US012729458B2

(12) United States Patent
Fox et al.

(10) Patent No.: US 12,729,458 B2
(45) Date of Patent: Sep. 8, 2026

(54) DISCOVERY AND EVOLUTION OF BIOLOGICALLY ACTIVE METABOLITES

(71) Applicant: The Regents of the University of Colorado, a Body Corporate, Denver, CO (US)

(72) Inventors: Jerome Fox, Boulder, CO (US); Ankur Sarkar, Boulder, CO (US)

(73) Assignee: The Regents of the University of Colorado, a Body Corporate, Denver, CO (US)

(*) Notice: Subject to any disclaimer, the term of this patent is extended or adjusted under 35 U.S.C. 154(b) by 1005 days.

(21) Appl. No.: 17/859,509

(22) Filed: Jul. 7, 2022

(65) Prior Publication Data

US 2023/0151354 A1 May 18, 2023

Related U.S. Application Data

(63) Continuation of application No. PCT/US2021/012621, filed on Jan. 8, 2021.

(60) Provisional application No. 62/958,368, filed on Jan. 8, 2020.

(51) Int. Cl.
*C40B 40/06* (2006.01)
*C12N 15/10* (2006.01)
*C40B 30/06* (2006.01)

(52) U.S. Cl.
CPC .......... *C40B 30/06* (2013.01); *C12N 15/1055* (2013.01)

(58) Field of Classification Search
None
See application file for complete search history.

(56) References Cited

U.S. PATENT DOCUMENTS 6,057,103 A * 5/2000 Short .................... C12N 15/52 536/25.4
6,200,759 B1 3/2001 Dove et al.
6,303,319 B1 10/2001 Rickles
6,428,951 B1 8/2002 Michnick et al.
7,927,794 B2 4/2011 Keasling et al.
8,586,725 B2 11/2013 Cummins et al.
8,716,460 B2 5/2014 Alfano et al.
8,859,232 B2 10/2014 Hahn et al.
10,385,332 B2 8/2019 Hill et al.
11,020,429 B2 6/2021 Thompson
11,472,847 B2 10/2022 Fox et al.
2002/0120947 A1 8/2002 Roch et al.
(Continued)

FOREIGN PATENT DOCUMENTS

CN 103160570 A 6/2013
EP 2116263 A1 11/2009
(Continued)

OTHER PUBLICATIONS

Badran et al. (2016) Nature vol. 533 pp. 58 to 63 and supplementary information (Year: 2016).*
(Continued)

*Primary Examiner* — Christian C Boesen
(74) *Attorney, Agent, or Firm* — WILSON SONSINI GOODRICH & ROSATI

(57) ABSTRACT

The disclosure provides systems, methods, reagents, apparatuses, vectors, and host cells for the discovery and evolution of metabolic pathways that produce small molecules that modulate enzyme function.

18 Claims, 54 Drawing Sheets

Specification includes a Sequence Listing.

(56) References Cited

U.S. PATENT DOCUMENTS

2002/0164587 A1 11/2002 Camonis et al.
2003/0170855 A1 9/2003 Zhang et al.
2003/0203471 A1 10/2003 Althoff et al.
2005/0040550 A1 2/2005 Short et al.
2005/0227357 A1 10/2005 Bohlmann et al.
2006/0292155 A1 12/2006 Golz et al.
2011/0046018 A1 2/2011 Chen et al.
2014/0315214 A1 10/2014 Taipale et al.
2018/0057545 A9 3/2018 Liu et al.
2018/0111929 A1 4/2018 Ibrahim et al.
2018/0230449 A1 8/2018 Niesert et al.
2020/0181598 A1 6/2020 Bode et al.
2020/0347428 A1 11/2020 Bode et al.

FOREIGN PATENT DOCUMENTS

WO WO-2004003550 A2 1/2004
WO WO-2004048549 A2 6/2004
WO WO-2008115420 A2 9/2008
WO WO-2011002977 A2 1/2011
WO WO-2011133493 A2 10/2011
WO WO-2012111772 A1 8/2012
WO WO-2013016693 A2 1/2013
WO WO-2014022434 A1 2/2014
WO WO-2015040197 A1 3/2015
WO WO-2015189428 A1 12/2015
WO WO-2018096150 A1 5/2018
WO WO-2019032628 A1 2/2019
WO WO-2019232025 A2 12/2019
WO WO-2020010364 A1 1/2020
WO WO-2021142207 A1 7/2021

OTHER PUBLICATIONS

Abraham et al., GROMACS: High performance molecular simulations through multi-level parallelism from laptops to supercomputers. SoftwareX. 1-2: 19-25 (2015).

Abu Bakar et al., Nonstructural proteins of alphavirus-potential targets for drug development. Viruses. 10(2):71 (2018).

Adams et al., Potent and selective inhibitors of the proteasome: dipeptidyl boronic acids. Bioorg Med Chem Lett. 8(4):333-338 (1998).

Aerts et al., Are public-private partnerships the solution to tackle neglected tropical diseases? A systematic review of the literature. Health Policy. 121(7):745-754 (2017).

Afonine et al. Towards automated crystallographic structure refinement with phenix.refine. Acta Crystallogr D Biol Crystallogr. 68(Pt 4):352-367 (2012).

Ajikumar et al. Isoprenoid pathway optimization for Taxol precursor overproduction in *Escherichia coli*. Science. 330(6000):70-74 (2010).

Akutsu et al., Molecular basis for ubiquitin and ISG15 cross-reactivity in viral ovarian tumor domains. Proc Natl Acad Sci USA. 108(6):2228-2233 (2011).

Aleshin et al., Activity, specificity, and probe design for the smallpox virus protease K7L. J Biol Chem. 287(47):39470-39479 (2012).

Aleshin et al., Structural evidence for regulation and specificity of flaviviral proteases and evolution of the Flaviviridae fold. Protein Sci. 16(5):795-806 (2007).

Alonso et al., Protein tyrosine phosphatases in the human genome. Cell. 117(6):699-711 (2004 ).

Amamuddy et al. Integrated computational approaches and tools for allosteric drug discovery. Int J Mol Sci. 21(3):847 (2020).

Anderie et al., Characterization of the C-terminal ER membrane anchor of PTP1B. Exp Cell Res. 313(15):3189-3197 (2007).

Antosch et al., Heterologous Reconstitution of Ikarugamycin Biosynthesis in *E. coli*. Angew Chem Int Ed Engl. 53(11):3011-3014 (2014).

Aramini et al., The RAS-binding domain of human BRAF protein serine/threonine kinase exhibits allosteric conformational changes upon binding HRAS. Structure. 23(8):1382-1393 (2015).

Arregui et al., Protein tyrosine phosphatase PTP1B in cell adhesion and migration. Cell Adh Migr. 7(5): 418-423 (2013).

Atanasov et al., Discovery and resupply of pharmacologically active plant-derived natural products: A review. Biotechnol Adv. 33(8):1582-1614 (2015).

Atanasov et al., Natural products in drug discovery: Advances and opportunities. Nat Rev Drug Discov. 20(3):200-216 (2021).

Attia et al., Molecular cloning and characterization of (+)-epi-α-bisabolol synthase, catalyzing the first step in the biosynthesis of the natural sweetener, hernandulcin, in Lippia dulcis. Arch Biochem Biophys. 527(1):37-44 (2012).

Auffinger et al., Halogen bonds in biological molecules. Proc Natl Acad Sci. USA. 101(48):16789-16794 (2004).

Auldridge et al., Bacterial phytochromes: more than meets the light. Crit Rev Biochem Mol Biol. 46(1):67-88 (2011).

Badran et al., Continuous evolution of Bacillus thuringiensis toxins overcomes insect resistance. Nature. 533(7601):58-63 (2016).

Banno et al., PTP1B and SHP2 in POMC neurons reciprocally regulate energy balance in mice. J Clin Invest. 120(3):120, 720-734 (2010).

Barr et al., Large-scale structural analysis of the classical human protein tyrosine phosphatome. Cell. 136(2):352-363 (2009).

Bence et al., Neuronal PTP1B regulates body weight, adiposity and leptin action. Nat Med. 12(8):917-924 (2006).

Benkert et al., Toward the estimation of the absolute quality of individual protein structure models. Bioinformatics. 27(3):343-350 (2011).

Bentires-Alj et al., Protein-tyrosine phosphatase 1B is required for HER2/Neu-induced breast cancer. Cancer Res. 67(6):2420-2424 (2007).

Bergmann et al., The refined crystal structure of the 3C gene product from hepatitis A virus: specific proteinase activity and RNA recognition. J Virol. 71(3): 2436-2448 (1997).

Bernhardt, Cytochromes P450 as versatile biocatalysts. J Biotechnol. 124(1):128-145 (2006).

Bohlmann et al., Terpenoid-based defenses in conifers: cDNA cloning, characterization, and functional expression of wound-inducible (E)-alpha-bisabolene synthase from grand fir (Abies grandis). 95(12): 6756-6761 (1998).

Boras et al., Preclinical characterization of an intravenous coronavirus 3CL protease inhibitor for the potential treatment of COVID19. Nat Commun. 12(1): 6055, 17pages (2021).

Boulware et al., Protease specificity determination by using cellular libraries of peptide substrates (CLIPS). Proc Natl Acad Sci USA. 103(20):7583-7588 (2006).

Bozhüyük et al., Modification and de novo design of non-ribosomal peptide synthetases using specific assembly points within condensation domains. Nat Chem. 11(7), 653-661 (2019).

Braun et al., MuteinDB: the mutein database linking substrates, products and enzymatic reactions directly with genetic variants of enzymes. Database (Oxford). 2012: bas028, 1-9 (2012).

Brown et al., Halogenase engineering for the generation of new natural product analogues. Chembiochem. 16(15): 2129-2135 (2015).

Bullock et al., Assessing helical protein interfaces for inhibitor design J Am Chem Soc. 133(36):14220-14223 (2011).

Burnham, K. P. & Anderson, D. R. Model Selection and Multimodel Inference: a Practical Information-theoretic Approach, 2nd edn. Springer-Verlag, New York. (2002).

Bussi et al., Canonical sampling through velocity rescaling. J Chem Phys. 126(1):014101 (2007).

Butler et al., Key mutations alter the cytochrome P450 BM3 conformational landscape and remove inherent substrate bias. J Biol Chem. 288(35):25387-25399 (2013).

Calla et al., Cytochrome P450 diversification and hostplant utilization patterns in specialist and generalist moths: Birth, death and adaptation. Mol Ecol. 26(21):6021-6035 (2017).

Camuesco et al., The intestinal anti-inflammatory effect of quercitrin is associated with an inhibition in iNOS expression. Br J Pharmacol. 143(7):908-918 (2004).

Carlson et al., Negative selection and stringency modulation in phage-assisted continuous evolution. Nat Chem Biol. 10(3):216-222 (2014).

(56) References Cited

OTHER PUBLICATIONS

Carter et al., Enthalpy-entropy compensation in biomolecular halogen bonds measured in DNA junctions. Biochemistry. 52(29):4891-4903 (2013).
Carter-Franklin et al., Vanadium haloperoxidase-catalyzed bromination and cyclization of terpenes. J Am Chem Soc. 125(13):3688-3689 (2003).
Chandramouli et al., Serotype-specific structural differences in the protease-cofactor complexes of the dengue virus family. J Virol. 84(6):3059-3067 (2010).
Chang et al., Production of isoprenoid pharmaceuticals by engineered microbes. Nat Chem Biol. 2(12):674-681 (2006).
Chang et al., Engineering *Escherichia coli* for production of functionalized terpenoids using plant P450s. Nat Chem Biol. 3(5):274-277 (2007).
Chatzivasileiou et al., Two-step pathway for isoprenoid synthesis. Proc Natl Acad Sci USA. 116(2):506-511 (2019).
Chaudhury et al., Identification of structural mechanisms of HIV-1 protease specificity using computational peptide docking: implications for drug resistance. Structure. 17(12):1636-1648 (2009).
Cheesman et al., Soluble and membrane-bound Drosophila melanogaster CYP6G1 expressed in *Escherichia coli*: purification, activity, and binding properties toward multiple pesticides. Insect Biochem Mol Biol. 43(5):455-465 (2013).
Chen et al., Allosteric inhibition of SHP2 phosphatase inhibits cancers driven by receptor tyrosine kinases. Nature. 535(7610):148-152 (2016).
Chen et al., Mechanisms of activation and inhibition of Zika virus NS2B-NS3 protease. Cell Res. 26(11):1260-1263 (2016).
Chen et al., Genomics and evolution of protein phosphatases. Sci Signal. 10(474):eaag1796. (2017).
Chen et al., A predictably selective aliphatic C-H oxidation reaction for complex molecule synthesis. Science. 318(5851):783-787 (2007).
Chen, X. et al., Statistical experimental design guided optimization of a one-pot biphasic multienzyme total synthesis of amorpha-4,11-diene. PLoS One. 8(11):e79650. (2013).
Chen, Y. et al., Emerging coronaviruses: Genome structure, replication, and pathogenesis. J Med Virol. 92(10):2249 (2020).
Cheng, Y. et al., Kidney disease is associated with in-hospital death of patients with COVID-19. Kidney Int. 97(5):829-838 (2020).
Cho, I. et al., Site-selective enzymatic C-H amidation for synthesis of diverse lactams. Science. 364(6440):575-578 (2019). Retraction (2020).
Choi, E. et al., Mitotic regulators and the SHP2-MAPK pathway promote IR endocytosis and feedback regulation of insulin signaling. Nat Commun. 10(1):1473 (2019).
Choi et al., Improvements to the ABSINTH force field for proteins based on experimentally derived amino acid specific backbone conformational statistics. J Chem Theory Comput. 15(2):1367-1382 (2019).
Choi, O. et al. Biosynthesis of plant-specific phenylpropanoids by construction of an artificial biosynthetic pathway in Escherichia coli. J Ind Microbiol Biotechnol. 38(10):1657-1665 (2011).
Choy et al., Conformational rigidity and protein dynamics at distinct timescales regulate PTP1B activity and allostery. Mol Cell 65(4):644-658 (2017).
Christianson, Structural biology and chemistry of the terpenoid cyclases. Chem Rev. 106(8):3412-3442 (2006).
Cortesio et al., Calpain 2 and PTP1B function in a novel pathway with Src to regulate invadopodia dynamics and breast cancer cell invasion. J Cell Biol. 180(5):957-971 (2008).
Cosentino et al., Engineering of a light-gated potassium channel. Science. 348(6235):707-710 (2015).
Cragg et al., Natural products: A continuing source of novel drug leads. Biochim Biophys Acta—Gen Subj. 1830(6):3670-3695 (2013).
Criswell et al., A single residue change leads to a hydroxylated product from the class II diterpene cyclization catalyzed by abietadiene synthase. Org Lett. 14(23):5828-5831 (2012).
Cui et al., A map of human cancer signaling. Mol Syst Biol. 3:152 (2007).
Culp et al., Evolution-guided discovery of antibiotics that inhibit peptidoglycan remodelling. Nature. 578(7796):582-587 (2020).
Cutler et al., The COVID-19 pandemic and the $16 trillion virus. Jama 324(15):1495-1496 (2020).
Dagliyan et al., Engineering extrinsic disorder to control protein activity in living cells. Science. 354(6318):1441-1444 (2016).
Danial et al., Cell death: critical control points. Cell. 116(2):205-219 (2004).
D'Arcy et al., Purification and crystallization of dengue and West Nile virus NS2B-NS3 complexes. Acta Crystallogr Sect F Struct Biol Cryst Commun. 62(Pt 2):157-162 (2006).
Darden et al., Particle mesh Ewald: An N.log(N) method for Ewald sums in large systems. J Chem Phys. 98:10089 (1993).
Davis et al., Directing evolution: The next revolution in drug discovery? Nat Rev Drug Discov. 16(10):681-698 (2017).
Davis, et al. Design, construction and characterization of a set of insulated bacterial promoters. Nucleic Acids Res. 39(3):1131-1141(2011).
De Sousa et al., Flavonoids as noncompetitive inhibitors of Dengue virus NS2B-NS3 protease: inhibition kinetics and docking studies. Bioorg Med Chem. 23(3):466-470 (2015).
Dempke et al., Targeting SHP-1, 2 and SHIP Pathways: A Novel Strategy for Cancer Treatment? Oncology. 95(5):257-269 (2018).
Dias et al., A Historical overview of natural products in drug discovery. Metabolites. 2(2):303-36 (2012).
Dietrich et al., A novel semi-biosynthetic route for artemisinin production using engineered substrate-promiscuous P450(BM3). ACS Chem Biol. 4(4):261-267 (2009).
Dietrich et al., High-throughput metabolic engineering: advances in small-molecule screening and selection. Annu Rev Biochem. 79:563-590 (2010).
Dong et al.; An interactive web-based dashboard to track COVID-19 in real time. Lancet Infect Dis. 20(5):533-534 (2020).
Douangamath et al., Crystallographic and electrophilic fragment screening of the SARS-CoV-2 main protease. Nat Commun. 11(1):5047 (2020).
Douzery et al., The timing of eukaryotic evolution: does a relaxed molecular clock reconcile proteins and fossils? Proc Natl Acad Sci. USA. 101(43):15386-15391 (2004).
Dove et al., Conversion of the ω subunit of *Escherichia coli* RNA polymerase into a transcriptional activator or an activation target. Genes Dev. 12(5):745-754 (1998).
Dove et al., Activation of prokaryotic transcription through arbitrary protein-protein contacts. Nature. 386(6625):627-630 (1997).
Dube et al., Genetic ablation of protein tyrosine phosphatase 1B accelerates lymphomagenesis of p53-null mice through the regulation of B-cell development. Cancer Res. 65(21):10088-10095 (2005).
Dubois et al., The SHP-1 protein tyrosine phosphatase negatively modulates glucose homeostasis. Nat Med. 12(5):549-556 (2006).
Dye, Flow cytometric analysis of Cfp-Yfp Fret as a marker for in vivo protein-protein interaction. Clin. Appl. Immunol. Rev. 5: 307-324 (2005).
Eche et al., Recombinant expression of HIV-1 protease using soluble fusion tags in *Escherichia coli*: A vital tool for functional characterization of HIV-1 protease. Virus Res. 295:198289 (2021).
Eden et al., Membrane contacts between endosomes and ER provide sites for PTP1B-epidermal growth factor receptor interaction. Nat Cell Biol. 12(3):267-72 (2010).
Edgar et al., Mechanistic insights into taxadiene epoxidation by taxadiene-5α-hydroxylase. ACS Chem. Biol. 11(2):460-469 (2016).
Emanuel et al., Fair allocation of scarce medical resources in the time of Covid-19. N Engl J Med. 382(21):2049-2055 (2020).
Emsley et al. Coot: model-building tools for molecular graphics. Acta Crystallogr D Biol Crystallogr. 60(Pt 12 Pt 1):2126-2132 (2004).
Erbel et al., Structural basis for the activation of flaviviral NS3 proteases from dengue and West Nile virus. Nat Struct Mol Biol. 13(4):372-373 (2006).
Esvelt et al., A system for the continuous directed evolution of biomolecules. Nature. 472(7344):499-503 (2011).
Faeder et al., Rule-based modeling of biochemical systems with BioNetGen. Methods Mol Biol. 500:113-167 (2009).

(56) References Cited

OTHER PUBLICATIONS

Fan et al., Optical control of biological processes by light-switchable proteins. Wiley Interdiscip Rev Dev Biol 4(5):545-554 (2015).
Fan et al., Protein-tyrosine phosphatase 1B antagonized signaling by insulin-like growth factor-1 receptor and kinase BRK/PTK6 in ovarian cancer cells. J Biol Chem. 288(34):24923-34 (2013).
Fasan, Tuning P450 enzymes as oxidation catalysts. ACS Catal. 2(4):647-666 (2012).
FDA Food and Drug Administration. Coronavirus (COVID-19) Drugs. at https://www.fda.gov/drugs/emergency-preparedness-drugs/coronavirus-covid-19-drugs (2022).
FDA Food and Drug Administration. Emergency Use Authorization. https://www.fda.gov/emergency-preparedness-and-response/mcm-legal-regulatory-and-policy-framework/emergency-use-authorization#coviddrugs (2022).
Fehr et al., In vivo imaging of the dynamics of glucose uptake in the cytosol of COS-7 cells by fluorescent nanosensors. J. Biol. Chem. 278: 19127-19133 (2003).
Felgner et al., Lipofection: a highly efficient, lipid-mediated DNA-transfection procedure. Proc Natl Acad Sci USA. 84(21):7413-7417 (1987).
Feiler et al., Directed evolution of mycobacterium tuberculosis ß-lactamase reveals gatekeeper residue that regulates antibiotic resistance and catalytic efficiency. PLoS One. 8(9):e73123 (2013).
Ferguson et al., Kinase inhibitors: The road ahead. Nat Rev Drug Discov. 17(5):353-377 (2018).
Ferreira et al., Molecular docking and structure-based drug design strategies. Molecules. 20(7): 13384-13421 (2015).
Fox et al., Interactions between Hofmeister anions and the binding pocket of a protein. J Am Chem Soc. 137(11):3859-3866 (2015).
Fox et al., Water-restructuring mutations can reverse the thermodynamic signature of ligand binding to human carbonic anhydrase. Angew Chem Int Ed Engl. 56(14):3833-3837 (2017).
Fox et al., The molecular origin of enthalpy/entropy compensation in biomolecular recognition. Annu Rev Biophys. 47:223-250 (2018).
Fürstenberg-Hägg et al., Plant defense against insect herbivores. Int J Mol Sci. 14(5):10242-10297 (2013).
Fujimori et al., What's new in enzymatic halogenations. Curr Opin Chem Biol. 11(5):553-560 (2007).
Fujisawa et al., Cloning and characterization of a novel gene that encodes (S)-ß-bisabolene synthase from ginger, Zingiber officinale. Planta 232(1):121-130 (2010).
Galanie et al., Complete biosynthesis of opioids in yeast. Science. 349(6252):1095-1100 (2015).
Gallagher, COVID19 therapeutics: Expanding the antiviral arsenal. EBioMedicine. 66:103289 (2021).
Gao et al., Structure of the RNA-dependent RNA polymerase from COVID-19 virus. Science. 368(6492):779-782 (2020).
Gautier et al., How to control proteins with light in living systems. Nat. Chem. Biol. 10: 533-41 (2014).
Gavory et al., Discovery and characterization of highly potent and selective allosteric USP7 inhibitors. Nat Chem Biol.14(2):118-125 (2018).
George et al., Isoprenoid drugs, biofuels, and chemicals—artemisinin, farnesene, and beyond. Adv Biochem Eng Biotechnol. 148: 355-389 (2015).
Gershenzon et al., The function of terpene natural products in the natural world. Nat Chem Biol. 3(7):408-414 (2007).
Gibbs et al., Inhibitor bound dengue NS2B-NS3pro reveals multiple dynamic binding modes. Biochemistry 57(10):1591-1602 (2018).
Gil-Parrado et al., lonomycin-activated calpain triggers apoptosis. A probable role for Bcl-2 family members. J Biol Chem. 277(30): 27217-27226 (2002).
Goldstein et al., Tyrosine dephosphorylation and deactivation of insulin receptor substrate-1 by protein-tyrosine phosphatase 1B. Possible facilitation by the formation of a ternary complex with the GRB2 adaptor protein. J Biol Chem. 275(6):4283-4289 (2000).
Gorbalenya et al., The species Severe acute respiratory syndrome-related coronavirus: classifying 2019-nCoV and naming it SARS-CoV-2. Nature Microbiology 5(4):536-544 (2020).
Gordon et al., A SARS-CoV-2-Human protein-protein interaction map reveals drug targets and potential drug-repurposing. Nature. 583(7816):459-468 (2020).
Govindarajan et al., Estimating the total number of protein folds. Proteins 35(4): 408-414 (1999).
Grangeasse et al., Bacterial tyrosine kinases: Evolution, biological function and structural insights. Philos Trans R Soc B Biol Sci. 367(1602):2640-2655 (2012).
Gruet et al., One-step generation of error-prone PCR libraries using Gateway® technology. Microb Cell Fact. 11:14 (2012).
Gu et al., COVID-19: gastrointestinal manifestations and potential fecal-oral transmission. Gastroenterology. 158(6):1518-1519 (2020).
Guex et al., Automated comparative protein structure modeling with SWISS-MODEL and Swiss-PdbViewer: a historical perspective. Electrophoresis. 30(Suppl 1):S162-S173 (2009).
Gunst et al., Efficacy of the TMPRSS2 inhibitor camostat mesilate in patients hospitalized with Covid-19-a double-blind randomized controlled trial. EClinicalMedicine. 35:100849 (2021).
Guo et al., Bisphosphonates target multiple sites in both cis- and trans-prenyltransferases. Proc Natl Acad Sci USA. 104(24):10022-10027(2007).
Guo et al., Discovery of reactive microbiota-derived metabolites that inhibit host proteases. Cell. 168(3):517-526.e18 (2017).
Haj et al., Imaging sites of receptor dephosphorylation by PTP1B on the surface of the endoplasmic reticulum. Science. 295(5560):1708-1711 (2002).
Haj et al., Regulation of signaling at regions of cell-cell contact by endoplasmic reticulum-bound protein-tyrosine phosphatase 1B. PLoS One. 7(5): e36633 (2012).
Halavaty et al., N- and C-terminal flanking regions modulate light-induced signal transduction in the LOV2 domain of the blue light sensor phototropin 1 from Avena sativa. Biochemistry. 46(49):14001-14009 (2007).
Hamberger et al., Evolution of diterpene metabolism: Sitka spruce CYP720B4 catalyzes multiple oxidations in resin acid biosynthesis of conifer defense against insects. Plant Physiol. 157(4): 1677-1695 (2011).
Hammamy et al., Development and Characterization of new peptidomimetic inhibitors of the West Nile Virus NS2B-NS3 Protease. ChemMedChem 8(2):231-241 (2013).
Hartenfeller et al., De novo drug design. Chemoinformatics and Computational Chemical Biology (ed. Bajorath, J.). 672: 299-323 (2010).
Harvey et al., The re-emergence of natural products for drug discovery in the genomics era. Nature reviews drug discovery 14(2):111-129 (2015).
Harvey, Natural products in drug discovery. Drug Discov. 13(19-20):894-901 (2008).
He et al., Protein tyrosine phosphatases as potential therapeutic targets. Acta Pharmacol Sin. 35(10):1227-1246 (2014).
Henrich et al., Matching the power of high throughput screening to the chemical diversity of natural products. Nat Prod Rep. 30(10):1284-1298 (2013).
Hert et al., Quantifying biogenic bias in screening libraries. Nat Chem Biol. 5(7): 479-483 (2009).
Hess et al., LINCS: A linear constraint solver for molecular simulations. J Comput Chem. 18:1463-1472 (1997).
Hjortness et al., Abietane-type diterpenoids inhibit protein tyrosine phosphatases by stabilizing an inactive enzyme conformation. Biochemistry 57(40):5886-5896 (2018).
Hjortness et al., Evolutionarily Conserved Allosteric Communication in Protein Tyrosine Phosphatases. Biochemistry. 57(45):6443-6451 (2018).
Ho et al., Critical assessment of the important residues involved in the dimerization and catalysis of MERS coronavirus main protease. PLOS One 10(12):e0144865 (2015).
Hoffman et al., SARS-CoV-2 cell entry depends on ACE2 and TMPRSS2 and is blocked by a clinically proven protease inhibitor. Cell. 181(2):271-280 (2020).

(56) References Cited

OTHER PUBLICATIONS

Hu et al., Kinetic, mutational, and structural studies of the Venezuelan equine encephalitis virus nonstructural protein 2 cysteine protease. Biochemistry 55(21):3007-3019 (2016).
Huang et al., Sesquiterpenes produced by truncated taxadiene synthase. Tetrahedron Lett. 41(50): 9701-9704 (2000).
Huang et al., CHARMM36m: An improved force field for folded and intrinsically disordered proteins. Nat Methods. 14(1): 71-73 (2017).
Huang et al., Understanding HIV-1 protease autoprocessing for novel therapeutic development. Future Med Chem. 5(11):1215-1229 (2013).
Hubbard et al., Protein tyrosine kinase structure and function. Annu Rev Biochem. 69:373-398 (2000).
Hubert et al., Dereplication strategies in natural product research: How many tools and methodologies behind the same concept? Phytochem Rev.16(1):55-95 (2017).
Hughes et al., Principles of early drug discovery. Br J Pharmacol. 162(6):1239-1249 (2011).
Ito et al., PTK6 inhibition suppresses metastases of triple-negative breast cancer via SNAIL-dependent E-cadherin regulation. Cancer Res. 76(15):4406-4417 (2016).
Jantan et al., Plant-derived immunomodulators: an insight on their preclinical evaluation and clinical trials. Front Plant Sci. 6:655 (2015).
Jendresen et al., Highly active and specific tyrosine ammonia-lyases from diverse origins enable enhanced production of aromatic compounds in bacteria and *Saccharomyces cerevisiae*. Appl Environ Microbiol. 81(13):4458-4476 (2015).
Jensen et al., Challenges and triumphs to genomics-based natural product discovery. J Ind Microbiol Biotechnol. 41(2):203-209 (2014).
Jensen, Natural products and the gene cluster revolution. Trends Microbiol. 24(12): 968-977 (2016).
Jewell et al., Hepatitis A virus 3C proteinase substrate specificity. Biochemistry 31(34): 7862-7869 (1992).
Jia et al., Extreme promiscuity of a bacterial and a plant diterpene synthase enables combinatorial biosynthesis. Metab Eng. 37: 24-34 (2016).
Jia et al., Combinatorial biosynthesis and the basis for substrate promiscuity in class I diterpene synthases. Metabolic Eng. 55:44-58 (2019).
Jiang et al., Natural products possessing protein tyrosine phosphatase 1B (PTP1B) inhibitory activity found in the last decades. Acta Pharmacol Sin. 33(10):1217-1245 (2012). doi:10.1038/aps.2012.90.
Jin et al., Structure of Mpro from SARS-CoV-2 and discovery of its inhibitors. Nature. 582(7811):289-293 (2020).
Johnson et al., Protein tyrosine phosphatase IB inhibitors for diabetes. Nat Rev Drug Discov. 1(9):696-709 (2002).
Johnston et al., Continuous bioactivity-dependent evolution of an antibiotic biosynthetic pathway. Nat. Commun. 11(1):4202 (2020).
Joosten et al., The PDB_REDO server for macromolecular structure model optimization. IUCrJ 1(Pt 4):213-220 (2014).
Jung et al., Cytochrome P450: taming a wild type enzyme. Curr Opin Biotechnol. 22(6):809-817 (2011).
Kaberniuk et al., A bacterial phytochrome-based optogenetic system controllable with near-infrared light. Nat Methods. 13(7):591-7 (2016).
Kachroo et al., Systematic humanization of yeast genes reveals conserved functions and genetic modularity. Science. 348(6237):921-925 (2015).
Kampranis et al., Rational conversion of substrate and product specificity in a Salvia monoterpene synthase: structural insights into the evolution of terpene synthase function. Plant Cell. 19(6):1994-2005 (2007).
Kaneko et al. Superbinder SH2 domains act as antagonists of cell signaling. Sci Signal. 5(243):ra68 (2012).
Karunarathne et al., Subcellular optogenetics—controlling signaling and single-cell behavior. J Cell Sci. 128(1):15-25 (2015).
Keedy et al., An expanded allosteric network in PTP1B by multitemperature crystallography, fragment screening, and covalent tethering. Elife. 7:e36307 (2018).
Kennedy, Signal-Processing Machines at the Postsynaptic Density. Science. 290(5492):750-754 (2000).
Kennedy, Managing the drug discovery/development interface. Drug Discov Today. 2(10):436-444 (1997).
Khaerunnisa et al., Potential Inhibitor of COVID-19 Main Protease (Mpro) from Several Medicinal Plant Compounds by Molecular Docking Study. Preprints. 14 pages (2020). doi:10.20944/preprints202003.0226.v1.
Khrimian et al., Absolute configurations of stink bug- and plant-produced sesquipiperitols via synthesis of all stereoisomers. J Nat Prod. 83(7)2281-2286 (2020).
Kitaoka et al., Optimization of recombinant expression enables discovery of novel cytochrome P450 activity in rice diterpenoid biosynthesis. Appl Microbiol Biotechnol. 99(18):7549-7558 (2015).
Klebe, Applying thermodynamic profiling in lead finding and optimization. Nat Rev Drug Discov. 14(2):95-110 (2015).
Koehn et al., The evolving role of natural products in drug discovery. Nat Rev Drug Discov. 4(3):206-220 (2005).
Koh et al., Current trends in modem pharmaceutical analysis for drug discovery. Drug Discov Today. 8(19): 889-897 (2003).
Konc et al., ProBiS-CHARMMing: web interface for prediction and optimization of ligands in protein binding sites. J Chem Inf Model. 55(11):2308-2314 (2015).
Kondo et al., Yellow fever virus NS2B/NS3 protease: hydrolytic properties and substrate specificity. Biochem Biophys Res Commun. 407(4):640-644 (2011).
Koren et al., Inhibition of the protein tyrosine phosphatase PTP1B: potential therapy for obesity, insulin resistance and type-2 diabetes mellitus. Best Pract Res Clin Endocrinol Metab. Metab. 21(4):621-640 (2007).
Krauss et al., LOVely enzymes—towards engineering light-controllable biocatalysts. Microb Biotechnol. 3(1):15-23 (2010).
Krimmer et al., Methyl, ethyl, propyl, butyl: futile but not for water, as the correlation of structure and thermodynamic signature shows in a congeneric series of thermolysin inhibitors. ChemMedChem 9(4):833-846 (2014).
Krishnan et al., Anxious moments for the protein tyrosine phosphatase PTP1B. Trends Neurosci. 38(8):462-465 (2015).
Krishnan et al., Targeting the disordered C terminus of PTP1B with an allosteric inhibitor. Nat Chem Biol. 10(7): 558-566 (2014).
Krishnan et al. PTP1B inhibition suggests a therapeutic strategy for Rett syndrome. J Clin Invest. 125(8):3163-3177 (2015).
Lancaster, J. et al., An IDS-type sesquiterpene synthase produces the pheromone precursor (Z)-α-bisabolene in Nezara viridula. J Chem Ecol. 45(2):187-197 (2019).
Lange et al., Enzymology of monoterpene functionalization in glandular trichomes. J Exp Bot. 70(4):1095-1108 (2019).
Lauchli et al., High-throughput screening for terpene-synthase-cyclization activity and directed evolution of a terpene synthase. Angew Chem Int Ed Engl. 52(21):5571-5574 (2013).
Lee et al., Identification of novel small molecule inhibitors against NS2B/NS3 serine protease from Zika virus. Antiviral Res. 139, 49-58 (2017).
Lee et al., Phosphorylation of the AMPA receptor GluR1 subunit is required for synaptic plasticity and retention of spatial memory. Cell. 112(5):631-643 (2003).
Lee et al. Proteasome inhibitors: valuable new tools for cell biologists. Trends Cell Biol. 8(10):397-403 (1998).
Lee et al., Surface sites for engineering allosteric control in proteins. Science. 322(5900):438-442 (2008).
Lehmann et al., Identification of human triple-negative breast cancer subtypes and preclinical models for selection of targeted therapies. J Clin Invest. 121(7):2750-2767 (2011).
Lei et al., Crystal structure of the papain-like protease of MERS coronavirus reveals unusual, potentially druggable active-site features. Antiviral Res. 109:72-82 (2014).
Lei et al., Crystal structure of Zika virus NS2B-NS3 protease in complex with a boronate inhibitor. Science. 353(6298):503-505 (2016).

(56) References Cited

OTHER PUBLICATIONS

Leonard et al., Combining metabolic and protein engineering of a terpenoid biosynthetic pathway for overproduction and selectivity control. Proc Natl Acad Sci USA. 107(31):13654-13659 (2010).
Lessard et al., PTP1B is an androgen receptor-regulated phosphatase that promotes the progression of prostate cancer. Cancer Res. 72(6):1529-1537 (2012).
Lessard et al., The two faces of PTP1B in cancer. Biochim Biophys Acta. 1804(3):613-619 (2010).
Lewis et al., Combinatorial alanine substitution enables rapid optimization of cytochrome P450BM3 for selective hydroxylation of large substrates. Chembiochem 11(18):2502-2505 (2010).
Li et al., Reprogramming the chemodiversity of terpenoid cyclization by remolding the active site contour of epi-isozizaene synthase. Biochemistry. 53(7):1155-1168 (2014).
Li et al., Therapeutic options for the 2019 novel coronavirus (2019-nCOV). Nat Rev Drug Discov. 19(3):149-150 (2020).
Li et al., Crystal Structure and Substrate Specificity of PTPN12. Cell Rep. 15(6):1345-1358 (2016).
Li et al., Production of plant-specific flavones baicalein and scutellarein in an engineered *E. coli* from available phenylalanine and tyrosine. Metab Eng. 52:124-133 (2019).
Li et al., Drug discovery and natural products: end of an era or an endless frontier? Science. 10;325(5937):161-165 (2009).
Li et al., Complete biosynthesis of noscapine and halogenated alkaloids in yeast. Proc Natl Acad Sci USA. 115(17):E3922-E3931 (2018).
Lim et al., (-)-α-Bisabolol production in engineered *Escherichia coli* expressing a novel (+)-α-Bisabolol synthase from the globe artichoke *Cynara cardunculus* var. scolymus. J Agric Food Chem. 69 (30):8492-8503 (2021).
Lim et al., Human coronaviruses: A review of virus-host interactions. Diseases. 4(3):26 (2016).
Lindner et al., The papain-like protease from the severe acute respiratory syndrome coronavirus is a deubiquitinating enzyme. J Virol. 79(24):15199-15208 (2005).
Ling et al., Cytostatic and cytotoxic natural products against cancer cell models. Molecules. 24(10):2012 (2019).
Liu et al., PTP1B promotes cell proliferation and metastasis through activating src and ERK1/2 in non-small cell lung cancer. Cancer Lett. 359(2):218-225 (2015).
Loehr et al., Yellow fever virus NS3 protease: peptide-inhibition studies. J Gen Virol. 88(Pt 8):2223-2227 (2007).
Lu et al., Co-expression of P450 BM3 and glucose dehydrogenase by recombinant *Escherichia coli* and its application in an NADPH-dependent indigo production system. J Ind Microbiol Biotechnol. 34(3):247-253 (2007).
Lukyanov et al., Innovation: Photoactivatable fluorescent proteins. Nat Rev Mol Cell Biol. 6(11):885-891 (2005).
Luo et al., Crystal structure of the NS3 protease-helicase from dengue virus. J Virol 82(1): 173-183 (2008).
Luo et al., Flexibility between the protease and helicase domains of the dengue virus NS3 protein conferred by the linker region and its functional implications. J Biol Chem. 285(24):18817-18827 (2010).
Luo et al., Complete biosynthesis of cannabinoids and their unnatural analogues in yeast. Nature. 567(7746):123-126 (2019).
Lv et al., HIV protease inhibitors: a review of molecular selectivity and toxicity. Hiv Aids (Auckl). 7:95-104. (2015).
Mackerell et al., All-atom empirical potential for molecular modeling and dynamics studies of proteins. J Phys Chem B. 102(18):3586-3616 (1998).
Mafu et al., Probing the promiscuity of ent -kaurene oxidases via combinatorial biosynthesis. Proc Natl Acad Sci USA. 113(9):2526-2531 (2016).
Maier, Design and synthesis of analogues of natural products. Org Biomol Chem. 13(19):5302-5343 (2015).
Malcolm et al., Expression and characterization of recombinant hepatitis A virus 3C proteinase. Biochemistry. 31(13):3358-3363 (1992).
Manguso et al. In vivo CRISPR screening identifies Ptpn2 as a cancer immunotherapy target. Nature. 547(7664):413-418 (2017).
Mao et al., Neurologic manifestations of hospitalized patients with coronavirus disease 2019 in Wuhan, China. JAMA Neurol. 77(6):683-690 (2020).
Martin et al., Engineering a mevalonate pathway in *Escherichia coli* for production of terpenoids. Nat Biotechnol. 21(7):796-802 (2003).
Martins et al., Marketed marine natural products in the pharmaceutical and cosmeceutical industries: tips for success. Mar drugs. 12(2):1066 -1101 (2014).
Matulka et al., PTP1B is an effector of activin signaling and regulates neural specification of embryonic stem cells. Cell Stem Cell. 13(6):706-719 (2013).
McAndrew et al., Structure of a three-domain sesquiterpene synthase: A prospective target for advanced biofuels production. Structure. 19(12):1876-1884 (2011).
McKibbin et al., The Global Macroeconomic Impacts of COVID-19: Seven Scenarios. SSRN Electronic Journal. CAMA Working Paper No. 19/2020: 45 pages (2020).
Medema et al., antiSMASH: rapid identification, annotation and analysis of secondary metabolite biosynthesis gene clusters in bacterial and fungal genome sequences. Nucleic Acids Res. 39(Web Server issue): W339-46 (2011).
Mehla et al., A comparison of two-hybrid approaches for detecting protein-protein interactions. Methods Enzymol. 586:333-358 (2017).
Mellott et al., A clinical-stage cysteine protease inhibitor blocks SARS-CoV-2 infection of human and monkey cells. ACS Chem Biol. 16(4):642-650 (2021).
Mendoza et al., Two detailed plaque assay protocols for the quantification of infectious SARS-CoV-2. Curr Protoc Microbiol. 57(1):ecpmc105 (2020).
Menon et al., RadH: A versatile halogenase for integration into synthetic pathways. Angew Chem Int Ed Engl. 56(39):11841-11845 (2017).
Merck. Merck and Ridgeback Biotherapeutics Provide Update on Results from MOVe-OUT Study of Molnupiravir, an Investigational Oral Antiviral Medicine, in At Risk Adults With Mild-to- Moderate COVID-19. at https://www.merck.com/news/merck-and-ridgeback-biotherapeutics-provide-update-on-results-from-move-out-study-of-molnupiravir-an-investigational-oral-antiviral-medicine-in-at-risk-adults-with-mild-to-moderate-covid-19/ (2021).
Merck. Merck and Ridgeback's Investigational Oral Antiviral Molnupiravir Reduced the Risk of Hospitalization or Death by Approximately 50 Percent Compared to Placebo for Patients with Mild or Moderate COVID-19 in Positive Interim Analysis of Phase 3 Study. at https://www.merck.com/news/merck-and-ridgebacks-investigational-oral-antiviral-molnupiravir-reduced-the-risk-of-hospitalization-or-death-by-approximately-50-percent-compared-to-placebo-for-patients-with-mild-or-moderat/ (2021).
Mobley et al., Predicting binding free energies: frontiers and benchmarks. Annu. Rev. Biophys. 46:531-558 (2017).
Montalibet et al., Using yeast to screen for inhibitors of protein tyrosine phosphatase 1B. Biochem Pharmacol. 68(9):1807-1814 (2004).
Montalibet et al. Residues distant from the active site influence protein-tyrosine phosphatase 1B inhibitor binding. J Biol Chem. 281(8):5258-5266 (2006).
Morrone et al., Increasing diterpene yield with a modular metabolic engineering system in *E. coli*: Comparison of MEV and MEP isoprenoid precursor pathway engineering. Appl Microbial Biotechnol. 85(6):1893-1906 (2010).
Muangphrom et al., Identification and characterization of a novel sesquiterpene synthase, 4-amorphen-11-ol synthase, from artemisia maritima. Plant Biotechnol. 35(2):113-121 (2018).
Muangphrom et al. Functional analysis of amorpha-4,11-diene synthase (ADS) homologs from non-artemisinin-producing artemisia species: The discovery of novel koidzumiol and (+)-α-Bisabolol synthases. Plant Cell Physiol. 57(8):1678-1688 (2016).
Murphy et al., WScore: A flexible and accurate treatment of explicit water molecules in ligand-receptor docking. J Med Chem. 59(9):4364-4384 (2016).
Muzzarelli et al., Structural and antiviral studies of the human norovirus GII.4 protease. Biochemistry. 58(7):900-907 (2019).

(56) References Cited

OTHER PUBLICATIONS

Nakagawa et al., A bacterial platform for fermentative production of plant alkaloids. Nat Commun. 2:326 (2011).
Nakamura et al., A norovirus protease structure provides insights into active and substrate binding site integrity. J Virol. 79(21):13685-13693 (2005).
Nalam et al., Evaluating the substrate-envelope hypothesis: structural analysis of novel HIV-1 protease inhibitors designed to be robust against drug resistance. J Virol. 84(10):5368-5378 (2010).
Namchuk, Early returns on small molecule therapeutics for SARS-CoV-2. ACS Infect Dis. 7(6):1298-1302 (2021).
Narwal et al., Crystal structure of chikungunya virus nsP2 cysteine protease reveals a putative flexible loop blocking its active site. Int J Biol Macromol. 116:451-462 (2018).
Needle et al., Structures of the middle east respiratory syndrome coronavirus 3C-like protease reveal insights into substrate specificity. Acta Crystallogr D Biol Crystallogr. 71(Pt 5):1102-1111 (2015).
Newman et al., Natural products as sources of new drugs from 1981 to 2014. Journal of Natural Products. 79(3):629-661 (2016).
Next Generation Sequencing: Amplicon-EZ. at https://www.genewiz.com/en/Public/Services/Next-Generation-Sequencing/Amplicon-Sequencing-Services/Amplicon-EZ (2022).
NIAID National Institute of Allergy and Infectious Diseases. Emerging Infectious Diseases/Pathogens. at https://www.niaid.nih.gov/research/emerging-infectious-diseases-pathogens (2018).
Nitsche et al., Peptide-boronic acid inhibitors of flaviviral proteases: medicinal chemistry and structural biology. J Med Chem. 60(1):511-516 (2017).
Nitsche, Proteases from dengue, West Nile and Zika viruses as drug targets. Biophys Rev. 11(2):157-165 (2019).
Noble et al., Ligand-bound structures of the dengue virus protease reveal the active conformation. J Virol. 86(1):438-446 (2012).
Noske et al., Structural characterization and polymorphism analysis of the NS2B-NS3 protease from the 2017 Brazilian circulating strain of Yellow Fever virus. Biochimica et Biophysica Acta (BBA)-General Subjects 1864(4):129521 (2020).
O'Brien et al., Inparanoid: A comprehensive database of eukaryotic orthologs. Nucleic Acids Res. 33(Database issue):D476-D480 (2005).
Oleinikovas et al., Understanding cryptic pocket formation in protein targets by enhanced sampling simulations. J Am Chem Soc. 138(43):14257-14263 (2016).
Olsson et al., The thermodynamics of protein-ligand interaction and solvation: insights for ligand design. J Mol Biol. 384(4):1002-1017 (2008).
O'Maille et al., Quantitative exploration of the catalytic landscape separating divergent plant sesquiterpene synthases. Nat Chem Biol. 4(10):617-623 (2008).
Otto et al., Cysteine proteases and their inhibitors. Chem Rev. 97(1):133-172 (1997).
Ouyang et al., Determination of hierarchical relationship of Src and Rac at subcellular locations with FRET biosensors. Proc Natl Acad Sci USA. 105(38):14353-14358 (2008).
Packer et al., Methods for the directed evolution of proteins. Nat Rev Genet. 16(7):379-394 (2015).
Paddon et al., Semi-synthetic artemisinin: a model for the use of synthetic biology in pharmaceutical development. Nat Rev Microbiol. 12(5):355-367 (2014).
Palazón-Riquelme et al., USP7 and USP47 deubiquitinases regulate NLRP3 inflammasome activation. EMBO Rep. 19(10):e44766 (2018).
Paling et al., Role of the protein tyrosine phosphatase SHP-1 (Src homology phosphatase-1) in the regulation of interleukin-3-induced survival, proliferation and signalling. Biochem. J. 368(Pt 3):885-894 (2002).
Pallesen et al., Immunogenicity and structures of a rationally designed prefusion MERS-CoV spike antigen. Proc Natl Acad Sci USA. 114(35):E7348-E7357 (2017).
Park et al., Whole-cell biocatalysis using cytochrome P450 monooxygenases for biotransformation of sustainable bioresources (fatty acids, fatty alkanes, and aromatic amino acids). Biotechnol Adv. 40:107504 (2020).
Parrinello, Polymorphic transitions in single crystals: A new molecular dynamics method. J Appl Phys. 52(12):7182 (1981).
Pastorino et al., Expression and biochemical characterization of nsP2 cysteine protease of Chikungunya virus. Virus Res.131(2):293-298 (2008).
Pastorino et al., Improvement of the purification of Saint Louis encephalitis virus NS2B-NS3 recombinant protease expressed in *Escherichia coli*. J Chromatogr B Analyt Technol Biomed Life Sci. 868(1-2):58-63 (2008).
Pathan et al., Basic opioid pharmacology: an update. Br J Pain. 6(1):11-16 (2012).
Paul et al., Tyrosine kinase—role and significance in Cancer. Int J Med Sci. 1(2):101-115 (2004).
Paul et al., How to improve R&D productivity: The pharmaceutical industry's grand challenge. Nat Rev Drug Discov. 9(3):203-214 (2010).
PCT/US2019/040896 International Preliminary Report on Patentability dated Jan. 12, 2021.
PCT/US2019/040896 International Search Report and Written Opinion dated Nov. 8, 2019.
PCT/US2021/012621 International Search Report and Written Opinion dated Apr. 6, 2021.
Pelander et al., In silica methods for predicting metabolism and mass fragmentation applied to quetiapine in liquid chromatography/time-of-flight mass spectrometry urine drug screening. Rapid Commun Mass Spectrom. 23(4):506-514 (2009).
Peralta-Yahya et al. Identification and microbial production of a terpene-based advanced biofuel. Nat Commun. 2:483 (2011).
Peter et al., Mechanism of signal transduction of the LOV2-Jα photosensor from Avena sativa. Nat Commun. 1:122 (2010).
Peters et al., Abietadiene synthase catalysis: mutational analysis of a prenyl diphosphate ionization-initiated cyclization and rearrangement. Proc Natl Acad Sci USA. 99(2):580-584 (2002).
Peters et al., Abietadiene synthase from grand fir (Abies grandis): Characterization and mechanism of action of the "pseudomature" recombinant enzyme. Biochemistry 39(50): 15592-15602 (2000).
Pfeifer et al., Biosynthesis of Yersiniabactin, a complex polyketide-nonribosomal peptide, using *Escherichia coli* as a heterologous host. Appl Environ Microbiol. 69(11):6698-6702 (2003).
Pfizer. Pfizer Seeks Emergency Use Authorization For Novel COVID-19 Oral Antiviral Candidate. at https://www.pfizer.com/news/press-release/press-release-detail/pfizer-seeks-emergency-use-authorization-novel-covid-19 (2021).
PHE Public Health Emergency. Pause in the Distribution of Bamlanivimab/Etesevimab. at https://www.phe.gov/emergency/events/COVID19/investigation-MCM/Bamlanivimab- etesevimab/Pages/bamlanivimab-etesevimab-distribution-pause.aspx (2021).
Phoo et al., Structures of Zika virus NS2B-NS3 protease in complex with peptidomimetic inhibitors. Antiviral Res. 160:17-24 (2018).
Pike et al., Protein tyrosine phosphatase 1B is a regulator of the interleukin-10-induced transcriptional program in macrophages. Sci Signal. 7(324):ra43 (2014).
Piserchio et al., Expression and purification of Src-family kinases for solution NMR studies. Methods Mol Biol. 831:111-131 (2012).
Porter et al., Cooperative changes in solvent exposure identify cryptic pockets, switches, and allosteric coupling. Biophys J. 116(5):818-830 (2019).
Price et al., FastTree 2—approximately maximum-likelihood trees for large alignments. PLoS One 5(3):e9490 (2010).
Qin et al., Chronic stress induces anxiety via an amygdalar intracellular cascade that impairs endocannabinoid signaling. Neuron. 85(6):1319-1331 (2015).
Rani et al., Drug development post COVID-19 pandemic: toward a better system to meet current and future global health challenges. Expert Opin Drug Discov. 16(4):365-371 (2021).
Ratia et al., Severe acute respiratory syndrome coronavirus papain-like protease: structure of a viral deubiquitinating enzyme. Proc Natl Acad Sci USA.103(15):5717-5722 (2006).
Repina et al., At light speed: Advances in optogenetic systems for regulating cell signaling and behavior. Annu Rev Chem Biomol Eng. 8:13-39 (2017).
Rhee et al., Protein tyrosine phosphatases in lymphocyte activation and autoimmunity. Nat Immunol. 13(5): 439-447 (2012).

(56) References Cited

OTHER PUBLICATIONS

Rinkel et al., Stereochemical investigations on the biosynthesis of achiral (Z)-γ-bisabolene in Cryptosporangium arvum. Beilstein J Org Chem. 15:789-794 (2019).
Rizzuti et al., Sub-micromolar inhibition of SARS-CoV-2 3CLpro by natural compounds. Pharmaceuticals (Basel) 14(9):892 (2021).
Ro et al., Production of the antimalarial drug precursor artemisinic acid in engineered yeast. Nature. 440(7086):940-943 (2006).
Robin et al., Structure of West Nile virus NS3 protease: ligand stabilization of the catalytic conformation. J Mol Biol. 385(5):1568-1577 (2009).
Robinson et al., Differential water thermodynamics determine PI3K-Beta/Delta selectivity for solvent-exposed ligand modifications. J Chem Inf Model. 56(5):886-894 (2016).
Rodrigues et al., Counting on natural products for drug design. Nature chemistry 8(6):531-541 (2016).
Rodriguez et al., The growing and glowing toolbox of fluorescent and photoactive proteins. Trends Biochem. Sci. 42(2):111-129 (2017).
Romsicki et al., Protein tyrosine phosphatase-1B dephosphorylation of the insulin receptor occurs in a perinuclear endosome compartment in human embryonic kidney 293 cells. J Biol Chem. 279(13): 12868-12875 (2004).
Rougéet al., Molecular understanding of USP7 substrate recognition and C-terminal activation. Structure. 24(8):1335-1345 (2016).
Rowland et al., ER contact sites define the position and timing of endosome fission. Cell 159(5):1027-1041 (2014).
Russo et al., The crystal structure of the Venezuelan equine encephalitis alphavirus nsP2 protease. Structure 14(9):1449-1458 (2006).
Rut et al., Profiling of flaviviral NS2B-NS3 protease specificity provides a structural basis for the development of selective chemical tools that differentiate Dengue from Zika and West Nile viruses. Antiviral Research 175:104731 (2020).
Rutledge et al. Discovery of microbial natural products by activation of silent biosynthetic gene clusters. Nat Rev Microbiol. 13(8):509-523 (2015).
Ruttkies et al., MetFrag relaunched: Incorporating strategies beyond in silica fragmentation. J Cheminform. 8:3 (2016).
Salis, The ribosome binding site calculator. Methods Enzymol. 498:19-42 (2011).
Sangster et al., New trends and future opportunities in the enzymatic formation of C-C, C-N, and C-O bonds. Chembiochem 23(6):e202100464. (2021).
Sarkar et al., Microbially guided discovery and biosynthesis of biologically active natural products. ACS Synth Biol 10(6):1505-1519 (2021).
Sarkar et al., Evolution-guided biosynthesis of terpenoid Inhibitors. ACS Synth Biol. 11(9):3015-3027 (2022).
Sarrade-Loucheur et al., Synthetic derivatives of (+)-epi-α-bisabolol are formed by mammalian cytochromes P450 expressed in a yeast reconstituted pathway. ACS Synth Biol. 9(2):368-380 (2020).
Sato et al., Fluorescent indicators for imaging protein phosphorylation in single living cells. Nat Biotechnol. 20(3):287-294 (2002).
Scott et al., Targeting protein tyrosine phosphatases for anticancer drug discovery. Curr Pharm Des. 16(16):1843-1862 (2010).
Seifert et al., Rational design of a minimal and highly enriched CYP102A1 mutant library with improved regio-, stereo- and chemoselectivity. Chembiochem 10(5):853-861 (2009).
Shang et al., Biochemical characterization of recombinant enterovirus 71 3C protease with fluorogenic model peptide substrates and development of a biochemical assay. Antimicrob Agents Chemother. 59(4):1827-1836 (2015).
Shchelkunov et al., Analysis of the monkeypox virus genome. Virology. 297(2):172-194 (2002).
Shepherd et al., A structure-guided switch in the regioselectivity of a tryptophan halogenase. Chembiochem 17(9):821-824 (2016).
Shi et al., Discovery and biosynthesis of guanipiperazine from a NRPS-like pathway. Chem Sci. 12(8):2925-2930 (2021).
Shimada et al., Selectivity of polycyclic inhibitors for human cytochrome P450s 1A1, 1A2, and 1B1. Chem. Res. Toxicol. 11(9):1048-1056 (1998).
Shin et al., Papain-like protease regulates SARS-CoV-2 viral spread and innate immunity. Nature. 587(7835):657-662 (2020).
Smanski et al., Synthetic biology to access and expand nature's chemical diversity. Nat Rev Microbiol. 14(3):135-149 (2016).
Snyder et al., Is it the shape of the cavity, or the shape of the water in the cavity? Eur Phys J. Special Topics. 223: 853-891 (2014).
Soysal et al., PTP1B expression is an independent positive prognostic factor in human breast cancer. Breast Cancer Res Treat. 137(2):637-644 (2013).
Stanford et al., Targeting tyrosine phosphatases: Time to end the stigma. Trends Pharmacol Sci. 38(6):524-540 (2017).
Steele et al., Sesquiterpene synthases from grand fir (Abies grandis). Comparison of constitutive and wound-induced activities, and cDNA isolation, characterization, and bacterial expression of delta-selinene synthase and gamma-humulene synthase J. Biol. Chem. 273(4):2078-2089 (1998).
Strickland et al., Rationally improving LOV domain-based photoswitches. Nat. Methods. 7(8):623-6 (2010).
Su et al., Anti-SARS-CoV-2 activities in vitro of Shuanghuanglian preparations and bioactive ingredients. Acta Pharmacol Sinica 41(9):1167-1177 (2020).
Su et al., Identification of pyrogallol as a warhead in design of covalent inhibitors for the SARS-CoV-2 3CL protease. Nat Commun. 12(1):3623 (2021).
Sun et al., Crystal structure of PTP1B complexed with a potent and selective bidentate inhibitor. J Biol Chem. 278(14):12406-12414 (2003).
Sun et al., Activity based fingerprinting of proteases using FRET peptides. 88(2):141-149 (2007).
Sycz et al., LOV Histidine kinase modulates the general stress response system and affects the virB operon expression in Brucella abortus. PLoS One. 10(5): e0124058 (2015).
Tachibana et al., Novel prenyltransferase gene encoding farnesylgeranyl diphosphate synthase from a hyperthermophilic archaeon, Aeropyrum pernix. Molecular evolution with alteration in product specificity. Eur J Biochem. 267(2):321-328 (2000).
Tan et al., 3C protease of enterovirus 68: structure-based design of Michael acceptor inhibitors and their broad-spectrum antiviral effects against picornaviruses. J Virol. 87(8):4339-4351 (2013).
Tautz et al., Targeting the PTPome in human disease. Expert Opin Ther Targets 10(1):157-177 (2006).
Teng et al., Structures, mechanisms and inhibitors of undecaprenyl diphosphate synthase: a cis-prenyltransferase for bacterial peptidoglycan biosynthesis. Bioorg Chem. 43:51-57 (2012).
Tholl, Biosynthesis and biological functions of terpenoids in plants. Adv Biochem Eng Biotechnol. 148:63-106 (2015).
Tian et al., Circular polymerase extension cloning of complex gene libraries and pathways. PLoS One. 4(7): e6441 (2009).
Tiganis et al., Epidermal growth factor receptor and the adaptor protein p52Shc are specific substrates of T-cell protein tyrosine phosphatase. Mol Cell Biol. 18(3):1622-1634 (1998).
Ting et al., Genetically encoded fluorescent reporters of protein tyrosine kinase activities in living cells. Proc Natl Acad Sci USA. 98(26):15003-15008 (2001).
Tonks et al., A brake becomes an accelerator: PTP1B—a new therapeutic target for breast cancer. Cancer Cell 11(3):214-216 (2007).
Tonks, Protein tyrosine phosphatases—from housekeeping enzymes to master regulators of signal transduction. FEBS J. 280(2):346-378 (2013).
Tonks, Protein tyrosine phosphatases: from genes, to function, to disease. Nat Rev Mol Cell Biol. 7(11):833-846 (2006).
Traves et al., Pivotal role of protein tyrosine phosphatase 1B (PTP1B) in the macrophage response to proinflammatory and anti-inflammatory challenge. Cell Death Dis. 5(3): e1125 (2014).
Traylor et al., Recombinant expression and characterization of Lucilia cuprina CYP6G3: Activity and binding properties toward multiple pesticides. Insect Biochem Mol Biol. 90:14-22 (2017).
Trouiller et al., Drug development for neglected diseases: a deficient market and a public-health policy failure. Lancet. 359(9324):2188-2194 (2002).
Tzeng et al., Protein activity regulation by conformational entropy. Nature. 488(7410):236-240 (2012).

(56) References Cited

OTHER PUBLICATIONS

Urlacher et.al.; Cytochrome P450 monooxygenases in biotechnology and synthetic biology. Trends Biotechnol. 37(8): 882-897 (2019).
Ursu et al., Understanding drug-likeness. Wiley Interdisciplinary Reviews: Computational Molecular Science 1, 760-781 (2011).
Vajda et al., Cryptic binding sites on proteins: definition, detection, and druggability. Curr Opin Chem Biol. 44:1-8 (2018).
Vallurupalli et al., Studying "invisible" excited protein states in slow exchange with a major state conformation. J. Am. Chem. Soc. 134(19):8148-8161 (2012).
Van Stokkum et al., The primary photophysics of the Avena sativa phototropin 1 LOV2 domain observed with time-resolved emission spectroscopy. Photochem Photobiol. 87(3): 534-541 (2011).
Van Vliet et al., Selective regulation of tumor necrosis factor-induced Erk signaling by Src family kinases and the T cell protein tyrosine phosphatase. Nat Immunol. 6(3):253-260 (2005).
Vanommeslaeghe, K. et al. CHARMM general force field: A force field for drug-like molecules compatible with the CHARMM all-atom additive biological force fields. J Comput Chem. 31(4): 671-690 (2010).
Varone et al., Shp1 in solid cancers and their therapy. Front Oncol. 10:935 (2020).
Varshavsky, N-degron and C-degron pathways of protein degradation. Proc Natl Acad Sci. USA. 116(2):358-366 (2019).
Veening et al., Phosphatases modulate the bistable sporulation gene expression pattern in Bacillus subtilis. Mol Microbiol. 56(6):1481-1494 (2005).
Vereb et al., Flow cytometric FRET analysis of protein interaction. Methods Mol Biol. 699:371-392 (2011).
Vidal et al., Library-based discovery and characterization of daphnane diterpenes as potent and selective HIV inhibitors in Daphne gnidium. J Nat Prod. 75(3):414-419 (2012).
Villamagna et al., The need for antiviral drugs for pandemic coronaviruses from a global health perspective. Front Med (Lausanne). 7:596587 (2020).
Viskovska et al., GII.4 norovirus protease shows pH-sensitive proteolysis with a unique Arg-His pairing in the catalytic site. J Virol. 93(6):e01479-18 (2019).
Vistoli et al., Assessing drug-likeness—what are we missing? Drug Discov Today. 13(7-8):285-294 (2008).
Vitalis et al., ABSINTH: A new continuum solvation model for simulations of polypeptides in aqueous solutions. J Comput Chem. 30(5):673-699 (2009).
Vitalis et al., Methods for Monte Carlo simulations of biomacromolecules. Annu Rep Comput Chem. 5:49-76 (2009).
Volinksy et al., Complexity of receptor tyrosine kinase signal processing. Cold Spring Harb Perspect Biol. 5(8): a009043 (2013).
Wang et al., Metabolic engineering of *Escherichia coli* for the biosynthesis of various phenylpropanoid derivatives. Metab Eng. 29:153-159 (2015).
Wang et al., Metabolic engineering of flavonoids in plants and microorganisms. Applied Microbiol Biotechnol. 91(4):949-956 (2011).
Wang et al., Structure of the Enterovirus 71 3C protease in complex with NK-1.8k and indications for the development of antienterovirus protease inhibitor. Antimicrob Agents Chemother. 61(7): e00298-17 (2017).
Waterhouse et al., SWISS-MODEL: Homology modelling of protein structures and complexes. Nucleic Acids Res. 46(W1):W296-W303 (2018).
Weaver, How Taxol/paclitaxel kills cancer cells. Mol Biol Cell. 25(18):2677-2681 (2014).
Weaver, Invadopodia: Specialized cell structures for cancer invasion. Clin Exp Metastasis. 23(2):97-105 (2006).
Weinert et al., Fast native-SAD phasing for routine macromolecular structure determination. Nature Methods. 12(2):131-133 (2015).
Welsch et al., Privileged scaffolds for library design and drug discovery. Curr Opin Chem Biol. 14(3):347-361 (2010).
Whitesides et al., Designing ligands to bind proteins. Q Rev Biophys. 38(4): 385-395 (2005).
WHO World Health Organization. Coronavirus disease 2019 (COVID-19): Situation Report-87. (2020).
WHO World Health Organization. Prioritizing diseases for research and development in emergency contexts. at https://www.who.int/activities/prioritizing-diseases-for-research-and- development-in-emergency-contexts (2022).
Wiesmann et al., Allosteric inhibition of protein tyrosine phosphatase 1B. Nat Struct Mol Biol. 11(8):730-737 (2004).
Wilderman et al., A single residue switch converts abietadiene synthase into a pimaradiene specific cyclase. J Am Chem Soc. 129(51):15736-15737 (2007).
Williams et al., Heterologous expression and characterization of a "pseudomature" form of taxadiene synthase involved in paclitaxel (Taxol) biosynthesis and evaluation of a potential intermediate and inhibitors of the multistep diterpene cyclization reaction. Arch Biochem Biophys. 379(1):137-146 (2000).
Winter, Xia2: An expert system for macromolecular crystallography data reduction. J Appl Cryst. 43:186-190 (2010).
Wrapp et al., Cryo-EM structure of the 2019-nCoV spike in the prefusion conformation. Science. 367(6483):1260-1263 (2020).
Wray et al., Inhibition of glycogen synthase kinase-3 alleviates Tcf3 repression of the pluripotency network and increases embryonic stem cell resistance to differentiation. Nat Cell Biol. 13(7):838-845 (2011).
Wu et al., A genetically encoded photoactivatable Rac controls the motility of living cells. Nature. 461(7260):104-108 (2009).
Wu et al., FDA-approved small-molecule kinase inhibitors. Trends Pharmacol Sci. 36(7):422-439 (2015).
Wu et al., Protein tyrosine phosphatase PTP1B is involved in neuroendocrine differentiation of prostate cancer. Prostate. 66(11):1125-1135 (2006).
Xue et al., Production of authentic SARS-CoV M(pro) with enhanced activity: application as a novel Tag-cleavage endopeptidase for protein overproduction. J Mol Biol. 366(3):965-975 (2007).
Yan et al., Resistance-gene-directed discovery of a natural-product herbicide with a new mode of action. Nature. 559(7714):415-418 (2018).
Yang et al., Targeting protein tyrosine phosphatase PTP-PEST (PTPN12) for therapeutic intervention in acute myocardial infarction. Cardiovasc Res. 116(5):1032-1046 (2020).
Yang et al., The crystal structures of severe acute respiratory syndrome virus main protease and its complex with an inhibitor. Proc Natl Acad Sci USA. 100(23):13190-13195 (2003).
Yang et al., Biological synthesis of coumarins in *Escherichia coli*. Microb Cell Fact. 14:65 (2015).
Yao et al., Discovery, X-ray crystallography and antiviral activity of allosteric inhibitors of flavivirus NS2B-NS3 protease. J Am Chem Soc. 141(17):6832-6836 (2019).
Yao et al., Estimation of the available free energy in a LOV2-J$\alpha$ photoswitch. Nat Chem Biol. 4(8):491-497 (2008).
Yesudhas et al., COVID-19 outbreak: history, mechanism, transmission, structural studies and therapeutics. Infection. 49(2):199-213 (2021).
Yildiz et al., Allosteric inhibition of the NS2B-NS3 protease from dengue virus. ACS Chem Biol. 8(12):2744-2752 (2013).
Yoshikuni et al., Designed divergent evolution of enzyme function. Nature. 440(7087):1078-1082 (2006).
Yu et al., GGTREE: an R package for visualization and annotation of phylogenetic trees with their covariates and other associated data. Methods Ecol. Evol. 8(1), 28-36 (2017).
Yu et al., Extension of the CHARMM general force field to sulfonyl-containing compounds and its utility in biomolecular simulations. J Comput Chem. 33(31):2451-2468 (2012).
Zabolotny et al., Protein-tyrosine phosphatase 1B expression is induced by inflammation in vivo. J Biol Chem. 283(21):14230-14241 (2008).
Zayner et al., The amino-terminal helix modulates light-activated conformational changes in AsLOV2. J Mol Biol. 419(1-2):61-74 (2012).
Zegzouti et al., ADP-Glo: A bioluminescent and homogeneous ADP monitoring assay for kinases. Assay Drug Dev Technol. 7(6):560-572 (2009).

(56) References Cited

OTHER PUBLICATIONS

Zhabinskii et al., Steroid plant hormones: Effects outside plant kingdom. Steroids. 97:87-97 (2015).
Zhang et al., Efflux transporter engineering markedly improves amorphadiene production in Escherichia coli. Biotechnol Bioeng. 113(8):1755-1763 (2016).
Zhang et al., Multidimensional heuristic process for high-yield production of astaxanthin and fragrance molecules in *Escherichia coli*. Nat Commun. 9(1):1858 (2018).
Zhang et al., Biosensors and their applications in microbial metabolic engineering. Trends Microbiol. 19(7):323-329 (2011).
Zhang et al., Crystal structure of SARS-CoV-2 main protease provides a basis for design of improved α-ketoamide inhibitors. Science, 368(6489):409-412 (2020).
Zhang et al., Genetic reduction of striatal-enriched tyrosine phosphatase (STEP) reverses cognitive and cellular deficits in an Alzheimer's disease mouse model. Proc Natl Acad Sci. 107(44):19014-19019 (2010).
Zhang et al., P450 fingerprinting method for rapid discovery of terpene hydroxylating P450 catalysts with diversified regioselectivity. J Am Chem Soc. 133(10):3242-3245 (2011).
Zhang et al., Complete biosynthesis of erythromycin A and designed analogs using *E. coli* as a heterologous host. Chem Biol. 17(11):1232-1240 (2010).
Zhang et al., Enzymatic assembly of carbon-carbon bonds via iron-catalysed sp3 C-H functionalization. Nature. 565(7737):67-72 (2019).
Zhang et al., PTP1B as a drug target: recent developments in PTP1B inhibitor discovery. Drug Discov Today. 12(9-10):373-381 (2007).
Zhang et al., Crystal structure of unlinked NS2B-NS3 protease from Zika virus. Science. 354(6319):1597-1600 (2016).
Zhao et al., Norovirus protease structure and antivirals development. Viruses. 13(10):2069 (2021).
Zhou et al., A pneumonia outbreak associated with a new coronavirus of probable bat origin. Nature. 579(7798):270-273 (2020).
Zhou et al., Optical control of cell signaling by single-chain photoswitchable kinases. Science. 355(6327):836-842 (2017).
Zhu et al., Antibacterial drug leads targeting isoprenoid biosynthesis. Proc Natl Acad Sci USA. 110(1):123-128 (2013).
Zhu et al., PTP1B contributes to the oncogenic properties of colon cancer cells through Src activation. Cancer Res. 67(21): 10129-10137 (2007).

* cited by examiner

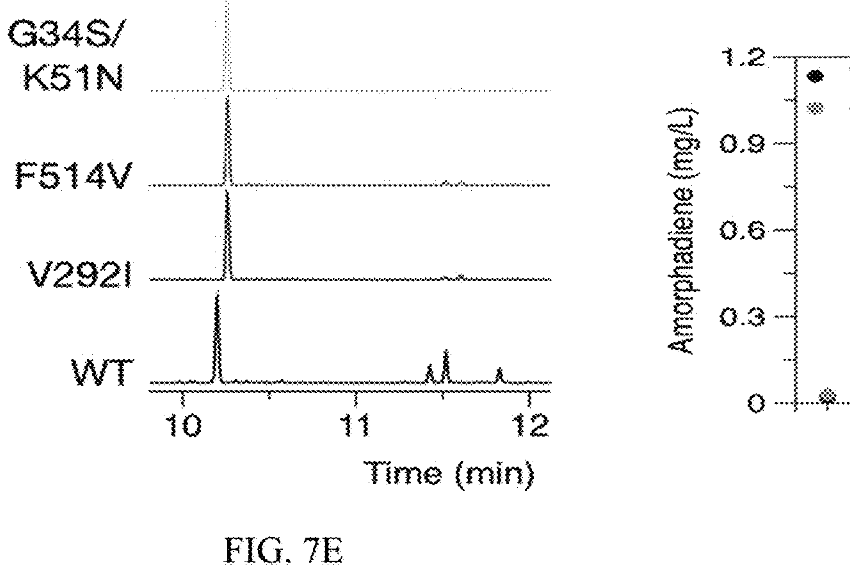
FIG. 7E
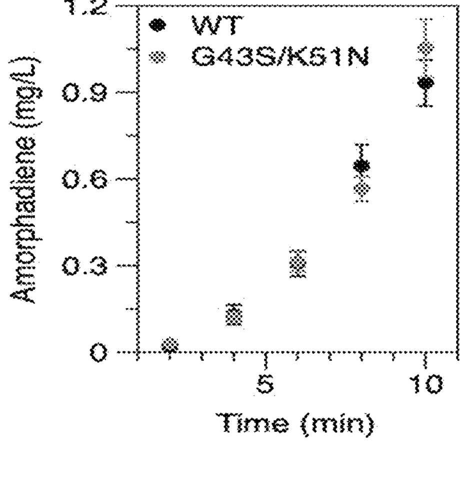
FIG. 7F
Spec (μg/ml)
200 400 600
WT B2Hx
G43S/ K51N B2Hx
FIG. 7G B2Hx
T455I
L450K
L450Y
A336V/M447H/I562T
Y415C
S484L
WT
W315P
A317N/A336S/S484C/I562V
L450G
B2H+
0
100
200
300
400
500
600
0
100
200
300
400
500
600

$IC_{50}$ = 19.9 (7.3) μM

DISCOVERY AND EVOLUTION OF BIOLOGICALLY ACTIVE METABOLITES

CROSS-REFERENCE

This application is a continuation of International Application No.: PCT/US2021/012621, filed Jan. 8, 2021, which claims the benefit under 35 U.S.C. § 119 (e) of U.S. provisional application No. 62/958,368, filed Jan. 8, 2020, each of which is incorporated by reference herein in its entirety.

STATEMENT AS TO FEDERALLY SPONSORED RESEARCH

This invention was made with government support under grant 1750244 awarded by the National Science Foundation. The government has certain rights to this invention.

SEQUENCE LISTING

The instant application contains a Sequence Listing which has been submitted electronically in XML file format and is hereby incorporated by reference in its entirety. Said XML copy, created on Dec. 22, 2022, is named 57123-702_301_SL.xml and is 192,400 bytes in size.

FIELD

Disclosed herein are systems, methods, reagents, apparatuses, vectors, and host cells for the discovery and evolution of metabolic pathways that produce small molecules that modulate enzyme function.

BACKGROUND

Natural products and their derivatives represent a long-standing source of pharmaceuticals and medicinal preparations[1-3]. These molecules-perhaps, as a result of their biological origin-tend to exhibit favorable pharmacological properties (e.g., bioavailability and "metabolite-likeness")[1,4] and can exert a striking variety of therapeutic effects (e.g., analgesic, antiviral, antineoplastic, anti-inflammatory, cytotoxic, immunosuppressive, and immunostimulatory)[5-10]. Recent advances in synthetic biology and metabolic engineering have suppled new approaches for the efficient biosynthesis and functionalization of known, pharmaceutically relevant natural products[11-13]; complementary methods for the discovery and optimization of new products with specific, therapeutically relevant activities, however, remain underdeveloped[14].

Existing strategies for natural product discovery are largely undirected and/or limited in scope. For example, screens of large natural product libraries—augmented, on occasion, with combinatorial (bio) chemistry[15-17]—have uncovered molecules with important medicinal properties[18], but these screens are resource-intensive and largely subject to serendipity[19]. Bioinformatic tools, by contrast, permit the identification of biosynthetic gene clusters[20,21], where co-localized resistance genes, if present, can reveal the biochemical function of their products[22]. The therapeutic activities of many pharmaceutically relevant metabolites, however, differ from their native functions[23], and most biosynthetic pathways can, when appropriately reconfigured, yield entirely new—and, perhaps, more effective—therapeutic molecules[12,24].

Microbial systems have emerged as powerful platforms for the biosynthesis of natural products from unculturable or low-yielding organisms.[25,26] Recent work showed that such systems can also permit the discovery and evolution of metabolic pathways with specific, therapeutically relevant activities (PCT/US2019/40896).

SUMMARY

Disclosed herein are systems, methods, reagents, apparatuses, vectors, and host cells for the discovery and evolution of metabolic pathways that produce small molecules that modulate enzyme function. For example, a microorganism is provided in which a first genetically encoded system links cell growth to the activity of a target enzyme and in which a second genetically encoded system—to be discovered or evolved—produces a metabolite that modulates the activity of the target enzyme. This disclosure applies this approach to a subset of target enzymes that post-translationally modify proteins, to metabolic pathways that produce phenylpropanoids or nonribosomal peptides, and to the discovery of cryptic metabolic pathways. Some aspects of this disclosure provide specific reconfigured or evolved pathways that produce specific modulators of enzyme activity, that yield improved titers of such modulators (relative to a starting pathway), and/or that exhibit reduced host toxicity (relative to a starting pathway). Metabolic products with specific inhibitory effects are also disclosed.

According to one aspect, methods for the discovery and evolution of metabolic pathways that produce molecules that modulate protein function are provided. The methods include contacting a population of host cells that comprise a protein of interest, such as an enzyme of interest, with a population of expression vectors comprising different metabolic pathways, wherein the host cells are amenable to transfer of the population of expression vectors; expressing the metabolic pathways in the population of host cells, wherein a cell or subset of the population of host cells produce a detectable output when the metabolic pathway within said cell or population of host cells produces a product that modulates the protein of interest, such as the enzyme of interest; screening the population of host cells under conditions that enable measurement of the detectable output in the cell or the subset of the population of host cells; isolating the cell or the subset of the population of host cells that produce a detectable output; isolating the expression vectors that yield detectable outputs higher than ($p<0.05$) the output of a reference vector that harbors a reference pathway, for example, a vector that encodes a pathway that does not produce molecules with concentrations and/or potencies sufficient to modulate the activity of a protein of interest, such as an enzyme of interest, in the cell or the subset of the population of host cells; and characterizing the products of the metabolic pathways encoded by the expression vectors that yield detectable outputs that are higher than the output of said reference vector in the cell or the subset of the population of host cells.

In some embodiments, the host cells comprise a genetically encoded system in which the activity of a protein of interest, such as an enzyme of interest, controls the assembly of a protein complex with an activity that is not possessed by either of two or more components of the complex and, thus, yields a detectable output in proportion to the amount of complex formed.

In some embodiments, the protein of interest is an enzyme that adds a post-translational modification that causes two proteins, which are initially dissociated, to be covalently linked or to form a noncovalent complex.

In some embodiments, the complex is formed by two proteins with a dissociation constant ($K_d$) less than or equal to the $K_d$ of the complexes formed between SH2 domains and their phosphorylated substrates.

In some embodiments, the enzyme of interest is an enzyme that adds a post-translational modification other than the addition or removal of a phosphate, and that modification causes two proteins, which are initially dissociated inside of the cell, to be covalently linked or to form a complex with a dissociation constant ($K_d$) less than or equal to the $K_d$ of the complex formed between a SH2 domain and a phosphorylated SH2-substrate domain (e.g., as shown in FIG. 1A).

In some embodiments, the metabolic pathways produce phenylpropanoids or nonribosomal peptides.

In some embodiments, the expression vectors comprising different metabolic pathways comprise a library of pathways generated by mutating one or more genes within a starting metabolic pathway.

In some embodiments, one or more of the metabolic pathways comprises a set of genes of unknown biosynthetic capability.

In some embodiments, one or more of the metabolic pathways that produces a detectable output higher than the output of the reference pathway produces a product that differs from the products of other metabolic pathways.

In some embodiments, one or more of the metabolic pathways that produces a detectable output higher than the output of the reference pathway produces a larger quantity of a product than the quantity of product generated by other metabolic pathways.

In some embodiments, one or more of the metabolic pathways that produces a detectable output higher than the output of the reference pathway exhibits a lower cellular toxicity than other metabolic pathways.

In some embodiments, the products of the metabolic pathways are characterized by standard analytical methods, preferably by gas chromatography-mass spectrometry (GC/MS), liquid chromatography-mass spectrometry (LC/MS), and/or nuclear magnetic resonance (NMR) spectroscopy.

In some embodiments, the methods further include isolating the products.

In some embodiments, the methods further include concentrating the products, preferably using a rotary evaporator.

In some embodiments, the methods further include testing the effects of the products on the protein of interest, such as the enzyme of interest.

In some embodiments, the protein of interest, such as the enzyme of interest, is a ubiquitin ligase, a SUMO transferase, a methyltransferase, a demethylase, an acetyltransferase, a glycosyltransferase, a palmitoyltransferase, or a related hydrolase.

In some embodiments, the products or molecules identified (e.g., amorphadiene and derivatives, taxadiene and derivatives, β-bisabolene and derivatives, α-bisabolene and derivatives, and α-longipinene and derivatives) are provided as drugs or drug leads for the treatment of diseases to which PTPs contribute, for example, type 2 diabetes, HER2-positive breast cancer, or Rett syndrome, as are methods of treatment of such diseases by administering an effective amount of the molecule(s) to a subject in need of such treatment.

According to another aspect, compositions or systems are provided that include a population of host cells that comprise a protein of interest and a population of expression vectors comprising different metabolic pathways, wherein a cell or subset of the population of host cells produce a detectable output when the metabolic pathway produces a product that modulates the protein of interest, and optionally wherein the expression vectors yield detectable outputs higher than the output of a reference vector that harbors a reference pathway, for example, a vector that encodes a pathway that does not produce molecules with concentrations and/or potencies sufficient to modulate the activity of a protein of interest, in the cell or the subset of the population of host cells.

In some embodiments, the host cells comprise a genetically encoded system in which the activity of a protein of interest controls the assembly of a protein complex with an activity that is not possessed by either of two or more components of the complex and, thus, yields a detectable output in proportion to the amount of complex formed.

In some embodiments, the protein of interest is an enzyme that adds a post-translational modification that causes two proteins, which are initially dissociated, to be covalently linked or to form a noncovalent complex.

In some embodiments, the complex is formed by two proteins with a dissociation constant ($K_d$) less than or equal to the $K_d$ of the complexes formed between SH2 domains and their phosphorylated substrates.

In some embodiments, the metabolic pathways produce phenylpropanoids or nonribosomal peptides.

In some embodiments, the expression vectors comprising different metabolic pathways comprise a library of pathways generated by mutating one or more genes within a starting metabolic pathway.

In some embodiments, one or more of the metabolic pathways comprises a set of genes of unknown biosynthetic capability.

In some embodiments, one or more of the metabolic pathways that produces a detectable output higher than the output of the reference pathway produces a product that differs from the products of other metabolic pathways.

In some embodiments, one or more of the metabolic pathways that produces a detectable output higher than the output of the reference pathway produces a larger quantity of a product than the quantity of product generated by other metabolic pathways.

In some embodiments, one or more of the metabolic pathways that produces a detectable output higher than the output of the reference pathway exhibits a lower cellular toxicity than other metabolic pathways.

In some embodiments, the protein of interest is a ubiquitin ligase, a SUMO transferase, a methyltransferase, a demethylase, an acetyltransferase, a glycosyltransferase, a palmitoyltransferase, or a related hydrolase.

According to another aspect, kits are provided that include a population of expression vectors as described herein. In some embodiments, the kits also include the population of host cells that comprise a protein of interest as described herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

FIG. 1A, A bacterial two-hybrid (B2H) system that detects phosphorylation-dependent protein-protein interactions: Major components include (i) a substrate domain fused to the omega subunit of RNA polymerase (yellow), (ii) an SH2 domain fused to the 434 phage cI repressor (light blue), (iii) an operator for 434cI (dark green), (iv) a binding site for RNA polymerase (purple), (v) Src kinase, and (vi) PTP1B. Src-catalyzed phosphorylation of the substrate domain enables a substrate-SH2 interaction that activates transcription of a gene of interest (GOI, black). PTP1B-catalyzed dephosphorylation of the substrate domain prevents that interaction; inhibition of PTP1B re-enables it. FIG. 1B, A version of the B2H system that both (i) lacks PTP1B and (ii) contains p130cas as the substrate domain and luxAB as the GOI. Inducible plasmids were used to increase expression of specific components in *E. coli*; secondary induction of Src from one such plasmid enhanced luminescence. FIG. 1C, A version of the B2H system that both (i) lacks PTP1B and Src and (ii) includes an SH2 domain (SH2*) with an enhanced affinity for phosphopeptides, a variable substrate domain, and LuxAB as the GOI. An inducible plasmid was used to increase expression of Src in *E. coli*. Sequences for substrates p130cas (SEQ ID NO: 24), MidT (SEQ ID NO: 25), EGFR (SEQ ID NO: 27), and ShcA (SEQ ID NO: 26) are shown. FIG. 1D, The B2H system from c with either p130cas or MidT as substrates. A second plasmid was used to overexpress either (i) Src and PTP1B or (ii) Src and an inactive variant of PTP1B (C215S) in *E. coli*. Right: Two single-plasmid B2H systems. FIG. 1E, The optimized system includes SH2*, the midT substrate, optimized promoters and ribosome binding sites (bb034 from FIG. 1D), and SpecR as the GOI. Inactivation of PTP1B enabled a strain of *E. coli* harboring this plasmid-borne system to survive at high concentrations of spectinomycin (>250 μg/ml). Error bars in FIG. 1B-FIG. 1D denote standard error with n=3 replicates.

FIG. 2A, A plasmid-borne pathway for terpenoid biosynthesis: (i) pMBIS, which harbors the mevalonate-dependent isoprenoid pathway of *S. cerevisiae*, converts mevalonate to isopentyl pyrophosphate (IPP) and farnesyl pyrophosphate (FPP). (ii) pTS, which encodes a terpene synthase (TS) and, when necessary, a geranylgeranyl diphosphate synthase (GGPPS), converts IPP and FPP to sesquiterpenes or diterpenes. FIG. 2B, Four terpene synthases: amorphadiene synthase (ADS), γ-humulene synthase (GHS), abietadiene synthase (ABS), and taxadiene synthase (TXS). FIG. 2C, The spectinomycin resistance of strains of *E. coli* that harbor both (i) the bacterial two-hybrid (B2H) system (ii) a TS-specific terpenoid pathway (pTS includes GGPPS only when ABS or TXS are present). ADS enabled survival in the presence of high concentrations of spectinomycin. Note: $ABS_{D404A/D621A}$ is catalytically inactive. B2H* contains $PTP1B_{C215S}$, which is inactive.

FIG. 3A, Error-prone PCR and/or site-saturation mutagenesis of a subset of genes within a metabolic pathway yield a library of metabolic pathways. FIG. 3B, Microbes, each of which harbors both (i) the B2H system and (ii) a member of the pathway library, are grown in liquid culture. Note: The system shown is an *E. coli* host that harbors both (i) the B2H system and (ii) mutated terpenoid pathways (i.e., pMBIS+pTS with mutations; see FIG. 2A). FIG. 3C, After liquid culture, the transformants are plated on solid media with different concentrations of antibiotic; hits comprise colonies that grow at antibiotic concentrations at which the wild-type pathway does not permit growth. FIG. 3D, The pathways of the hits are sequenced; their mutations are reintroduced into the wild-type pathway; and these reconstructed pathway variants are rescreened with drop-based plating (10 μL) on solid media with different concentrations of antibiotic. This step removes false positives (e.g., colonies that survived because of mutations located outside of the target genes). FIG. 3E, The confirmed hits are grown in liquid culture; their products are extracted with a hexane overlay, as needed, and concentrated in a rotary evaporator. FIG. 3F, GC/MS enables the identification and quantification of mutant products; NMR can assist with identification. FIG. 3G, Interesting metabolites (purchased or purified from culture extract) are characterized with in vitro kinetic measurements or cell studies of target modulation and/or ITC analyses of target-metabolite binding.

FIG. 4A, A genetically encoded system that detects metabolite-mediated activation of enzymes E1 and/or E2. E1 adds a PTM to protein P1, allowing it to bind to P2; the newly formed P1-P2 complex activates transcription of a gene of interest (GOI, black). E2 removes the PTM from P1 and, thus, prevents complex formation. When the GOI confers a fitness advantage, inhibitors of E2 or activators of E1 enhance cell survival. When the GOI is toxic, inhibitors of E1 or activators of E2 enhance cell survival. FIG. 4B, An alternative detection system. E1 adds a PTM to protein P1, allowing it to bind to P2; the newly formed P1-P2 complex assembles a split protein (e.g., a fluorescent protein, a luciferase, or an enzyme that confers antibiotic resistance). E2 removes the PTM from P1 and, thus, prevents complex formation. When the reconstituted split protein confers a fitness advantage, inhibitors of E2 or activators of E1 enhance cell survival. When, by contrast, the reconstituted protein is toxic, inhibitors of E1 or activators of E2 enhance cell survival. FIG. 4C, A genetically encoded system that detects metabolite-mediated activation of PTM enzymes that control protein ligation (e.g., a SUMO transferase, a ubiquitin ligase, or associated peptidases). E1 attaches P1 to a lysine residue (K) of P2, and the newly formed P1-P2 complex activates transcription of a GOI. E2 breaks this complex apart. FIG. 4D, An alternative system. E1 attaches P1 to P2, and the newly formed P1-P2 complex permits the assembly of a split protein. E2-mediated proteolysis breaks this complex apart.

FIG. 5A, Phenylpropanoid pathways developed by Young-Soo Hong and colleagues[45]. Abbreviations: TAL, ammonia-lyase from *S. espanaensis*; Sam5, 4-coumarate 3-hydroxylase form *S. espanaensis*; COM, O-methyltransferase from *A. thaliana*; ScCCL, cinnamate/4-coumarate: CoA ligase from *Streptomyces coelicolor*; CHS, chalcone synthase from *A. thaliana*; STS, stilbene synthase from *Arachis hypogaea*. FIG. 5B, The pathways encoded by the plasmids from FIG. 5A. FIG. 5C, A genetically encodable yersiniabactin (Ybt) synthetase, as described by Khosla and colleagues[46]. Ybt is a polyketide-nonribosomal peptide. The substrates necessary for Ybt production appear in blue. Abbreviations: ArCP, aryl carrier protein; A, adenylation; PCP, peptidyl carrier proteins; Cy, cyclization; KS, ketosynthase; ACP, acyl carrier protein; AT, acyltransferase; KR, NADPH-dependent ketoreductase; MT, methyltransferase; SAM, S-adenosyl-methionine; TE, thioesterase. See the text for details on biosynthesis.

FIG. 6A, Mutagenesis and/or reorganization of a multi-step pathway inactivates a biosynthetic gene and, thus, permits the accumulation of a metabolic intermediate. FIG. 6B, Mutagenesis and/or reorganization of a multi-step pathway inactivates a repressor gene and, thus, permits the expression of pathway genes.

FIGS. 7A-7I. Microbial evolution of terpenoid inhibitors. FIG. 7A-7B, Homology models for (FIG. 7A) ADS and (FIG. 7B) GHS show the locations of residues targeted for site-saturation mutagenesis (SSM). A substrate analogue from an aligned structure of 5-epi-aristolochene synthase (pdb entry 5eat) appears in blue. FIG. 7C-7D, Measurements of the spectinomycin resistance conferred by mutants of (c) ADS (LB plates) and (FIG. 7D) GHS (TB plates). ALP corresponds to a quintuple mutant of GHS (A336C/T445C/S484C/1562L/M565L) that generates α-longipinene as a major product. Shades denote colony densities: diffuse (≥10 colonies, light gray), circular diffuse (gray), and circular lawn (black). FIG. 7E, The product profiles of mutants of ADS that enable growth at higher antibiotic concentrations than the wild-type enzyme. FIG. 7F, $ADS_{G43S/K51N}$ and ADS yield similar amorphadiene titers in liquid cultures. FIG. 7G, $ADS_{G43S/K51N}$ yields higher colony densities than the wild-type enzyme in the presence of an inactive B2H system (B2Hx); these densities suggest that $ADS_{G43S/K51N}$ is less toxic than ADS. FIG. 7H, The product profiles of wild-type GHS and several GHS mutants that yield enhanced antibiotic resistance; discrepancies between profiles of these mutants suggest differences in the composition of intracellular terpenoids that might give rise to enhanced antibiotic resistance. FIG. 7I, $GHS_{A319Q}$ yields a higher terpenoid titer than GHS. Error bars in FIG. 7F and FIG. 7I denote standard deviation with n=3 biological replicates.

FIG. 8A, Analysis of the antibiotic resistance conferred by mutants of ADS. Images show the growth of *E. coli* on LB plates seeded from drops of liquid culture (10 μL). Each mutant was prepared by using site-directed mutagenesis to introduce mutations identified in the selection experiment (i.e., hits) into the starting ADS plasmid. Shades denote colony densities: diffuse (≥10 colonies, light gray), circular diffuse (gray), and circular lawn (black) FIG. 8B, A replicate of the experiment described in FIG. 8A. FIG. 8C, Analysis of the antibiotic resistance conferred by mutants of GHS. Images show the growth of *E. coli* on TB plates seeded from drops of liquid culture (10 μL). FIG. 8D, A replicate of the experiment described in FIG. 8C. In FIG. 8A-FIG. 8D, blue highlights denote mutants that enabled growth at higher concentrations of spectinomycin than the wild-type enzymes in two biological replicates (i.e., these mutants appear in FIGS. 3C and 3*d*).

FIG. 9A, Titers of the dominant terpenoids (i.e., amorphadiene, γ-humulene, taxadiene, or abietadiene) generated by each TS-specific strain in the absence (top) and presence (bottom) of the B2H system. Similar titers indicate that the B2H system does not interfere with terpenoid biosynthesis. FIG. 9B, GC/MS chromatograms of the terpenoids generated by each strain in the absence (top) and presence (bottom) of the B2H system (m/z=204). Similar profiles indicate that the B2H system does not alter product distributions. FIG. 9C, Analysis of the contributions of either (i) TS activity or (ii) B2H function to the death and survival of various strains. Inactivation of GHS does not enhance the survival of the GHS strain, an indication that this enzyme does not produce growth-inhibiting terpenoids. Inactivation of either ADS or the B2H system, by contrast, weakens the antibiotic resistance of the ADS strain, an indication that maximal resistance requires both terpenoid production and B2H activation. Labels denote the following controls: $GHS_{D/A}$, an inactive GHS; $ADS_{D/A}$, an inactive ADS; B2H*, a constitutively active B2H; $B2H_x$, an inactive B2H. Note: The left and right images show LB plates seeded with drops of liquid culture (10 μL) from two biological replicates. Error bars in FIG. 9A denote standard error for n≥3 biological replicates.

FIG. 10A, Chromatograms show expected dominant products (*) for each TS-specific strain from FIG. 2C (the B2H system is present). FIG. 10B, Titers of major products generated by ADS and TXS. FIG. 10C, Initial rates of PTP1B-catalyzed hydrolysis of pNPP in the presence of increasing concentrations of amorphadiene and taxadiene. Lines show fits to a Michaelis-Menten model, which provides evidence of noncompetitive inhibition (amorphadiene) and mixed inhibition (taxadiene). FIG. 10D, A depiction of a HEK293T/17 cell. Insulin stimulates phosphorylation of the membrane-bound insulin receptor (IR); PTP1B dephosphorylates IR, and the inhibition of PTP1B restores phosphorylation. FIG. 10E, ELISA-based measurements of IR phosphorylation in starved wild-type HEK293T/17 cells exposed to 3% dimethyl sulfoxide (DMSO, n=2), 930 μM amorphadiene (AD, in 3% DMSO, n=3), and 405 μM α-bisabolene (Abis, 3% DMSO, n=1) for 10 minutes. The results indicate that both amorphadiene and α-bisabolene can cross the cell membrane, inhibit intracellular PTP1B, and, thus, increase IR phosphorylation. Error bars in FIG. 10B denote standard error with n=3 biological replicates. Error bars in FIG. 10C denote standard error with n≥3 measurements. Error bars in FIG. 10E denote standard error with n values indicated (we note: for these measurements, we subtracted a reference signal produced by lysis buffer alone, n=3).

FIG. 11A-FIG. 11B, The spectinomycin resistance of strains of *E. coli* that harbor (i) an active or inactive bacterial two-hybrid system (B2H and B2Hx, respectively, as in FIGS. 1, 2, and 7-9) and (ii) the terpenoid pathway from FIG. 2 with each of the following terpene synthases: γ-humulene synthase from *Abies grandis* (GHS), β-bisabolene synthase from *Zingiber officinale* (ZoBBA), β-bisabolene synthase from Santalum album (SaBBA), and α-bisabolene synthase (ABB) from *Abies grandis* (ABS). SaBBA and, most prominently, ABB enable survival at high concentrations of spectinomycin. FIG. 11C, chemical structures of β-bisabolene and α-bisabolene. FIG. 11D, analysis of PTP1B activity on p-nitrophenyl phosphate (pNPP) in the presence of increasing concentrations of α-bisabolene (measured as amorphadiene equivalents) purified from culture extract. Lines show fits to a Michaelis-Menten Model.

FIG. 12A, Initial rates of pNPP hydrolysis by $PTP1B_{321}$, $TCPTP_{292}$, and $PTP1B_{282}$ in the presence of increasing concentrations of amorphadiene. Lines show fits to models of inhibition. A comparison of the first and second plots (or, more specifically, the $IC_{50}$'s derived from the plotted data) indicates that amorphadiene is a ~five-fold more potent inhibitor of $PTP1B_{321}$ than $TCPTP_{292}$, the most closely related PTP in the human genome (by sequence identity); this selectivity suggests that amorphadiene binds outside of the active site of PTP1B. A comparison of the second and third plots, in turn, indicate that amorphadiene inhibits $PTP1B_{282}$ ~four-fold less potently than $PTP1B_{321}$; this discrepancy suggests that the α7 helix, which is present in $PTP1B_{321}$ but missing in $PTP1B_{282}$ (and which is proximal to a known allosteric binding site of PTP1B), is involved in the $PTP1B_{321}$-amorphadiene interaction. FIG. 12B, the chemical structure of amorphadiene. FIG. 12C, a preliminary crystal structure of PTP1B bound to amorphadiene. FIG. 12D, Data used to solve the structure in FIG. 12C shows electron density near the allosteric site of PTP1B (F280 appears on the left of this image); this density is consistent with the structure of amorphadiene. FIG. 12E, the chemical structure of α-bisabolol, a structural analogue of α-bisabolene. FIG. 12F, a preliminary crystal structure of PTP1B bound to α-bisabolol. FIG. 12G, Data used to solve the structure in FIG. 12F shows electron density near the allosteric site of PTP1B (F280 appears in the upper left of this image); this density is consistent with the structure of α-bisabolol.

FIG. 13, We optimized the transcriptional response of the B2H system by adjusting the strength of various genetic elements. In three sequential phases, we changed (1) the promoter for Src/CDC37, (2) the ribosome binding site (RBS) for Src/CDC37, and (3) and the RBS for PTP1B. In phases 1 and 2, we used a PTP1B-deficient system with either a wild-type (WT, EPQYEEIPYL (SEQ ID NO: 1)) or non-phosphorylatable (Mut, EPQFEEIPYL (SEQ ID NO:2)) substrate domain. Here, "none" indicates that absence of an additional promoter; the labeled "Pro1" controls the transcription of all five genes to its left. In phase 3, we used a complete B2H system with either a wild-type (WT) or catalytically inactive (C215S, Mut) variant of PTP1B. The remaining B2H component of each phase are detailed in TABLE 2. Error bars denote standard error with n≥3 biological replicates.

FIG. 14, A comparison of the antibiotic resistance conferred by B2H systems with different RBSs for PTP1B (see TABLE 2 for the remaining components of each system). Images show the growth of *E. coli* on agar plates (LB) seeded from drops of liquid culture (10 μL) with two biological replicates for each condition. The RBS bb034 confers a greater sensitivity to spectinomycin on agar plates; concentrations of spectinomycin in the liquid culture, by contrast, do not have a strong influence on bacterial growth. Informed by this analysis, we incorporated bb034 into our "optimized" B2H system and ceased adding spectinomycin to liquid culture.

FIG. 15A, A GC chromatogram of pure amorphadiene (purchased from Ambeed). FIG. 15B, The mass spectrum of the indicated peak from FIG. 15A.

FIG. 16A, A GC chromatogram shows the production of γ-humulene by a strain of *E. coli* engineered to produce it (i.e., pMBIS+pGHS). FIG. 16B, The mass spectrum of the indicated peak from FIG. 16A.

FIG. 17A, A GC chromatogram shows the production of abietadiene by a strain of *E. coli* engineered to produce it (i.e., pMBIS+pABS). FIG. 17B, The mass spectrum of the indicated peak from FIG. 17A.

FIG. 18A, A GC chromatogram shows the production of pure taxadiene (a kind gift from Phil Baran). FIG. 18B, The mass spectrum of the indicated peak from FIG. 18A.

FIG. 19A, A GC chromatogram shows the production of β-bisabolene by a strain of *E. coli* engineered to produce it (i.e., pMBIS+pGHSL450G). FIG. 19B, The mass spectrum of the indicated peak from FIG. 19A.

FIG. 21A, A bacterial two-hybrid (B2H) system in which a phosphorylation-dependent protein-protein interaction modulates transcription of a gene of interest (GOI, black). Major components include (i) a substrate domain fused to the omega subunit of RNA polymerase (yellow), (ii) an SH2 domain fused to the 434 phage cI repressor (light blue), (iii) Src kinase and PTP1B, (iv) an operator for 434cI (dark green), (v) a binding site for RNA polymerase (purple), and (vi) a gene of interest (GOI, black). FIG. 21B, The luminescence generated by a B2H system with a p130cas substrate, LuxAB as the GOI, and no PTP1B. We used an inducible plasmid to increase expression of specific components. FIG. 21C, The luminescence generated by B2H systems with an SH2 domain that exhibits enhanced affinity for phosphopeptides (SH2*), one of four substrate domains, LuxAB as the GOI, and no Src or PTP1B. We used an inducible plasmid to control the expression of Src. Sequences for substrates p130cas (SEQ ID NO: 24), MidT (SEQ ID NO: 25), EGFR (SEQ ID NO: 27), and ShcA (SEQ ID NO: 26) are shown. FIG. 21D, The B2H system from c with either p130cas or MidT substrates. We used a second plasmid to control the expression of Src and an active or inactive (C215) variant of PTP1B. Right: Two optimized single-plasmid systems. FIG. 21E, The final B2H system. Inactivation of PTP1B enabled a strain of *E. coli* harboring this system to survive at high concentrations of spectinomycin (>250 μg/ml). Error bars in FIGS. 21B-21D denote standard error with n=3 biological replicates.

FIG. 22A, The plasmid-borne pathway for terpenoid biosynthesis: (i) $pMBIS_{CmR}$, which harbors the mevalonate-dependent isoprenoid pathway of *S. cerevisiae*, converts mevalonate to isopentyl pyrophosphate (IPP) and farnesyl pyrophosphate (FPP). (ii) pTS, which encodes a terpene synthase (TS) and, when necessary, a geranylgeranyl diphosphate synthase (GGPPS), converts IPP and FPP to sesquiterpenes or diterpenes. FIG. 22B, Five terpene synthases examined in this study: amorphadiene synthase (ADS), γ-humulene synthase (GHS), α-bisabolene synthase (ABA), abietadiene synthase (ABS), and taxadiene synthase (TXS). FIG. 22C, The spectinomycin resistance of strains of *E. coli* that harbor both (i) the bacterial two-hybrid (B2H) system (ii) a TS-specific terpenoid pathway. Note: ABS*, a positive control, has a constitutively active B2H (i.e., it includes $PTP1B_{C215S}$). FIG. 22D, Chromatograms show expected major products (i.e., namesake; *) for each TS-specific strain from c in the presence of the B2H system. Values are normalized to the largest peak within a given sample. FIG. 22E, Initial rates of PTP1B-catalyzed hydrolysis of pNPP in the presence of increasing concentrations of (AD) amorphadiene or (AB) α-bisabolene. Lines show the best-fit kinetic models of inhibition (TABLE 12). FIG. 22F, Estimated $IC_{50}$'s. FIG. 22G, Titers of the major products generated by ADS and ABA. Error bars denote (FIG. 22E) standard error and (FIG. 22F) 95% confidence intervals for n≥3 independent measurements, and (FIG. 22G) standard deviation for n=3 biological replicates.

FIG. 23A. Aligned X-ray crystal structures of PTP1B bound to TCS401, a competitive inhibitor (yellow protein, orange highlights, and green spheres; pdb entry 5k9w), and BBR, an allosteric inhibitor (gray protein, blue highlights, and light blue spheres; pdb entry 1t4j). FIG. 23B, Aligned structures of PTP1B bound to BBR (white protein and light blue ligand) and amorphadiene (cyan protein and dark blue ligand, pdb entry 6W30). FIG. 23C, Dihydroartemisinic acid (DHA), a structural analogue of amorphadiene with a carboxyl group likely to disrupt binding to the hydrophobic cleft. FIG. 23D, DHA is eight-fold less potent than amorphadiene. Lines show the best-fit kinetic models of inhibition (TABLE 12). Error bars denote standard error for n=3 independent measurements with a 95% confidence interval for the $IC_{50}$. FIG. 23E, Dixon plot showing $V_o^{-1}$ vs. [TCS401] at various concentrations of AD (black, blue, purple markers). The parallel lines indicate that TCS401 and AD cannot bind simultaneously. FIG. 23F, Dixon plot showing $V_o^{-1}$ vs. [orthovanadate] at various concentrations of AD (black, blue, purple markers). The intersecting lines indicate that orthovanadate and AD can bind simultaneously. FIG. 23G, Both amorphadiene and α-bisabolene inhibit PTP1B much more potently than TC-PTP; the removal of the α7 helix (or equivalent) from both enzymes reduces the selectivity of AD, but not AB. Error bars show propagated 95% confidence intervals estimated from n≥3 independent measurements at each condition. FIG. 23H, Amorphadiene (930 μM) and α-bisabolene (405 μM) stimulate IR phosphorylation in HEK293T/17 cells; at the same concentrations, dihydroartemisinic acid (DHA) and α-bisabolol (ABOL) exhibit reduced signals consistent with their reduced potencies (#: $p<0.05$, compared to negative control, *: $p<0.05$). All inhibitors are dissolved in 3% DMSO (v/v; negative control). Error bars in FIGS. 23D-f denote standard error for n=3-12 biological replicates. Error bars in FIG. 23G denote propagated 95% confidence intervals for n≥3 independent measurements. Error bars in FIG. 23H denote standard error propagated from a buffer-only control (n=3 biological replicates).

FIG. 24A, A bioinformatic analysis of terpene synthases. We assembled a cladogram of 4,464 members of the largest terpene synthase family (PF03936) and annotated it with functional data. We selected three genes from each of eight clades (curved boxes): six with no characterized genes (i.e., genes with known functions) and two with no characterized genes. FIG. 24B, The spectinomycin resistance conferred by the selected genes alongside $pMBIS_{CmR}$ and $pB2H_{opt}$. Hits with robust growth beyond 400 μg/mL spectinomycin appear in blue. "n.m." indicates the condition was not measured. FIG. 24C, A0A0C9VSL7 produces (+)-1 (10),4-cadinadiene as a dominant product (m/z=204). FIG. 24D, Structure of (+)-1 (10),4-cadinadiene. FIG. 24E, The inhibition of PTP1B by (+)-1 (10),4-cadinadiene (85% purity, 10% DMSO). Lines show the best-fit kinetic models of inhibition (TABLE 12).

FIG. 25A, The spectinomycin resistance of strains harboring B2H systems modified to detect the inactivation of different disease-relevant PTPs. Inactivating mutations[86-88] confer survival at high concentrations of antibiotic. FIG. 25B, A comparison of the resistance conferred by PTP1B- and TC-PTP-specific B2H systems in the presence of metabolic pathways for amorphadiene and α -bisabolene (i.e., $pMBIS_{CmR}$+ADS or ABA). The PTP1B-specific system exhibits a prominent survival advantage, a finding consistent with the selectivity of both terpenoids for this enzyme. FIG. 25C, The titers of AD and AB in strains harboring both the B2H systems and associated metabolic pathways are indistinguishable between strains.

FIG. 26A, Total terpene titers generated by each TS-specific strain in the absence (red) and presence (blue) of the B2H system. These results indicate that the B2H system does not disrupt terpenoid biosynthesis. FIG. 26B, GC/MS chromatograms of the terpenoids generated by the diterpene synthases in the absence (top) and presence (bottom) of the B2H system (m/z=272). FIG. 26C, GC/MS chromatograms of the terpenoids generated by the sesquiterpene synthases in the absence (top) and presence (bottom) of the B2H system (m/z=204). Similar profiles in FIG. 26B and FIG. 26C indicate that the B2H system does not alter product distributions. FIG. 26D, Analysis of the contributions of either (i) TS activity or (ii) B2H function to the death and survival of GHS, ADS, and ABA strains. Inactivation of GHS does not enhance survival, an indication that this enzyme does not produce growth-inhibiting terpenoids. Inactivation of either ADS, ABA, or the B2H system, by contrast, weakens the antibiotic resistance of the ADS and ABA strains; maximal resistance thus requires both terpenoid production and B2H activation. Labels denote the following controls: D/A, an inactive terpene synthase (contains a D/A mutation at the catalytic aspartic acid, preventing the initial metal-binding step in terpene cyclization); *, a constitutively active B2H (contains $PTP1B_{C215S}$, preventing dephosphorylation); X, an inactive B2H (contains a substrate domain with a Y/F mutation, prohibiting phosphorylation and thus binding with the SH2 domain). Images show LB plates seeded with drops of liquid culture (10 μL) from two biological replicates. TABLE 2 details the B2H systems used for these analyses. Error bars in FIG. 26A denote standard deviation for n≥3 biological replicates.

FIG. 32A, Snapshots from molecular dynamics (MD) simulations of PTP1B bound to amorphadiene (AD). Arrows indicate clusters of ligand. FIG. 32B, A crystal structure of PTP1B bound to AD highlights residues that undergo high-frequency contacts. Here, contacts have residue-ligand distances <4 Å, and high frequencies exceed 10% of all snapshots in the MD simulations. FIG. 32C, Estimates of the average root-mean-square deviation (RMSD) of the complete system (PL), the protein (P), the protein core ($P_{core}$; residues 1-287), the disordered region of the protein ($P_{tail}$; residues 288-321), and the ligand (L) over MD simulations indicate that both AD and the disordered region of the protein are mobile (the latter more so than the former), while the protein core remains fixed. The average RMSDs of both (i) the re-centered ligand (Int), a metric for rotational and vibrational fluctuations, and (ii) the center of mass (COM) of the ligand, a metric for its positional deviation, are large, an indication that the ligand can adopt multiple bound conformations and/or positions.

FIG. 33A, Aligned crystal structures of PTP1B (gray, pdb entry 5k9w) and TC-PTP (blue, pdb entry 118k). Highlights on PTP1B: a competitive inhibitor (orange), the α7 helix (red), and truncation points used for kinetic studies (281 and 283, the 281-equivalent of TC-PTP). FIG. 33B, Sequence alignment of the α6/7 regions of PTP1B (SEQ ID NO: 140) and TC-PTP (SEQ ID NO: 141). The truncation points used in our kinetics analysis. FIG. 33C, aligned structures of the binding sites of BBR (gray, pdb entry 1t4j) and amorphadiene (blue). FIG. 33D-FIG. 33M, Initial rates of pNPP hydrolysis by various PTPs in the presence of increasing concentrations of (FIG. 33D-FIG. 33G) amorphadiene, (FIG. 33H-FIG. 33K) α-bisabolene, (FIG. 33L) dihydroartimesinic acid, and (FIG. 33M) α-bisabolol inhibition. In all figures, lines show the best-fit models of inhibition (TABLE 12). Error bars in FIG. 33D-FIG. 33M represent standard error of at least 3 measurements. Error in $IC_{50}$'s represent 95% confidence intervals determined from fits to models of inhibition (TABLE 12).

FIG. 34A, Initial rate data for AD inhibition of SHP1. The lower panel shows the same data as % inhibition for a subset of points at two different substrate concentrations (open vs. closed circles). FIG. 34B, Initial rate data for AD inhibition of SHP2. The lower panel shows the same data as % inhibition for a subset of points at two different substrate concentrations (open vs. closed circles). FIG. 34C, Initial rate data for AB inhibition of SHP1. The lower panel shows the same data as % inhibition for a subset of points at two different substrate concentrations (open vs. closed circles). FIG. 34D, Initial rate data for AB inhibition of SHP2. The lower panel shows the same data as % inhibition for a subset of points at two different substrate concentrations (open vs. closed circles). In FIG. 34A, FIG. 34C, and FIG. 34D, our inability to measure inhibition >25% (lower panel) at the solubility limit of AD, in combination with the high $K_m$ for 4-methylumbelliferyl phosphate (4-MUP), precluded accurate inhibition model fitting, $K_I$, and $IC_{50}$ determination. However, the weak inhibition observed suggests AD/AB are less potent inhibitors of these enzymes than PTP1B. In all panels, error bars denote standard error of n=3 biological replicates and lines show fit to a noncompetitive inhibition model.

FIG. 35A, A depiction of insulin signaling in HEK293T/17 cells. Extracellular insulin binds to the transmembrane insulin receptor (IR), triggering phosphorylation of its intracellular domain. PTP1B, which localizes to the endoplasmic reticulum (ER) of mammalian cells, dephosphorylates this domain to regulate downstream signaling pathways. In starved cells, exogenously supplied inhibitors can permeate the cell membrane and inhibit PTP1B-mediated dephosphorylation of the IR. FIG. 35B, A screen of inhibitor concentrations for enzyme-linked immunosorbent assay (ELISAs). An enzyme-linked immunosorbent assay (ELISA) of IR phosphorylation in HEK293T/17 cells incubated with various concentrations of amorphadiene, α-bisabolene, and their structural analogues. We used this screen to identify biologically active concentrations of amorphadiene and α-bisabolene to study further. FIG. 35C, ELISA-based measurements of IR phosphorylation in HEK293T/17 cells incubated with amorphadiene (AD), α-bisabolene (AB), dihydroartimesnic acid (DHA), and α-bisabolol (ABOL). Curves denote fits to the four-parameter logistic equation: y=d+ (a−d)/(1+ (x/c)^b), where y is absorbance at 450 nm, and x is the sample dilution (e.g., 1 denotes no dilution, 0.5 denotes a 2-fold dilution, and so on). These signals indicate that amorphadiene and α-bisabolene can increase IR phosphorylation over a negative control (3% DMSO) and their less inhibitory analogs. Error bars denote standard error with n≥3 biological replicates.

FIG. 36A, Biological replicates for FIG. 22C. FIG. 36B, Biological replicates for FIG. 25A. FIG. 36C, Biological replicates for FIG. 25B. Orange highlights correspond to the data displayed in FIGS. 2C and 5A-5B.

FIG. 37A, A GC/MS chromatogram shows the production of α-bisabolene by a strain of *E. coli* engineered to produce it (i.e., pMBIS+pABA). FIG. 37B, The mass spectrum of the indicated peak from FIG. 37A.

FIG. 38A, A GC/MS chromatogram shows the production of (+)-1 (10),4-Cadinadiene by a strain of *E. coli* engineered to produce it (i.e., pMBIS+pA0A0C9VSL7). FIG. 38B, The mass spectrum of the indicated peak from FIG. 38A.

FIG. 39A, We dissolved different amounts of p-nitrophenol (p-NP) in 100 μL buffer (50 mM HEPES, pH=7.3) and measured the absorbance of the resulting solutions with a SpectraMax M2 plate reader. A linear fit to this curve allowed us to convert absorbance measurements taken during kinetic assays (pNPP) to p-NP concentrations. FIG. 39B, We dissolved different amounts of 4-methyl umbelliferone (4-MU) in 100 μL buffer (50 mM HEPES, pH=7.3) and measured the FLUORESCECE of the resulting solutions with a SpectraMax M2 plate reader. A linear fit to this curve allowed us to convert absorbance measurements taken during kinetic assays (4-MUP) to 4-MU concentrations.

DETAILED DESCRIPTION

Figure 1A:
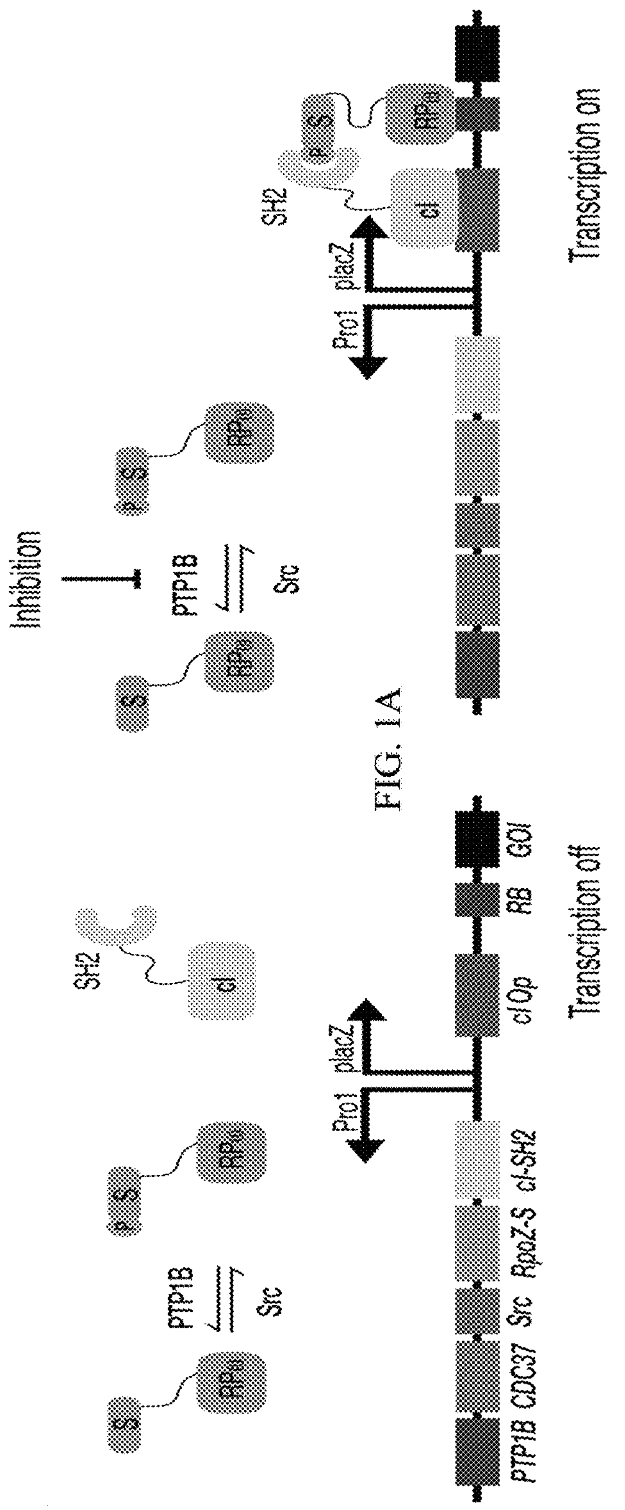
FIGS. 1A-1E. Development of a bacterial-two hybrid system that links the inhibition of PTP1B to antibiotic resistance.

*E. coli* is a valuable platform for the production of terpenoids[27-29]. The inventors hypothesized that a strain of *E. coli* programmed to detect the inactivation of a human drug target might enable the rapid discovery and biosynthesis of terpenoids that inhibit that target. To program such a strain, a bacterial two-hybrid (B2H) system was assembled in which a protein tyrosine kinase (PTK) and protein tyrosine phosphatase (PTP) from *H. sapiens* control gene expression. PTKs are targets of over 30 FDA-approved drugs[30]; PTPs lack clinically approved inhibitors but contribute to an enormous number of diseases[31,32]. The first proof-of-concept system was specifically designed to detect inhibitors of protein tyrosine phosphatase 1B (PTP1B), an elusive therapeutic target for the treatment of type 2 diabetes, obesity, and breast cancer (FIG. 1A)[31-35]. In this system, Src kinase phosphorylates a substrate domain, enabling a protein-protein interaction that activates transcription of a gene of interest (GOI). PTP1B dephosphorylates the substrate domain, preventing that interaction, and the inactivation of PTP1B re-enables it. *E. coli* is a particularly good host for this detection system because its proteome is sufficiently orthogonal to the proteome of *H. sapiens* to minimize off-target growth defects that can result from the regulatory activities of Src and PTP1B36.

Figure 1B:
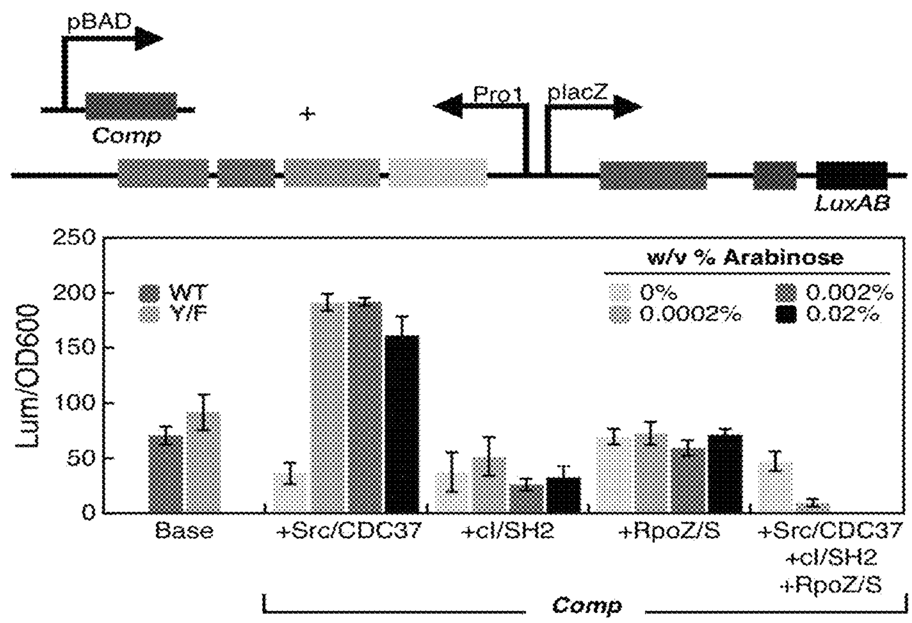
Figure 1C:
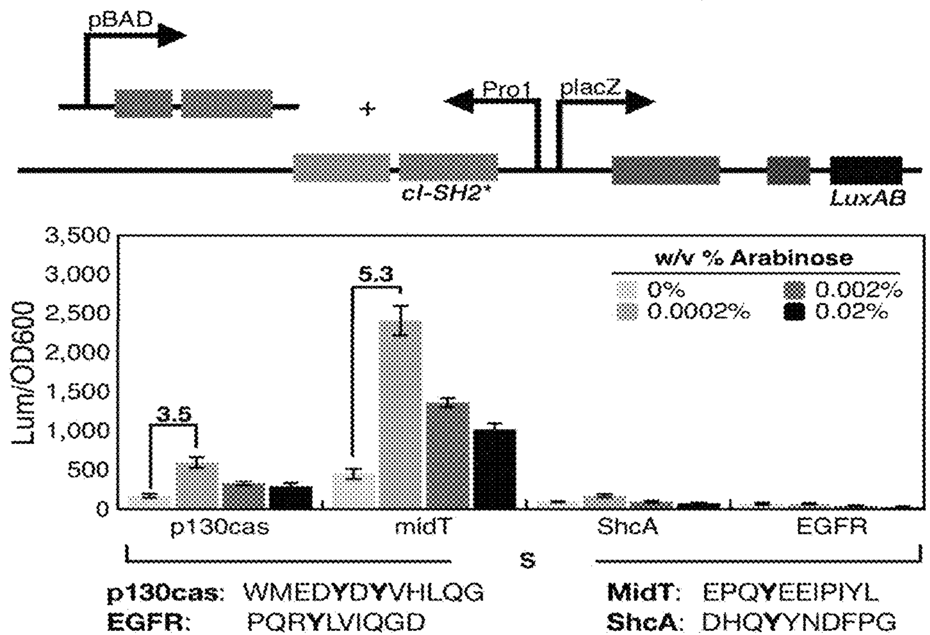
Figure 1D:
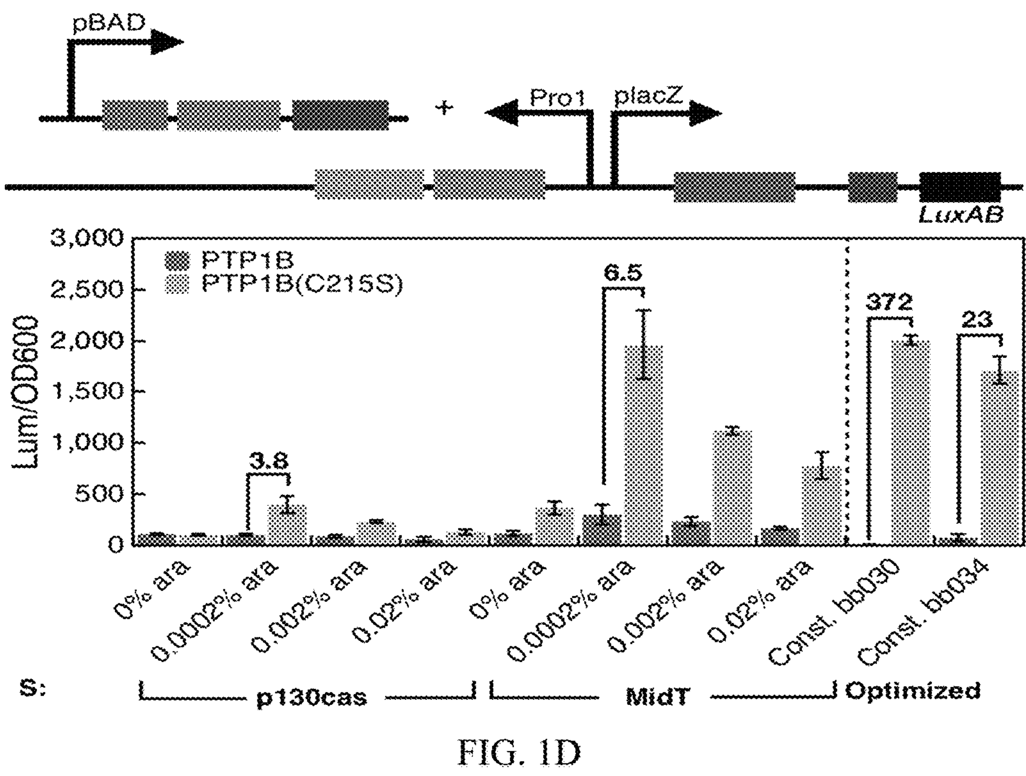
Figure 1E:
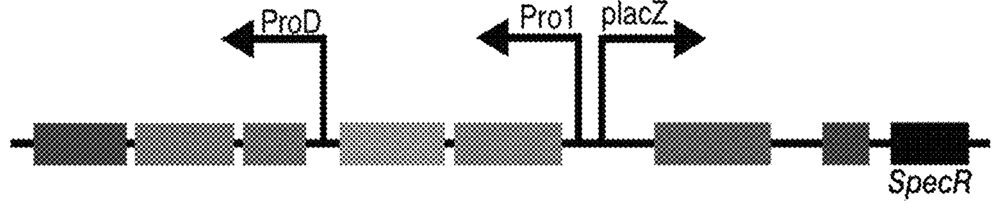
Figure 1E:
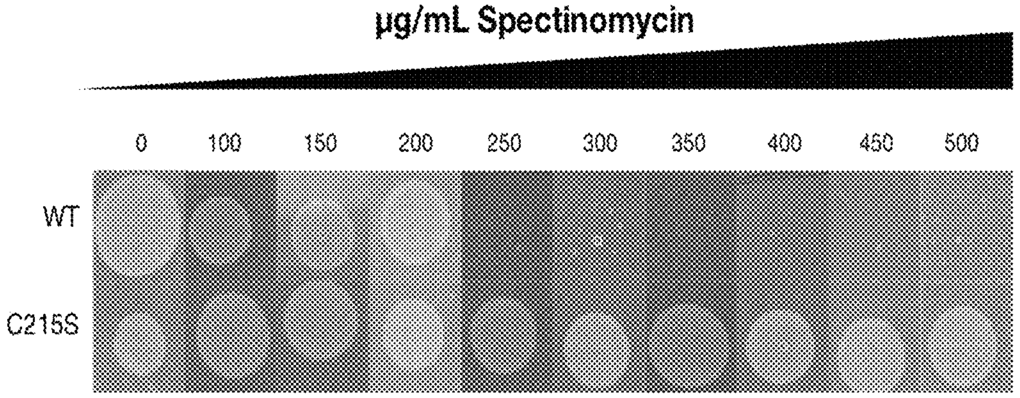
Figure 13:
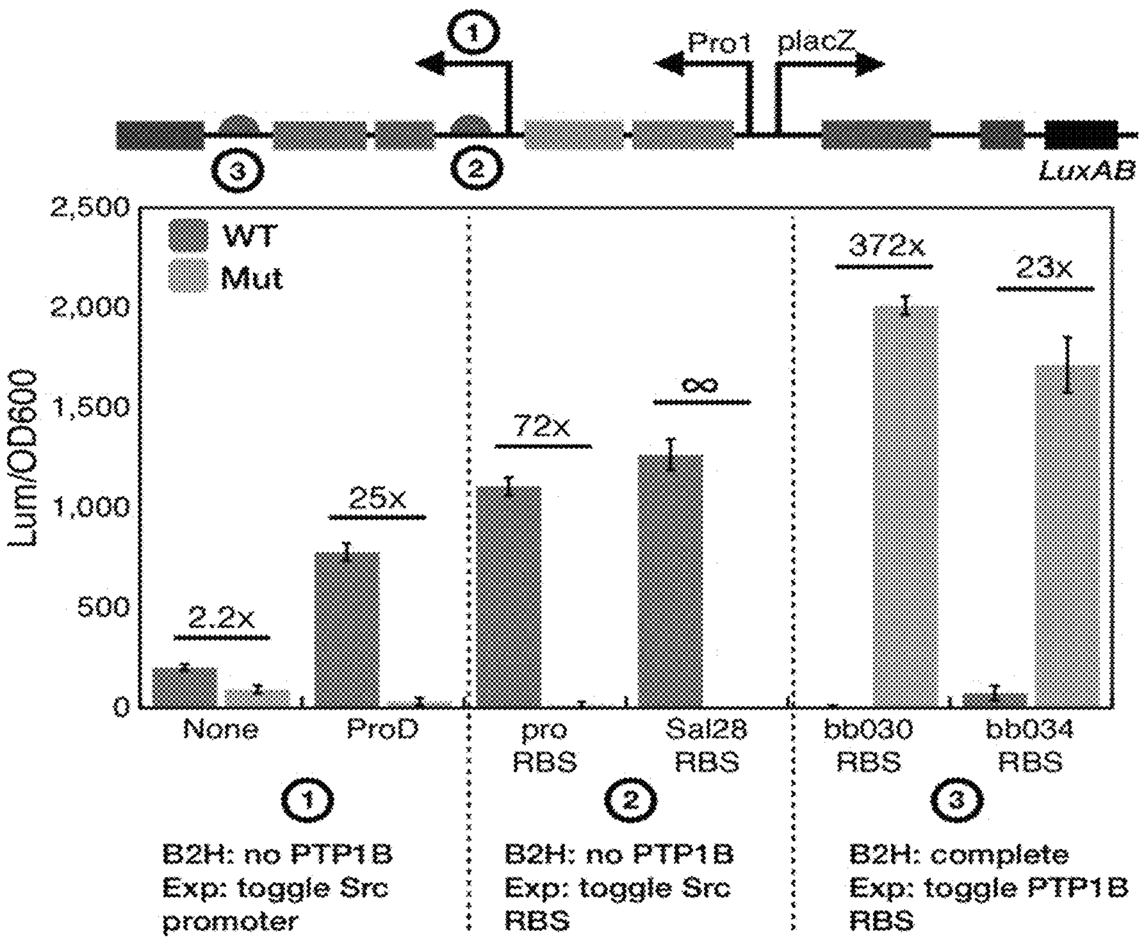
FIG. 13. Optimization of the bacterial-two hybrid (B2H) system.
Figure 14:
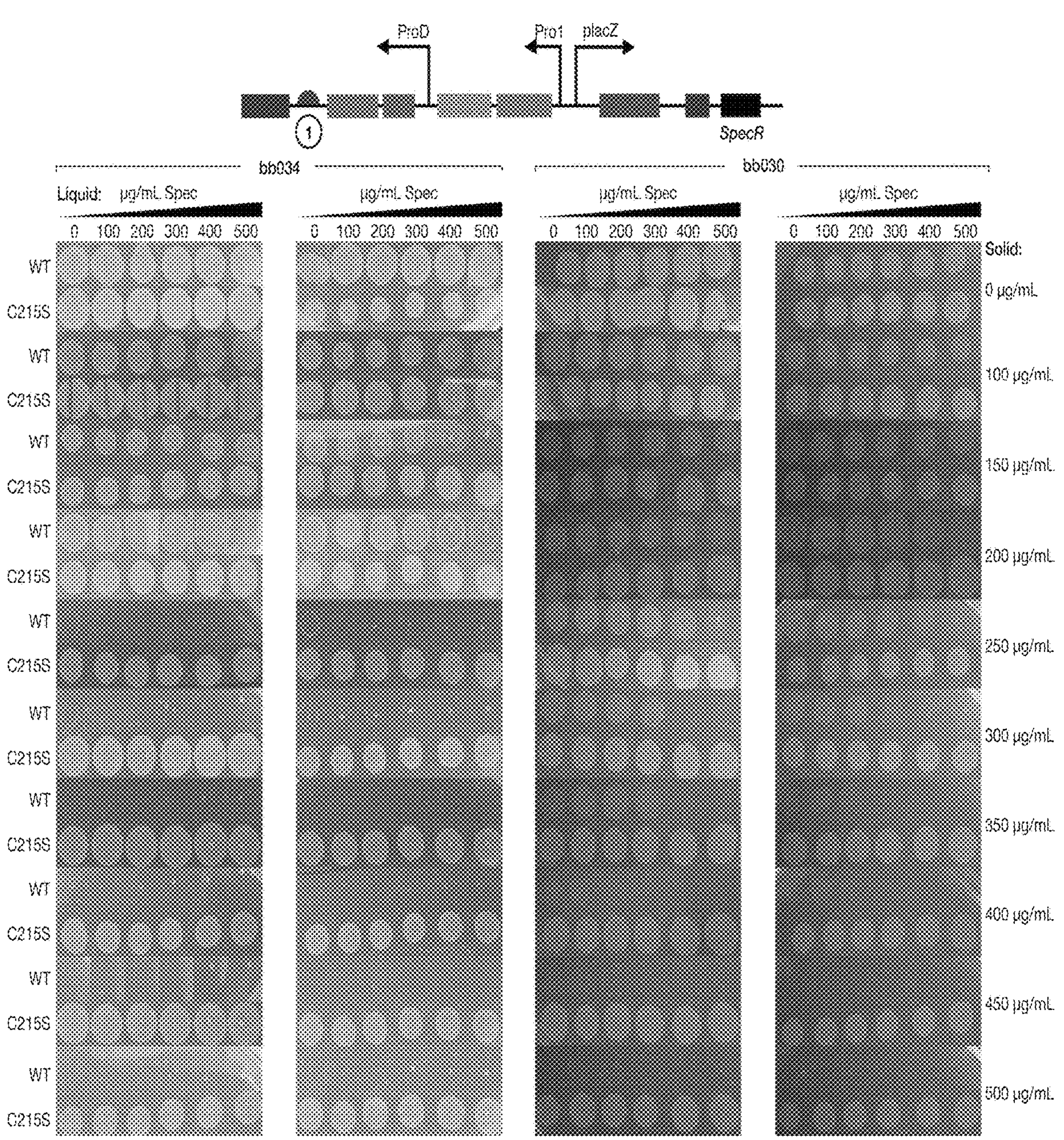
FIG. 14. Analysis of different selection conditions.
Figure 15A:
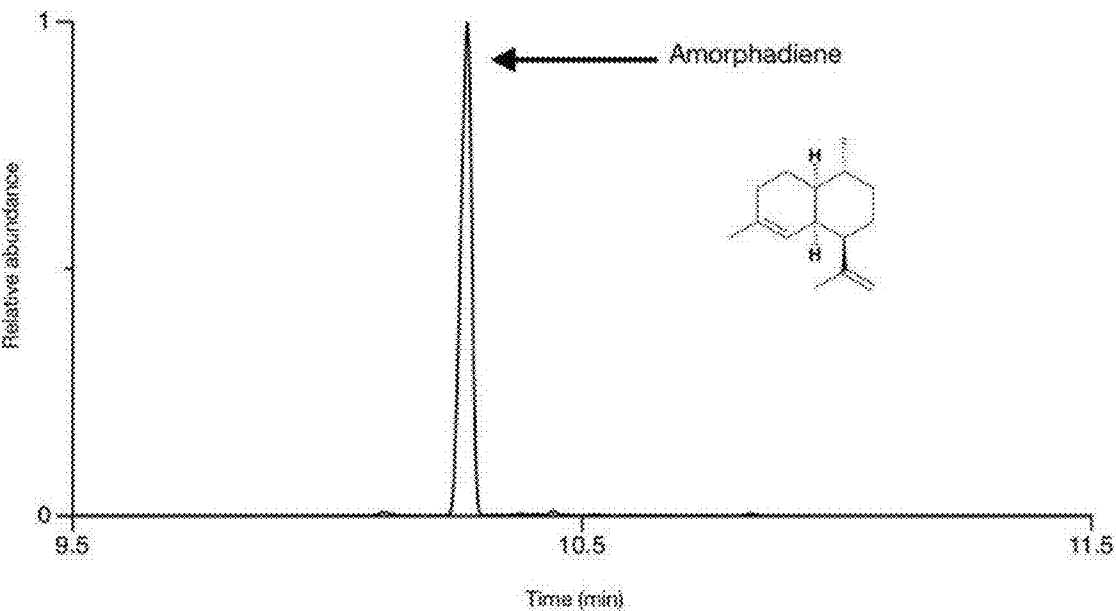
FIGS. 15A-15B.
Figure 15B:
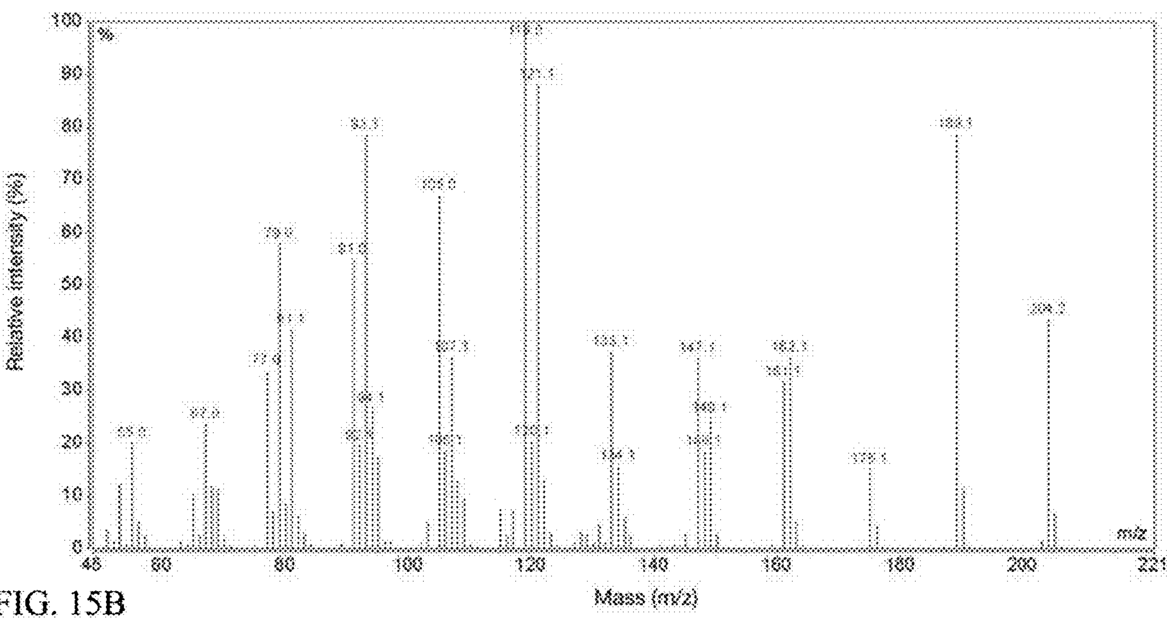
Figure 16A:
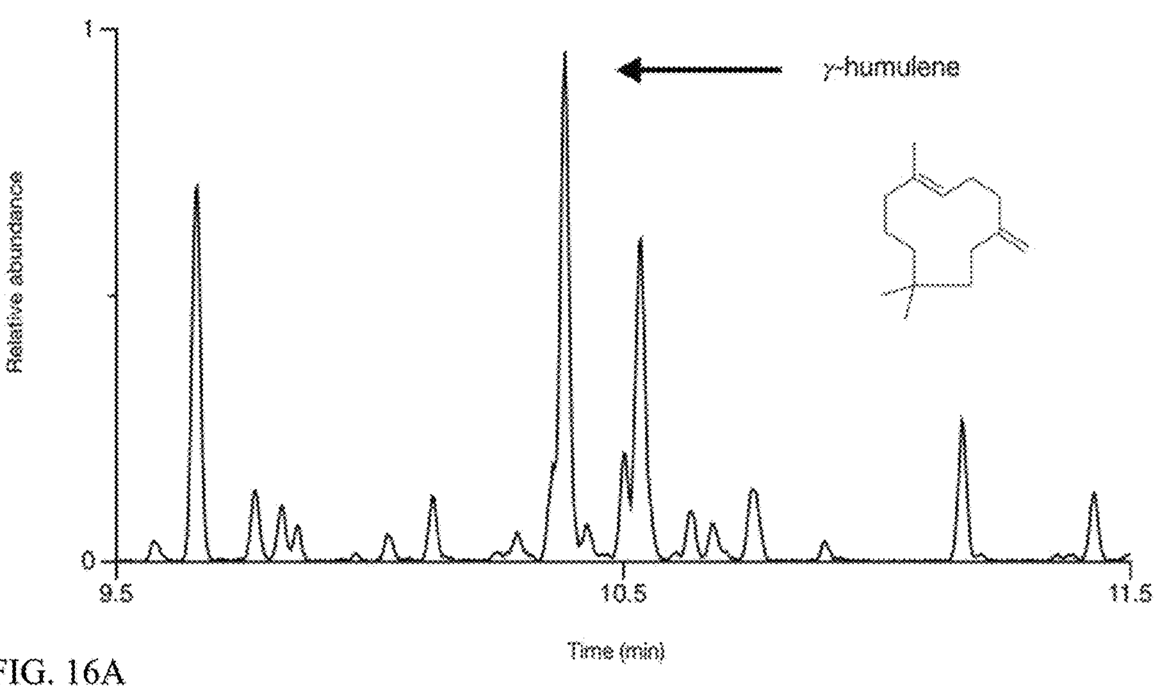
FIGS. 16A-16B. GC/MS analysis of γ-humulene production.
Figure 16B:
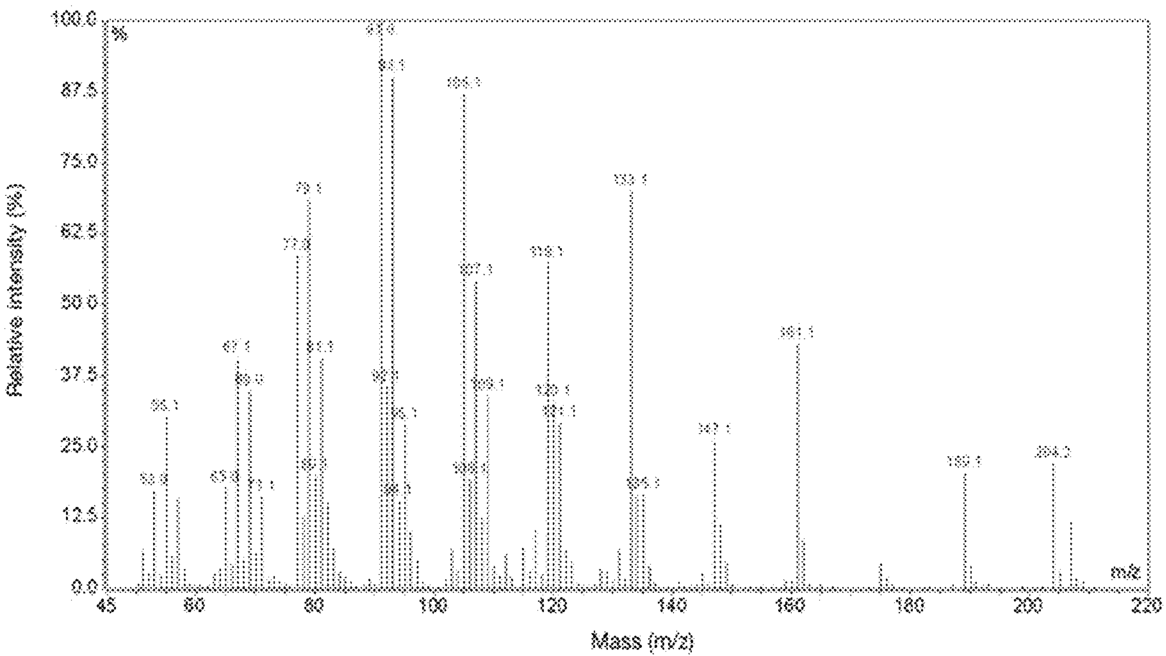
Figure 17A:
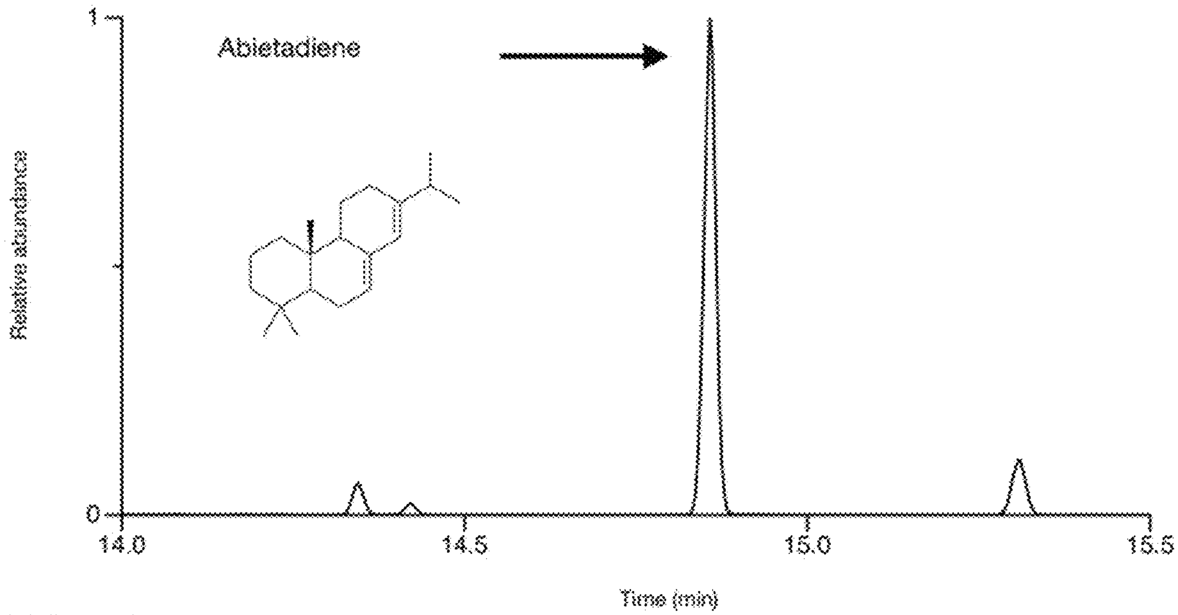
FIGS. 17A-17B. Supplementary FIG. 4|GC/MS analysis of abietadiene production.
Figure 17B:
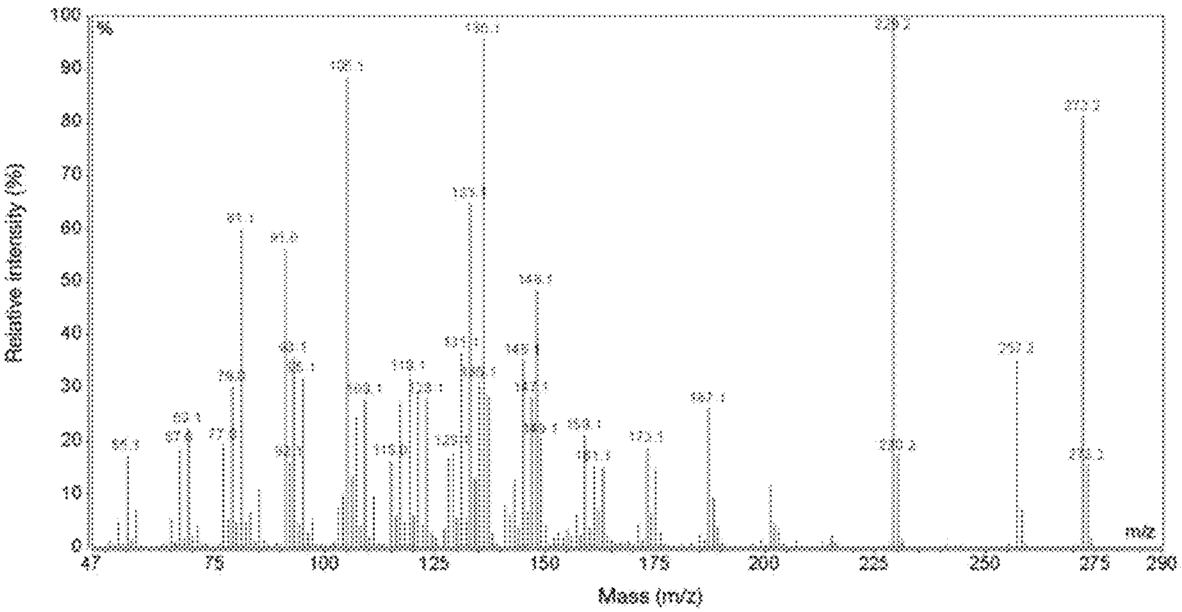
Figure 18A:
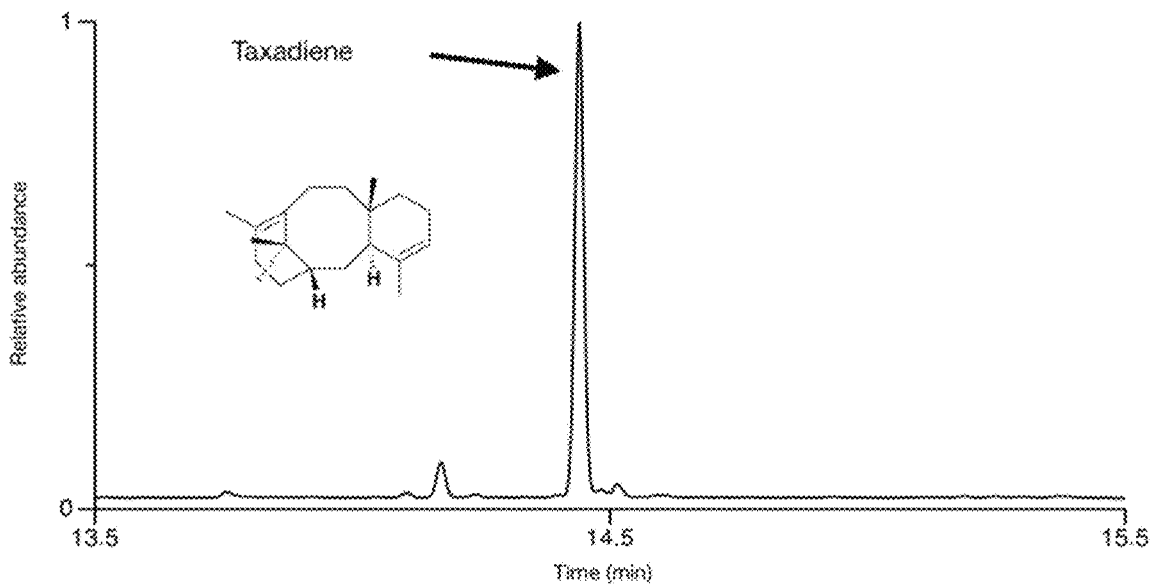
FIGS. 18A-18B. GC/MS analysis of taxadiene production.
Figure 18B:
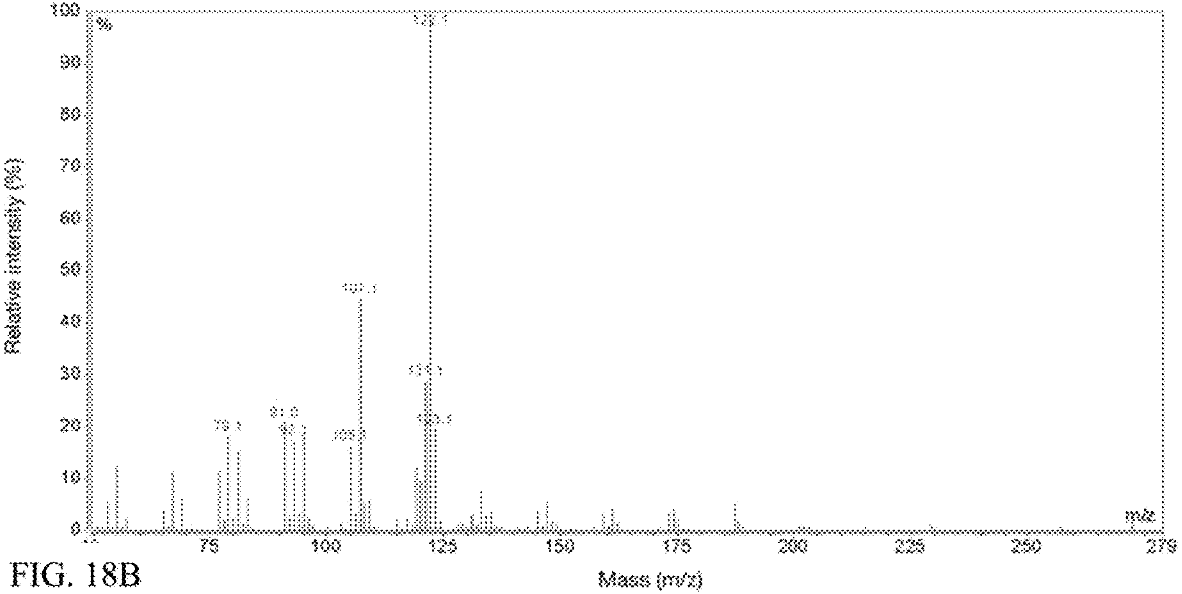
Figures 19A, 19B:
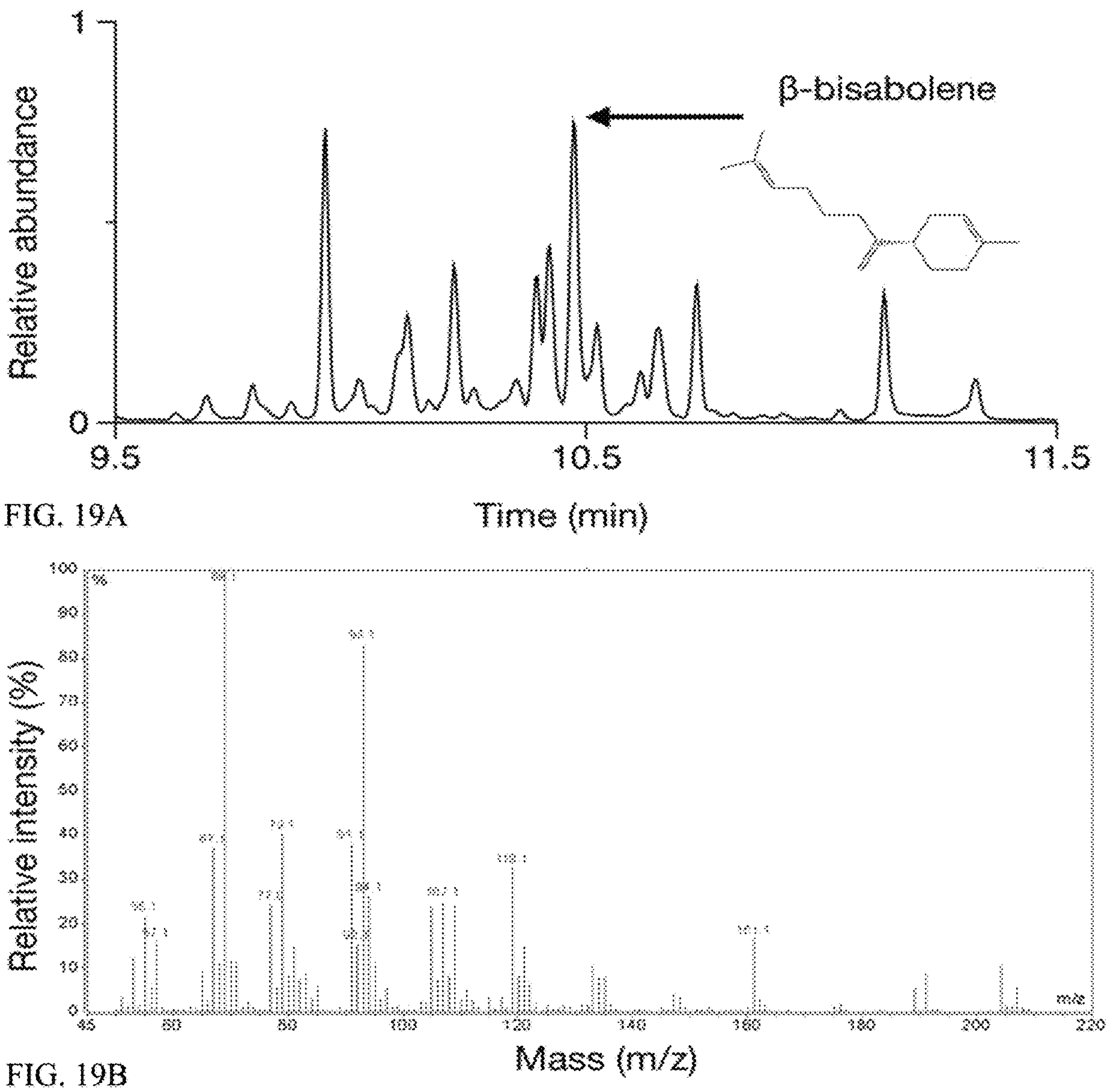
FIGS. 19A-19B. GC/MS analysis of β-bisabolene production.
Figure 20:
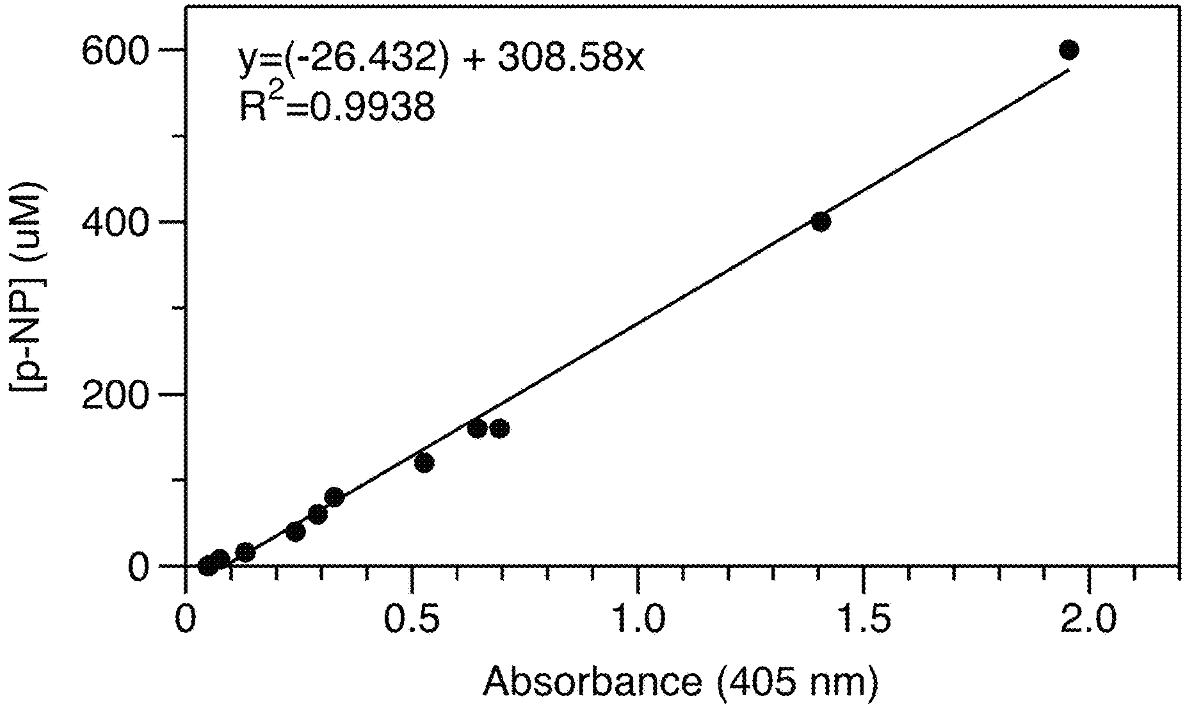
FIG. 20. Standard curve for pNPP assay. This standard curve was generated by dissolving various concentrations of p-nitrophenol (p-NP) in 100 μL water and measuring their absorbance with a plate reader. Absorbance measurements collected in our pNPP kinetics analysis were converted to concentrations using this curve.

B2H development was carried out in several steps. To begin, a luminescent "base" system was assembled in which Src modulates the binding of a substrate domain to a substrate homology 2 (SH2) domain; this system was based on a previous design in which protein-protein association controls GOI expression[37]. The initial system did not yield a phosphorylation-dependent transcriptional response, however, so it was complemented with inducible plasmids—each harboring a different system component—to identify proteins that might exhibit suboptimal activities. Notably, secondary induction of Src increased luminescence, an indication that insufficient substrate phosphorylation depressed GOI expression in the base system (FIG. 1B). Accordingly, this system was modified by swapping in different substrate domains, by adding mutations to the SH2 domain that enhance its affinity for phosphopeptides[38], and by removing the gene for Src. With this configuration, induction of Src from a second plasmid increased luminescence most prominently for the MidT substrate (FIG. 1C); simultaneous induction of both Src and PTP1B, in turn, prevented that increase (FIG. 1D). The MidT system was finalized by integrating genes for Src and PTP1B, by adjusting promoters and ribosome binding sites to amplify its transcriptional response further (FIGS. 1D, 13, and 14), and by adding a gene for spectinomcyin resistance (SpecR) as the GOI. The final plasmid-borne detection system required the inactivation of PTP1B to permit growth at high antibiotic concentrations (FIG. 1E).

Figures 2A, 2B, 2C:
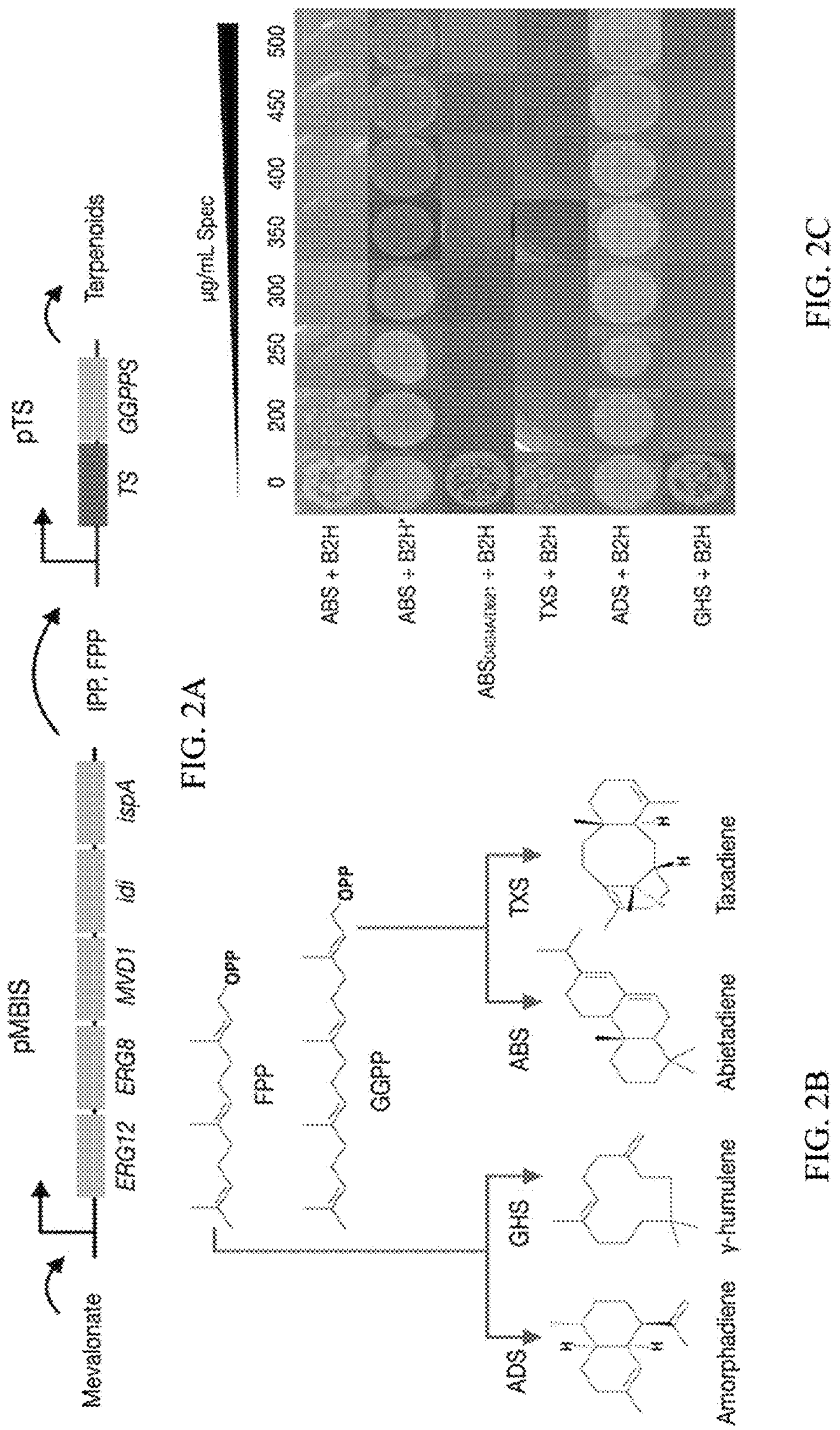
FIGS. 2A-2C. Biosynthesis of PTP1B-inhibiting terpenoids enables cell survival.

The B2H system was used to identify new inhibitors of PTP1B by coupling it with metabolic pathways that might generate such molecules in *E. coli*. Previous screens of plant extracts have identified structurally complex terpenoids that inhibit PTP1B[39]; pathways were, thus, constructed for several simpler terpenoid scaffolds that lack established inhibitory effects: amorphadiene, γ-humulene, abietadiene, and taxadiene. Abietadiene is a metabolic precursor to a weak inhibitor of PTP1B[40]; the other three terpenoids represent a structurally diverse set of molecules. Each pathway consisted of two plasmid-borne modules (FIG. 2A): (i) the mevalonate-dependent isoprenoid pathway from *S. cerevisiae*[41] and (ii) a terpene synthase supplemented—when necessary for diterpenoid production—with a geranylgeranyl diphosphate synthase. These modules enabled terpenoid titers of 0.5-100 μM in *E. coli* (FIG. 9).

Figure 9A:
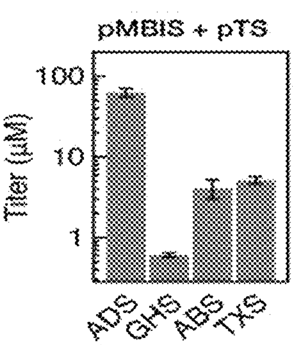
FIGS. 9A-9C. Analysis of the products of different terpene synthases.
Figure 9A:
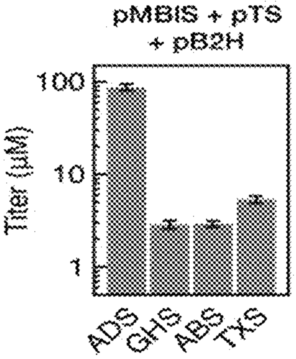
Figure 9B:
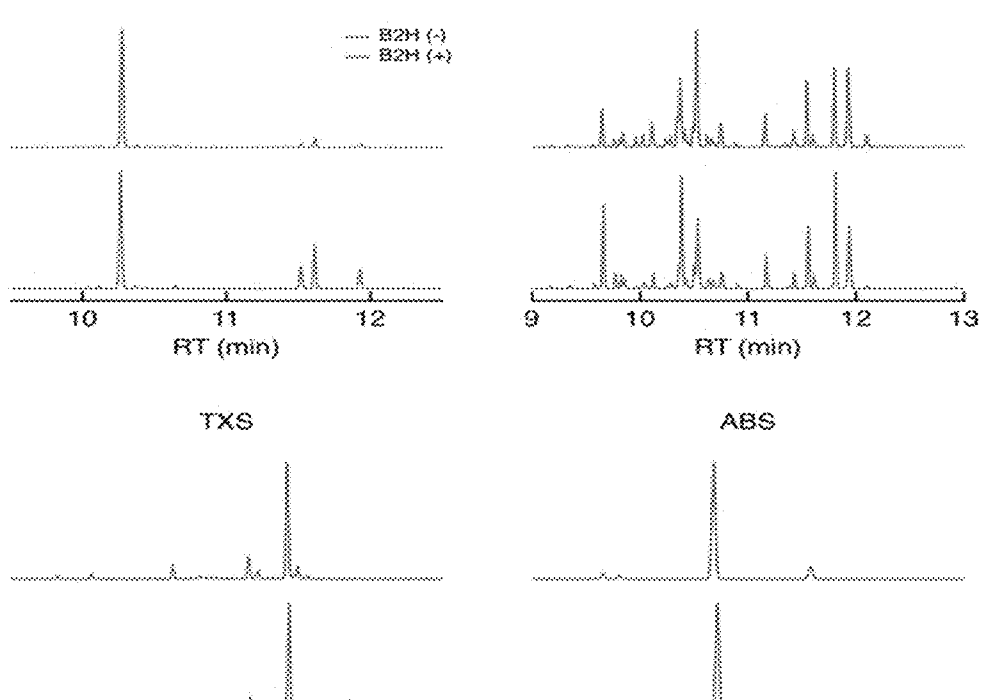
Figure 9C:
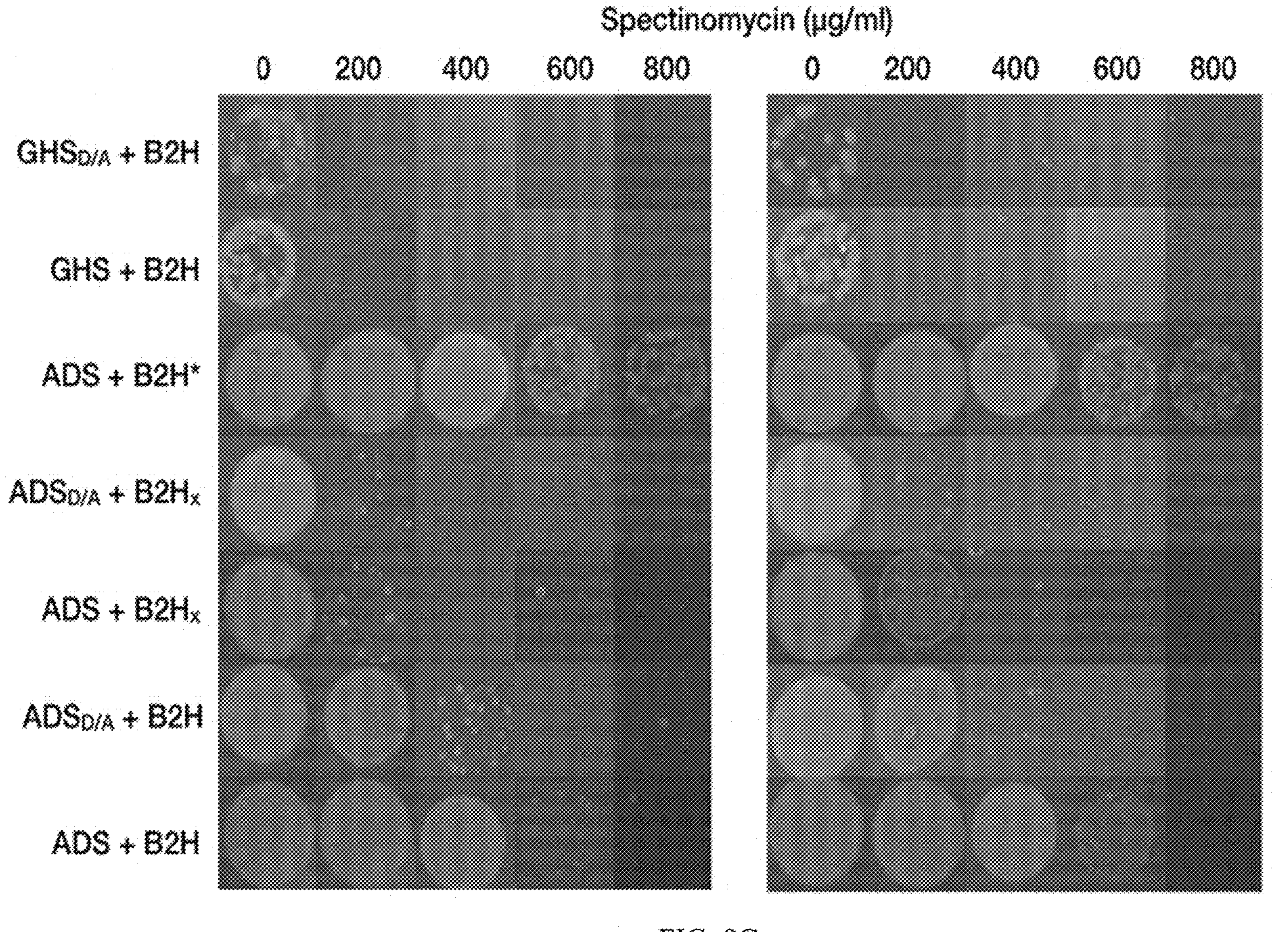

Each pathway was screened for its ability to produce inhibitors of PTP1B by transforming *E. coli* with plasmids harboring both the pathway of interest and the B2H system. GC-MS traces confirmed that all pathways generated terpenoids in the presence of the B2H system (FIG. 2D). Surprisingly, the amorphadiene pathway permitted survival at high concentrations of antibiotic; importantly, maximal resistance required a functional B2H system (FIG. 9C). This result suggests that the amorphadiene pathway produces an inhibitor of PTP1B.

Figures 3A, 3B, 3C, 3D, 3E, 3F, 3G:
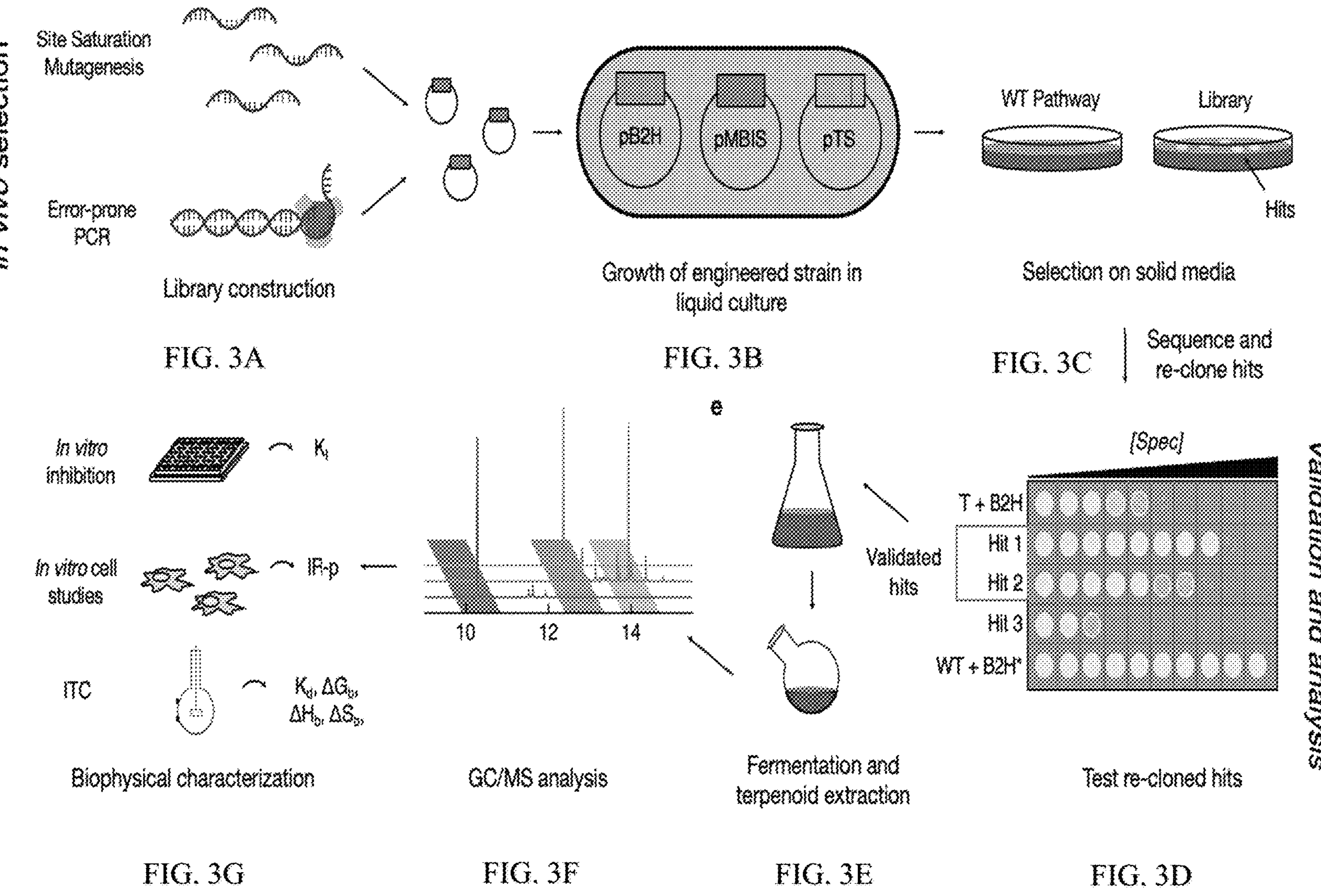
FIGS. 3A-3G. Strategy for microbially assisted directed evolution (MADE).

Microbially-assisted directed evolution (MADE) refers to the approach described herein for using microbial systems to discover and evolve metabolic pathways that produce inhibitors or activators of a therapeutically relevant enzyme target, wherein both the metabolic pathway and the target enzyme exist within a host cell, for example, an *E. coli* cell (FIG. 3). Some aspects of this approach provide a method for building a genetically encoded system that detects the activity of a target enzyme within a host cell, for example a system that links changes in the activity of a target enzyme to changes in the antibiotic resistance of the host cell (FIG. 1).

Previous work demonstrated (i) the assembly of a detection system that links the activities of a protein kinase and a protein phosphatase to antibiotic resistance (FIG. 1) and (ii) the use of that system, in combination with MADE, to discover inhibitors of a protein phosphatase (FIG. 2). These results are detailed in PCT/US2019/40896.

Described herein are strategies, systems, methods, and reagents to expand the scope of capabilities of MADE and to address the needs of previously described evolution experiments. The MADE methods herein utilize one or more of the following: 1) target enzymes that post-translationally modify proteins (PTM enzymes) in a manner other than adding or removing a phosphate group; 2) a metabolic pathway that generates phenylpropanoids or nonribosomal peptides; 3) a cryptic gene cluster that encodes putative natural products; and 4) natural products with specific inhibitory effects.

In some embodiments, provided are methods for using MADE to discover and evolve metabolic pathways that produce inhibitors or activators of PTM enzymes (FIG. 3), wherein said PTM enzymes modulate a protein-protein interaction that controls a detectable output, wherein both the PTM enzymes and the detectable output are encoded by at least one plasmid or one genome, wherein a metabolic pathway that produces natural products is encoded by at least one plasmid or one genome, and wherein said plasmids and genomes exist within the same host cell. In some embodiments, a pool of said host cells, each of which contains a different metabolic pathway, is screened for a detectable output, and the cells that yield the highest detectable output are selected as hits. These hits are analyzed with the following steps: 1) their metabolic pathways are reassembled from a starting pathway; 2) the re-assembled pathways are re-screened in host cells (a confirmation step); 3) the cells that yield the highest detectable outputs are, once again, selected as hits; 4) these selected cells are grown in liquid culture; 5) the products generated in said liquid culture are identified and quantified with standard analytical methods, for example, gas chromatography-mass spectrometry (GC/MS); 6) the products generated in liquid culture are concentrated with a rotary evaporator; and 7) the modulatory effects of the concentrated products are tested on purified PTM enzymes (FIG. 3).

In some embodiments, the target PTM enzyme naturally inhibits the growth of a host cell, for example, an *S. cerevisiae* cell in which a heterologously expressed kinase slows cell growth.

Figures 4A, 4B, 4C, 4D:
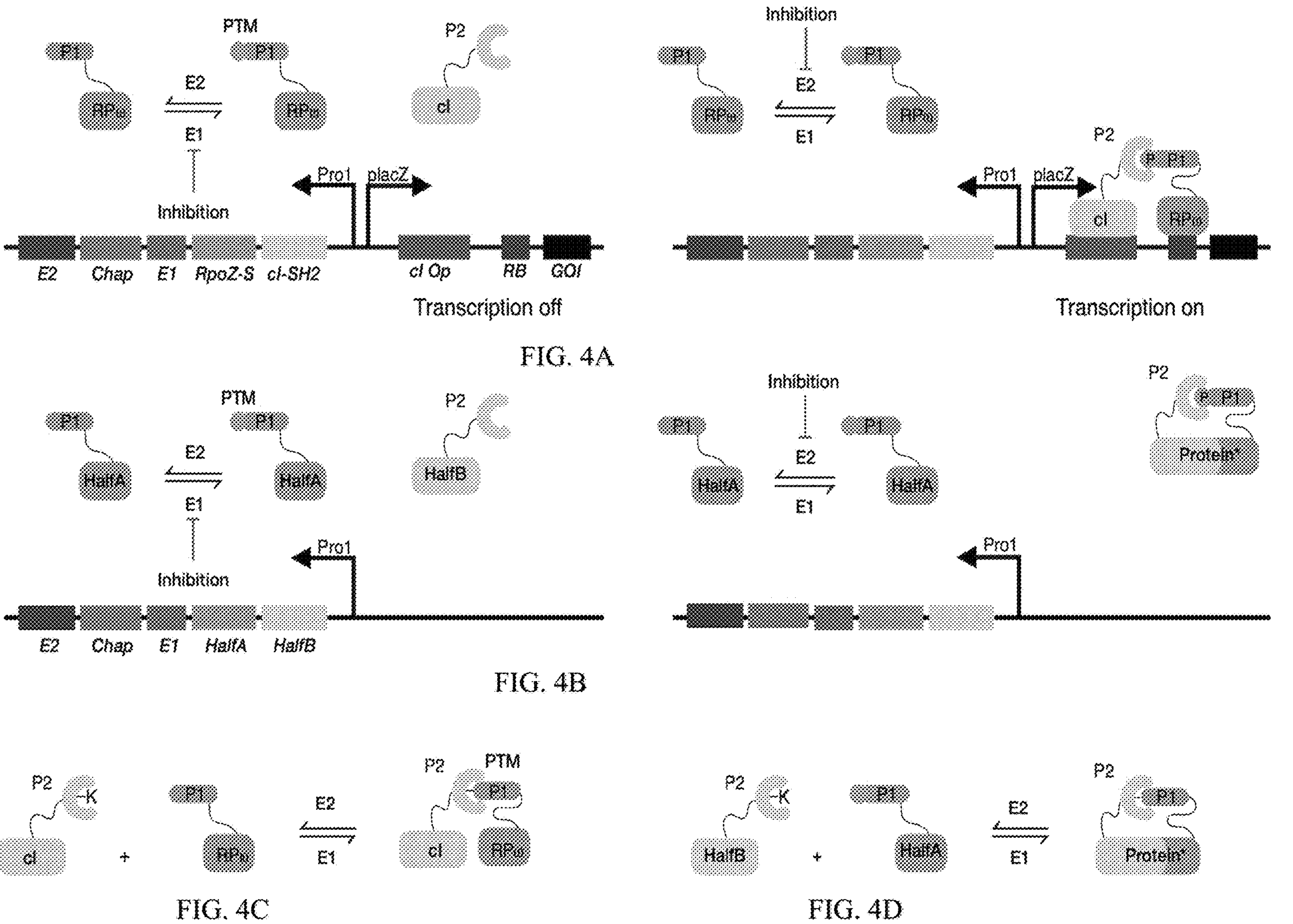
FIGS. 4A-4D. Genetically encoded systems that detect metabolite-mediated modulation of post-translational modification (PTM) enzymes.
Figure 5A:
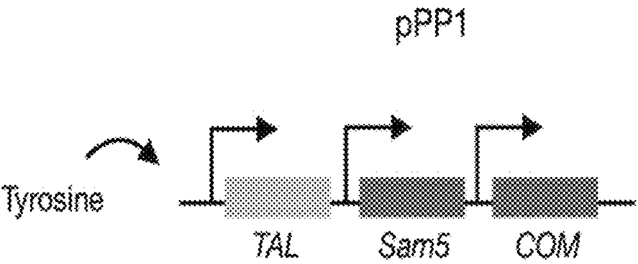
FIGS. 5A-5C. Alternative metabolic pathways.
Figure 5A:
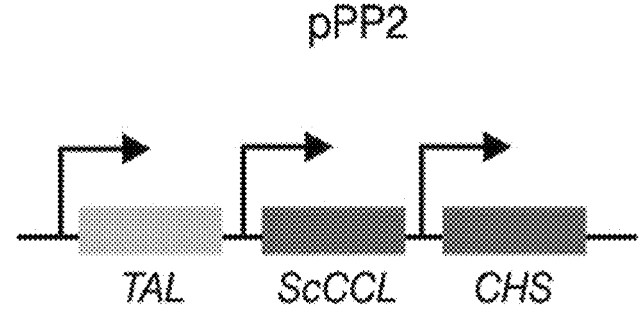
Figure 5A:
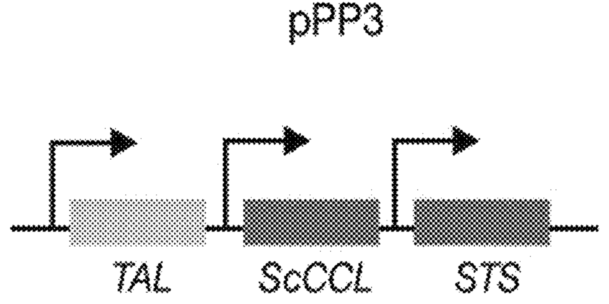
Figures 5B, 5C:
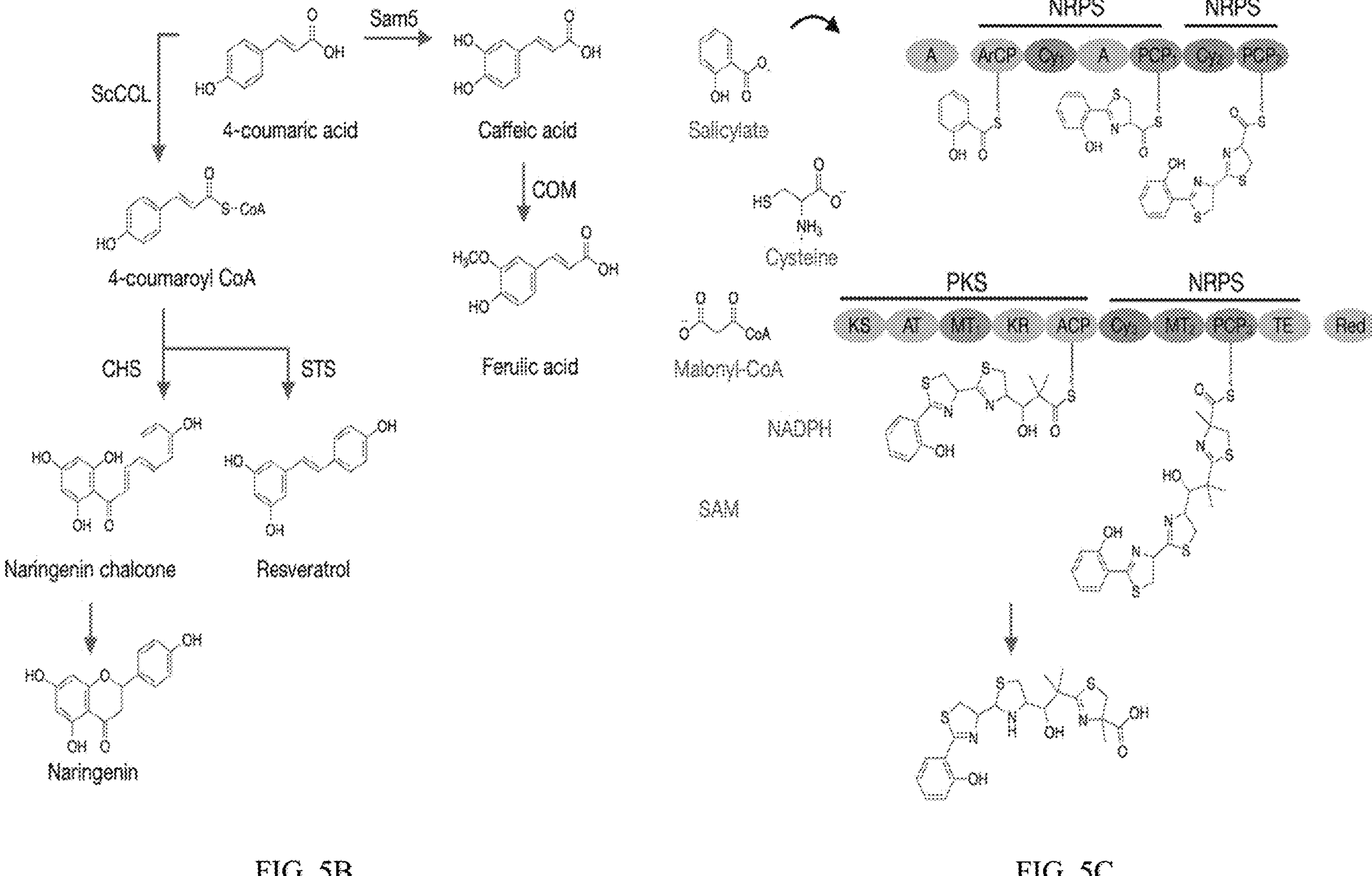

In some embodiments, the PTM enzymes are ubiquitin ligases, SUMO transferases, methyltransferases, demethylases, acetyltransferases, glycosyltransferases, palmitoyltransferases, and/or related hydrolases. In some embodiments, a bacterial two-hybrid (B2H) system links the activity of one or more PTM enzymes to the transcription of a gene of interest (GOI; FIG. 4A). In some embodiments, the PTM enzymes modulate the assembly of a split protein, for example, a fluorescent protein, a luciferase, or an enzyme that confers antibiotic resistance (FIG. 4B). In some embodiments, the target enzymes covalently link or proteolyze two proteins, wherein the assembly of these proteins activates the transcription of a gene of interest (FIG. 4C) or reassembles a split protein (FIG. 4D).

In some embodiments, provided are methods for the discovery and evolution of phenylpropanoids or nonribosomal peptides that inhibit or activate a target enzyme, wherein a metabolic pathway that produces phenylpropanoids or nonribosomal peptides is encoded by at least one plasmid or one genome (FIG. 5), wherein said plasmid and said genome exist within a host cell, wherein mutagenesis and/or modulation of said metabolic pathways permit the production of an inhibitor or activator of the target enzyme, and wherein MADE enables the identification of pathways thus mutated and/or reconfigured.

Figures 6A, 6B:
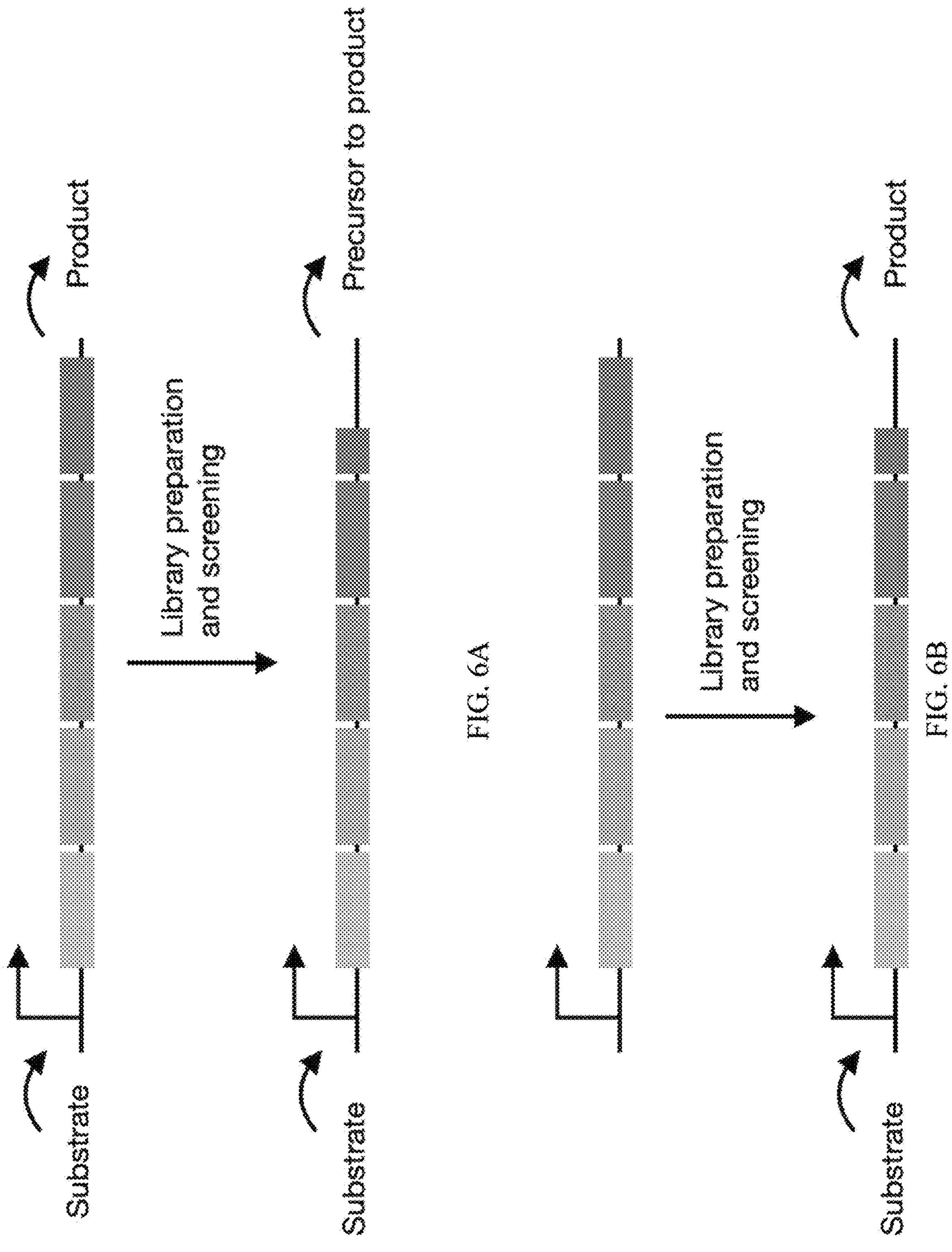
FIGS. 6A-6B. An approach for the discovery of cryptic metabolic pathways.

In some embodiments, provided are methods for the discovery and evolution of cryptic metabolic pathways that generate inhibitors or activators of a target enzyme, wherein said cryptic metabolic pathways comprise a set of genes with unknown or poorly characterized products, or wherein said cryptic metabolic pathways comprise a set of genes in which one gene hinders the biosynthesis of an important product, wherein subsequent mutagenesis and/or reconfiguration of said pathway causes it to generate more of that product, and wherein MADE enables the discovery of a pathway thus mutated and/or reconfigured. For example, the removal of a biosynthetic gene may enable the accumulation of a metabolic intermediate that modulates the activity of a target enzyme (FIG. 6A); alternatively, the removal of a gene for a transcriptional repressor may permit the activation of the entire metabolic pathway (FIG. 6B).

In some embodiments, provided are methods for the discovery and evolution of metabolic pathways with higher titers and/or lower toxicities, wherein starting pathways are mutated and/or reconfigured to create a library of pathways, and said library of pathways is screened using MADE to identify pathways that (i) produce higher quantities of inhibitor or activator than the starting pathway and/or (ii) exhibit a lower toxicity than the starting pathway (FIG. 7). For example, mutagenized and/or reconfigured pathways may contain genes for a mutant enzyme, for example, a terpene synthase, that exhibits a higher activity than the wild-type enzyme; alternatively, mutagenized and/or reconfigured pathways may contain genes for a mutant terpene synthase that is more soluble or otherwise less toxic than a wild-type enzyme.

Some aspects of this disclosure provide molecules that inhibit protein tyrosine phosphatases (PTPs), for example, protein tyrosine phosphatase 1B (PTP1B; FIGS. 9 and 10). Examples include amorphadiene and derivatives, taxadiene and derivatives, β-bisabolene and derivatives, α-bisabolene and derivatives, and α-longipinene and derivatives. In some embodiments, these molecules are provided as drugs or drug leads for the treatment of diseases to which PTPs contribute, for example, type 2 diabetes[42], HER2-positive breast cancer[43], or Rett syndrome[44], as are methods of treatment of such diseases by administering an effective amount of the molecule(s) to a subject in need of such treatment.

Also provided are compositions or systems that include a population of host cells that comprise a protein of interest and a population of expression vectors comprising different metabolic pathways, wherein a cell or subset of the population of host cells produce a detectable output when the metabolic pathway produces a product that modulates the protein of interest, and optionally wherein the expression vectors yield detectable outputs higher than the output of a reference vector that harbors a reference pathway, for example, a vector that encodes a pathway that does not produce molecules with concentrations and/or potencies sufficient to modulate the activity of a protein of interest, in the cell or the subset of the population of host cells.

In some embodiments, the host cells comprise a genetically encoded system in which the activity of a protein of interest controls the assembly of a protein complex with an activity that is not possessed by either of two or more components of the complex and, thus, yields a detectable output in proportion to the amount of complex formed. In some embodiments, the protein of interest is an enzyme that adds a post-translational modification that causes two proteins, which are initially dissociated, to be covalently linked or to form a noncovalent complex. In some embodiments, the complex is formed by two proteins with a dissociation constant ($K_d$) less than or equal to the $K_d$ of the complexes formed between SH2 domains and their phosphorylated substrates.

In some embodiments, the metabolic pathways encoded by the expression vectors produce phenylpropanoids or nonribosomal peptides. In some embodiments, the expression vectors comprising different metabolic pathways comprise a library of pathways generated by mutating one or more genes within a starting metabolic pathway. In some embodiments, one or more of the metabolic pathways comprises a set of genes of unknown biosynthetic capability.

In some embodiments, one or more of the metabolic pathways that produces a detectable output higher than the output of the reference pathway produces a product that differs from the products of other metabolic pathways. In some embodiments, one or more of the metabolic pathways that produces a detectable output higher than the output of the reference pathway produces a larger quantity of a product than the quantity of product generated by other metabolic pathways. In some embodiments, one or more of the metabolic pathways that produces a detectable output higher than the output of the reference pathway exhibits a lower cellular toxicity than other metabolic pathways.

In some embodiments, the protein of interest is a ubiquitin ligase, a SUMO transferase, a methyltransferase, a demethylase, an acetyltransferase, a glycosyltransferase, a palmitoyltransferase, or a related hydrolase.

Also provided herein are kits that include a population of expression vectors as described herein. In some embodiments, the kits also include the population of host cells that comprise a protein of interest as described herein.

The summary above is meant to illustrate, in a non-limiting manner, some of the embodiments, advantages, features, and uses of the technology described herein. Other embodiments, advantages, features, and uses of the technology disclosed herein will be apparent from the Detailed Description, Drawings, Examples, and Claims.

Definitions

The term "metabolic pathway," as used herein, refers to a collection of genes that enable the synthesis of metabolite.

The term "metabolite," as used herein, refers to an organic molecule assembled within a living system.

The term "small molecule," as used herein, refers to a molecule with a molecular weight less than 900 daltons.

The term "phenylpropanoids," as used herein, refers to an organic compound synthesized from the amino acids phenylalanine and/or tyrosine.

The term "nonribosomal peptide," as used herein, refers to peptides synthesized without messenger RNA. For example, peptides synthesized from nonribosomal peptide synthases.

The term "modulator," as used herein, refers to a molecule, peptide, protein, polynucleotide, or entity that changes the activity of another molecule, peptide, protein, polynucleotide, or entity.

The term "inhibitor," as used herein, refers to a small molecule that reduces the activity of an enzyme.

The term "activator," as used herein, refers to a small molecule that increases the activity of an enzyme.

The term "natural product," as used herein, refers to a chemical compound or substance produced by a living organism.

The term "detection system," as used herein, refers to a system that links the activity of a target enzyme to a detectable output.

The term "bacterial two-hybrid (B2H) system," as used herein, refers to a genetically encoded system that links a protein-protein interaction to a detectable output.

The term "detectable output," as used herein, refers to an output that can be detected with standard analytical instrumentation. Examples include fluorescence, luminescence, antibiotic resistance, or microbial growth.

The term "split protein," as used herein, refers to a protein that exists as two separate halves, which, upon reassembly, restore the function of the protein.

The term "substrate domain," as used herein, refers to a protein that includes a peptide fragment or protein component acted upon by a protein of interest. For example, a substrate domain may include the peptide fragment of a receptor protein targeted by a kinase or phosphatase of interest.

The term "vector," as used herein, refers to a deoxyribonucleic acid (DNA) molecule used as a vehicle to artificially carry foreign genetic material into a cell.

The term "host cell," as used herein, refers to a cell that can host the genetically encoded systems, on vectors or genomes, necessary for MADE. For example, as host cell may contain plasmids that encode both (i) a genetically encoded detection system that links the activity of a target enzyme to a detectable output and (ii) a metabolic pathway capable of synthesizing molecules that might or might not inhibit said target enzyme.

EXAMPLES

Example 1

Figures 10A, 10B, 10C, 10D, 10E:
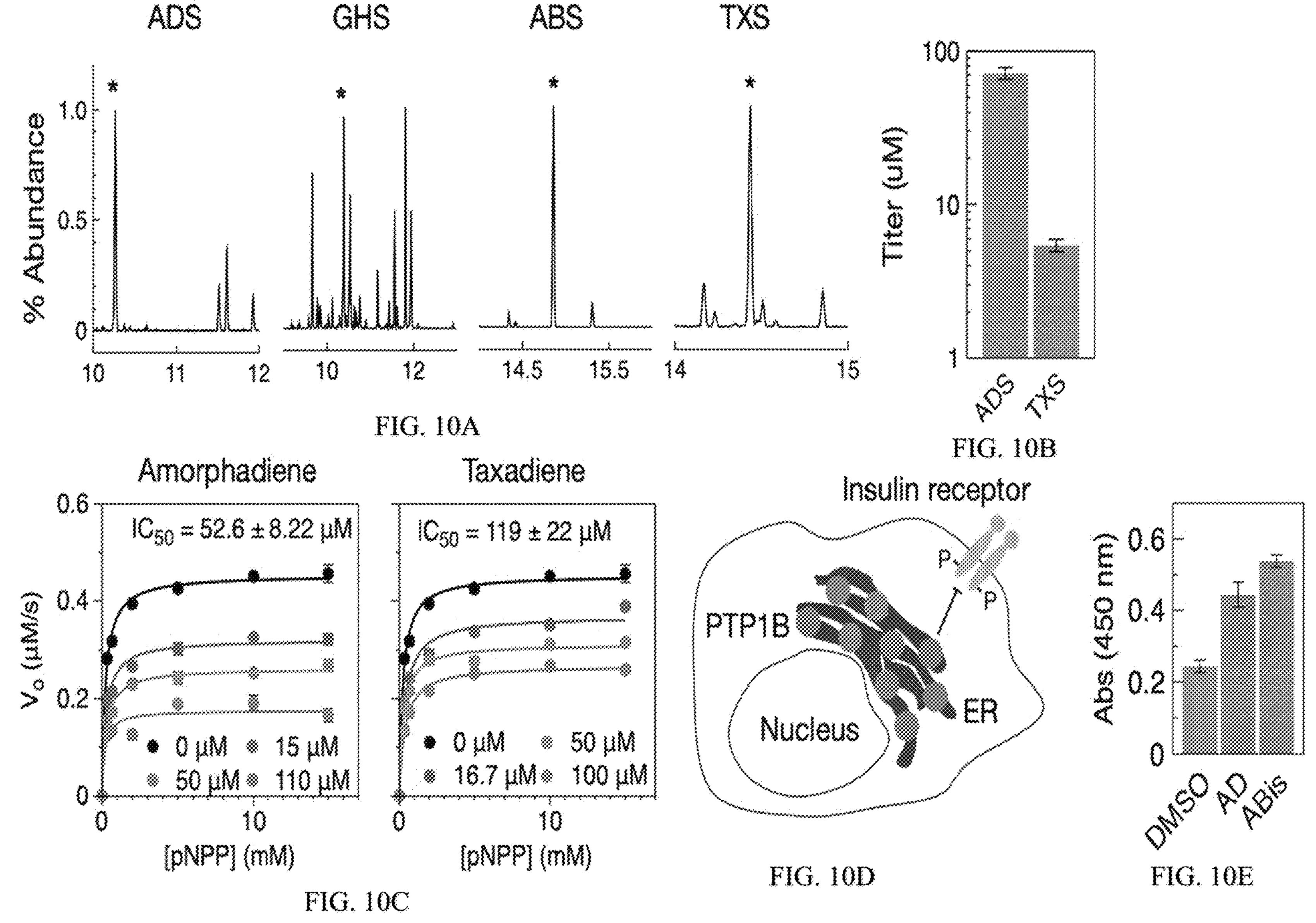
FIGS. 10A-10E. Analysis of the products of various terpenoids.

In previous work, a strain of *E. coli* was generated with two genetically encoded modules—a B2H system that links the inhibition of PTP1B to the expression of a gene for antibiotic resistance, and a metabolic pathway for the production of amorphadiene—exhibited greater antibiotic resistance that similar strains with different metabolic pathways (FIG. 2). In recent work, this result was explored further. First, it was shown that maximal resistance required both an active amorphadiene synthase (ADS) and a functional B2H system (FIG. 9). Second, the inhibitory effect of amorphadiene, the dominant product of ADS, was confirmed by measuring its influence on PTP1B-catalyzed hydrolysis of p-nitrophenyl phosphate (pNPP; FIG. 10C). Initial rates exhibited a saturation behavior characteristic of noncompetitive or uncompetitive inhibition; most importantly, the $IC_{50}$ for amorphadiene was ~53 μM, a concentration lower than the 72 μM generated in liquid culture. For comparison, the $IC_{50}$ for taxadiene was 119 μM, a concentration far lower than its titer in liquid culture. Results of the in vitro studies thus indicate that amorphadiene confers antibiotic resistance by inhibiting PTP1B. Finally, an enzyme-linked immunosorbent assay (ELISA) was used to demonstrate the ability of amorphadiene to inhibit PTP1B inside of a HEK293T/17 cell (FIG. 10D-10E).

Figure 7A:
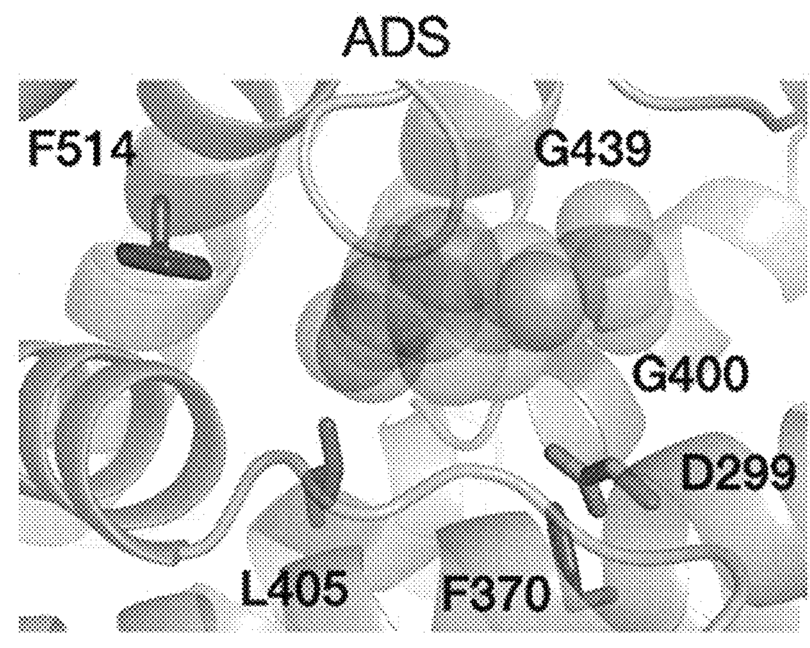
Figure 7B:
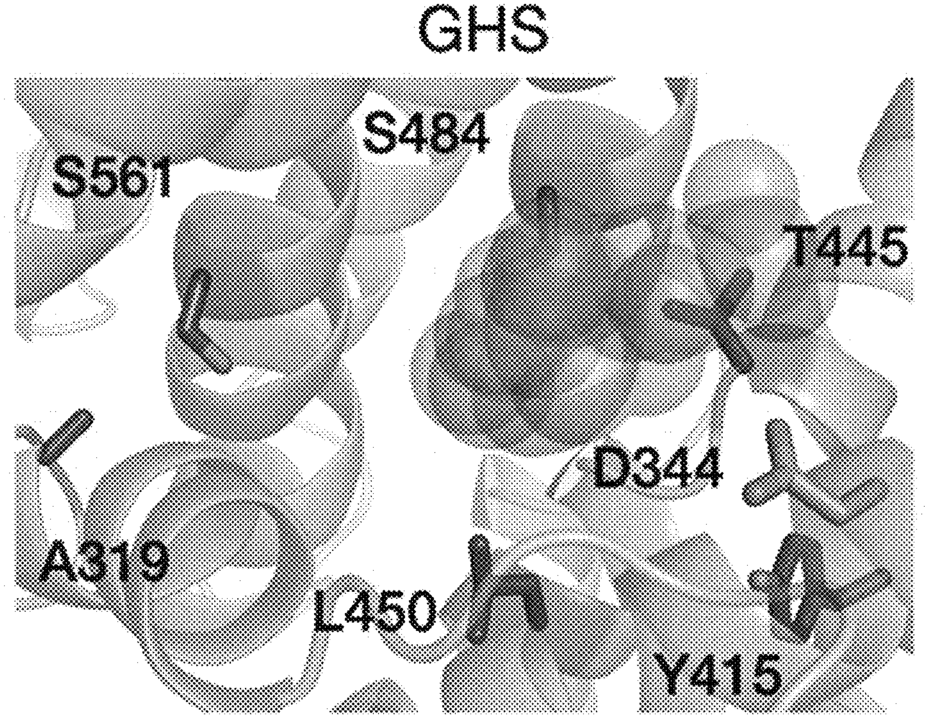
Figure 7C:
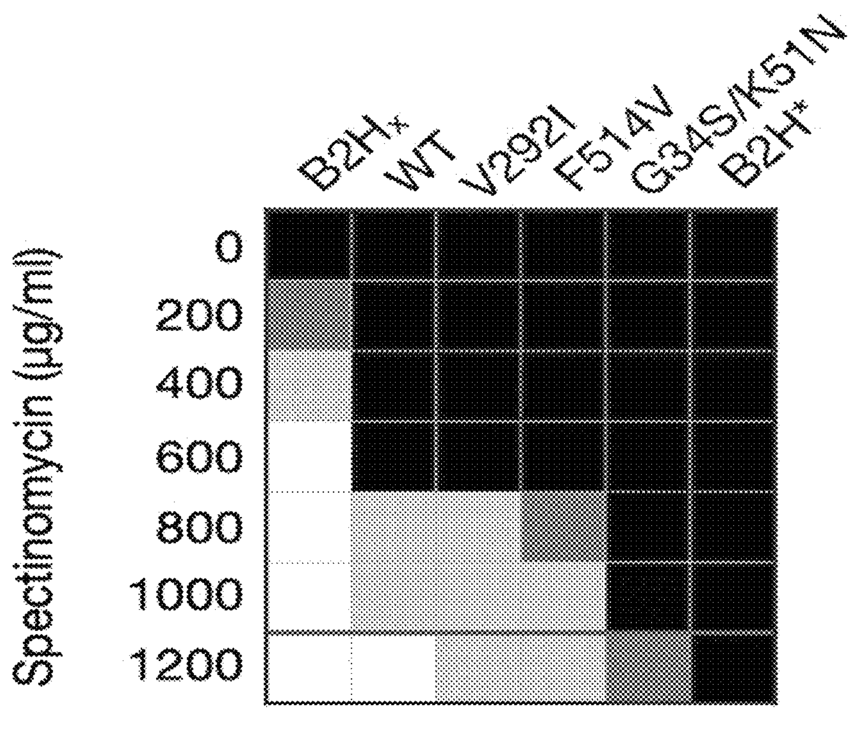
Figure 7D:
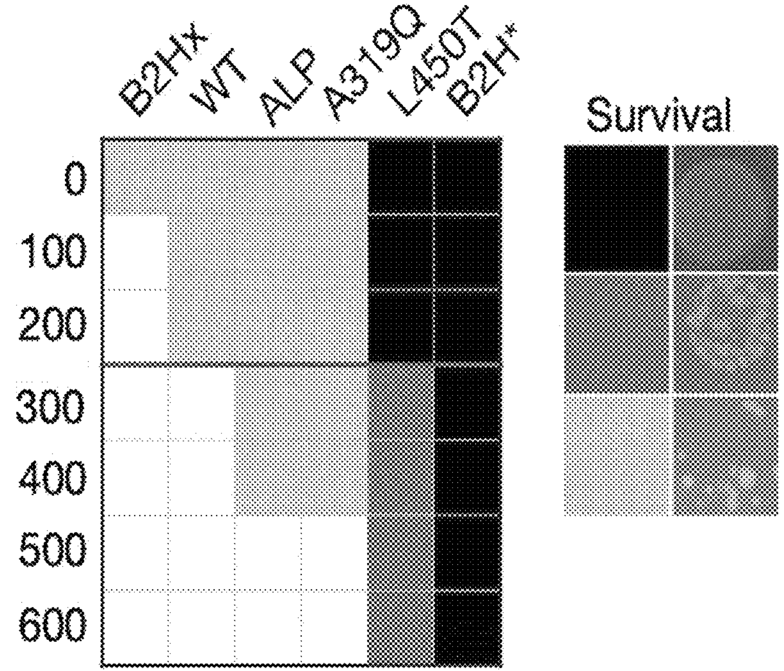

The microbial system provides an interesting opportunity to explore how metabolic pathways evolve to generate functional molecules. To look for evolutionarily accessible changes in the activities ADS and GHS that improve their ability to generate inhibitors of PTP1B, mutants of both enzymes were prepared. For ADS, error-prone PCR and site-saturation mutagenesis of poorly conserved residues was used; for GHS, site-saturation mutagenesis of the wild-type enzyme was paired with a screen of several previously developed mutants with distinct product profiles[47] (FIGS. 7A, 7B). At least one mutant from each library consistently conferred survival at higher antibiotic concentrations than the wild-type enzyme (FIG. 7C, 7D).

The G34S/K51N mutant of ADS, which improved antibiotic resistance more than other mutants, is particularly intriguing because its mutated residues are located outside of the active site and alter neither product profile nor titer (FIG. 7E, 7F). It was hypothesized that these mutations might reduce a minor growth deficiency caused by heterologous ADS expression (e.g., they might reduce the formation of inclusion bodies). To test this hypothesis, the survival conferred by wild-type and mutant strains in the presence of an inactive B2H system was compared; the mutant strain showed more robust growth at high concentrations of antibiotic (FIG. 7G). These results suggest that the engineered strain can select for less toxic enzyme mutants which, in the presence of other stresses, might improve production of inhibitory metabolites.

Figure 7H:
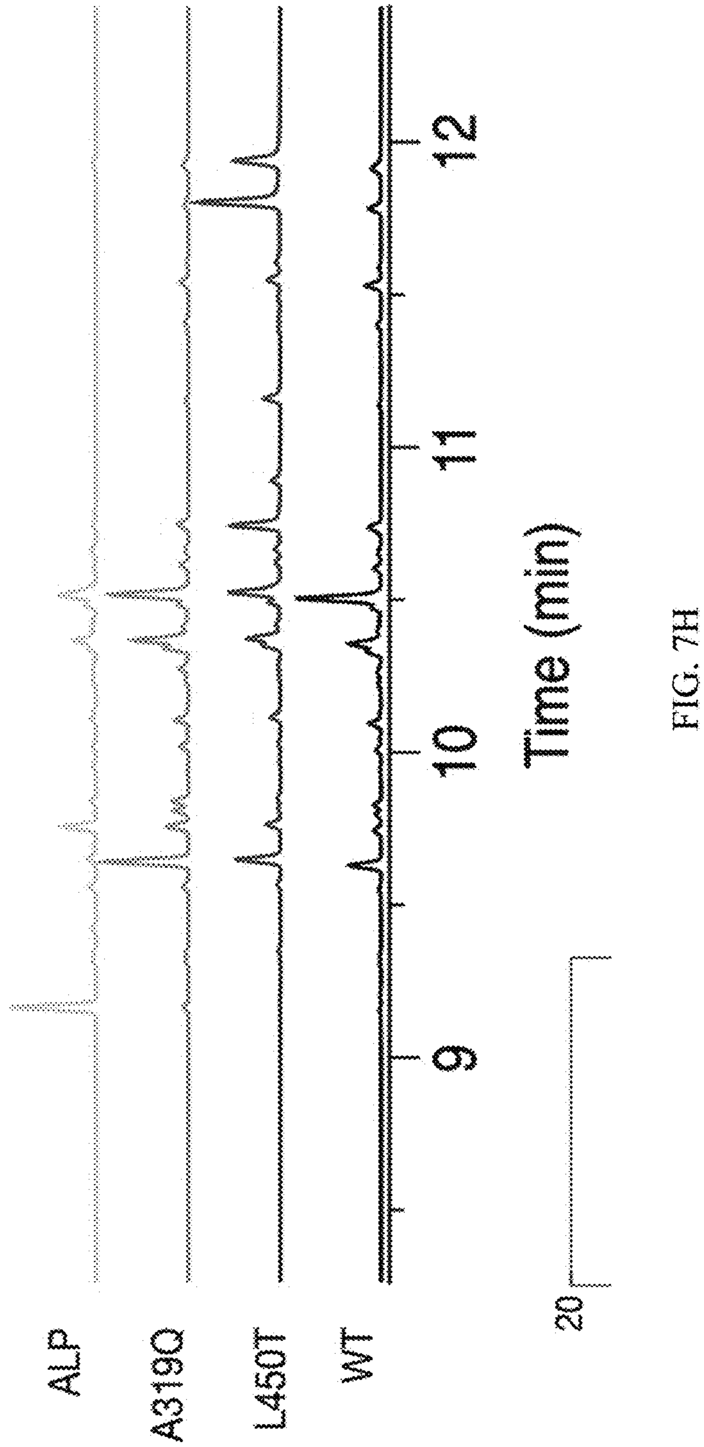
Figure 7I:
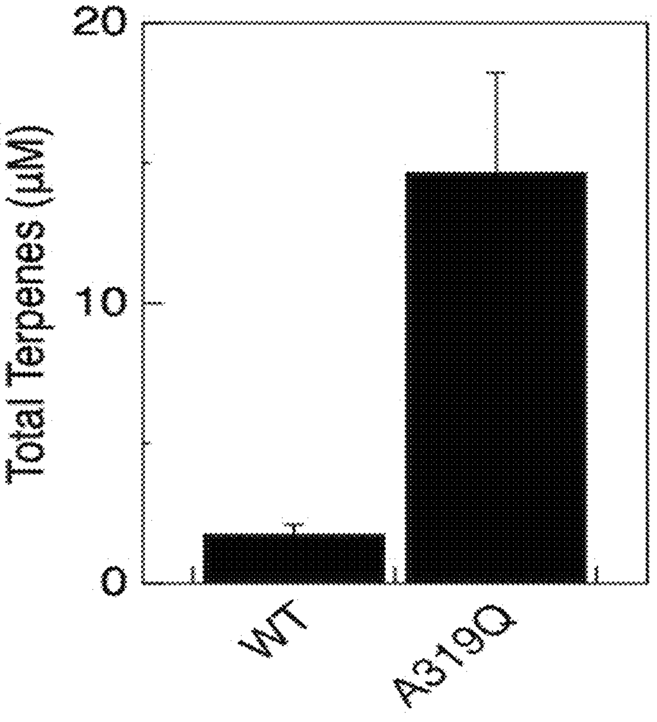
Figure 8A:
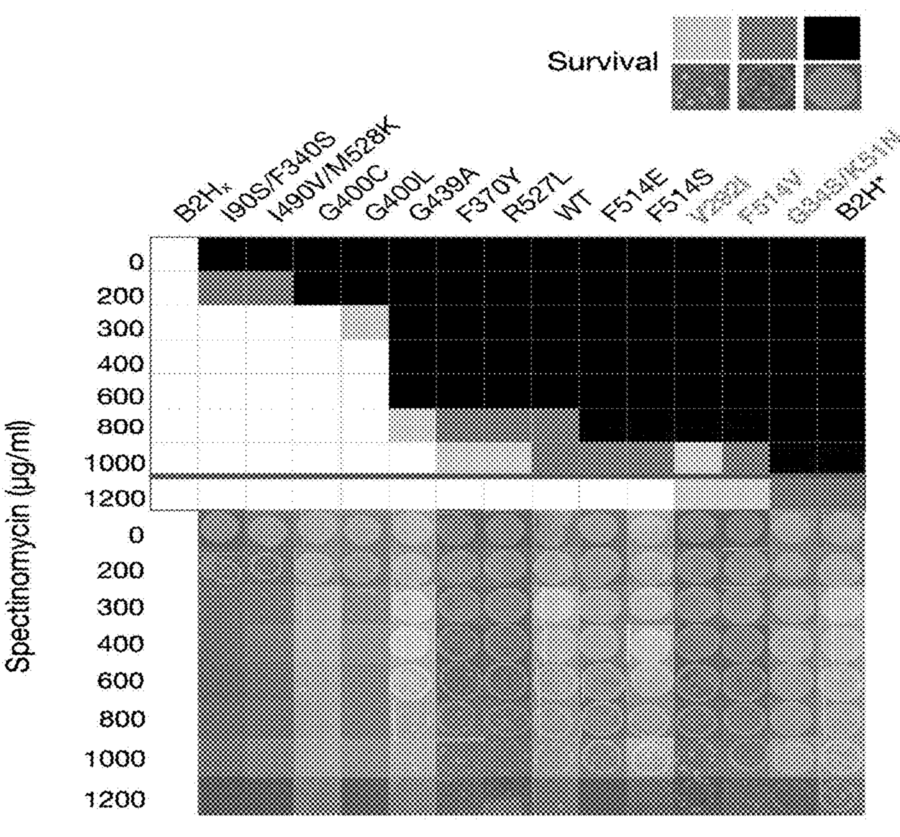
FIGS. 8A-8D. Analysis of evolved mutants.
Figure 8B:
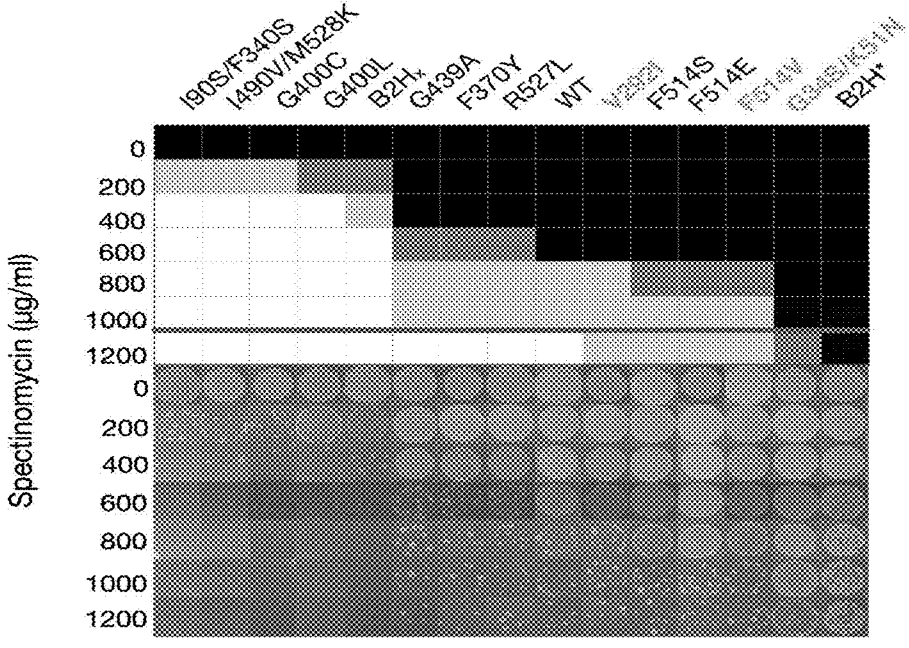
Figures 8C, 8D:
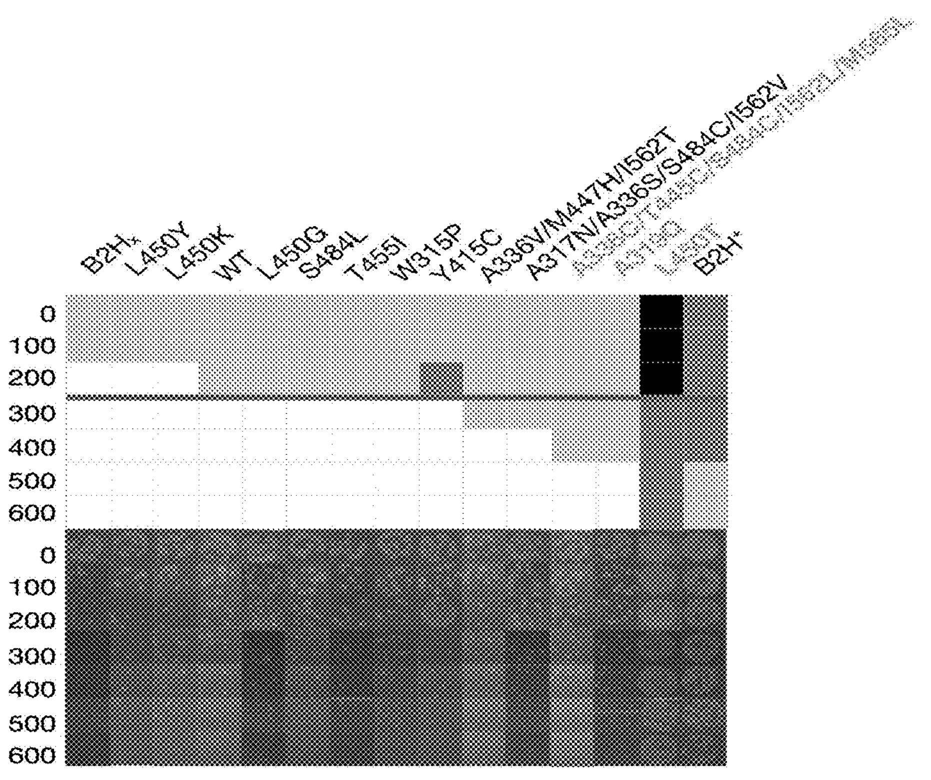

Intriguingly, the mutants of GHS that conferred enhanced antibiotic resistance (relative to the wild-type enzyme) altered product profile and/or titer (FIGS. 7H and 7I). Two examples include $GHS_{A336C/T445C/S484C/I562L/M565L}$ (or ALP), which primarily generates α-longipinene, and $GHS_{A319Q}$, which enhances terpenoid titer by ~tenfold. The GHS mutants thus indicate that the engineered strain can select for enzyme mutants that generate different products and/or higher titers than a starting wild-type enzyme.

Figures 11A, 11B:
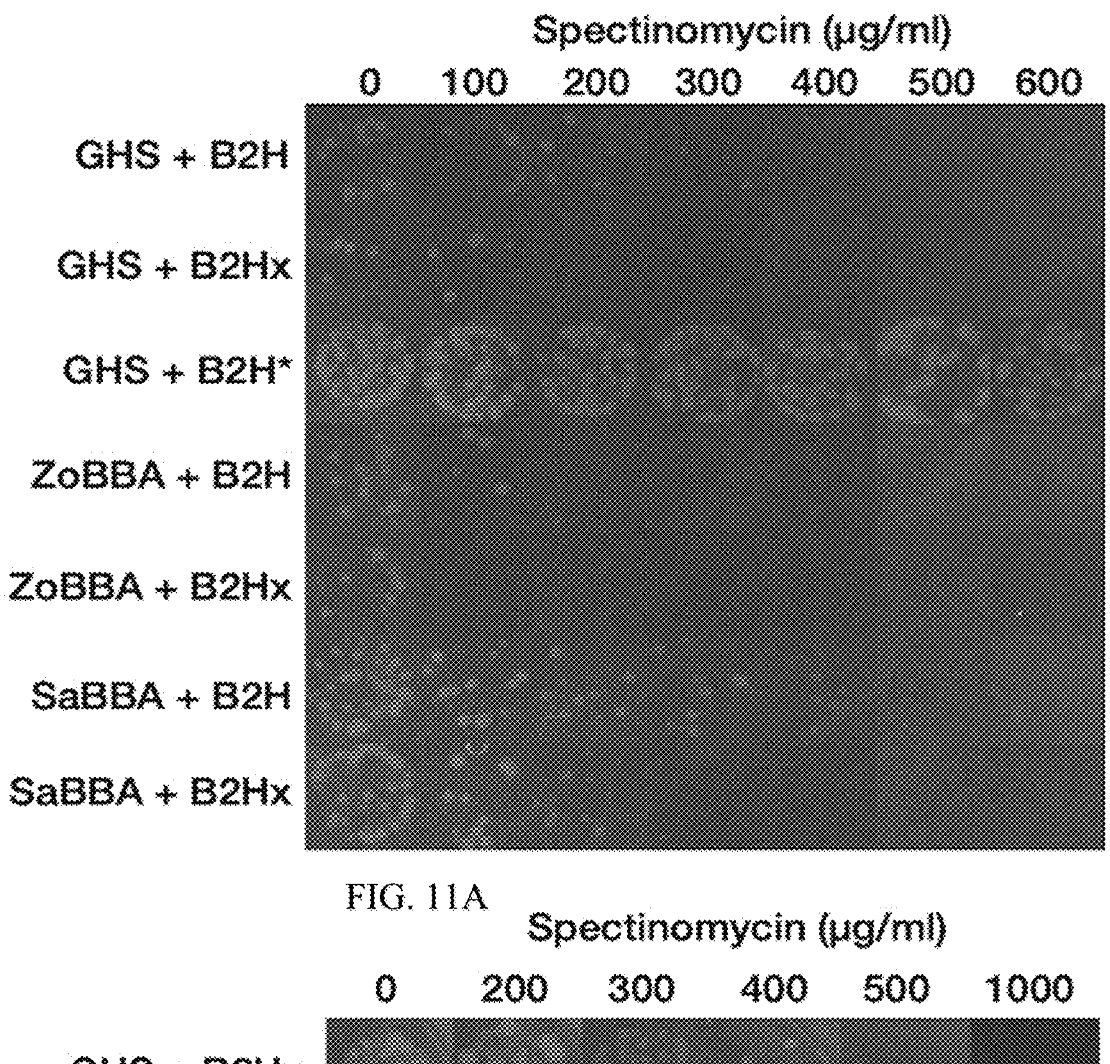
FIGS. 11A-11*d*. Analysis of alternative terpene synthases.
Figure 11C:
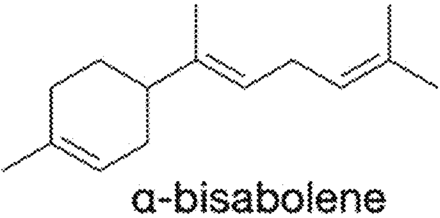
Figure 11D:
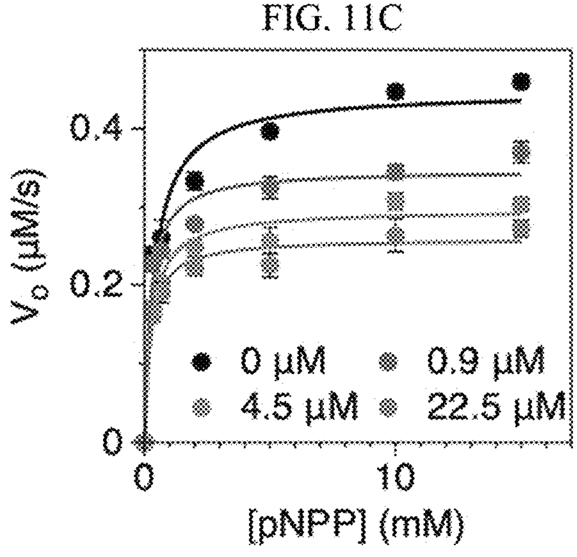
Figure 12A:
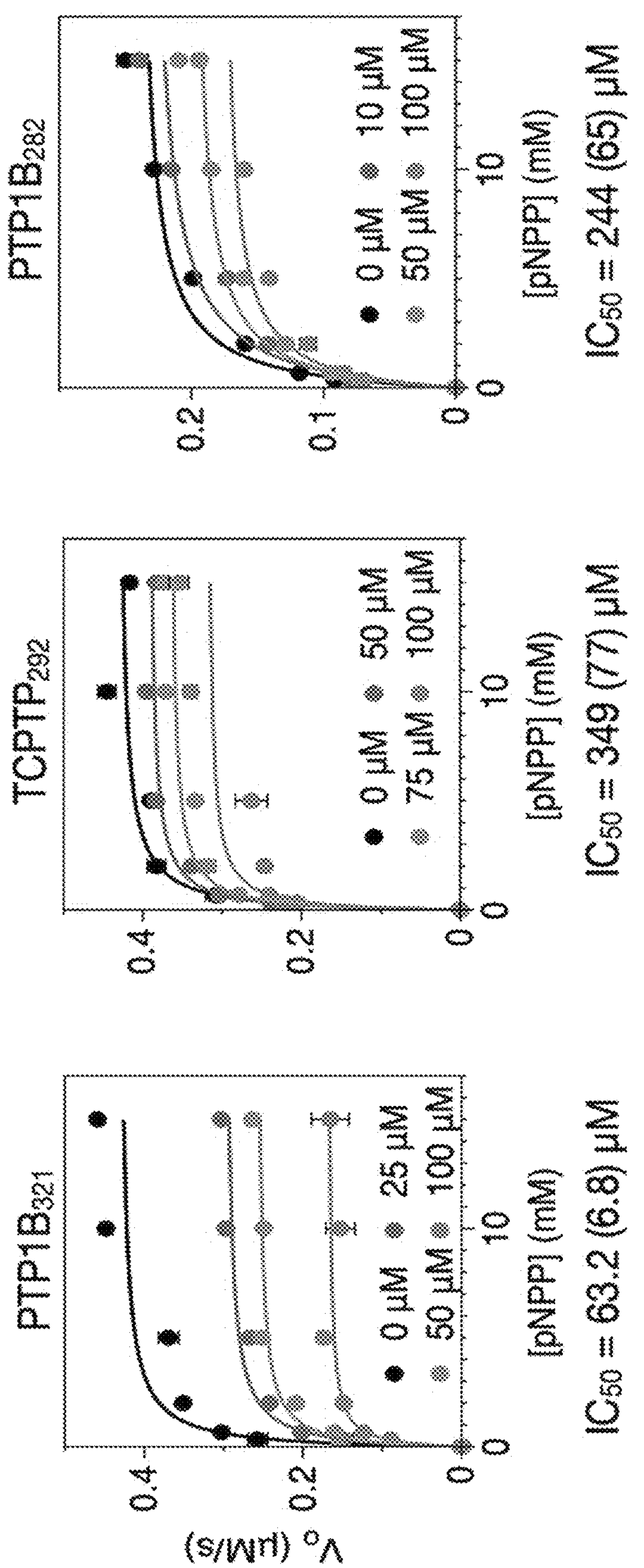
FIGS. 12A-12G. Analysis of selective inhibitors of PTP1B.
Figures 12B, 12C, 12D, 12E, 12F, 12G:
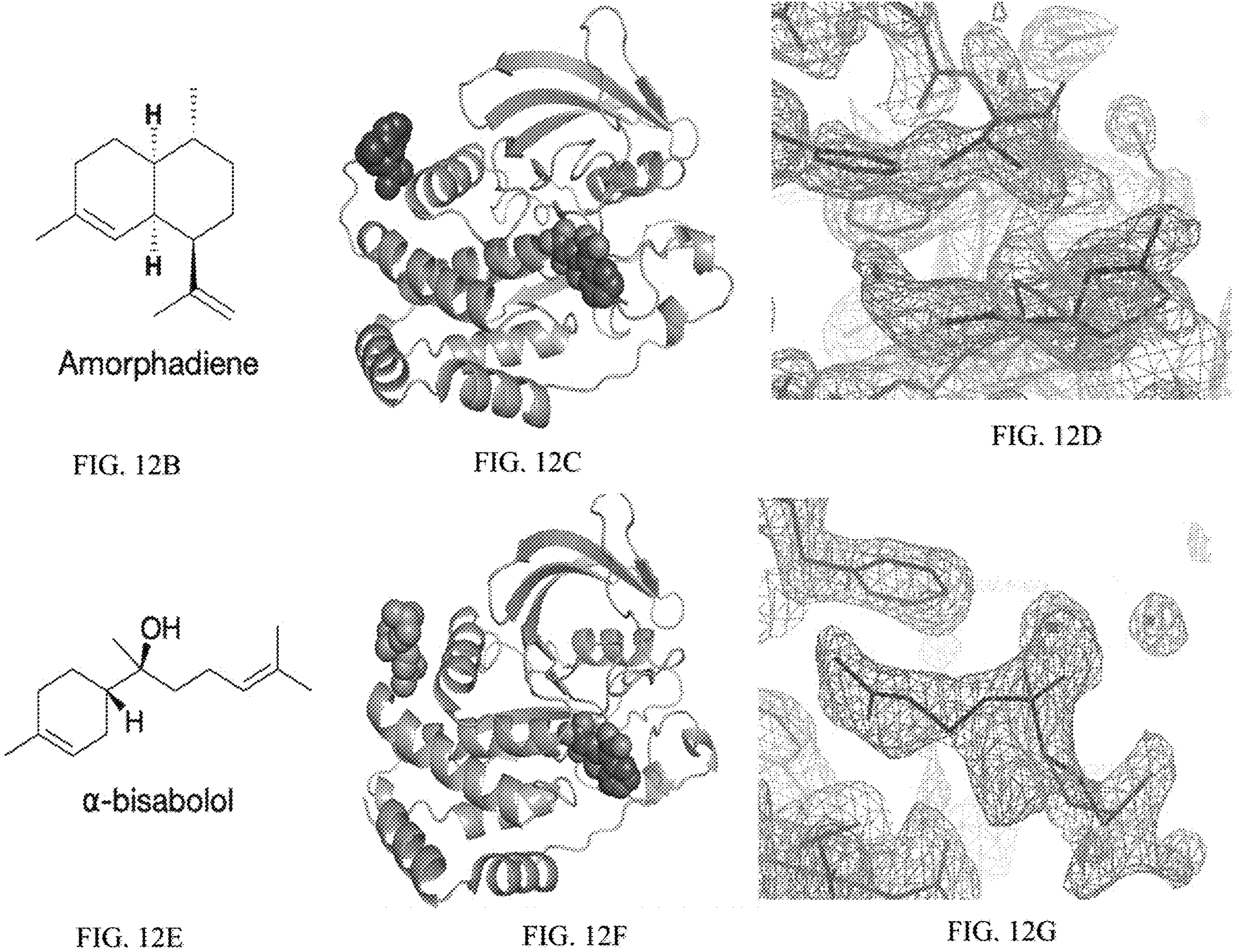

To expand the study, the survival conferred by terpene synthases that primarily generate β-bisabolene and α-bisabolene was also examined. Both of these enzymes enhanced antibiotic resistance; strikingly, kinetic studies of α-bisabolene purified from culture supernatant indicate that this molecule is particularly potent (i.e., $IC_{50}$~20 μM in 10% DMSO; FIG. 11).

The results of the analyses of terpene synthases suggest that amorphadiene and derivatives, taxadiene and derivatives, α-longipinene and derivatives, β-bisabolene and derivatives, and α-bisabolene and derivatives, and may provide an important source of pharmaceutically relevant PTP inhibitors.

Methods

Bacterial strains. *E. coli* DH10B, chemically competent NEB Turbo, or electrocompetent One Shot Top10 (Invitrogen) were used to carry out molecular cloning and to perform preliminary analyses of terpenoid production; *E. coli* BL2-DE31 were used to express proteins for in vitro studies; and *E. coli* s1030[48] were used for luminescence studies and for all experiments involving terpenoid-mediated growth (i.e., evolution studies).

For all strains, chemically competent cells were generated by carrying out the following steps: (i) each strain was plated on LB agar plates with the required antibiotics. (ii) One colony of each strain was used to inoculate 1 mL of LB media (25 g/L LB with appropriate antibiotics listed in TABLE 2) in a glass culture tube, and this culture was grew overnight (37° C., 225 RPM). (iii) The 1-mL culture was used to inoculate 100-300 mL of LB media (as above) in a glass shake flask, and this culture was grown for several hours (37° C., 225 RPM). (iv) When the culture reached an OD of 0.3-0.6, the cells were centrifuged (4,000×g for 10 minutes at 4° C.), the supernatant was removed, and the cells were resuspended in 30 mL of ice cold TFB1 buffer (30 mM potassium acetate, 10 mM $CaCl_2$), 50 mM $MnCl_2$, 100 mM RbCl, 15% v/v glycerol, water to 200 mL, pH=5.8, sterile filtered), and the suspension was incubated at 4° C. for 90 min. (v) Step iv was repeated, but resuspended in 4 mL of ice cold TFB2 buffer (10 mM MOPS, 75 mM $CaCl_2$), 10 mM $RbCl_2$, 15% glycerol, water to 50 mL, pH=6.5, sterile filtered). (iv) The final suspension as split into 100 μL aliquots and frozen at −80° C. until further use.

Electrocompetent cells were generated by following an approach similar to the one above. In step iv, however, the cells were resuspended in 50 mL of ice cold MilliQ water and repeated this step twice—first with 50 mL of 20% sterile glycerol (ice cold) and, then, with 1 mL of 20% sterile glycerol (ice cold). The pellets were frozen as before.

Materials. Methyl abietate was purchased from Santa Cruz Biotechnology; trans-caryophyllene, farnesol, tris(2-carboxyethyl)phosphine (TCEP), bovine serum albumin (BSA), M9 minimal salts, phenylmethylsulfonyl fluoride (PMSF), and DMSO (dimethyl sulfoxide) were purchased from Millipore Sigma; glycerol, bacterial protein extraction reagent II (B-PERII), and lysozyme from were purchased VWR; cloning reagents were purchased from New England Biolabs; amorphadiene was purchased from Ambeed, Inc.; and all other reagents (e.g., antibiotics and media components) were purchased from Thermo Fisher. Taxadiene was a kind gift from Phil Baran of the The Scripps Research Institute. Mevalonate was prepared by mixing 1 volume of 2 M DL-mevalanolactone with 1.05 volumes of 2 M KOH and incubating this mixture at 37° C. for 30 minutes.

Cloning and molecular biology. All plasmids were constructed by using standard methods (i.e., restriction digest and ligation, Golden Gate and Gibson assembly, Quikchange mutagenesis, and circular polymerase extension cloning). TABLE 1 describes the source of each gene; TABLES 2 and 3 describe the composition of all final plasmids.

Construction of the B2H system was begun by integrating the gene for HA4-rpoZ from pAB094a into pAB078d and by replacing the ampicillin resistance marker of pAB078d with a kanamycin resistance marker (Gibson Assembly). The resulting "combined" plasmid was modified, in turn, by replacing the HA4 and SH2 domains with kinase substrate and substrate recognition (i.e., SH2) domains, respectively (Gibson assembly), and by integrating genes for Src kinase, CDC37, and PTP1B in various combinations (Gibson assembly). The functional B2H system was finalized by modifying the SH2 domain with several mutations known to enhance its affinity for phosphopeptides (K15L, T8V, and C10A, numbered as in Kaneko et. al.[40]), by exchanging the GOI for luminescence (LuxAB) with one for spectinomycin resistance (SpecR), and by toggling promoters and ribosome binding sites to enhance the transcriptional response (Gibson assembly and Quickchange Mutagenesis, Agilent Inc.). Note: For the last step, Pro1 to ProD was also converted by using the Quikchange protocol. When necessary, plasmids with arabinose-inducible components were constructed by cloning a single component from the B2H system into pBAD (Golden Gate assembly). TABLES 4 and 5 list the primers and DNA fragments used to construct each plasmid.

Pathways for terpenoid biosynthesis were assembled by purchasing plasmids encoding the first module (pMBIS) and sesquiterpene synthases (ADS or GHS in pTRC99a) from Addgene, and by building the remaining plasmids. Genes for ABS, TXS, and GGPPS were integrated into pTRC99t (i.e., pTRC99a without BsaI sites), and a version of pADS was modified by adding a gene for $P450_{BM3}$ with three mutations that enable the epoxidation of amorphadiene (F87A, R47L, and Y51F; $P450_{G3}$; Gibson Assembly and Quickchange Mutagenesis) 49. TABLE 6 lists the primers and DNA fragments used to construct each plasmid.

Luminescence assays. Preliminary B2H systems (which contained LuxAB as the GOI) were characterized with luminescence assays. In brief, necessary plasmids were transformed into *E. coli* s1030 (TABLE 2), the transformed cells were plated onto LB agar plates (20 g/L agar, 10 g/L tryptone, 10 g/L sodium chloride, and 5 g/L yeast extract with antibiotics described in TABLE 2), and all plates were incubated overnight at 37° C. Individual colonies were used to inoculate 1 ml of terrific both (TB at 2%, or 12 g/L tryptone, 24 g/L yeast extract, 12 mL/L 100% glycerol, 2.28 g/L $KH_2PO_4$, 12.53 g/L $K_2HPO_4$, pH=7.0, and antibiotics described in TABLE 2), and we incubated these cultures overnight (37° C. and 225 RPM). The following morning, each culture was diluted by 100-fold into 1 ml of TB media (above), and these cultures were incubated in individual wells of a deep 96-well plate for 5.5 hours (37° C., 225 RPM). (Note: When pBAD was present, the TB media was supplemented with 0-0.02 w/v % arabinose). An amount of 100 μL of each culture was transferred into a single well of a standard 96-well plate and measured both $OD_{600}$ and luminescence (gain: 135, integration time: 1 second, read height: 1 mm) on a Biotek Synergy plate reader. Analogous measurements of cell-free media were performed to measure background signals, which were subtracted from each measurement prior to calculating OD-normalized luminescence (i.e., Lum/$OD_{600}$).

Analysis of antibiotic resistance. The spectinomycin resistance conferred by various B2H systems in the absence of terpenoid pathways was evaluated by carrying out the following steps: (i) *E. coli* were transformed with the necessary plasmids (TABLE 2) and the transformed cells were plated onto LB agar plates (20 g/L agar, 10 g/L tryptone, 10 g/L sodium chloride, 5 g/L yeast extract, 50 μg/ml kanamycin, 10 μg/ml tetracycline). (ii) Individual colonies were used to inoculate 1-2 ml of TB media (12 g/L tryptone, 24 g/L yeast extract, 12 mL/L 100% glycerol, 2.28 g/L $KH_2PO_4$, 12.53 g/L $K_2HPO_4$, 50 μg/ml kanamycin, 10 μg/ml tetracycline, pH=7.0), and these cultures were incubated overnight (37° C., 225 RPM). In the morning, each culture was diluted by 100-fold into 4 ml of TB media (as above) with 0-500 μg/ml spectinomycin (spectinomycin was used only for the results depicted in FIG. 14), and these cultures were incubated in deep 24-well plates until wells containing 0 μg/ml spectinomycin reached an $OD_{600}$ of 0.9-1.1. (iv) Each 4-ml culture was diluted by 10-fold into TB media with no antibiotics and plated 10-μL drops of the diluent onto agar plates with various concentrations of spectinomycin. (v) Plates were incubated overnight (37° C.) and photographed the following day.

To examine terpenoid-mediated resistance, steps i and ii were performed as described above with the addition of 34 μg/ml chloramphenicol and 50 μg/ml carbenicillin in all liquid/solid media. The experiment then proceeded with the following steps: (iii) Samples were diluted from 1-ml cultures to an $OD_{600}$ of 0.05 in 4.5 ml of TB media (supplemented with 12 g/L tryptone, 24 g/L yeast extract, 12 mL/L 100% glycerol, 2.28 g/L $KH_2PO_4$, 12.53 g/L $K_2HPO_4$, 50 g/ml kanamycin, 10 μg/ml tetracycline, 34 μg/ml chloramphenicol, and 50 μg/ml carbenicillin), which were incubated in deep 24-well plates (37° C., 225 RPM). (iv) At an $OD_{600}$ of 0.3-0.6, 4 ml of each culture was transferred to a new well of a deep 24-well plate, 500 μM isopropyl β-D-1-thiogalactopyranoside (IPTG) and 20 mM of mevalonate was added, and incubated for 20 hours (22° C., 225 RPM). (v) Each 4-ml culture was diluted to an $OD_{600}$ of 0.1 with TB media and plated 10 μL of the diluent onto either LB or TB plates supplemented with 500 μM IPTG, 20 mM mevalonate, 50 μg/ml kanamycin, 10 μg/ml tetracycline, 34 μg/ml chloramphenicol, 50 μg/ml carbenicillin, and 0-1200 μg/ml spectinomycin (for both plates, 20 g/L agar was used with media and buffer components described above). Note: to control the range of antibiotic resistance, LB plates were used for ADS and its mutants, and TB plates, which improve terpenoid titers, were used for GHS and its mutants. (iv) All plates were incubated at 30° C. and photographed after 2 days.

Terpenoid biosynthesis. *E. coli* were prepared for terpenoid production by transforming cells with plasmids harboring requisite pathway components (TABLE 2) and plating them onto LB agar plates (20 g/L agar, 10 g/L tryptone, 10 g/L sodium chloride, and 5 g/L yeast extract with antibiotics described in TABLE 2). One colony from each strain was used to inoculate 2 ml TB (12 g/L tryptone, 24 g/L yeast extract, 12 mL/L 100% glycerol, 2.28 g/L $KH_2PO_4$, 12.53 g/L $K_2HPO_4$, pH=7.0, and antibiotics described in TABLE 2) in a glass culture tube for ~16 hours (37° C. and 225 RPM). These cultures were diluted by 75-fold into ml of TB media and the new cultures were incubated in 125 mL glass shake flasks (37° C. and 225 RPM). At an $OD_{600}$ of 0.3-0.6, 500 μM IPTG and 20 mM mevalonate were added. After 72-88 hours of growth (22° C. and 225 RPM), terpenoids were extracted from each culture.

To measure terpenoid production over time, the approach described above was used with the following modifications: (i) Overnight cultures were diluted with 1:75 mL in 4.5 mL TB supplemented with antibiotics in a glass culture tube. (ii) When cultures reached an $OD_{600}$ of 0.3-0.6, 4 mL of each culture were moved to a new culture tube and 500 μM IPTG, 20 mM mevalonate, 0-800 μg/mL spectinomycin, and 1 mL dodecane were added (to extract terpenoids). Every 4 hours, 100 μL of the dodecane sample was removed for GC/MS analysis.

Protein expression and purification. PTPs were expressed and purified as described previously[42]. Briefly, *E. coli* BL21 (DE3) cells were transformed with pET21b vectors, and induced with 500 μM IPTG at 22° C. for 20 hours. PTPs were purified from cell lysate by using desalting, nickel affinity, and anion exchange chromatography (HiPrep 26/10, HisTrap HP, and HiPrep Q HP, respectively; GE Healthcare). The final protein (30-50 μM) was stored in HEPES buffer (50 mM, pH 7.5, 0.5 mM TCEP) in 20% glycerol at −80° C.

Extraction and purification of terpenoids. Hexane was used to extract terpenoids generated in liquid culture. For 10-mL cultures, 14 mL of hexane was added to 10 ml of culture broth in 125-mL glass shake flasks, the mixture (100 RPM) shaken for 30 minutes, centrifuged (4000×g), and 10 mL of the hexane layer was withdrawn for further analysis. For 4-mL cultures, 600 μL hexane were added to 1 mL of culture broth in a microcentrifuge tube, the tubes were vortexed for 3 minutes, the tubes were centrifuged for 1 minute (17000×g), and 300-400 μL of the hexane layer was saved for further analysis.

To purify amorphadiene, 500-1000 mL culture broth was supplemented with hexane (16.7% v/v), the mixture was shaken for 30 minutes (100 RPM), the hexane layer was isolated with a separatory funnel, the isolated organic phase was centrifuged (4000×g), and the hexane layer withdrawn. To concentrate the terpenoid products, excess hexane was evaporated in a rotary evaporator to bring the final volume to 500 μL, and the resulting mixture was passed over a silica gel one or two times (Sigma-Aldrich; high purity grade, 60 Å pore size, 230-400 mesh particle size)). Elution fractions (100% hexane) were analyzed on the GC/MS and pooled fractions with the compound of interest (amorphadiene). Once purified, pooled fractions were dried under a gentle stream of air, the terpenoid solids were resuspended in DMSO, and the final samples were quantified as outlined below.

GC-MS analysis of terpenoids. Terpenoids generated in liquid culture were measured with a gas chromatograph/mass spectrometer (GC-MS; a Trace 1310 GC fitted with a TG5-SilMS column and an ISQ 7000 MS; Thermo Fisher Scientific). All samples were prepared in hexane (directly or through a 1:100 dilution of DMSO) with 20 μg/ml of caryophyllene or methyl abietate as an internal standard. When the peak area of an internal standard exceeded ±30% of the average area in hexane samples containing only standard, the corresponding samples were re-analyzed. For all runs, the following GC method was used: hold at 80° C. (3 min), increase to 250° C. (15° C./min), hold at 250° ° C. (6 min), increase to 280° ° C. (30° C./min), and hold at 280° C. (3 min). To identify various analytes, m/z ratios were scanned from 50 to 550.

Sesquiterpenes generated by variants of ADS were examined by using select ion mode (SIM) to scan for the molecular ion (m/z=204). For quantification, we used Eq. 1:

$$C_i = C_{std} * \frac{A_i}{A_{std}} * R \quad \text{(Eq. 1)}$$

$$R = \frac{A_{std,o}/C_{std,o}}{A_{ref,o}/C_{ref,o}} \quad \text{(Eq. 2)}$$

where $A_i$ is the area of the peak produced by analyte i, $A_{std}$ is the area of the peak produced by $C_{std}$ of caryophyllene in the sample, and R is the ratio of response factors for caryophyllene and amorphadiene in a reference sample.

Sesquiterpenes generated by variants of GHS were quantified by using the aforementioned procedure with several modifications: Methyl abietate was used as an internal standard (several mutants of GHS generate caryophyllene as a product); both m/z=204 and m/z=121, a common ion between sesquiterpenes and methyl abietate were scanned for; a ratio of response factors for amorphadiene and methyl abietate at m/z=121 for R was used; and peak areas were calculated at m/z=121. For all analyses, the analysis was focused on peaks with areas that exceeded 1% of the total area of all peaks at m/z=204. Diterpenoids were quantified by, once again, accompanying the general procedure with several modifications: A different molecular ion (m/z=272) and an ion common to both diterpenoids and caryophyllene (m/z=93) was scanned for; a ratio of response factors for pure taxadiene (a kind gift from Phil Baran) and caryophyllene at m/z=93 was used; and peak areas m/z=93 were calculated. For all analyses, only peaks with areas that exceeded 1% of the total area of all peaks at m/z=272 were examined.

Molecules were identified by using the NIST MS library and, when necessary, this identification was confirmed with analytical standards or mass spectra reported in the literature. Note: The assumption of a constant response factor for different terpenoids (e.g., all sesquiterpenes and diterpenes ionize like amorphadiene and taxadiene, respectively) can certainly yield error in estimates of their concentrations; the analyses described herein, which are consistent with those of other studies of terpenoid production in microbial systems[50, 51] thus supply rough estimates of concentrations for all compounds except amorphadiene and taxadiene (which had analytical standards).

Homology modeling of ADS and GHS. Homology models of ADS and GHS were constructed by using SWISS-MODEL with structures for α-bisabolol synthase (pdb entry 4gax) and α-bisabolene synthase (pdb entry 3sae) as templates, respectively[52]. This software package uses ProMod3 to build models from a target-template alignment, which preserves the structures of conserved regions and remodels insertions and deletions with a fragment library[53,54].

Preparation of mutant libraries. Libraries of enzyme mutants were prepared by using site-saturation mutagenesis (SSM) and error-prone PCR (ePCR). For SSM, the following steps were performed: (i) Genes were amplified with NNK primers that targeted select sites. (ii) The amplified genes were digested with DpnI, purified with gel electrophoresis, and either Gibson Assembly or circular polymerase extension cloning (CPEC)[55] was used to integrate them into plasmids ($pTS_{xx}$). (iii) Heat shock was used to transform the fully assembled plasmids into chemically competent NEB Turbo cells. (iv) Library size was determined by plating dilutions of the transformation reactions on several LB agar plates (20 g/L agar, 10 g/L tryptone, 10 g/L sodium chloride, 5 g/L yeast extract, 50 μg/ml carbenicillin), and all remaining cells were plated over 9-10 plates for subsequent analysis. (v) Colonies were sequenced to verify that at least 5 of 6 transformants contained mutated genes. (vi) Plates were scraped into LB media (25 g/L LB broth mix, no antibiotics) and the final transformants were miniprepped to recover the DNA Library. (vii) All final libraries were frozen in MilliQ water at −20° C.

For ePCR, the Genemorph II kit (Agilent) was used with ~0.5-2.5 mutations/kb. The final plasmids were dialyzed and electroporated into One Shot electrocompetent Top 10 cells, and the final plasmids were sequenced, extracted, and stored as described above.

Analysis of mutant libraries. Each mutant library was screened by carrying out the following steps: (i) 100 ng of each site-specific SSM library for a given terpene synthase was pooled. (ii) Each complete library (i.e., ePCR or pooled SSM) was dialyzed for 2 hours. (iii) Up to 10 μL (<1 μg) of each library was electroporated into a strain of *E. coli* harboring both the pMBIS pathway and the B2H system. (iv) 1 mL of SOC was added to the transformed cells and incubated for 1 hour (37° C. and 225 RPM). (v) 100 μL of the SOC outgrowth was serial diluted and plated onto LB agar plates (20 g/L agar, 10 g/L tryptone, 10 g/L sodium chloride, 5 g/L yeast extract, 50 μg/ml carbenicillin, 10 μg/ml tetracycline, 50 μg/ml kanamycin, and 34 μg/ml chloramphenicol) and the plates were incubated overnight (37° C.). This step allowed for quantification of the number of transformants screened (i.e., a number determined by counting colonies). (vi) The remaining 900 μL of transformed cells was added to 100 mL of TB (12 g/L tryptone, 24 g/L yeast extract, 12 mL/L 100% glycerol, 2.28 g/L $KH_2PO_4$, 12.53 g/L $K_2HPO_4$, 50 g/ml carbenicillin, 10 μg/ml tetracycline, 34 μg/ml chloramphenicol, 50 μg/ml kanamycin, pH=7.0) in 500-mL Erlenmeyer flasks, and these flasks were incubated overnight (37° C. and 225 RPM). (vii) In the morning, an aliquot of each culture was diluted to an $OD_{600}$ of 0.05 in 4 mL of TB and incubated in glass culture tubes (37° C. and 225 RPM). (viii) At an $OD_{600}$ of 0.3-0.6, terpenoid production was induced by adding 5-20 mM mevalonate and 500 μM IPTG, and the resulting cultures were incubated for 20 hours (22° C. and 225 RPM). (ix) Each culture was diluted to an $OD_{600}$ of 0.001 and 100 μL of diluent was plated onto agar plates containing 500 μM IPTG, 5-20 mM mevalonate, 50 μg/ml kanamycin, 10 μg/ml tetracycline, 34 μg/ml chloramphenicol, 50 μg/ml carbenicillin, and 0-1000 μg/ml spectinomycin. (x) Colonies that survived high concentrations of spectinomycin were used to inoculate 4 mL of LB media (25 g/L LB broth mix, 50 μg/ml carbenicillin, 10 μg/ml tetracycline, 34 μg/ml chloramphenicol, 50 g/ml kanamycin, which was incubated overnight (37° C., 225 RPM). (xi) Plasmid DNA was extracted from the overnight culture for Sanger sequencing.

The influence of interesting mutations- and a check for false positive-were confirmed by rescreening them in freshly prepared mutants. Site directed mutagenesis was used to introduce mutations found in the hits and then their antibiotic resistance was analyzed using the drop-based plating method described above.

Enzyme kinetics. To examine terpenoid-mediated inhibition, PTP1B-catalyzed hydrolysis of p-nitrophenyl phosphate (pNPP) was measured in the presence of various concentrations of terpenoids. Each reaction included PTP1B (0.05 M), pNPP (0.33, 0.67, 2, 5, 10, and 15 mM), inhibitors (110 μM, 50 μM, and 15 μM for amorphadiene; 100 μM, 50 μM, and 16.7 μM for taxadiene), and buffer (50 mM HEPES pH=7.5, 0.5 mM TCEP, 50 μg/ml BSA, 10% DMSO). The formation of p-nitrophenol was monitored by measuring absorbance at 405 nm every 10 seconds for 5 minutes on a Spectramax M2 plate reader.

Kinetic models were evaluated in three steps: (i) Initial-rate measurements collected in the absence and presence of inhibitors were fitted to Michaelis-Menten and inhibition models, respectively (here, the nlinfit and fminsearch functions from MATLAB were used). (ii) An F-test was used to compare the mixed model to the single-parameter model with the least sum squared error (here, the fcdf function from MATLAB was used to assign p-values), and the mixed model was accepted when $p<0.05$. (iii) The Akaike's Information Criterion (AIC) was used to compare the best-fit single parameter model to each alternative single parameter model, and the "best-fit" model was accepted when the difference in AIC ($\Delta_i$) exceed 10 for all comparisons.[56] Note: For amorphadiene, this criterion was not met; both noncompetitive and uncompetitive models, however, yielded indistinguishable $IC_{50}$'s.

The half maximal inhibitory concentration ($IC_{50}$) of inhibitors were estimated by using the best-fit kinetic models to determine the concentration of inhibitor required to reduce initial rates of PTP-catalyzed hydrolysis of 15 mM of pNPP by 50%. The MATLAB function "nlparci" was used to determine the confidence intervals of kinetic parameters, and those intervals were propagated to estimate corresponding confidence on $IC_{50}$'s.

REFERENCES FOR EXAMPLE 1

1. Newman, D. J. & Cragg, G. M. Natural Products as Sources of New Drugs from 1981 to 2014. *Journal of Natural Products* 79, 629-661 (2016).
2. Koehn, F. E. & Carter, G. T. The evolving role of natural products in drug discovery. *Nature Reviews Drug Discovery* 4, 206-220 (2005).
3. Harvey, A. L., Edrada-Ebel, R. & Quinn, R. J. The re-emergence of natural products for drug discovery in the genomics era. *Nat. Rev. Drug Discov.* 14, 111-129 (2015).
4. Rodrigues, T., Reker, D., Schneider, P. & Schneider, G. Counting on natural products for drug design. *Nature Chemistry* 8, 531-541 (2016).
5. Pathan, H. & Williams, J. Basic opioid pharmacology: an update. *Br. J. Pain* 6, 11-16 (2012).
6. Vidal, V. et al. Library-Based Discovery and Characterization of Daphnane Diterpenes as Potent and Selective HIV Inhibitors in Daphne gnidium. (2011). doi: 10.1021/np200855d
7. Weaver, B. A. How Taxol/paclitaxel kills cancer cells. 25, (2014).
8. Camuesco, D. et al. The intestinal anti-inflammatory effect of quercitrin is associated with an inhibition in iNOS expression. *Br. J. Pharmacol.* 143, 908-918 (2004).
9. Ling, T., Lang, W. H., Maier, J., Quintana Centurion, M. & Rivas, F. Cytostatic and Cytotoxic Natural Products against Cancer Cell Models. *Molecules* 24, 2012 (2019).
10. Jantan, I., Ahmad, W. & Bukhari, S. N. A. Plant-derived immunomodulators: An insight on their preclinical evaluation and clinical trials. *Frontiers in Plant Science* 6, (2015).
11. Galanie, S., Thodey, K., Trenchard, I. J., Filsinger Interrante, M. & Smolke, C. D. Complete biosynthesis of opioids in yeast. *Science.* 349, 1095-1100 (2015).
12. Luo, X. et al. Complete biosynthesis of cannabinoids and their unnatural analogues in yeast. *Nature* (2019). doi: 10.1038/s41586-019-0978-9
13. Zhang, R. K. et al. Enzymatic assembly of carbon-carbon bonds via iron-catalysed sp 3 C—H functionalization. *Nature* (2019). doi: 10.1038/s41586-018-0808-5
14. Davis, A. M., Plowright, A. T. & Valeur, E. Directing evolution: The next revolution in drug discovery? *Nature Reviews Drug Discovery* 16, 681-698 (2017).
15. Maier, M. E. Design and synthesis of analogues of natural products. *Organic and Biomolecular Chemistry* 13, 5302-5343 (2015).
16. Chen, M. S. & White, M. C. A predictably selective aliphatic C—H oxidation reaction for complex molecule synthesis. *Science.* 318, 783-787 (2007).
17. Cho, I., Jia, Z. J. & Arnold, F. H. Site-selective enzymatic C—H amidation for synthesis of diverse lactams. *Science.* 364, 575-578 (2019).
18. Harvey, A. L. Natural products in drug discovery. *Drug Discovery Today* 13, 894-901 (2008).
19. Henrich, C. J. & Beutler, J. A. Matching the power of high throughput screening to the chemical diversity of natural products. *Nat. Prod. Rep.* 30, 1284-1298 (2013).
20. Medema, M. H. et al. AntiSMASH: Rapid identification, annotation and analysis of secondary metabolite biosynthesis gene clusters in bacterial and fungal genome sequences. *Nucleic Acids Res.* 39, (2011).
21. Jensen, P. R. Natural Products and the Gene Cluster Revolution. *Trends Microbiol.* 24, 968-977 (2016).
22. Yan, Y. et al. Resistance-gene-directed discovery of a natural-product herbicide with a new mode of action. (2018). doi: 10.1038/s41586-018-0319-4
23. Zhabinskii, V. N., Khripach, N. B. & Khripach, V. A. Steroid plant hormones: Effects outside plant kingdom. *Steroids* 97, 87-97 (2015).
24. Li, Y. et al. Complete biosynthesis of noscapine and halogenated alkaloids in yeast. *Proc. Natl. Acad. Sci. U.S.A* 115, E3922-E3931 (2018).
25. Zhang, H., Wang, Y., Wu, J., Skalina, K. & Pfeifer, B. A. Complete biosynthesis of erythromycin A and designed analogs using *E. coli* as a heterologous host. *Chem. Biol.* 17, 1232-1240 (2010).
26. Antosch, J., Schaefers, F. & Gulder, T. A. M. Heterologous Reconstitution of Ikarugamycin Biosynthesis in *E. coli. Angew. Chemie Int. Ed.* 53, 3011-3014 (2014).
27. Choi, O. et al. Biosynthesis of plant-specific phenylpropanoids by construction of an artiWcial biosynthetic pathway in *Escherichia coli. J. Ind. Microbiol. Biotechnol.* (2011). doi: 10.1007/s10295-011-0954-3
28. Pfeifer, B. A., Wang, C. C. C., Walsh, C. T. & Khosla, C. Biosynthesis of Yersiniabactin, a Complex Polyketide-Nonribosomal Peptide, Using *Escherichia coli* as a Heterologous Host. *Appl. Environ. Microbiol.* (2003). doi: 10.1128/AEM.69.11.6698-6702.2003
29. Ajikumar, P. K. et al. Isoprenoid pathway optimization for Taxol precursor overproduction in *Escherichia coli. Science* 330, 70-74 (2010).

30. Chang, M. C. Y., Eachus, R. A., Trieu, W., Ro, D.-K. & Keasling, J. D. Engineering *Escherichia coli* for production of functionalized terpenoids using plant P450s. *Nat. Chem. Biol.* 3, 274-277 (2007).

31. Morrone, D. et al. Increasing diterpene yield with a modular metabolic engineering system in *E. coli*: Comparison of MEV and MEP isoprenoid precursor pathway engineering. *Appl. Microbiol. Biotechnol.* 85, 1893-1906 (2010).

32. Ferguson, F. M. & Gray, N. S. Kinase inhibitors: The road ahead. *Nature Reviews Drug Discovery* 17, 353-376 (2018).

33. Stanford, S. M. & Bottini, N. Targeting Tyrosine Phosphatases: Time to End the Stigma. *Trends in Pharmacological Sciences* (2017). doi: 10.1016/j.tips.2017.03.004

34. Tonks, N. K. Protein tyrosine phosphatases: from genes, to function, to disease. *Nat. Rev. Mol. Cell Biol.* 7, 833-846 (2006).

35. Tautz, L., Pellecchia, M. & Mustelin, T. Targeting the PTPome in human disease. *Expert Opin. Ther. Targets* 10, 157-77 (2006).

36. Tonks, N. K. Protein tyrosine phosphatases—From housekeeping enzymes to master regulators of signal transduction. *FEBS Journal* 280, 346-378 (2013).

37. Scott, L. M., Lawrence, H. R., Sebti, S. M., Lawrence, N. J. & Wu, J. Targeting protein tyrosine phosphatases for anticancer drug discovery. *Curr. Pharm. Des.* 16, 1843-62 (2010).

38. Montalibet, J. & Kennedy, B. P. Using yeast to screen for inhibitors of protein tyrosine phosphatase 1B. *Biochem. Pharmacol.* 68, 1807-1814 (2004).

39. Badran, A. H. et al. Continuous evolution of *Bacillus thuringiensis* toxins overcomes insect resistance. *Nature* 533, 58-63 (2016).

40. Kaneko, T. et al. Superbinder SH2 domains act as antagonists of cell signaling. *Sci. Signal.* 5, (2012).

41. Jiang, C.-S., Liang, L.-F. & Guo, Y.-W. Natural products possessing protein tyrosine phosphatase 1B (PTP1B) inhibitory activity found in the last decades. *Acta Pharmacol. Sin.* 33, 1217-1245 (2012).

42. Hjortness, M. K. et al. Abietane-Type Diterpenoids Inhibit Protein Tyrosine Phosphatases by Stabilizing an Inactive Enzyme Conformation. *Biochemistry* 57, 5886-5896 (2018).

43. Martin, V. J. J., Pitera, D. J., Withers, S. T., Newman, J. D. & Keasling, J. D. Engineering a mevalonate pathway in *Escherichia coli* for production of terpenoids. *Nat. Biotechnol.* 21, 796-802 (2003).

44. He, R., Yu, Z., Zhang, R. & Zhang, Z. Protein tyrosine phosphatases as potential therapeutic targets. *Acta Pharmacol. Sin.* 35, 1227-1246 (2014).

45. Bentires-Alj, M. & Neel, B. G. Protein-tyrosine phosphatase 1B is required for HER2/Neu-induced breast cancer. *Cancer Res.* (2007). doi: 10.1158/0008-5472.CAN-06-4610

46. Krishnan, N. et al. PTP1B inhibition suggests a therapeutic strategy for Rett syndrome. *J. Clin. Invest.* (2015). doi: 10.1172/JCI80323

47. Yoshikuni, Y., Ferrin, T. E. & Keasling, J. D. Designed divergent evolution of enzyme function. *Nature* 440, 1078-1082 (2006).

48. Carlson, J. C., Badran, A. H., Guggiana-Nilo, D. A. & Liu, D. R. Negative selection and stringency modulation in phage-assisted continuous evolution. *Nat. Chem. Biol.* 10, 216-222 (2014).

49. Dietrich, J. A. et al. A novel semi-biosynthetic route for artemisinin production using engineered substrate-promiscuous P450BM3. *ACS Chem. Biol.* 4, 261-267 (2009).

50. Edgar, S. et al. Mechanistic Insights into Taxadiene Epoxidation by Taxadiene-5α-Hydroxylase. *ACS Chem. Biol.* 11, 460-469 (2016).

51. Chen, X. et al. Statistical experimental design guided optimization of a one-pot biphasic multienzyme total synthesis of amorpha-4,11-diene. *PLoS One* 8, e79650 (2013).

52. Waterhouse, A. et al. SWISS-MODEL: Homology modelling of protein structures and complexes. *Nucleic Acids Res.* (2018). doi: 10.1093/nar/gky427

53. Guex, N., Peitsch, M. C. & Schwede, T. Automated comparative protein structure modeling with SWISS-MODEL and Swiss-PdbViewer: A historical perspective. *Electrophoresis* (2009). doi: 10.1002/elps.200900140

54. Benkert, P., Biasini, M. & Schwede, T. Toward the estimation of the absolute quality of individual protein structure models. *Bioinformatics* (2011). doi: 10.1093/bioinformatics/btq662

55. Tian, J. Q. and J. & Quan, J. Circular Polymerase Extension Cloning of Complex Gene Libraries and Pathways. *PLoS One* 4, e6441 (2009).

56. Burnham, K. P. & Anderson, D. R. *Model Selection and Multimodel Inference: a Practical Information-theoretic Approach, 2nd edn. Springer-Verlag, New York. New York Springer* 60, (2002).

57. Davis, J. H., Rubin, A. J. & Sauer, R. T. Design, construction and characterization of a set of insulated bacterial promoters. *Nucleic Acids Res.* 39, 1131-1141 (2011).

58. Salis, H. M. The ribosome binding site calculator. *Methods Enzymol.* 498, 19-42 (2011).

59. Sato, M., Ozawa, T., Inukai, K., Asano, T. & Umezawa, Y. Fluorescent indicators for imaging protein phosphorylation in single living cells. *Nat Biotechnol* 20, 287-294 (2002).

Example 2

The design of small molecules that inhibit disease-relevant proteins represents a longstanding challenge of medicinal chemistry. Here, we describe an approach for encoding this challenge—the inhibition of a human drug target—into a microbial host and using it to guide the discovery and biosynthesis of targeted, biologically active natural products. This approach identified two previously unknown terpenoid inhibitors of protein tyrosine phosphatase 1B (PTP1B), an elusive therapeutic target for the treatment of diabetes and cancer. At least one inhibitor targets an allosteric site, which confers unusual selectivity; both can inhibit PTP1B in living cells. A screen of 24 uncharacterized terpene synthases from a pool of 4,464 genes uncovered additional hits, demonstrating a scalable discovery approach, and the incorporation of different PTPs into the microbial host yielded PTP-specific detection systems. Findings illustrate the potential for using microbes to discover and build natural products that exhibit precisely defined biochemical activities yet possess unanticipated structures and/or binding sites.

Despite advances in structural biology and computational chemistry, the design of small molecules that bind tightly and selectively to disease-relevant proteins remains exceptionally difficult[1]. The free energetic contributions of rearrangements in the molecules of water that solvate binding partners and structural changes in the binding partners themselves are particularly challenging to predict and, thus, to incorporate into molecular design[2,3]. Drug development, as a result, often begins with screens of large compound libraries[4].

Nature has endowed living systems with the catalytic machinery to build an enormous variety of biologically active molecules—a diverse natural library[5]. These molecules evolved to carry out important metabolic and ecological functions (e.g., the phytochemical recruitment of predators of herbivorous insects[6]) but often also exhibit useful medicinal properties. Over the years, screens of environmental extracts and natural product libraries—augmented, on occasion, with combinatorial (bio) chemistry[7-9]—have uncovered a diverse set of therapeutics, from aspirin to paclitaxel[10]. Unfortunately, these screens tend to be resource intensive[11], limited by low natural titers[12], and largely subject to serendipityl[3]. Bioinformatic tools, in turn, have permitted the identification of biosynthetic gene clusters[14,15], where co-localized resistance genes can reveal the biochemical function of their products[16,17]. The therapeutic applications of many natural products, however, differ from their native functions[18], and many biosynthetic pathways can, when appropriately reconfigured, produce entirely new and, perhaps, more effective therapeutic molecules[19,20]. Methods for efficiently identifying and building natural products that inhibit specific disease-relevant proteins remain largely undeveloped.

Protein tyrosine phosphatases (PTPs) are an important class of drug targets that could benefit from new approaches to inhibitor discovery. These enzymes catalyze the hydrolytic dephosphorylation of tyrosine residues and, together with protein tyrosine kinases (PTKs), contribute to an enormous number of diseases (e.g., cancer, autoimmune disorders, and heart disease, to name a few)[21,22]. The last several decades have witnessed the construction of many potent inhibitors of PTKs, which are targets for over 30 approved drugs[23]. Therapeutic inhibitors of PTPs, by contrast, have proven difficult to develop. These enzymes possess well conserved, positively charged active sites that make them difficult to inhibit with selective, membrane-permeable molecules[24]; they lack targeted therapeutics of any kind.

In this study, we describe an approach for using microbial systems to find natural products that inhibit difficult-to-drug proteins. We focused on protein tyrosine phosphatase 1B (PTP1B), a therapeutic target for the treatment of type 2 diabetes, obesity, and HER2-positive breast cancer[25]. PTP1B possesses structural characteristics that are generally representative of the PTP family[26] and regulates a diverse set of physiological processes (e.g., energy expenditure[27], inflammation[28], and neural specification in embryonic stem cells[29]). In brief, we assembled a strain of *Escherichia coli* with two genetic modules—(i) one that links cell survival to the inhibition of PTP1B and (ii) one that enables the biosynthesis of structurally varied terpenoids. In a study of five well-characterized terpene synthases, this strain identified two previously unknown terpenoid inhibitors of PTP1B. Both inhibitors were selective for PTP1B, exhibited distinct binding mechanisms, and increased insulin receptor phosphorylation in mammalian cells. A screen of 24 uncharacterized terpene synthases from eight phylogenetically diverse clades uncovered additional hits, demonstrating a scalable approach for finding inhibitor-synthesizing genes. A simple exchange of PTP genes, in turn, permitted the facile extension of our genetically encoded detection system to new targets. Our findings illustrate a versatile approach for using microbial systems to find targeted, readily synthesizable inhibitors of disease-relevant enzymes.

Development of a Genetically Encoded Objective

Figures 21A, 21B, 21C:
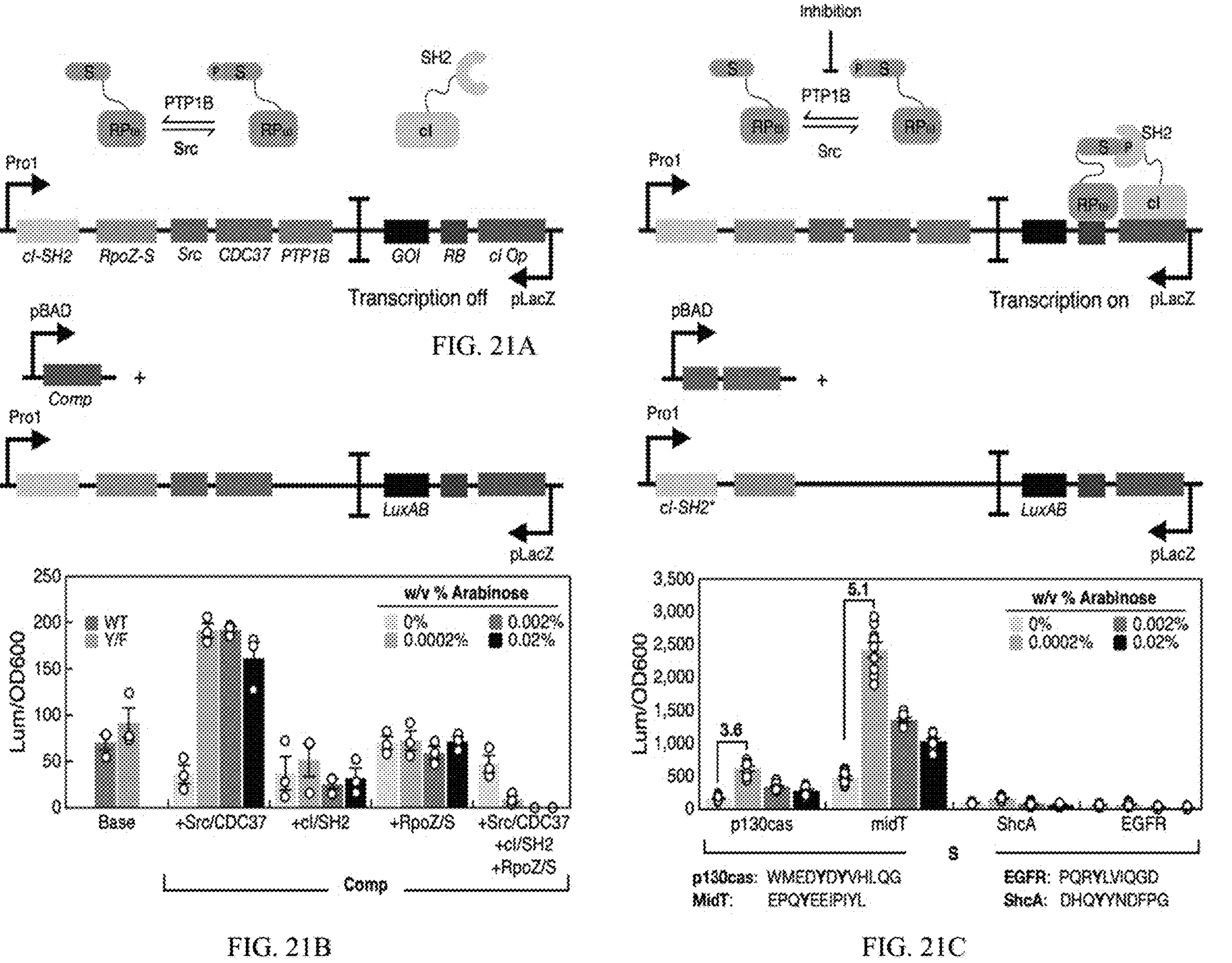
FIGS. 21A-21E. Development of a bacterial-two hybrid system that links the inhibition of PTP1B to antibiotic resistance. This figure elaborates on FIG. 1 by including the orientation of genes.

*E. coli* is a versatile platform for building natural products from unculturable or low-yielding organisms[30,31]. We hypothesized that a strain of *E. coli* programmed to detect the inactivation of PTP1B (i.e., a genetically encoded objective) might enable the discovery of natural products that inhibit it (i.e., molecular solutions to the objective). To program such a strain, we assembled a bacterial two-hybrid (B2H) system in which PTP1B and Src kinase control gene expression (FIG. 21A). In this system, Src phosphorylates a substrate domain, enabling a protein-protein interaction that activates transcription of a gene of interest (GOI). PTP1B dephosphorylates the substrate domain, preventing that interaction, and the inactivation of PTP1B re-enables it. *E. coli* is a particularly good host for this detection system because its proteome is sufficiently orthogonal to the proteome of *H. sapiens* to minimize off-target growth defects that can result from the regulatory activities of Src and PTP1B (Note 1)[32].

Figure 21E:
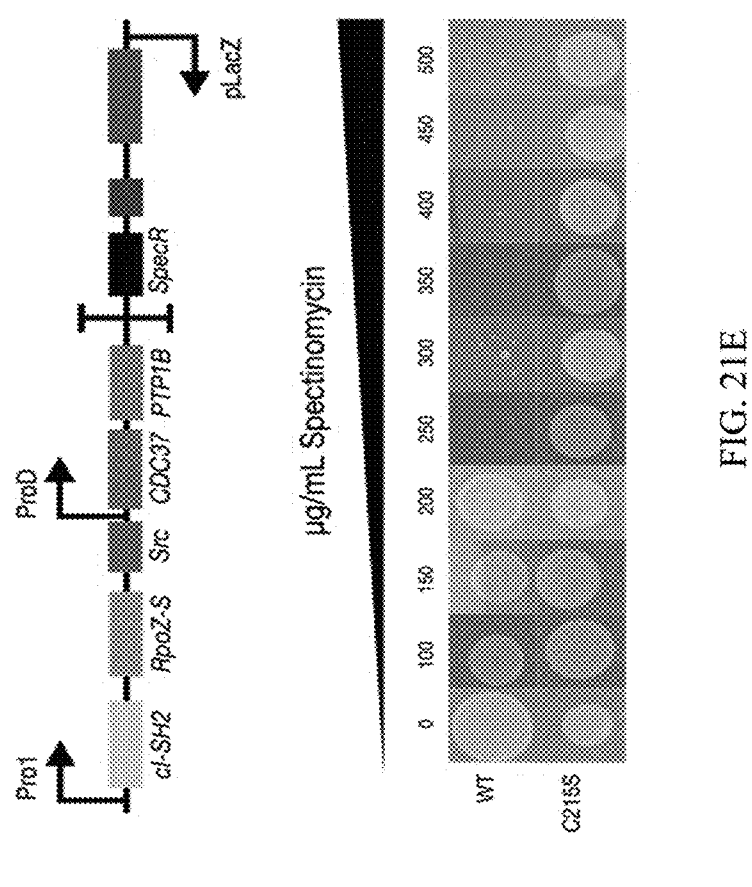
Figure 21D:
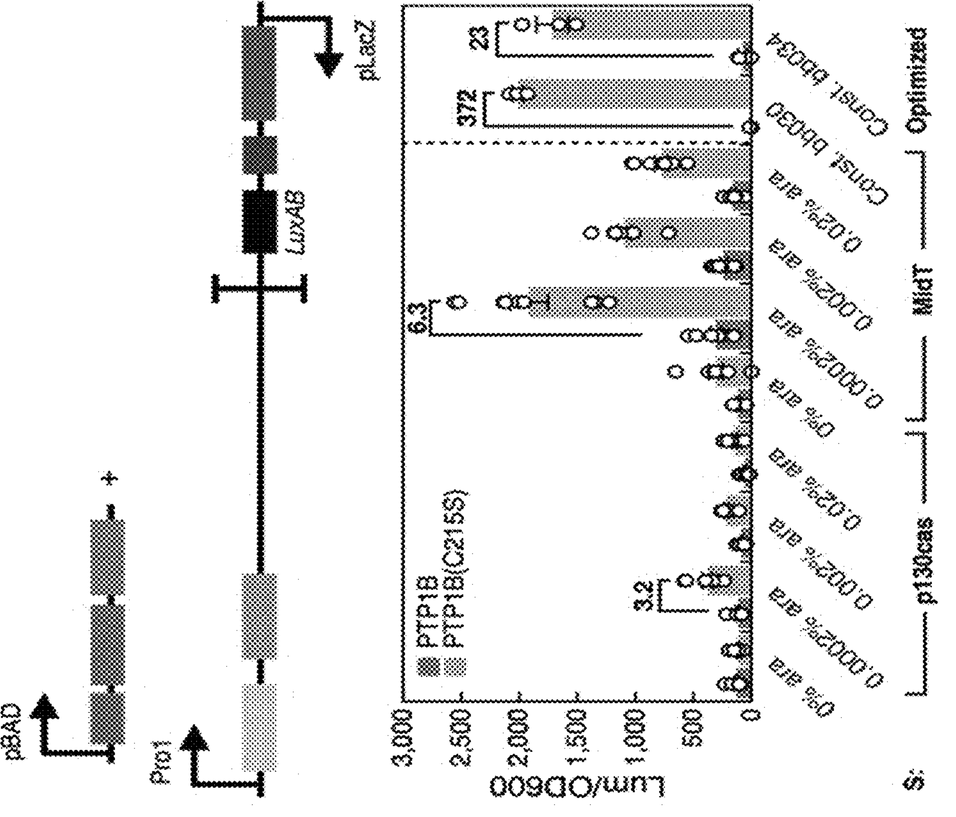

We carried out B2H development in several steps. To begin, we assembled a luminescent "base" system in which Src modulates the binding of a substrate domain to an Src homology 2 (SH2) domain (FIG. 21B); this system, which includes a chaperone that helps Src to fold (Cdc37)[33], is similar to other B2H designs that detect protein-protein binding[34]. Unfortunately, our initial system did not yield a phosphorylation-dependent transcriptional response, so we complemented it with inducible plasmids—each harboring a different system component—to identify proteins with suboptimal expression levels (FIG. 21*b*). Interestingly, secondary induction of Src increased luminescence, an indication that insufficient substrate phosphorylation and/or weak substrate-SH2 binding depressed GOI expression in our base system. We modified this system by swapping in different substrate domains, by adding mutations to the SH2 domain that enhance its affinity for phosphopeptides[35], and by removing the gene for Src—a modification that allowed us to control expression exclusively from a second plasmid. With this configuration, induction of Src increased luminescence most prominently for the MidT substrate (FIG. 1C), and simultaneous induction of both Src and PTP1B prevented that increase—an indication of intracellular PTP1B activity (FIG. 21D). We finalized the MidT system by incorporating genes for PTP1B and Src, by adjusting promoters and ribosome binding sites to amplify its transcriptional response further (FIG. 21D, FIG. 13, and FIG. 14), and by adding a gene for spectinomycin resistance (SpecR) as the GOI. The final plasmid-borne detection system required the inactivation of PTP1B to permit growth at high concentrations of antibiotic (FIG. 21E).

Biosynthesis of PTP1B Inhibitors

Figures 26A, 26B, 26C:
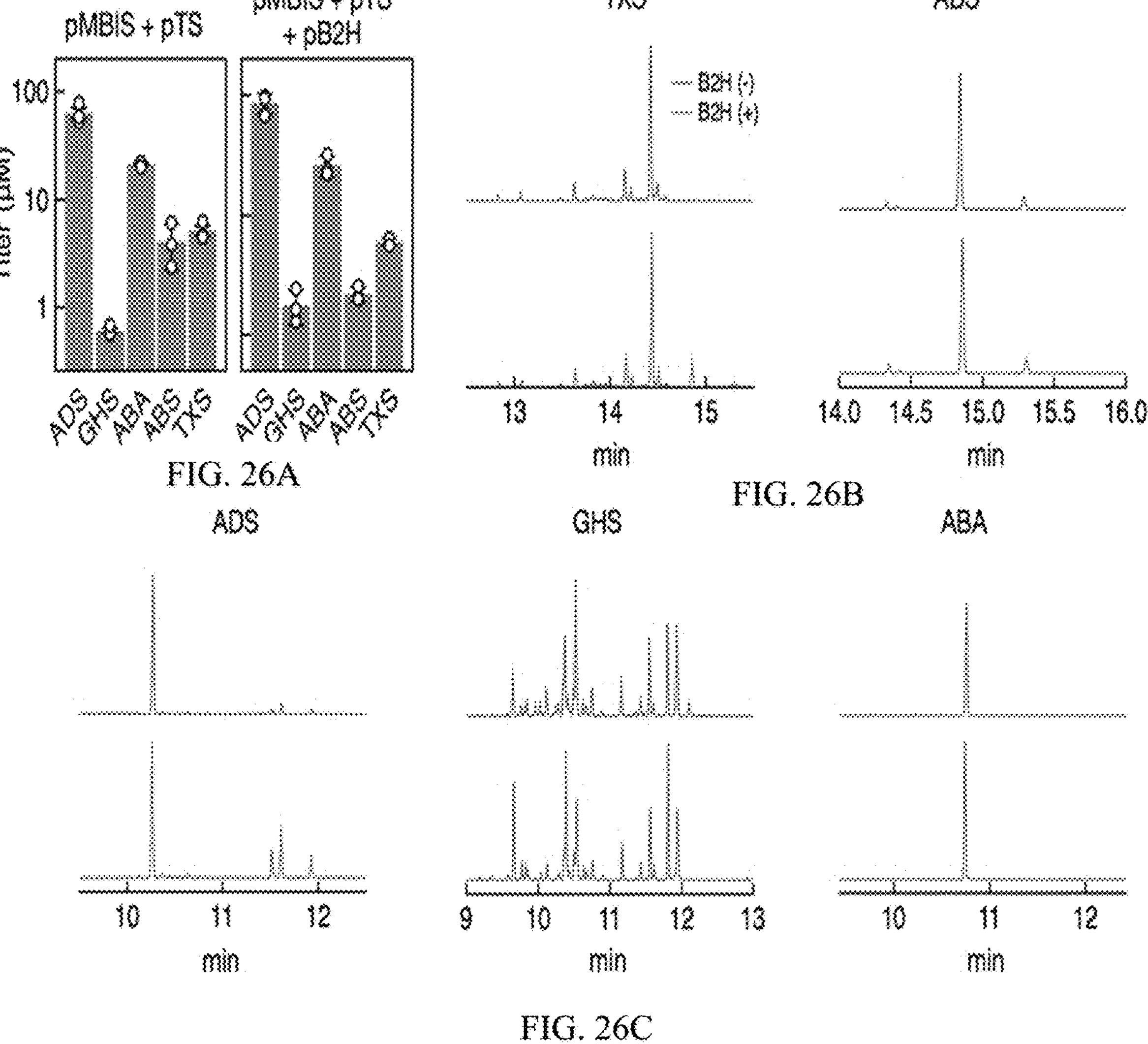
FIG. 26A-26D. Analysis of the products of different terpene synthases. This figure builds on FIG. 9 by including additional measurements.

To search for inhibitors of PTP1B that bind outside of its active site, we coupled the B2H system with metabolic pathways for terpenoids, a structurally diverse class of secondary metabolites with largely nonpolar structures (FIG. 22A), some of which are known to inhibit PTP1B[36,37]. Terpenoids include over 80,000 known compounds and represent nearly one-third of all characterized natural products[38] (the basis of approximately 50% of clinically approved drugs[39]). To begin, we focused on a handful of structurally diverse terpenoids without established inhibitory effects (FIG. 22B): Amorphadiene (AD), Y-humulene, α-bisabolene (AB), abietadiene, and taxadiene. Each terpenoid pathway consisted of two plasmid-borne modules: (i) the mevalonate-dependent isoprenoid pathway from *S. cerevisiae* (optimized for expression in *E. coli*[40]) and (ii) a terpene synthase previously demonstrated to express and produce one of the five selected terpenoids in *E. coli*[40-44]. The terpene synthase was supplemented, when necessary for diterpenoid production, with a geranylgeranyl diphosphate synthase. These modules generated terpenoids at titers of 0.3-18 mg/L in *E. coli* (FIG. 26).

Figures 22A, 22B, 22C:
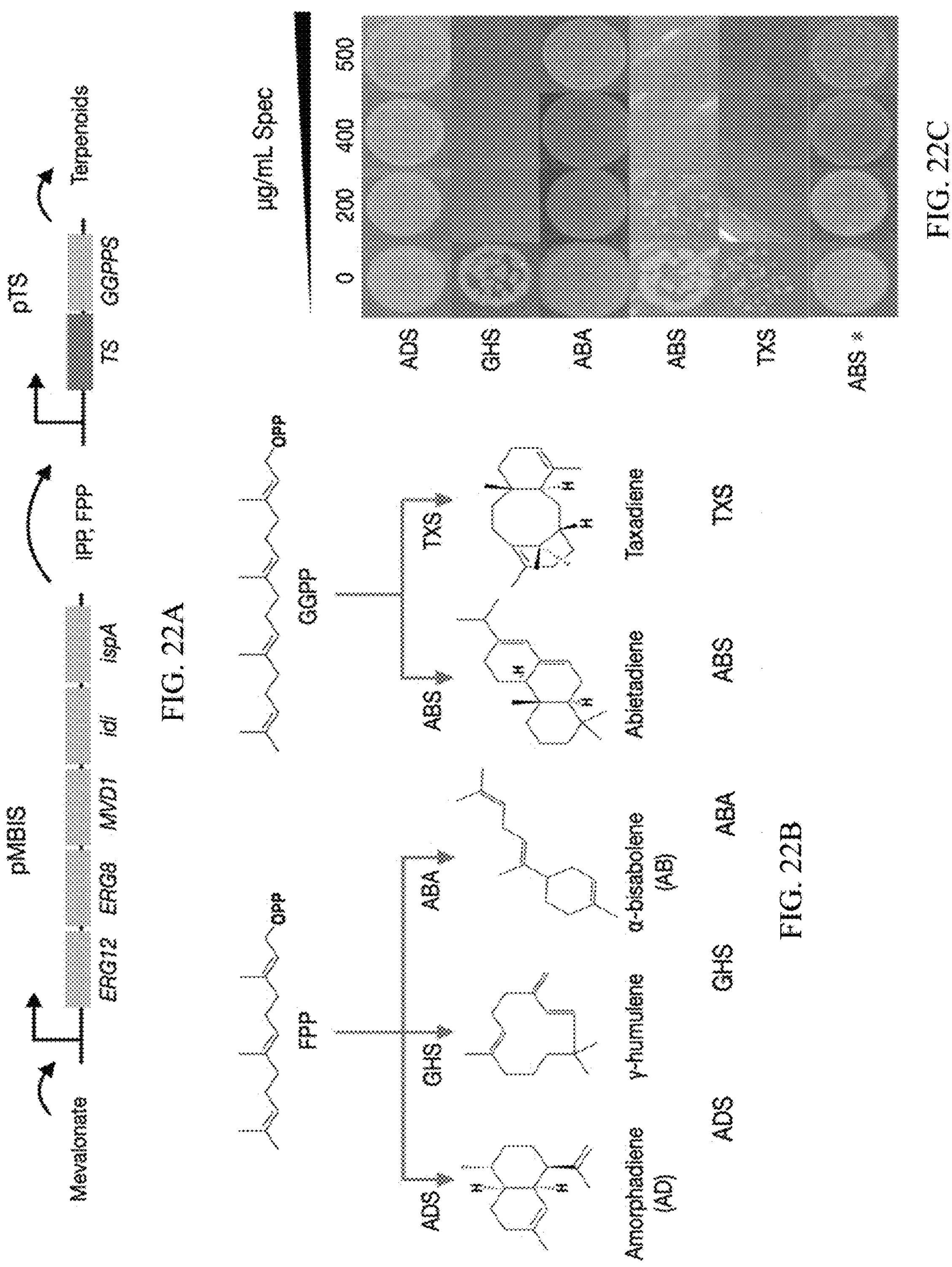
FIGS. 22A-22G. Biosynthesis of PTP1B-inhibiting terpenoids enables cell survival. This figure elaborates on FIGS. 2 and 10.
Figure 26D:
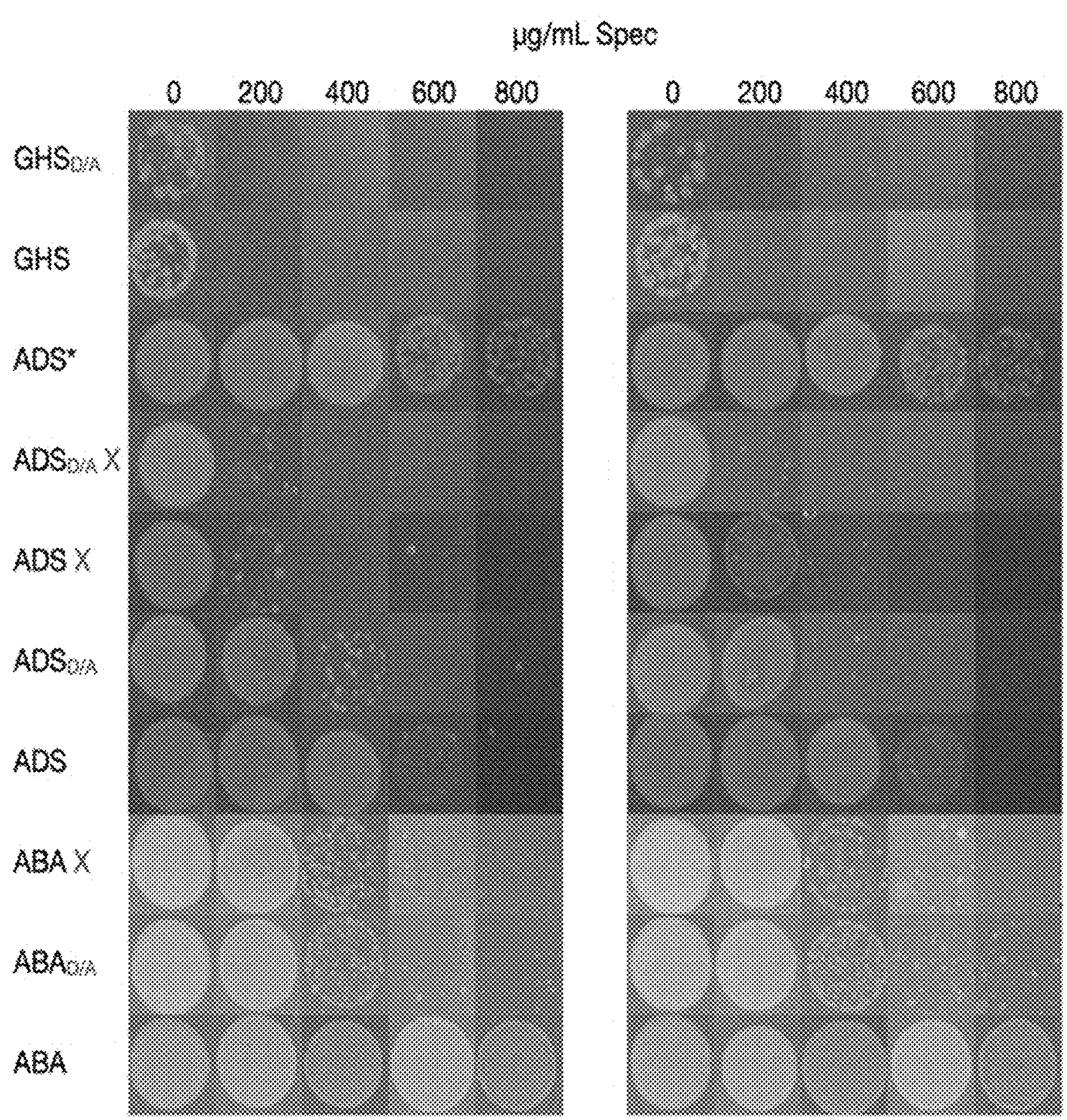

We screened each pathway for its ability to produce inhibitors of PTP1B by transforming *E. coli* with plasmids harboring both the pathway of interest and the B2H system (FIG. 22C). To our surprise, pathways for AD and AB permitted survival at high concentrations of antibiotic. Critically, GC-MS traces confirmed that all pathways generated terpenoids in the presence of the B2H system (FIG. 22D, FIG. 26), and maximal resistance of the AD- and AB-producing strains required both an active terpene synthase and a functional B2H system (FIG. 26D).

Figures 22D, 22E, 22F, 22G:
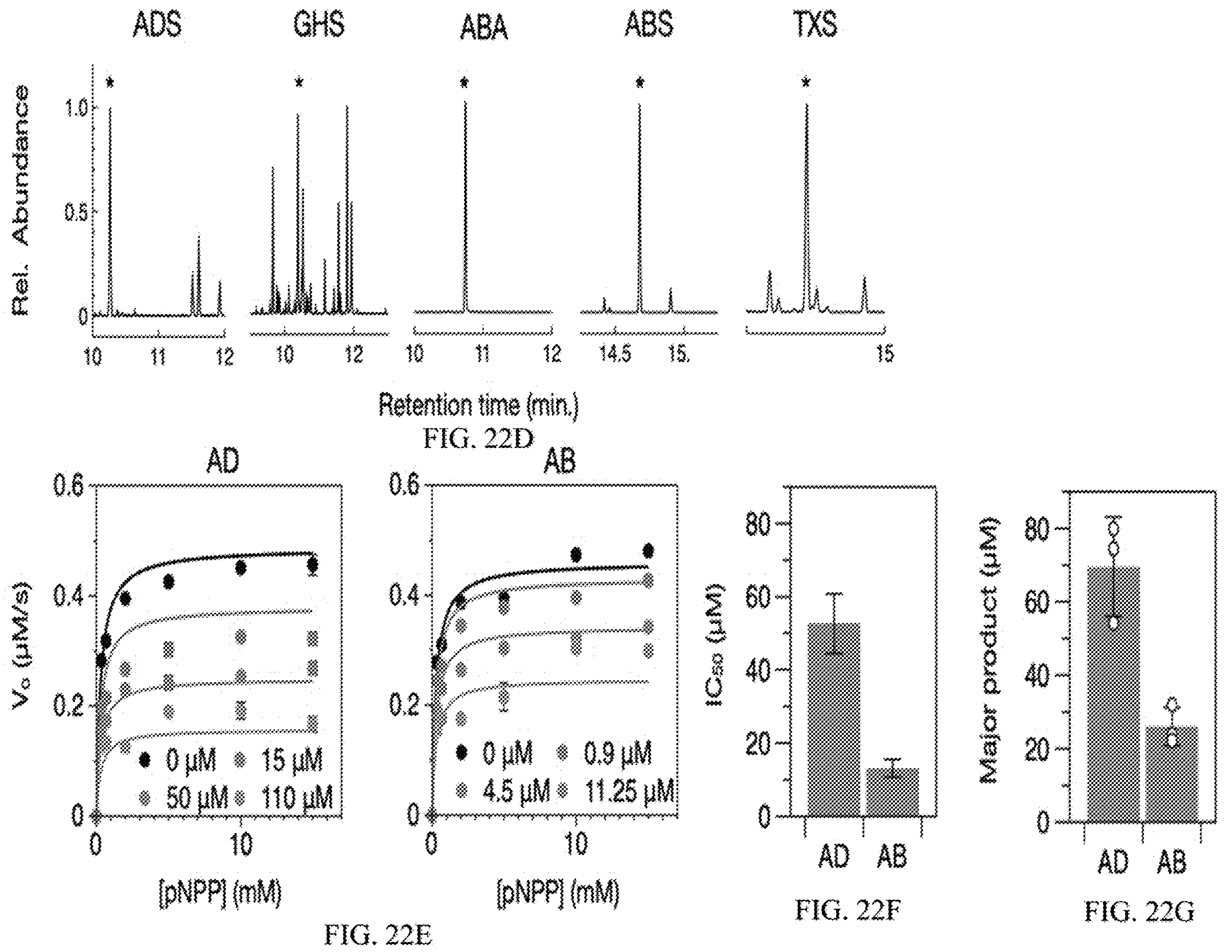

We confirmed the inhibitory effects of purified terpenoids by examining their influence on PTP1B-catalyzed hydrolysis of p-nitrophenyl phosphate (pNPP; FIG. 22E, TABLE 12). The $IC_{50}$s for AD and AB were 53±8 μM and 13±2 μM, respectively, in 10% DMSO (FIG. 22F). These $IC_{50}$s are surprisingly strong for small, unfunctionalized hydrocarbons; the ligand efficiencies of both inhibitors are high (TABLE 15), and their potencies are similar to those of larger molecules that form hydrogen bonds and other stabilizing interactions with PTP1B[21,45]. Both $IC_{50}$s are also similar to the respective terpenoid concentrations in liquid culture (FIG. 22G), a finding consistent with in vivo inhibition (terpenoids tend to accumulate intracellularly[46], so in vivo concentrations may be even higher). Our growth-coupled assays, kinetic assays, and production measurements, taken together, indicate that AD and AB activate the B2H system by inhibiting PTP1B inside the cell.

Biophysical Analysis of PTP1B Inhibitors

Figures 23A, 23B, 23C, 23D, 23E, 23F, 23G, 23H:
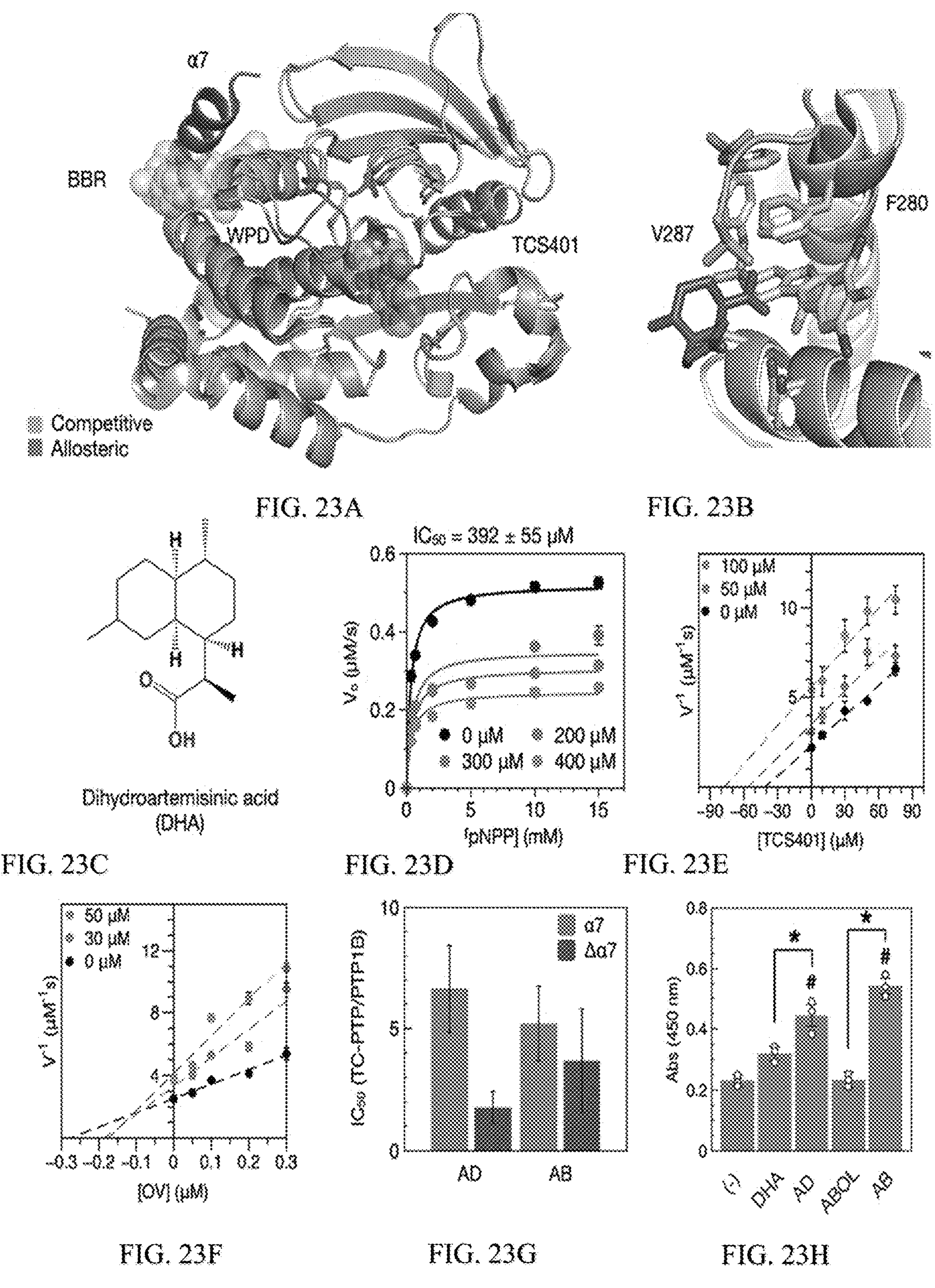
FIGS. 23A-23H. Biophysical analysis of terpenoid-mediated inhibition. This figure builds on FIG. 12 by including additional kinetic measurements.

Allosteric inhibitors of PTPs are valuable starting points for drug development. These molecules bind outside of the well conserved, positively charged active sites of PTPs and tend to have improved selectivities and membrane permeabilities over substrate analogs[21]. Motivated by these considerations, an early screen identified a benzbromarone derivative that inhibited PTP1B weakly ($IC_{50}$=350 μM) without competing with substrates; subsequent optimization of this compound led to two improved inhibitors ($IC_{50}$'s=8 and 22 μM) that bind to an allosteric site[45] (FIG. 23A). Over the next 15 years, efforts to find new inhibitors that bind to this or other allosteric regions on the catalytic domain have been largely unsuccessful[47]. Benzbromarone derivatives are the only allosteric inhibitors with crystallographically verified binding sites. (Although, an allosteric inhibitor that binds to a disordered region of the full-length protein has been characterized with NMR[25]). New approaches for finding allosteric inhibitors are clearly needed.

Figure 30:
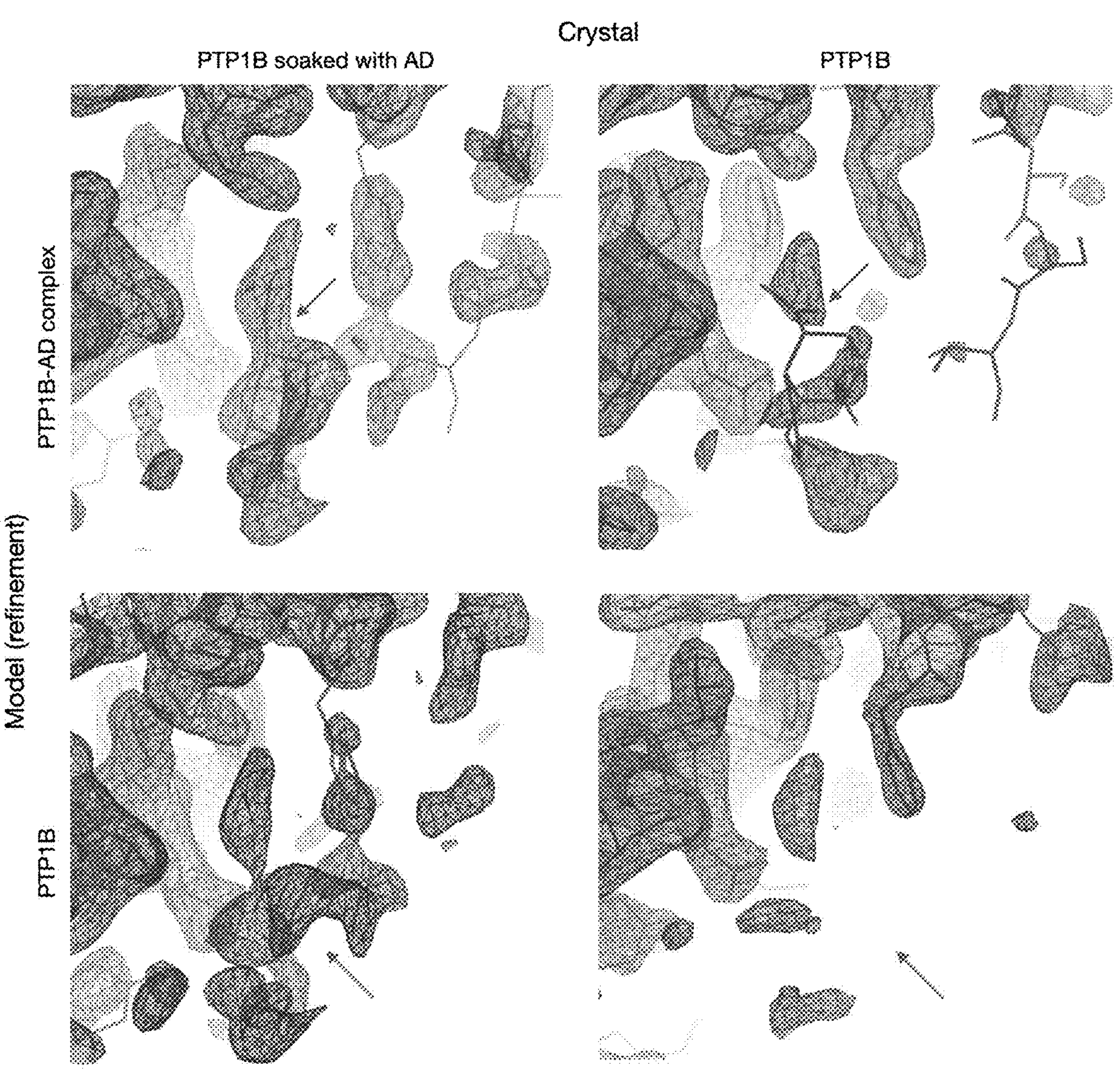
FIG. 30. Crystallographic analysis of PTP1B bound to AD. Crystal structures of PTP1B collected in the (left) presence or (right) absence of AD. Resolutions: 2.10 Å (PTP1B-AD) and 1.94 Å (PTP1B). We refined these structures by modeling (top) the PTP1B-AD complex or (bottom) the apo form PTP1B. For PTP1B soaked with AD (left), the 1.0 σ2Fo-Fc electron density supports the modeled position of AD but suggest multiple conformations; this density appears even when AD is excluded from the model. For apo PTP1B (right), the 1.0 σ2Fo-Fc electron does not support a bound AD molecule; small regions of unexplained density may reflect water molecules or partial occupancy of the α7 helix[15].
Figure 31:
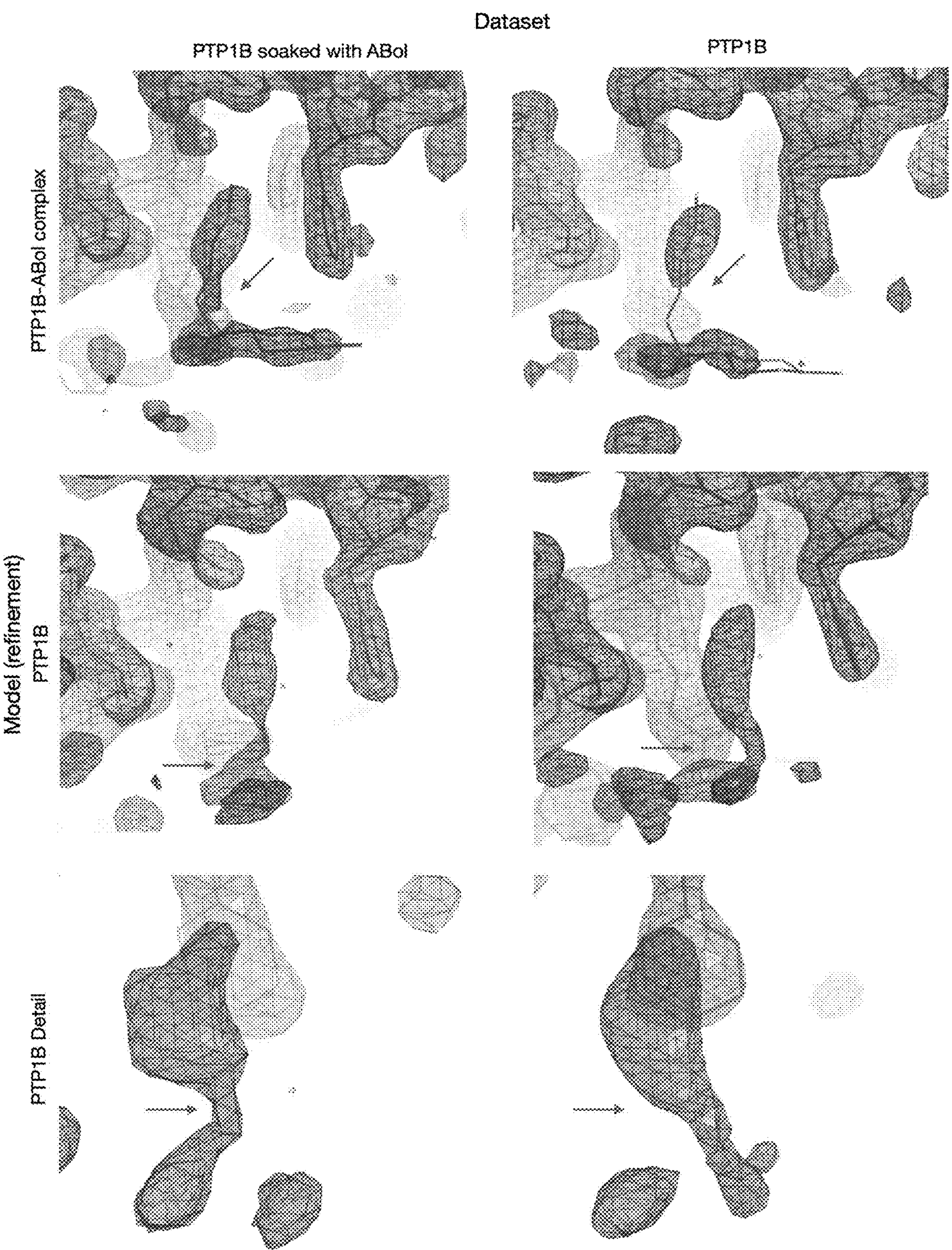
FIG. 31. Crystallographic analysis of PTP1B bound to ABol. Crystal structures of PTP1B collected in the (left) presence or (right) absence of ABol. Resolutions: 2.11 Å (PTP1B-ABol) and 1.94 Å (PTP1B). We refined these structures by modeling (top) the PTP1B-ABol complex or (middle/bottom) the apo form PTP1B. For PTP1B soaked with ABol (left), the 0.90 σ2Fo-Fc electron density is consistent with the modeled position of ABol, but it becomes less pronounced when ABol is excluded from the model. The apo form of PTP1B (right) shows similar density for both models; small differences in the shape of the 0.90 σ2Fo-Fc electron density between datasets suggests that this density may have a different origin (e.g., a ligand vs. partial occupancy of the α7 helix). The unambiguous determination of a binding site for α-bisabolol requires additional data.
Figure 32A:
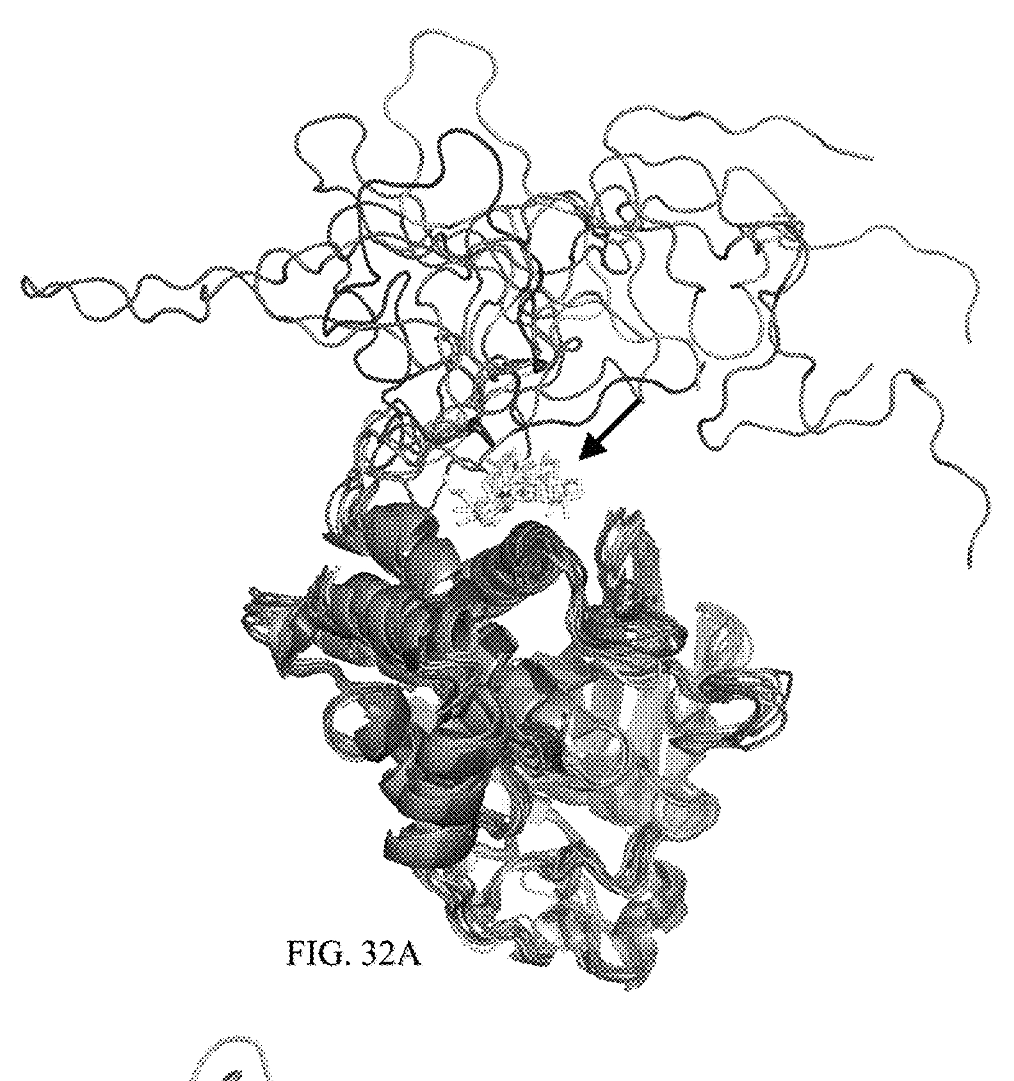
FIGS. 32A-32C. Evidence of multiple bound conformations.
Figure 32B:
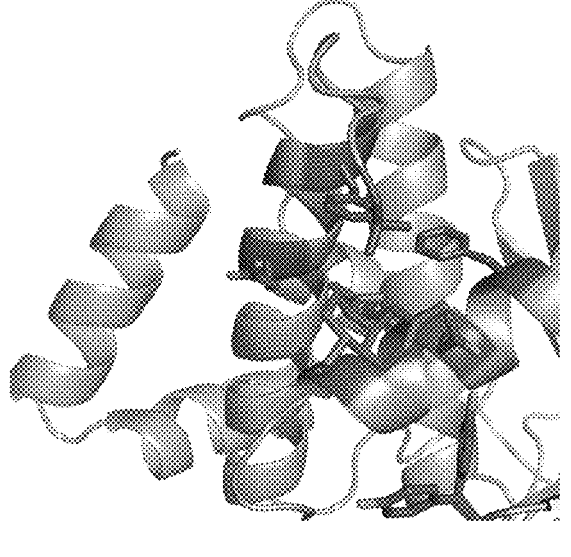
Figure 32C:
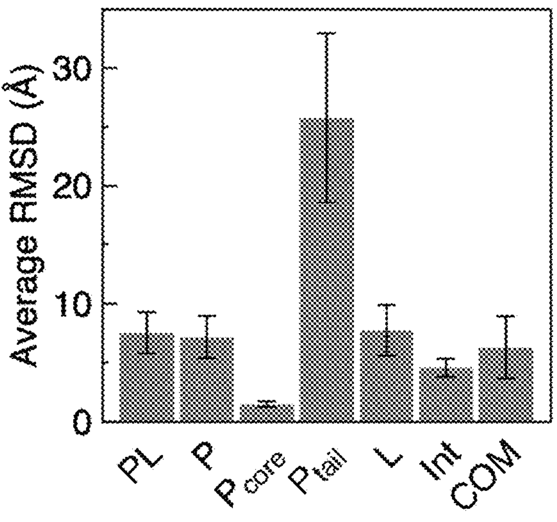

Our microbial system could grant access to new compounds that bind in unexpected ways. AD and AB provide examples. They are highly nonpolar and, thus, incapable of engaging in the hydrogen bonds and electrostatic interactions on which most other PTP inhibitors rely[21,45]. To examine their binding mechanisms in detail, we sought to collect X-ray crystal structures of PTP1B bound to AD and α-bisabolol, a soluble analogue of AB (a ligand for which poor solubility precluded soaking experiments). Unfortunately, only the structure of PTP1B bound to AD was sufficient for unambiguous determination of a binding site (FIG. 30 and FIG. 31). This inhibitor binds to the same allosteric site targeted by benzbromarone derivatives. Its binding mode, however, is distinct: (i) AD causes the α7 helix of PTP1B to reorganize to create a hydrophobic cleft (FIG. 23B); this type of reorganization is interesting because it is typically slow (micro- to millisecond)[48] and difficult to incorporate into computational ligand design[49]. (ii) It likely adopts multiple bound conformations (i.e., the electron density indicates regions of disorder; FIG. 30). This behavior, which is supported by molecular dynamics simulations, is consistent with prior work on the binding of proteins to hydrocarbon moieties, which tend to be "mobile" in their binding pockets.

Figures 33A, 33B, 33C, 33D, 33E, 33F, 33G:
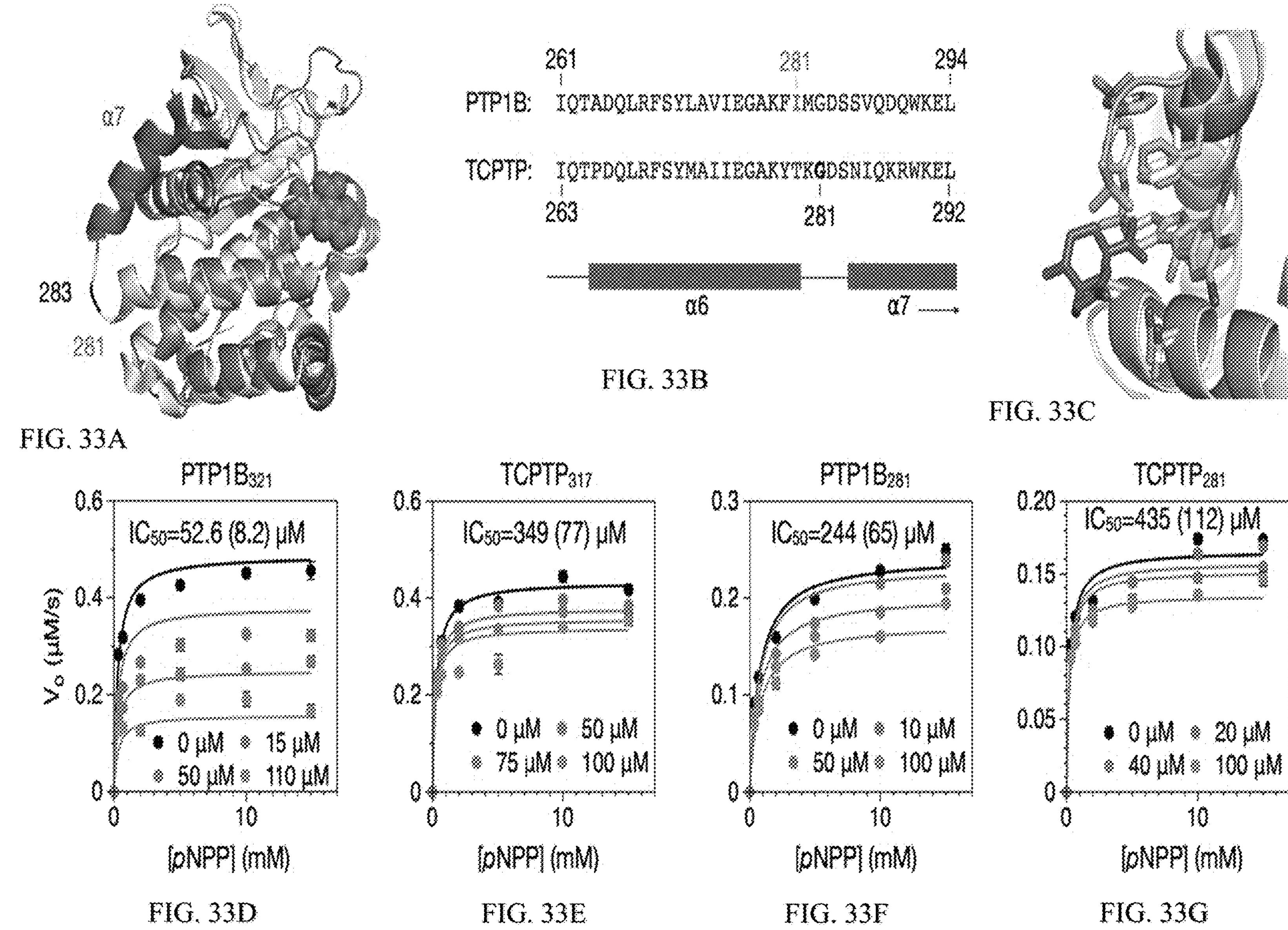
FIGS. 33A-33M. Summary of kinetics analyses.
Figures 33H, 33I, 33J, 33K, 33L, 33M:
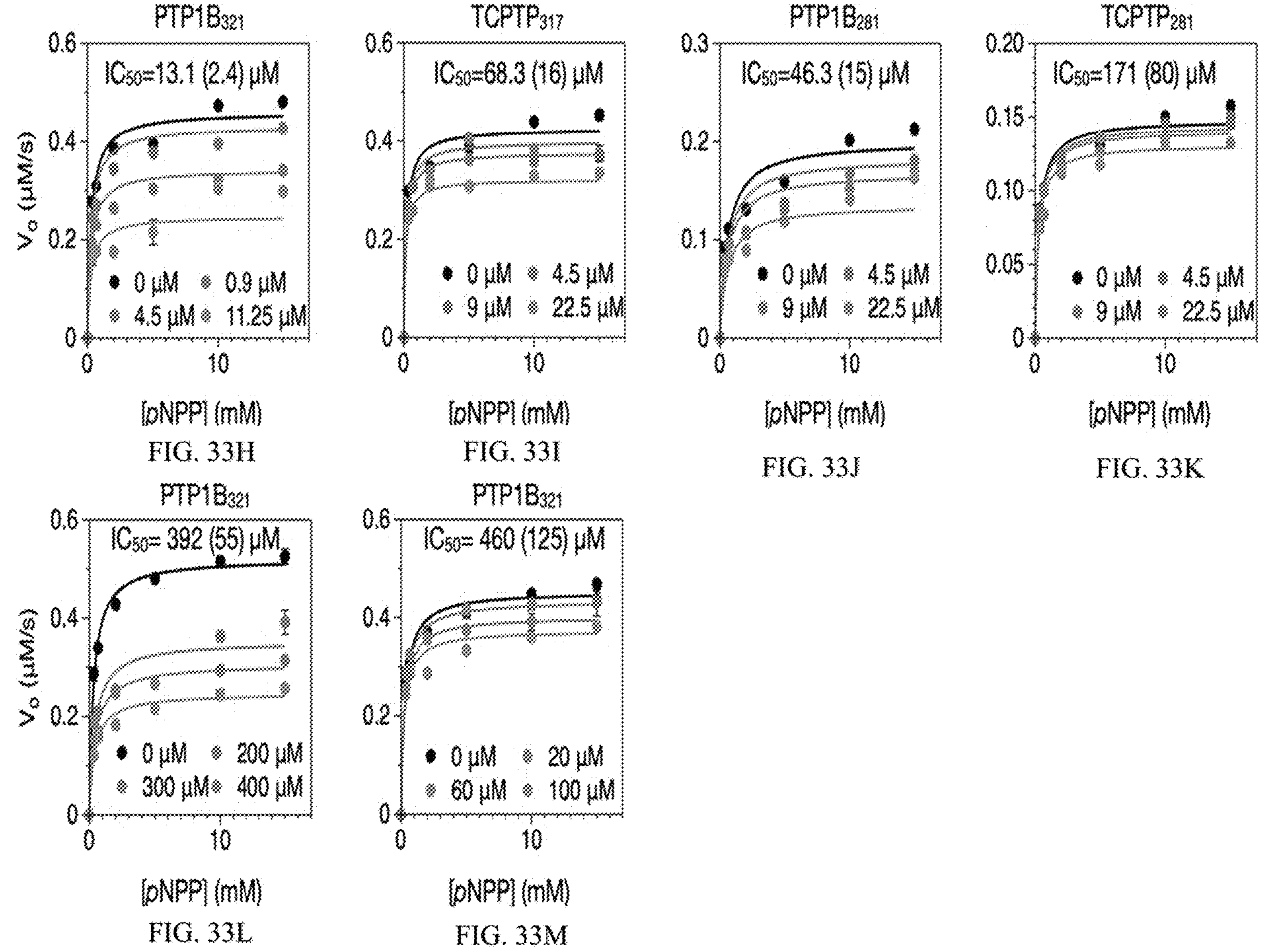

We probed the binding of AD and AB further with several additional analyses. First, we examined the inhibition of PTP1B by dihydroartemisinic acid. This structural analogue of AD has a carboxyl group that, according to our crystal structure, should interfere with binding to the hydrophobic cleft created by the α7 helix (FIG. 23C). The $IC_{50}$ of this molecule was eight-fold higher than that of AD, a reduction in potency consistent with its crystallographic pose (FIG. 23*d* and FIG. 33). Second, we studied the competition between AD and two inhibitors that bind to the active site: (i) TCS401, which causes the WPD loop to adopt a closed conformation, and (ii) orthovanadate, which does not. For background, benzobromarones, upon binding to the C-terminal allosteric site, stabilize the WPD loop in an open conformation that is incompatible with the binding of TCS401, but not orthovanadate. Our kinetic data suggest that AD behaves similarly (FIG. 23E and FIG. 23F), a finding consistent with a shared binding site and mechanism of modulation. Finally, we assessed the inhibitory effects of AD and AB against TC-PTP, the closest homolog of PTP1B. Intriguingly, both molecules inhibited TC-PTP five- to six-fold less potently than PTP1B (FIG. 23G and FIG. 33). This finding is consistent with binding to the poorly conserved allosteric site. Importantly, this selectivity may seem modest, but it matches or exceeds the selectivities of most pre-optimized inhibitors (including benzobromarone derivatives) and is exceedingly rare for unfunctionalized hydrocarbons[50]. We assessed the contribution of the α7 helix to selectivity, in turn, by removing the equivalent region from PTP1B and TC-PTP (FIG. 23G). This modification caused a four-fold reduction in the selectivity of AD, an effect consistent with the involvement of the α7 helix in its binding. Intriguingly, the selectivity of AB was insensitive to this modification; the unambiguous determination of the binding site of this ligand requires additional data.

Figure 35A:
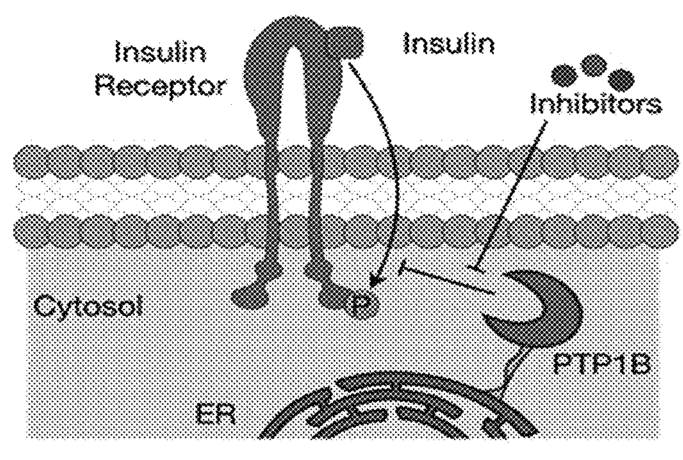
FIG. 35A-35C. Analysis of PTP1B-mediated IR dephosphorylation.

AD and AB are lipophilic molecules that could be valuable for their ability to pass through the membranes of mammalian cells. To examine the biological activity of these molecules, we incubated them with HEK293T/17 cells and used an enzyme-linked immunosorbent assay to measure shifts in insulin receptor (IR) phosphorylation. IR is a receptor tyrosine kinase that undergoes PTP1B-mediated dephosphorylation from the cytosolic side of the plasma membrane (PTP1B, in turn, localizes to the endoplasmic reticulum of the cell). Both molecules increased IR phosphorylation over a negative control (FIG. 23H and FIG. 35). We checked for off-target contributions to this signal, in turn, by repeating the ELISA with equivalent concentrations of dihydroartemisinic acid and α-bisabolol. To our satisfaction, both molecules led to a reduction in signal consistent with their reduced potencies.

Figures 34A, 34B, 34C, 34D:
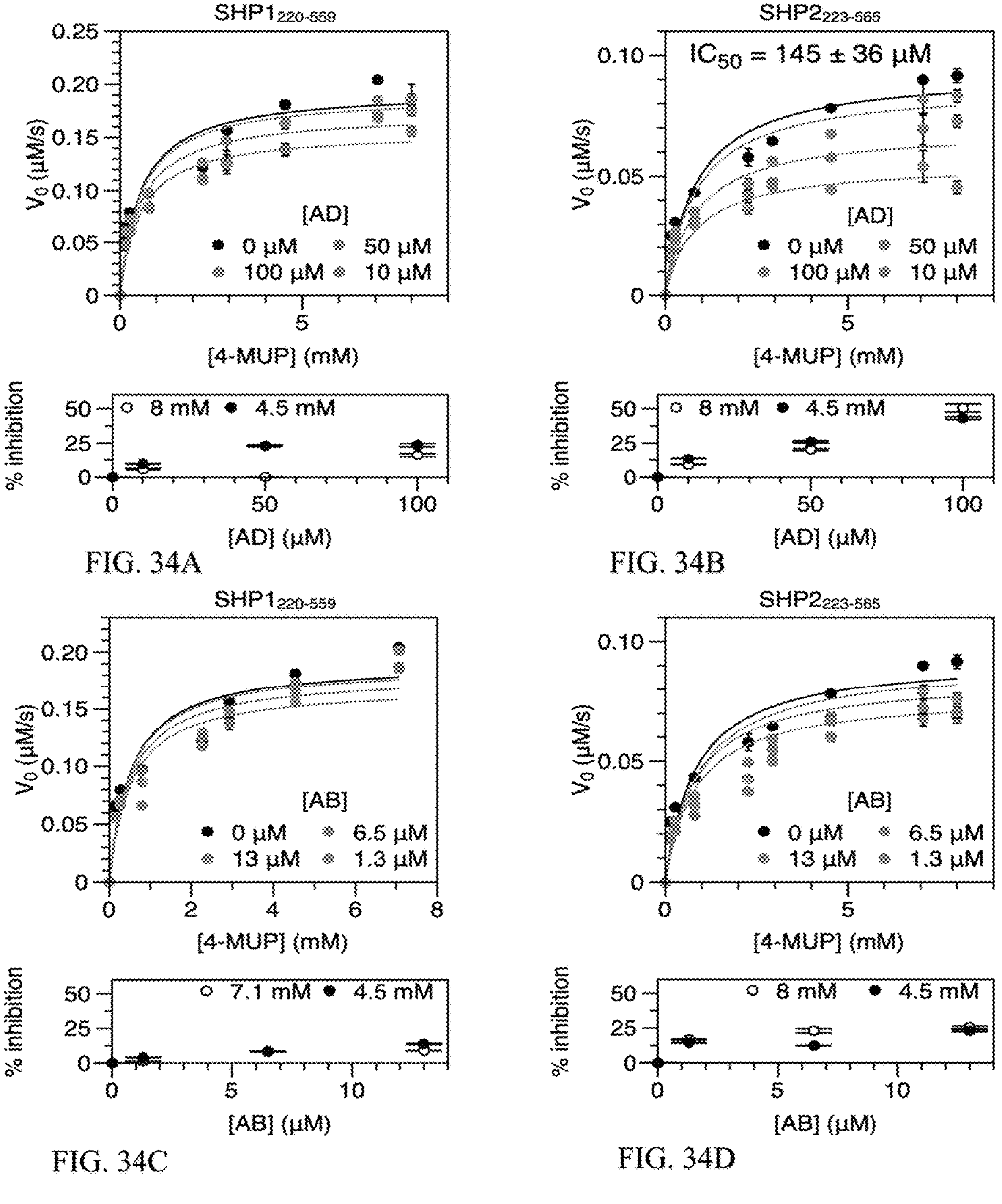
FIGS. 34A-34D. Expanded analysis of selectivity.

Other PTPs can promote IR dephosphorylation; SHP1 and SHP2 provide two examples[51-53]. To examine the potential contribution of these enzymes to the increase in IR phosphorylation observed in our ELISA, we measured their inhibition by AD and AB. Briefly, AD inhibited SHP2 three-fold less potently than PTP1B, and its inhibition of SHP1 was too weak to measure (FIGS. 34A-34B). The low potency of AB against SHP1 and SHP2 also precluded experimental measurement (FIGS. 34C-34D). These potencies, together with the aforementioned analysis of weakly inhibitory structural analogs, suggest that the inhibition of PTP1B by AD and AB is the primary cause of the increase in IR phosphorylation observed in our ELISA experiments.

a Scalable Approach to Molecular Discovery

Figures 24A, 24B, 24C, 24D, 24E:
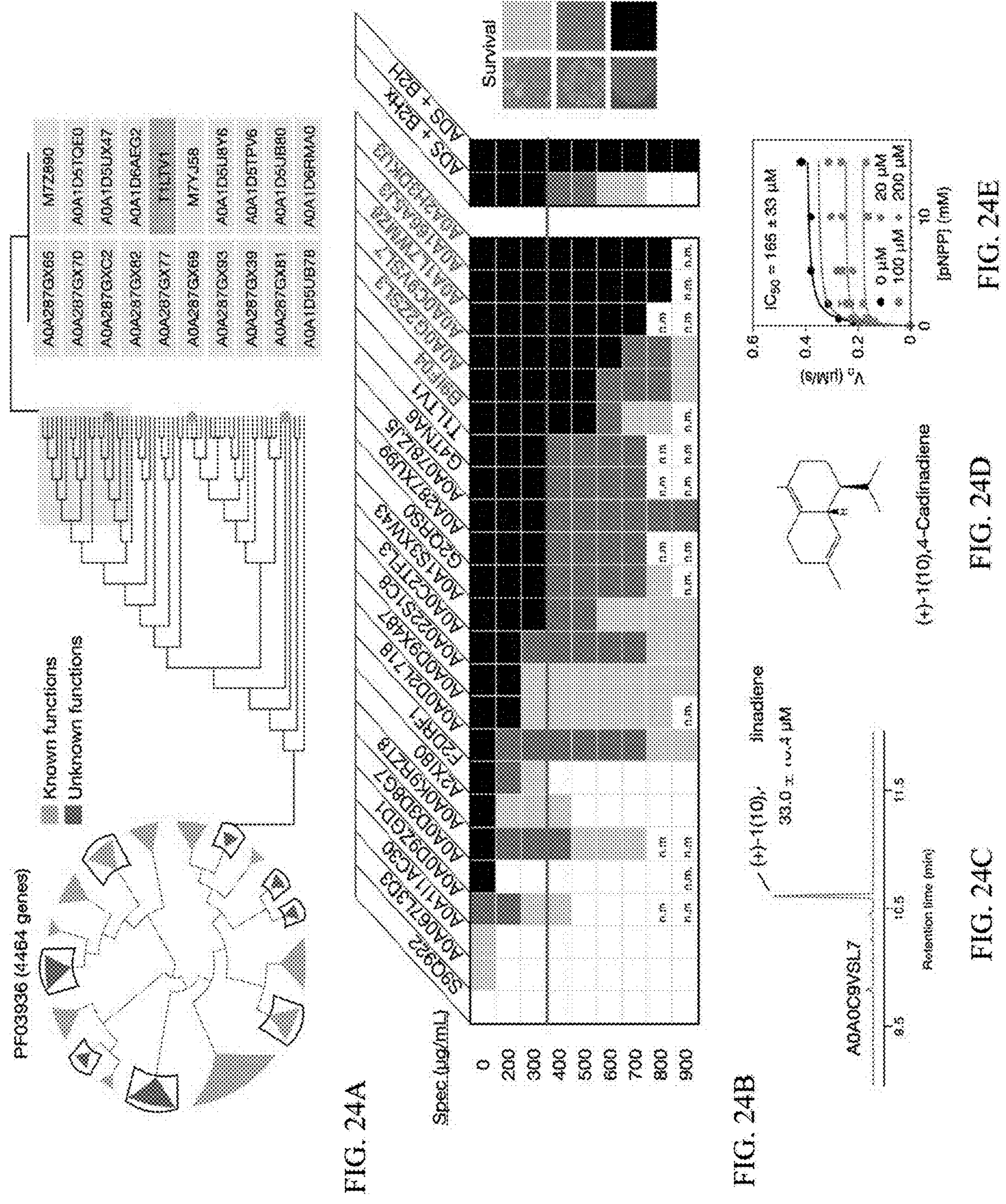
FIGS. 24A-24E. Analysis of uncharacterized terpene synthase genes.
Figure 27:
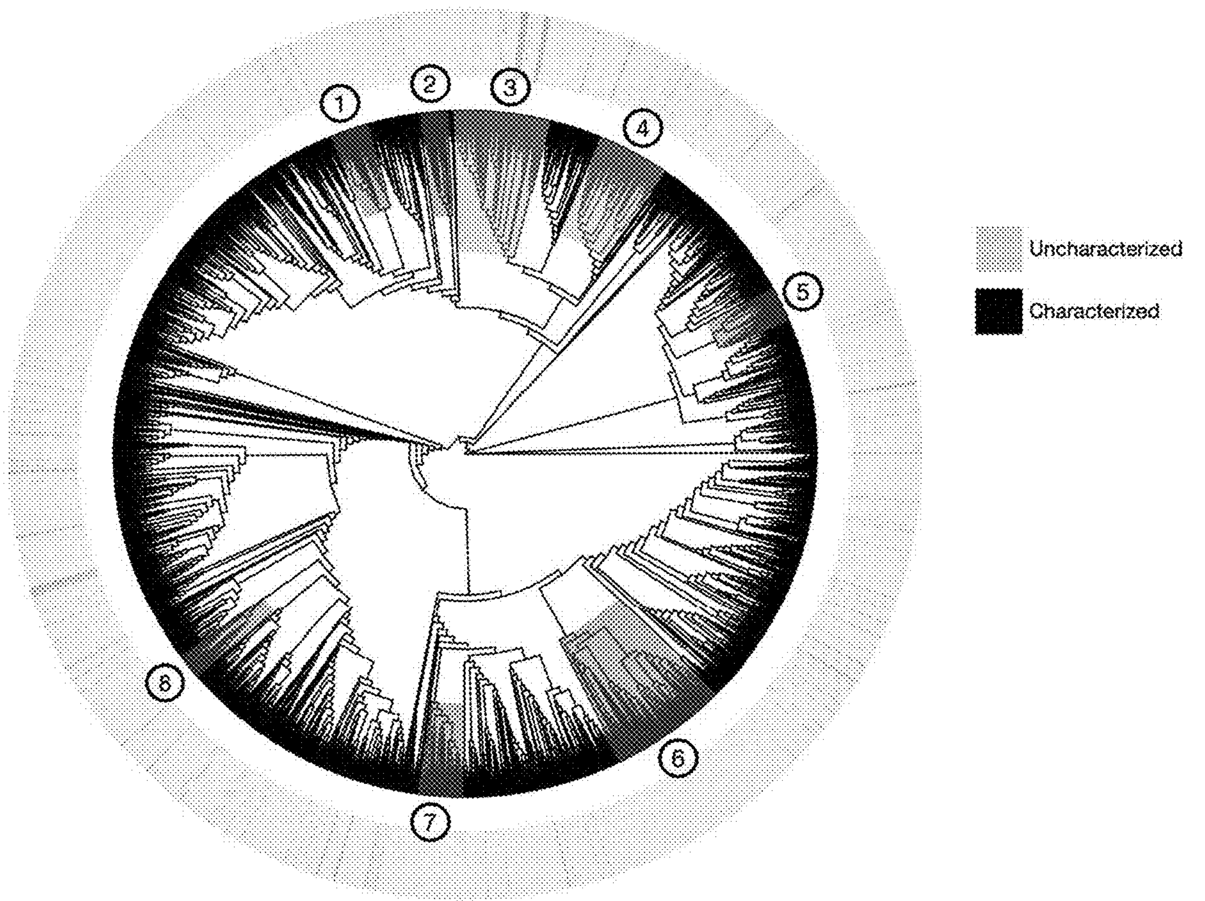
FIG. 27. An annotated cladogram of terpene synthases. This cladogram of the PF03936 family is surrounded by a heatmap that shows the presence/absence of known EC numbers of the form 4.2.3. #(which includes terpene cyclization reactions) from the Uniprot database. We selected three genes from each of eight clades: six with no characterized genes (red) and two with characterized genes (blue). TABLE 1 summarizes the genes.

Our microbial strain provides a powerful tool for screening genes for their ability to generate novel PTP1B inhibitors. Most terpenoids, as a case study, are not commercially available, and even when their metabolic pathways are known, their biosynthesis, purification, and in vitro analysis is a resource-intensive process that is difficult to parallelize with existing methods[54]. Our B2H system offers a potential solution: It can identify inhibitor-synthesizing genes with a simple growth-coupled assay. We explored its application to discovery efforts by using it to screen a diverse set of uncharacterized biosynthetic genes. In brief, we carried out a bioinformatic analysis of the largest terpene synthase family (PF03936) by building and annotating a cladogram of its 4,464 constituent members (FIG. 27); from here, we synthesized three uncharacterized genes from each of eight clades: six with no characterized genes and two with some characterized genes (FIG. 24A). We reasoned that these 24 phylogenetically diverse genes (8 from fungi, 13 from plants, and 3 from bacteria) might encode enzymes with distinct product profiles and potentially, through the inclusion of uncharacterized clades, novel sesquiterpene scaffolds.

Figure 28:
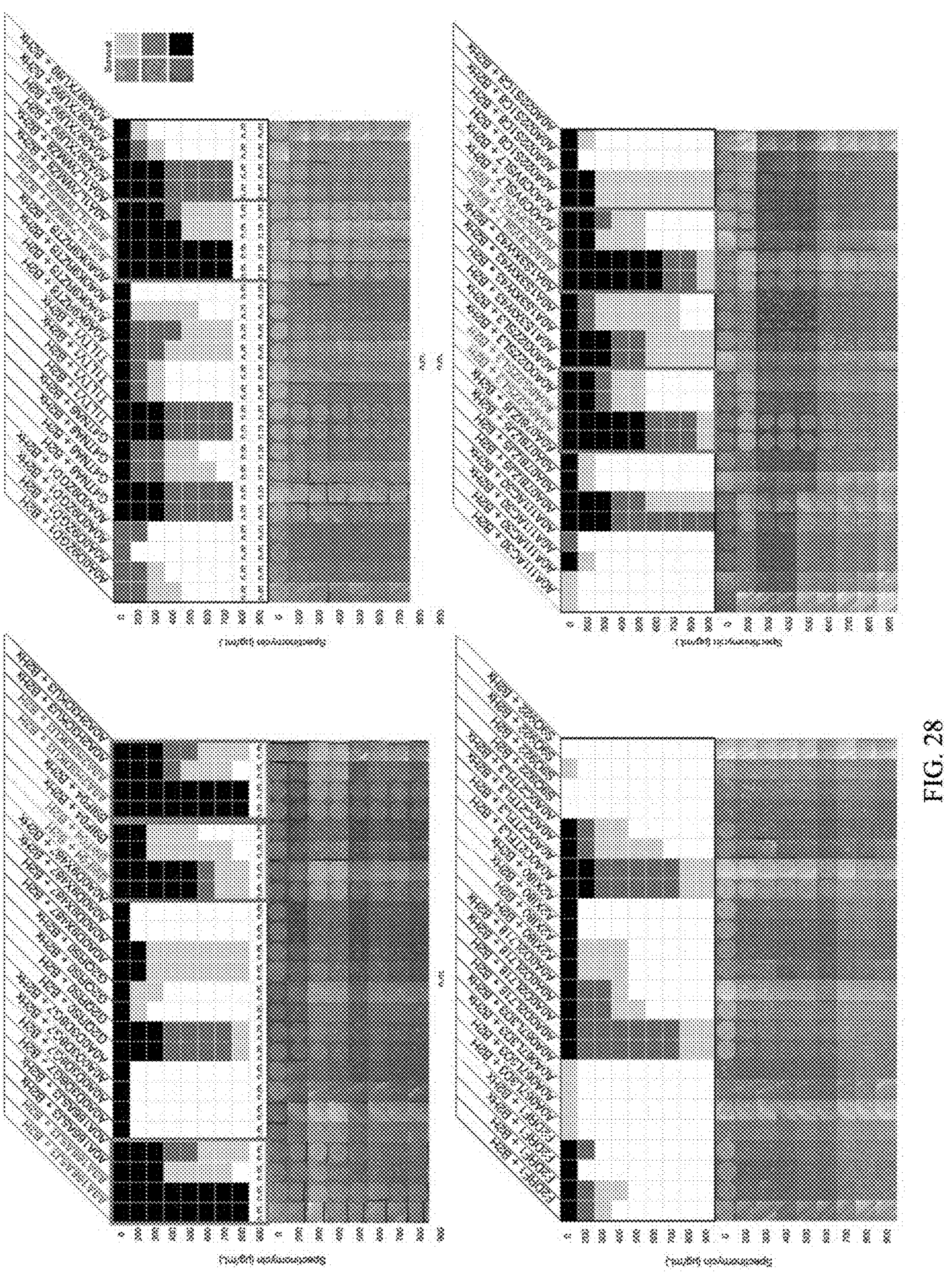
FIG. 28. Analysis of selected genes. We searched for sesquiterpene inhibitors of PTP1B by screening each of the 24 uncharacterized genes alongside the FPP pathway (i.e., pMBIS). These pictures show the antibiotic resistance conferred by each gene. We selected strains with antibiotic resistance exceeding 400 μg/ml as hits (blue). Importantly, for these genes, the reduced survival of B2Hx controls indicates that enhanced resistance requires activation of the B2H system. In the top diagrams, n.m. indicates conditions that were not measured.
Figure 29:
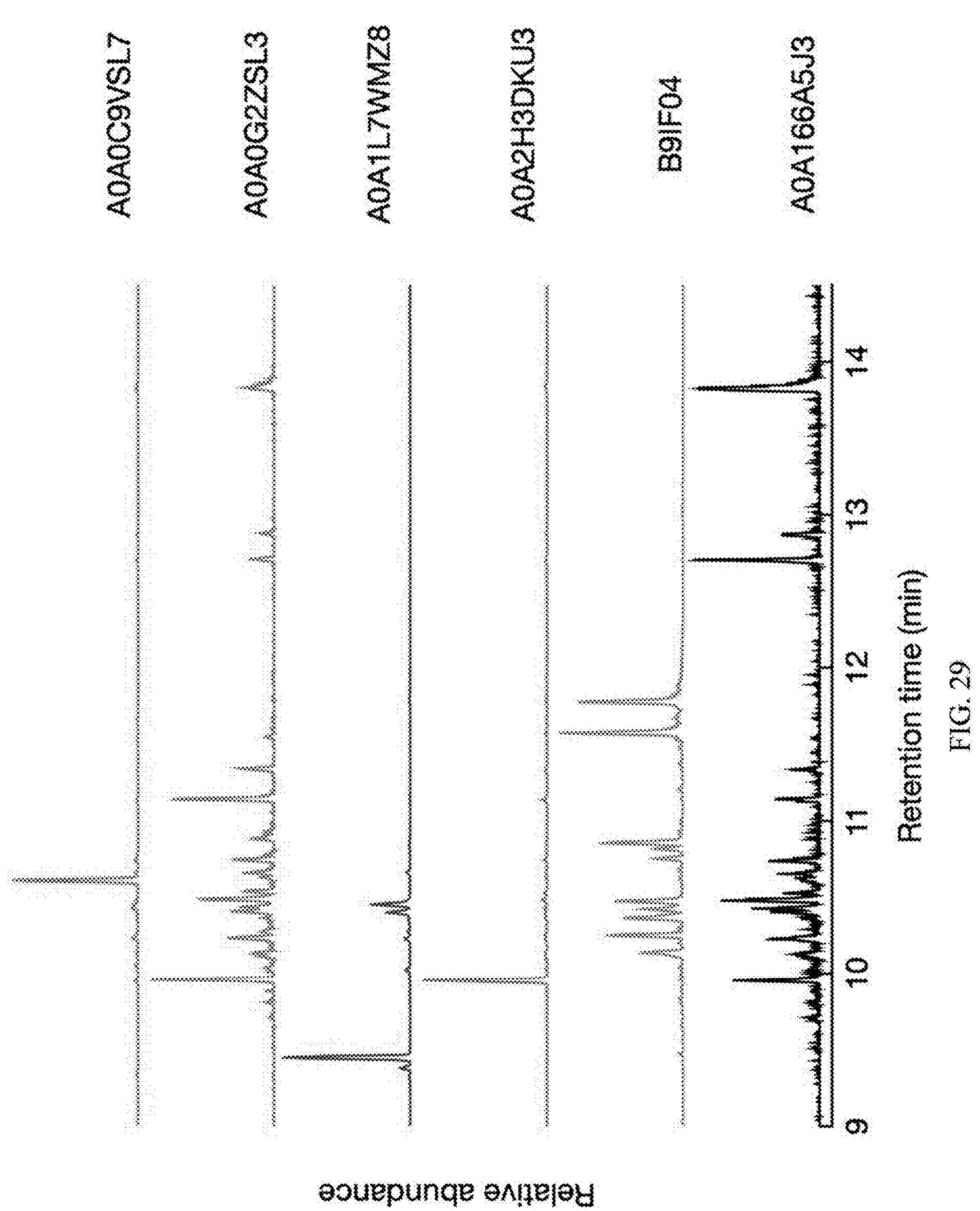
FIG. 29. Product profiles of selected hits. The product profiles of selected hits (extracted ion chromatograms, m/z=204). In brief, we grew up hits (i.e., $pB2H_{opt}$, pMBIS$_{CmR}$, and pTS). in liquid culture for 72 hours. With the exception of A0A0G2ZSL3, all hits were grown in 10 mL of 2% TB; A0A0G2ZSL3 was grown in a 4-mL culture of 2% TB. Notably, both A0A0C9VSL7 and A0A2H3DKU3 generate one dominant product: (+)-1 (10),4-cadinadiene and β-farnesene, respectively. We focused on A0A0C9VSL7 because (+)-1 (10),4-cadinadiene is a structural analog of amorphadiene, an inhibitor identified in our initial screen.

Guided by our initial screen, we searched for sesquiterpene inhibitors by pairing each of the uncharacterized genes with the FPP pathway. To our surprise, six genes conferred a significant survival advantage (FIG. 24B), and maximal resistance required an active B2H system (FIG. 28). Each hit generated distinct product profiles (FIG. 29); we focused our analysis on A0A0C9VSL7, which produced mostly (+)-1(10),4-cadinadiene as a major product (FIGS. 24C-24D). This terpenoid is a structural analog of AD but has a weaker potency ($IC_{50}$=165±33 μM; FIG. 24E); a titer of 33±18 μM suggests that intracellular accumulation may allow it to inhibit PTP1B inside the cell. Our ability to detect a weak inhibitor suggests that the B2H system can capture a broad set of scaffolds in molecular discovery efforts. The purification and analysis of additional hits, the incorporation of isoprenoid substrates of different sizes (through the use of geranyl diphosphate synthase or geranyl geranyl diphosphate synthase), and the inclusion of more uncharacterized genes could expand the scope of such efforts.

Design of Alternative PTP-Specific Objectives

Figures 25A, 25B, 25C:
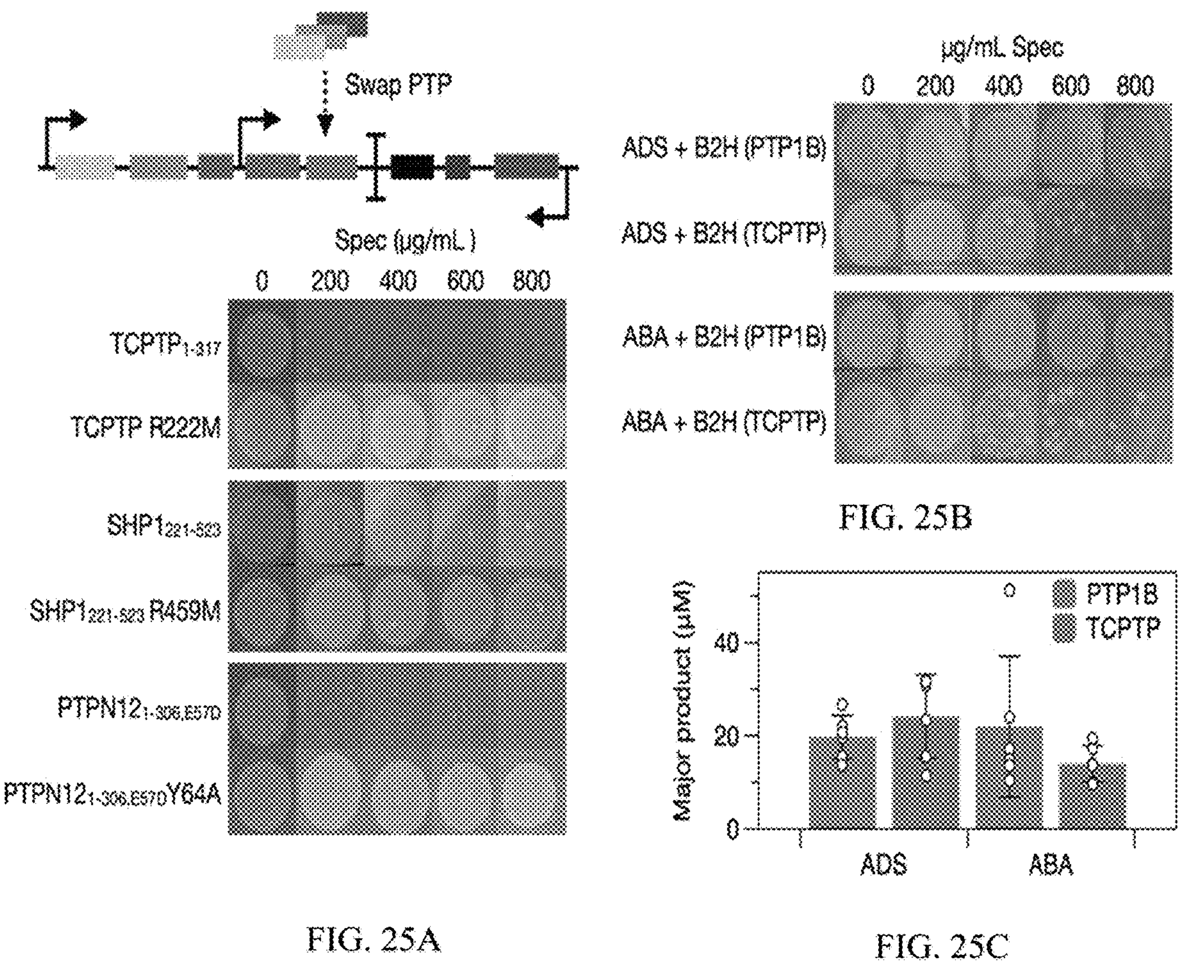
FIGS. 25A-25C.| Extension to other disease-related PTPs.

We explored the versatility of our B2H system by assessing its ability to detect the inactivation of several other diseases-relevant PTPs. In short, we swapped out the gene for PTP1B with genes for PTPN2, PTPN6, or PTPN12; these enzymes are targets for immunotherapeutic enhancement[55], the treatment of ovarian cancer[56], and acute myocardial infarction[57], respectively. Their catalytic domains share 31-65% sequence identity with the catalytic domain of PTP1B. Interestingly, the new B2H systems were immediately functional; PTP inactivation permitted growth at high concentrations of spectinomycin (FIG. 25A). This finding suggests that our detection system can be easily extended to other members of the PTP family.

PTP-specific B2H systems could facilitate the identification of natural products that selectively inhibit one PTP over another. We explored this application by comparing the antibiotic resistance conferred by PTP1B- and TC-PTP-specific systems in response to metabolic pathways for AD and α-bisabolene (FIG. 25B). As expected, the PTP1B-specific system permitted growth at higher concentrations of antibiotic, a result consistent with the selectivity of both terpenoids for PTP1B. Indistinguishable terpenoid titers between the two strains suggest that this survival advantage does not result from difference in intracellular concentration (FIG. 25C). Findings thus indicate that a simple comparison of B2H systems—a potential secondary screen—offers a simple approach for evaluating the selectivity PTP-inhibiting gene products. Notably, high concentrations of inhibitors in two strains could swamp out selective effects; in such cases, terpenoid levels could be reduced with lower mevalonate concentrations.

This study addresses an important challenge of medicinal chemistry—the design of molecular structures that inhibit disease-relevant enzymes—by using a desired biochemical activity (i.e., an objective) as a genetically encoded constraint to guide molecular biosynthesis. This approach enabled the identification of two selective, biologically active inhibitors of PTP1B, an elusive drug target[58]. These molecules are not drugs, but they are promising scaffolds for lead development. Their mechanisms of modulation—which elicit allosteric conformational changes yet appear to rely on loose, conformationally flexible binding—are unusual (and computationally elusive[59]), and demonstrate the ability of microbial systems to find new solutions to difficult challenges in molecular design. Our identification of unusual inhibitors in relatively small libraries, in turn, suggests that microbial systems can access a rich molecular landscape that is not efficiently explored by existing approaches to molecular discovery.

The B2H system at the core of our approach is a valuable tool for identifying biologically active natural products, which are structurally complex, difficult to synthesize, and often hidden in cryptic gene clusters[60]. It has several key advantages over contemporary approaches to inhibitor discovery: (i) It incorporates synthesizability as a search criterion—an important attribute of drug leads[61]. (ii) It is scalable. We used a growth-coupled assay to screen 24 uncharacterized terpene synthases; this type of assay is also compatible with very large mutagenesis libraries (e.g., $10^{10}$) [62]. (iii) It can use cellular machinery to stabilize proteins (e.g., CDC37 for Src); this capability could facilitate the integration of unstable and/or disordered targets. Future efforts to exploit these advantages by incorporating large libraries of mutated and/or reconfigured pathways, alternative biosynthetic enzymes (e.g., cytochromes P450, halogenases, and methyltransferases), or new classes of disease-relevant enzymes would be informative.

The B2H system also has important limits. When used alongside metabolic pathways, it links survival not only to the potency of metabolites, but also to their titers, off-target effects, and pathway toxicities. These limitations can be beneficial; they bias the discovery process toward potent, readily synthesizable inhibitors and could, thus, facilitate post-discovery efforts to improve the titers of interesting molecules[63]. Nonetheless, they will exclude some types of structurally complex molecules that are difficult to synthesize in *E. coli*. The use of similar activity-based screens in other organisms (e.g., *Streptomyces*) could be interesting.

The compatibility of our discovery approach with different PTPs is valuable in light of their increasingly well validated potential as a rich- and essentially untapped-source of new therapeutic targets[64]. We anticipate that some PTPs will require the use of chaperones and/or transcriptional adjustments to be incorporated into B2H systems. Our systematic optimization of the PTP1B-based system provides an experimental framework for exploring these modifications. Side-by-side comparisons of B2H systems, in turn, offer a promising strategy for evaluating inhibitor selectivity in secondary screens. In future work, new varieties of objectives (e.g., B2H systems or genetic circuits that detect the selective inhibition—or, perhaps, activation—of one PTP over another) could facilitate the discovery of molecules with sophisticated mechanisms of modulation in primary screens. The versatility of genetically encoded objectives highlights the power of using microbial systems to find targeted, biologically active molecules.

Note 1: The orthogonality of proteomes. *E. coli* and *S. cerevisiae* are both well-developed platforms for the production of pharmaceutically relevant natural products[20,65,66]. We chose to use *E. coli* for this study because its machinery for phosphorylating proteins is dissimilar from that of eukaryotic cells and thus less likely to interfere with the function of genetically encoded systems that link the inhibition of PTP1B to cellular growth[67]. By contrast, the overexpression of Src kinase in *S. cerevisiae* is lethal and is mitigated by PTP1B[68]; these effects are inconsistent with our biochemical objective. More broadly, *S. cerevisiae* and humans, despite having evolved from a common ancestor approximately 1 billion years ago[69], share many functionally equivalent proteins; orthologous genes, in fact, account for more than one-third of the yeast genome[70]. Most strikingly, a recent study found that nearly half (47%) of 414 essential genes from *S. cerevisiae* could be replaced with human orthologs without growth defects[71]. This finding suggests that yeast is a particularly restrictive host for genetically encoded systems that link arbitrary changes in the activities of human regulatory enzymes to fitness advantage.

Methods

Bacterial strains. We used *E. coli* DH10B, chemically competent NEB Turbo, or electrocompetent One Shot Top10 (Invitrogen) to carry out molecular cloning and to perform preliminary analyses of terpenoid production; we used *E. coli* BL2-DE31 to express proteins for in vitro studies; and we used *E. coli* s103072 for our luminescence studies and for all experiments involving terpenoid-mediated growth (i.e., evolution studies).

For all strains, we generated chemically competent cells by carrying out the following steps: (i) We plated each strain on LB agar plates with the required antibiotics. (ii) We used one colony of each strain to inoculate 1 mL of LB media (25 g/L LB with appropriate antibiotics listed in TABLE 8) in a glass culture tube, and we grew this culture overnight (37° C., 225 RPM). (iii) We used the 1-mL culture to inoculate 100-300 mL of LB media (as above) in a glass shake flask, and we grew this culture for several hours (37° C., 225 RPM). (iv) When the culture reached an OD of 0.3-0.6, we centrifuged the cells (4,000×g for 10 minutes at 4° C.), removed the supernatant, resuspended them in 30 mL of ice cold TFB1 buffer (30 mM potassium acetate, 10 mM $CaCl_2$, 50 mM $MnCl_2$, 100 mM RbCl, 15% v/v glycerol, water to 200 mL, pH=5.8, sterile filtered), and incubated the suspension at 4° C. for 90 min. (v) We repeated step iv, but resuspended in 4 mL of ice cold TFB2 buffer (10 mM MOPS, 75 mM $CaCl_2$), 10 mM $RbCl_2$, 15% glycerol, water to 50 mL, pH=6.5, sterile filtered). (iv) We split the final suspension into 100 μL aliquots and froze them at −80° C. until further use.

We generated electrocompetent cells by following an approach similar to the one above. In step iv, however, we resuspended the cells in 50 mL of ice cold MilliQ water and repeated this step twice-first with 50 mL of 20% sterile glycerol (ice cold) and, then, with 1 mL of 20% sterile glycerol (ice cold). We froze the pellets as before.

Materials. We purchased methyl abietate from Santa Cruz Biotechnology; trans-caryophyllene, tris(2-carboxyethyl) phosphine (TCEP), bovine serum albumin (BSA), M9 minimal salts, phenylmethylsulfonyl fluoride (PMSF), and DMSO (dimethyl sulfoxide) from Millipore Sigma; glycerol, bacterial protein extraction reagent II (B-PERII), and lysozyme from VWR; cloning reagents from New England Biolabs; AD from Ambeed, Inc.; and all other reagents (e.g., antibiotics and media components) from Thermo Fisher. Taxadiene was a kind gift from Phil Baran of the The Scripps Research Institute. We prepared mevalonate by mixing 1 volume of 2 M DL-mevalanolactone with 1.05 volumes of 2 M KOH and incubating this mixture at 37° C. for 30 minutes.

Cloning and molecular biology. We constructed all plasmids by using standard methods (i.e., restriction digest and ligation, Golden Gate and Gibson assembly, Quikchange mutagenesis, and circular polymerase extension cloning). TABLE 7 describes the source of each gene; TABLE 8 and TABLE 3 describe the composition of all final plasmids.

We began construction of the B2H system by integrating the gene for HA4-RpoZ from pAB094a into pAB078d and by replacing the ampicillin resistance marker of pAB078d with a kanamycin resistance marker (Gibson Assembly). We modified the resulting. "combined" plasmid, in turn, by replacing the HA4 and SH2 domains with kinase substrate and substrate recognition (i.e., SH2) domains, respectively (Gibson assembly), and by integrating genes for Src kinase, CDC37, and PTP1B in various combinations (Gibson assembly). We finalized the functional B2H system by modifying the SH2 domain with several mutations known to enhance its affinity for phosphopeptides (K15L, T8V, and C10A, numbered as in Kaneko et. al.[35]), by exchanging the GOI for luminescence (LuxAB) with one for spectinomycin resistance (SpecR), and by toggling promoters and ribosome binding sites to enhance the transcriptional response (Gibson assembly and Quickchange Mutagenesis, Agilent Inc.). We note: For the last step, we also converted Pro1 to ProD by using the Quikchange protocol. When necessary, we constructed plasmids with arabinose-inducible components by cloning a single component from the B2H system into pBAD (Golden Gate assembly). TABLE 4, TABLE 9, and TABLE 10 list the primers and DNA fragments used to construct each plasmid.

We assembled pathways for terpenoid biosynthesis by purchasing plasmids encoding the first module (pMBIS) and various sesquiterpene synthases (ADS or GHS in pTRC99a) from Addgene, and by building the remaining plasmids. We replaced the tetracycline resistance in pMBIS with a gene for chloramphenicol resistance to create $pMBIS_{CmR}$. We integrated genes for ABS, TXS, ABA, and GGPPS into pTRC99t (i.e., pTRC99a without BsaI sites). TABLE 4, TABLE 9, and TABLE 10 list the primers and DNA fragments used to construct each plasmid.

Luminescence assays. We characterized preliminary B2H systems (which contained LuxAB as the GOI) with luminescence assays. In brief, we transformed necessary plasmids into *E. coli* s1030 (TABLE 8), plated the transformed cells onto LB agar plates (20 g/L agar, 10 g/L tryptone, 10 g/L sodium chloride, and 5 g/L yeast extract with antibiotics described in TABLE 8), and incubated all plates overnight at 37° C. We used individual colonies to inoculate 1 ml of terrific both (TB at 2%, or 12 g/L tryptone, 24 g/L yeast extract, 12 mL/L 100% glycerol, 2.28 g/L $KH_2PO_4$, 12.53 g/L $K_2HPO_4$, pH=7.3, and antibiotics described in TABLE 8), and we incubated these cultures overnight (37° C. and 225 RPM). The following morning, we diluted each culture by 100-fold into 1 ml of TB media (above), and we incubated these cultures in individual wells of a deep 96-well plate for 5.5 hours (37° C., 225 RPM). (We note: When pBAD was present, we supplemented the TB media with 0-0.02 w/v % arabinose). We transferred 100 μL of each culture into a single well of a standard 96-well clear plate and measured both $OD_{600}$ and luminescence on a Biotek Synergy plate reader (gain: 135, integration time: 1 second, read height: 1 mm). Analogous measurements of cell-free media allowed us to measure background signals, which we subtracted from each measurement prior to calculating OD-normalized luminescence (i.e., Lum/$OD_{600}$).

Analysis of antibiotic resistance. We evaluated the spectinomycin resistance conferred by various B2H systems in the absence of terpenoid pathways by carrying out the following steps: (i) We transformed *E. coli* with the necessary plasmids (TABLE 8) and plated the transformed cells onto LB agar plates (20 g/L agar, 10 g/L tryptone, 10 g/L sodium chloride, 5 g/L yeast extract, 50 μg/ml kanamycin, 10 μg/ml tetracycline). (ii) We used individual colonies to inoculate 1-2 ml of TB media (12 g/L tryptone, 24 g/L yeast extract, 12 mL/L 100% glycerol, 2.28 g/L $KH_2PO_4$, 12.53 g/L $K_2HPO_4$, 50 μg/ml kanamycin, 10 μg/ml tetracycline, pH=7.3), and we incubated these cultures overnight (37° C., 225 RPM). In the morning, we diluted each culture by 100-fold into 4 ml of TB media (as above) with 0-500 μg/ml spectinomycin (we used spectinomycin in the liquid culture only for FIG. 14), and we incubated these cultures in deep 24-well plates until wells containing 0 μg/ml spectinomycin reached an $OD_{600}$ of 0.9-1.1. (iv) We diluted each 4-ml culture by 10-fold into TB media with no antibiotics and plated 10-μL drops of the diluent onto agar plates with various concentrations of spectinomycin. (v) We incubated plates overnight (37° C.) and photographed them the following day.

To examine terpenoid-mediated resistance, we began with steps i and ii as described above with the addition of 34 μg/ml chloramphenicol and 50 μg/ml carbenicillin in all liquid/solid media. We then proceeded with the following steps: (iii) We diluted samples from 1-ml cultures to an $OD_{600}$ of 0.05 in 4.5 ml of TB media (supplemented with 12 g/L tryptone, 24 g/L yeast extract, 12 mL/L 100% glycerol, 2.28 g/L $KH_2PO_4$, 12.53 g/L $K_2HPO_4$, 50 μg/ml kanamycin, 10 μg/ml tetracycline, 34 μg/ml chloramphenicol, and 50 μg/ml carbenicillin), which we incubated in deep 24-well plates (37° C., 225 RPM). (iv) At an $OD_{600}$ of 0.3-0.6, we transferred 4 ml of each culture to a new well of a deep 24-well plate, added 500 μM isopropyl β-D-1-thiogalactopyranoside (IPTG) and 20 mM of mevalonate, and incubated for 20 hours (22° C., 225 RPM). (v) We diluted each 4-ml culture to an $OD_{600}$ of 0.1 with TB media and plated 10 μL of the diluent onto either LB or TB plates supplemented with 500 μM IPTG, 20 mM mevalonate, 50 μg/ml kanamycin, 10 μg/ml tetracycline, 34 μg/ml chloramphenicol, 50 μg/ml carbenicillin, and 0-1200 μg/ml spectinomycin (for both plates, we used 20 g/L agar with media and buffer components described above).

Terpenoid biosynthesis. We prepared *E. coli* for terpenoid production by transforming cells with plasmids harboring requisite pathway components (TABLE 8) and plating them onto LB agar plates (20 g/L agar, 10 g/L tryptone, 10 g/L sodium chloride, and 5 g/L yeast extract with antibiotics described in TABLE 8). We used one colony from each strain to inoculate 2 ml TB (12 g/L tryptone, 24 g/L yeast extract, 12 mL/L 100% glycerol, 2.28 g/L $KH_2PO_4$, 12.53 g/L $K_2HPO_4$, pH=7.0, and antibiotics described in TABLE 8) in a glass culture tube for ~16 hours (37° C. and 225 RPM). We diluted these cultures by 75-fold into 10 ml of TB media and incubated the new cultures in 125 mL glass shake flasks (37° C. and 225 RPM). At an $OD_{600}$ of 0.3-0.6, we added 500 μM IPTG and 20 mM mevalonate. After 72-88 hours of growth (22° C. and 225 RPM), we extracted terpenoids from each culture as outlined below.

Protein expression and purification. We expressed and purified PTPs as described previously[73]. Briefly, we transformed *E. coli* BL21 (DE3) cells with pET16b or pET21b vectors (see TABLE 8 for details), and we induced with 500 μM IPTG at 22° C. for 20 hours. We purified PTPs from cell lysate by using desalting, nickel affinity, and anion exchange chromatography (HiPrep 26/10, HisTrap HP, and HiPrep Q HP, respectively; GE Healthcare). We stored the final protein (30-50 μM) in HEPES buffer (50 mM, pH 7.5, 0.5 mM TCEP) in 20% glycerol at −80° C.

Extraction and purification of terpenoids. We used hexane to extract terpenoids generated in liquid culture. For 10-mL cultures, we added 14 mL of hexane to 10 ml of culture broth in 125-mL glass shake flasks, shook the mixture (100 RPM) for 30 minutes, centrifuged it (4000×g), and withdrew 10 mL of the hexane layer for further analysis. For 4-mL cultures, we added 600 μL hexane to 1 mL of culture broth in a microcentrifuge tube, vortexed the tubes for 3 minutes, centrifuged the tubes for 1 minute (17000×g), and saved 300-400 μL of the hexane layer for further analysis.

To purify AD, AB, and (+)-1 (10),4-cadinadiene, we supplemented 500-1000 mL culture broth with hexane (16.7% v/v), shook the mixture for 30 minutes (100 RPM), isolated the hexane layer with a separatory funnel, centrifuged the isolated organic phase (4000×g), and withdrew the hexane layer. To concentrate the terpenoid products, we evaporated excess hexane in a rotary evaporator to bring the final volume to 500 μL, and we passed the resulting mixture over a silica gel 1-3 times (Sigma-Aldrich; high purity grade, 60 Å pore size, 230-400 mesh particle size). We analyzed elution fractions (100% hexane) on the GC/MS and pooled fractions with the compound of interest (AD). Once purified, we dried pooled fractions under a gentle stream of air, resuspended the concentrated terpenoids in DMSO, and quantified the final samples as outlined below. We repeated the purification process until samples (in DMSO) were >95% pure by GC/MS unless otherwise noted.

GC-MS analysis of terpenoids. We measured terpenoids generated in liquid culture with a gas chromatograph/mass spectrometer (GC-MS; a Trace 1310 GC fitted with a TG5-SilMS column and an ISQ 7000 MS; Thermo Fisher Scientific). We prepared all samples in hexane. (directly or through a 1:100 dilution of DMSO) with 20 μg/ml of caryophyllene as an internal standard. Highly concentrated samples were diluted 10-20× prior to preparation to bring concentrations within the MS detection limit. When the peak area of an internal standard exceeded ±40% of the average area of all samples containing that standard, we re-analyzed the corresponding samples. For all runs, we used the following GC method: hold at 80° C. (3 min), increase to 250° C. (15° C./min), hold at 250° C. (6 min), increase to 280° C. (30° C./min), and hold at 280° C. (3 min). To identify various analytes, we scanned m/z ratios from 50 to 550.

We examined sesquiterpenes generated by variants of ADS by using select ion mode (SIM) to scan for the molecular ion (m/z=204). For quantification, we used Eq. 1: where $A_i$ $$C_i = C_{std} * \frac{A_i}{A_{std}} * R \quad \text{(Eq. 1)}$$

$$R = \frac{A_{std,o}/C_{std,o}}{A_{ref,o}/C_{ref,o}} \quad \text{(Eq. 2)}$$

is the area of the peak produced by analyte i, $A_{std}$ is the area of the peak produced by $C_{std}$ of caryophyllene in the sample, and R is the ratio of response factors for caryophyllene and AD in a reference sample. TABLE 11 provides the concentrations of all standards and reference compounds used in this analysis.

We quantified diterpenoids by, once again, accompanying our general procedure with several modifications: We scanned for a different molecular ion (m/z=272) and an ion common to both diterpenoids and caryophyllene (m/z=93); we used a ratio of response factors for pure taxadiene (a kind gift from Phil Baran) and caryophyllene at m/z=93; and we calculated peak areas m/z=93. For all analyses, we examined only peaks with areas that exceeded 1% of the total area of all peaks at m/z=272.

We identified molecules by using the NIST MS library and, when necessary, confirmed this identification with analytical standards or mass spectra reported in the literature. We note: The assumption of a constant response factor for different terpenoids (that is, the assumption that all sesquiterpenes and diterpenes ionize like AD and taxadiene, respectively) can certainly yield error in estimates of their concentrations; our analyses, which are consistent with those of other studies of terpenoid production in microbial systems[74,75], supply rough estimates of concentrations for all compounds except AD and taxadiene (which had analytical standards).

Bioinformatics. We used a bioinformatic analysis to identify a phylogenetically diverse set of terpene synthases. Briefly, we downloaded (i) all constituent genes of PF03936 (the largest terpene synthase family grouped by a C-terminal domain) from the PFAM Database and (ii) all enzymes with Enzyme Commission (EC) number of 4.2.3. # from the Uniprot Database; this string, which defines carbon oxygen lyases that act on phosphates, includes terpene synthases. We cleaned both datasets in Excel (i.e., we ensured that every identifier had only one row), and we used a custom R script to designate each PF03936 member as characterized (i.e., in possession of a Uniprot-based EC number) or uncharacterized. Finally, we used FastTree[76] with default settings to create a phylogenetic tree of the PF03936 family and the R-package ggtree[77] to visualize the resulting tree and function data as a cladogram and heatmap.

After annotating the cladogram by hand, we selected three genes from each of six clades: six with no characterized genes and two with some characterized genes. We avoided clades proximal to known monoterpene synthases or diterpene synthases known to act on GGPP isomers absent in our system (e.g., ent-copalyl diphosphate); these enzymes are unlikely to act on FPP, the primary product of $pMBIS_{CmR}$. When selecting enzymes within clades, we biased our choice towards bacterial/fungal species and selected genes with a minimal number of common ancestors within the clade. The selected genes were synthesized and cloned into the pTrc99a vector by Twist Biosciences and assayed for antibiotic resistance as described above.

Enzyme kinetics. To examine terpenoid-mediated inhibition, we measured PTP-catalyzed hydrolysis of p-nitrophenyl phosphate (pNPP) or 4-methylumbelliferyl phosphate (4-MUP, used when KM for pNPP was large) in the presence of various concentrations of terpenoids. Each reaction included PTP (0.05 μM PTP1B/TCPTP or 0.1 μM SHP1/SHP2 in 50 mM HEPES, 0.5 mM TCEP, 50 μg/ml BSA), pNPP (0.33, 0.67, 2, 5, 10, and 15 mM) or 4-MUP (0.13, 0.27, 0.8, 2.27, 2.93, 4.53, 7.07, and 8 mM), inhibitor (with concentrations listed in the figures), buffer (50 mM HEPES pH=7.3, 50 μg/ml BSA), and DMSO at 10% v/v. We monitored the formation of p-nitrophenol by measuring absorbance at 405 nm every 10 seconds for 5 minutes on a SpectraMax M2 plate reader and the formation of 4-methylumbelliferyl by measuring fluorescence at 450 nm (370 nm ex, 435 nm cutoff, medium gain).

Figures 39A, 39B:
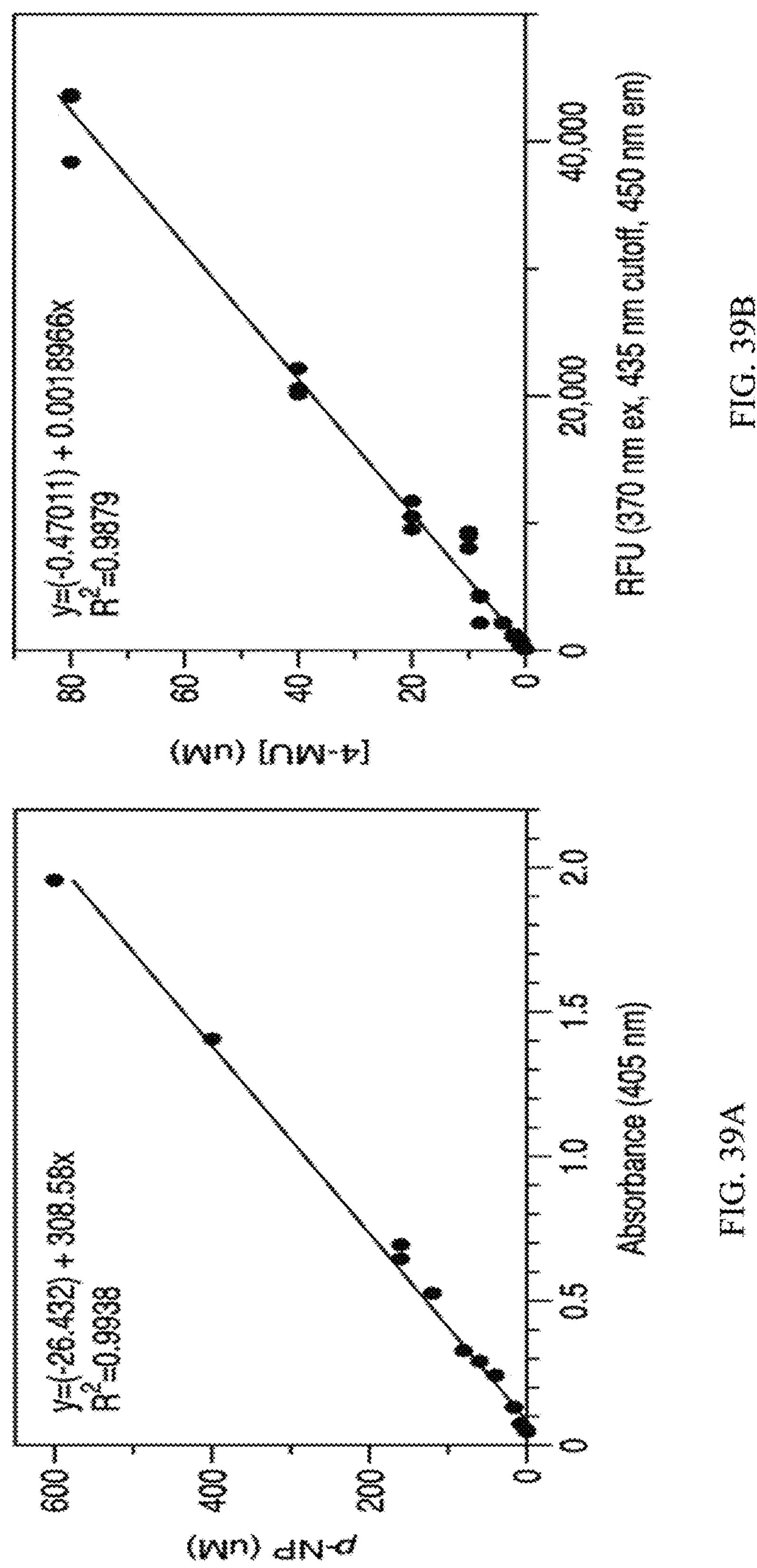
FIGS. 39A-39B. A standard curve for p-nitrophenol (p-NP). This figure elaborates on FIG. 20 by including additional measurements.

We used a custom MATLAB script to process all raw kinetic data. This script removed all concentration values that fell outside of either (i) the range of our standard curve (absorbance/fluorescence vs. μM; FIG. 39) or (ii) the initial rate regime (>10% of the pNPP or 4-MUP concentration used in the assay). When this step reduced kinetic dataset to fewer than ten points, we re-measured those datasets to collect at least ten. We fit final datasets, in turn, with a linear regression model (using Matlab's backslash operator).

We evaluated kinetic models in three steps: (i) We fit initial-rate measurements collected in the absence and presence of inhibitors to Michaelis-Menten and inhibition models, respectively (here, we used the nlinfit and fminsearch functions from MATLAB; TABLE 12). (ii) We used an F-test to compare the mixed model to the single-parameter model with the least sum squared error (here, we used the fcdf function from MATLAB to assign p-values), and we accepted the mixed model when $p<0.05$. (iii) We used the Akaike's Information Criterion (AIC) to compare the best-fit single parameter model to each alternative single parameter model, and we accepted the "best-fit" model when the difference in AIC ($\Delta_i$) exceed 5 for all comparisons.[78] We note: For AD, AB, and (+) 1-(10),4-cadinadiene this criterion was not met; both noncompetitive and uncompetitive models, however, yielded indistinguishable ICso's.

We estimated the half maximal inhibitory concentration ($IC_{50}$) of inhibitors by using the best-fit kinetic models to determine the concentration of inhibitor required to reduce initial rates of PTP-catalyzed hydrolysis of 15 mM of pNPP by 50%. We used the MATLAB function "nlparci" to determine the confidence intervals of kinetic parameters, and we propagated those intervals to estimate corresponding confidence intervals for each $IC_{50}$.

X-ray crystallography. We prepared crystals of PTP1B by using hanging drop vapor diffusion. In brief, we added 2 μL of PTP1B (~600 μM PTP1B, 50 mM HEPES, pH 7.3) to 6 μL of crystallization solution (100 mM HEPES, 200 mM magnesium acetate, and 14% polyethylene glycol 8000, pH 7.5) and incubated the resulting droplets over crystallization solution for one week at 4° C. (EasyXtal CrystalSupport, Qiagen). We soaked crystals with ligand by transferring them to droplets formed with 6 μL of crystallization solution and 1 μL of ligand solution (10 mM in DMSO), which we incubated for 2-5 days at 4° C. We prepared all ligands for freezing by soaking them in cryoprotectant formed from a 70/30 (v/v) mixture of buffer (100 mM HEPES, 200 mM magnesium acetate, and 25% polyethylene glycol 8000, pH 7.5) and glycerol.

We collected X-ray diffraction data through the Collaborative Crystallography Program at Lawrence Berkeley National Lab (ALS ENABLE, beamline 8.2.1, 100 K, 1.00003 Å). We performed integration, scaling, and merging of X-ray diffraction data using the xia2 software package[79], and we carried out molecular replacement and structure refinement with the PHENIX graphical interface,[80] supplemented with manual model adjustment in COOT[81] and one round of PDB-REDO[82] (the latter, only for the PTP1B-AD complex).

Molecular dynamics (MD) simulations. Full-length PTP1B contains a disordered region that extends beyond the α7 helix (i.e., 299-435). In this study, we used a well-studied truncation variant (i.e., $PTP1B_{1-321}$) that includes residues from the disordered region. To model PTP1B, we used CAMPARI v.2[83] to generate structures of the disordered region of each complex (i.e., residues 288-321 for PTP1B-AD) from a crystal structure without a disordered tail. To quickly thermalize the tail structures, we ran short Monte Carlo (MC) simulations using the ABSINTH implicit-solvent force field[84,85], fixing the coordinates of the atoms in the ligand and the protein core.

We performed MD simulations using GROMACS 2020[86]. Briefly, we used the CHARMM36m protein force field[87], a CHARMM-modified TIP3P water model[88], and ligand parameters generated by CGenFF[89,90]. We solvated each PTP1B-ligand complex (initialized from the corresponding crystal structure) in a dodecahedral box with edges positioned ≥10 Å from the surface of the complex, and we added six sodium ions to neutralize each system. We used the LINCS algorithm[91] to constrain all bonds involving hydrogen atoms, the Verlet leapfrog algorithm to numerically integrate equations of motion with a 2-fs time step, and the particle-mesh Ewald summation[92] (cubic interpolation with a grid spacing of 0.16 nm) to calculate long-range electrostatic interactions; we used a cutoff of 1.2 nm, in turn, for short-range electrostatic and Lennard-Jones interactions. We independently coupled the protein-ligand complex and solvent molecules to a temperature bath (300K) using a modified Berendsen thermostat[93] with a relaxation time of 0.1 ps, and we fixed pressure coupling to 1 bar using the Parrinello-Rahman algorithm[94] with a relaxation time of 2 ps and isothermal compressibility of $4.5\times10^{-5}$ $bar^{-1}$.

For each system, we carried out 30 independent MD simulations to reduce sampling bias. For each MD trajectory, we minimized energy using the steepest decent method followed by 100-ps solvent relaxation in the NVT ensemble and 100-ps solvent relaxation in the NPT ensemble. After an additional 5-ns NPT equilibration, we carried out production runs for 5 ns in the NPT ensemble and registered coordinate data every 10 ps.

Analysis of PTP1B inhibition in HEK293TCells. We prepared HEK293T/17 cells for an enzyme-linked immunosorbent assay (ELISA) by growing them in 75 $cm^2$ culture flasks (Corning) with DMEM media supplemented with 10% FBS, 100 units/ml penicillin, and 100 units/ml streptomycin. We replaced the media every day for 3-5 days until the cells reached 80-100% confluency.

Figure 35B:
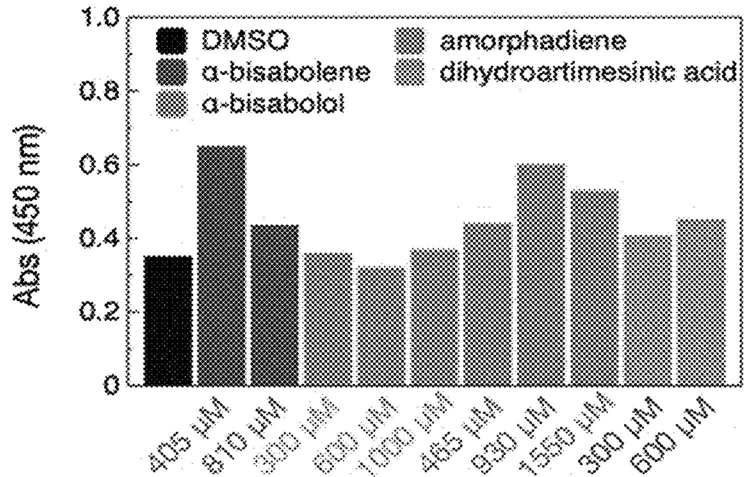
Figure 35C:
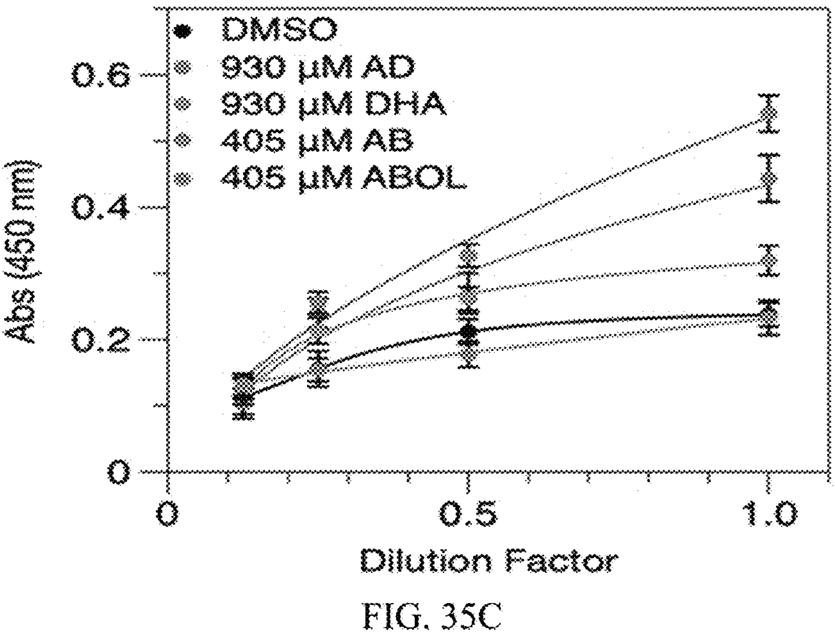
Figures 36A, 36B, 36C:
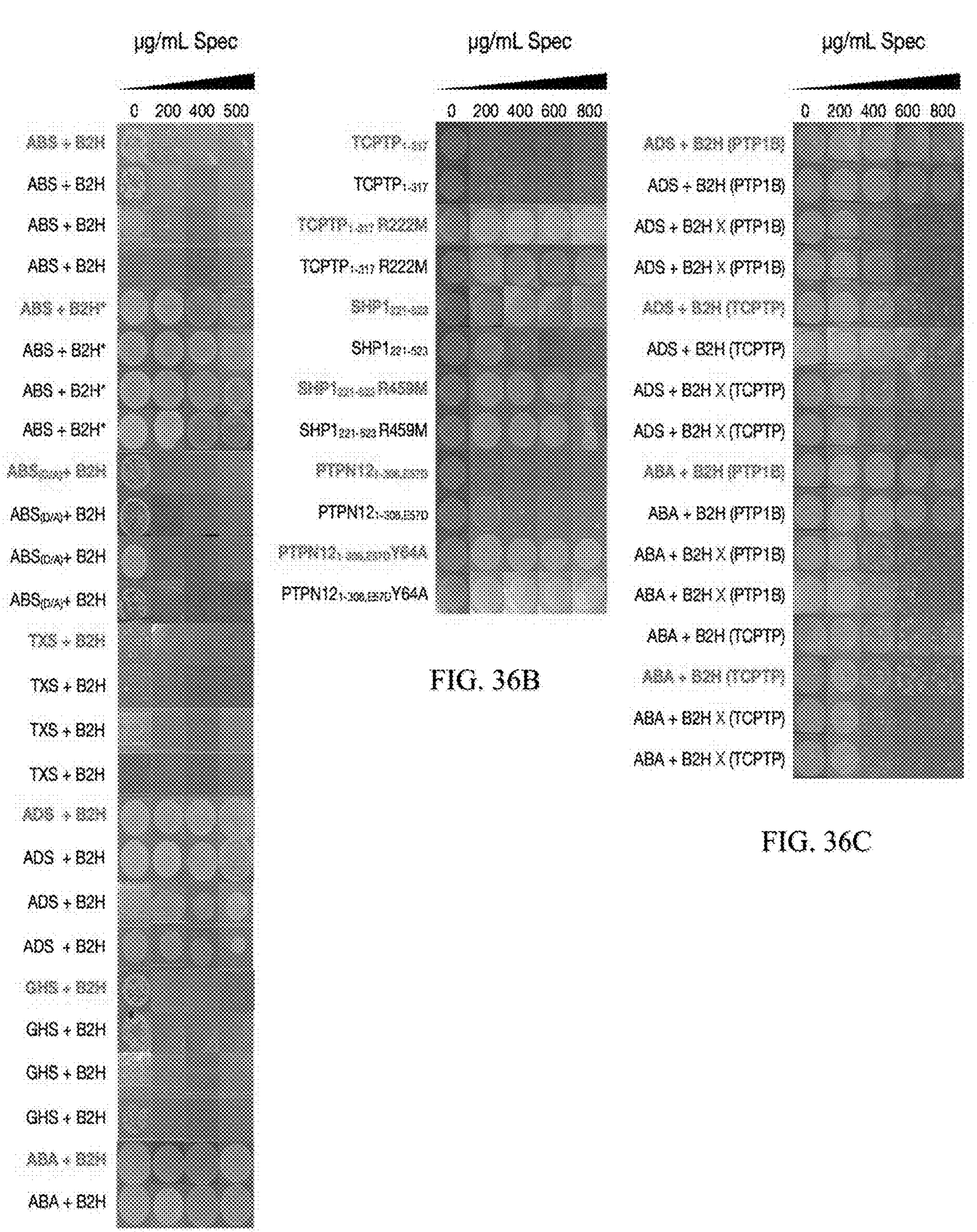
FIGS. 36A-36C. Full datasets for B2H-mediated antibiotic resistance.
Figures 37A, 37B:
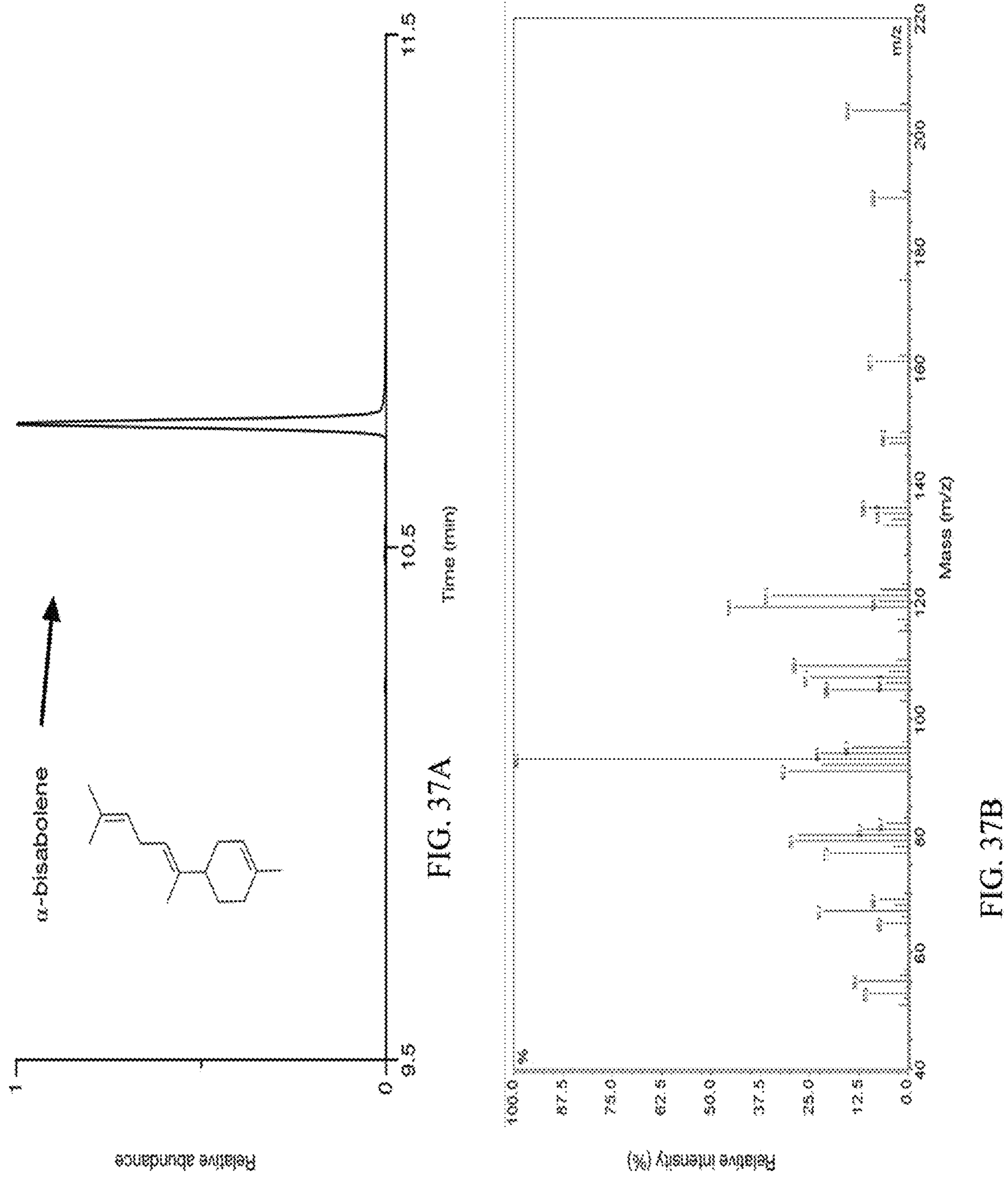
FIGS. 37A-37B. GC/MS analysis of α-bisabolene production.
Figure 38A:
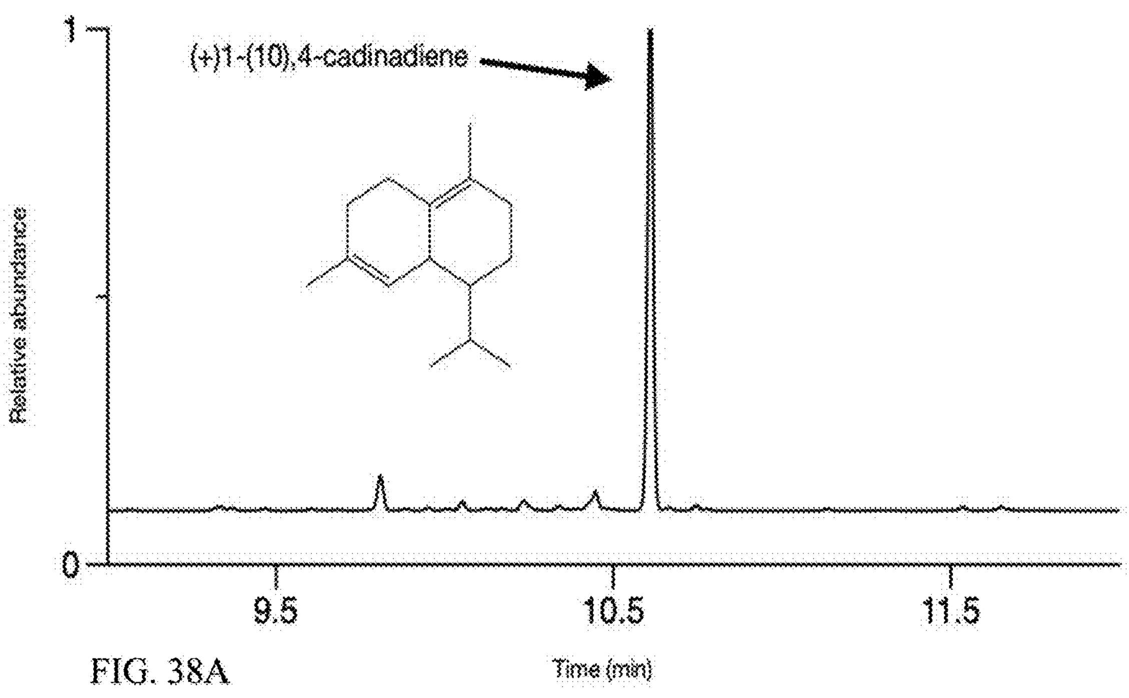
FIGS. 38A-38B. Supplementary FIG. 20|GC/MS analysis of (+)-1 (10),4-Cadinadiene.
Figure 38B:
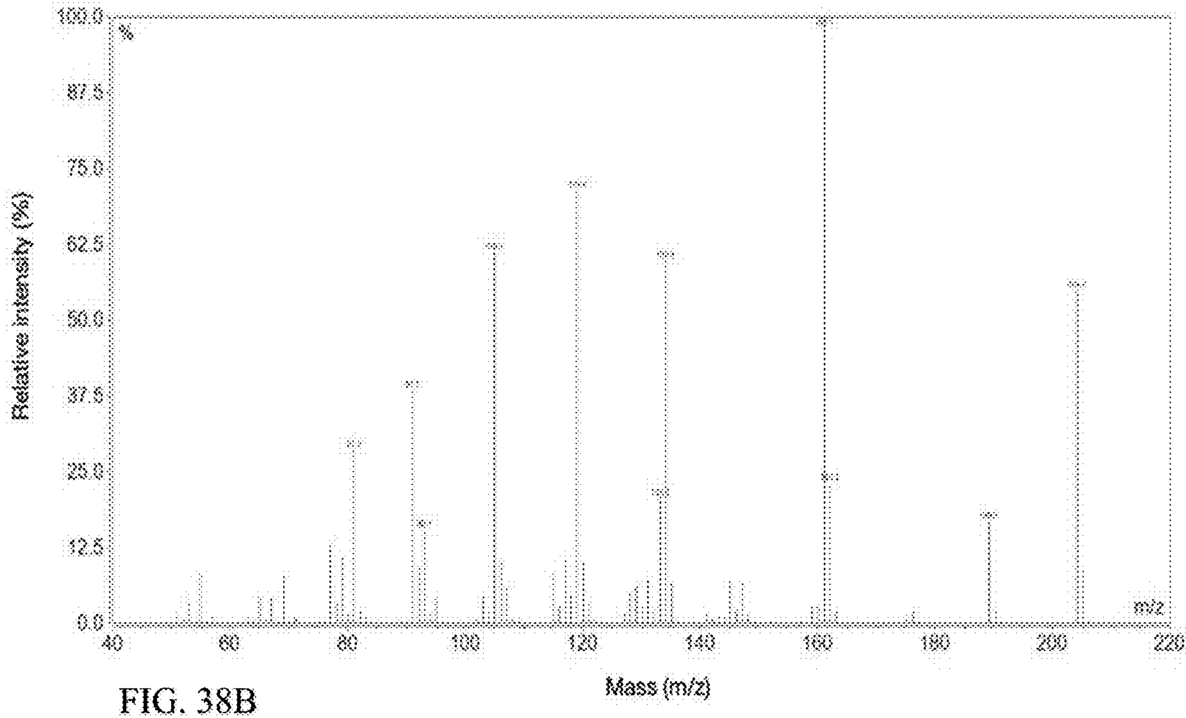

We measured the influence of inhibitors on insulin receptor (IR) phosphorylation by using an IR-specific ELISA (FIG. 35). Briefly, we starved cells for 48 hours in FBS-free media and incubated the with inhibitors (all at 3% DMSO) for 10 minutes. After incubation, we lysed cells with lysis buffer (9803, Cell Signaling Technology) supplemented with 1× halt phosphatase inhibitor cocktail and 1× halt protease inhibitor cocktail (Thermo Fisher Scientific) for 10 min, pelleted the cell debris, and used the lysis buffer to dilute each sample to 60 mg/ml total protein. We measured IR phosphorylation in subsequent dilutions of the 60 mg/ml samples with the PathScan® Phospho-Insulin Receptor β (panTyr) Sandwich ELISA Kit (Cell Signaling Technology; #7082). We note: To identify biologically active concentrations of AB and AD, we screened several concentrations and chose those that gave the highest signal (405 UM for AB and 930 μM for AD); similar concentrations of weak inhibitors did not yield a detectable signal (FIGS. 35B and 35C).

Statistical analysis and reproducibility. We determined statistical significance (FIG. 23H) with a two-tailed Student's t-test (details in TABLE 14), and we used an F-test to compare one- and two-parameter models of inhibition (TABLE 12).

REFERENCES FOR EXAMPLE 2

1. Olsson, T. S. G., Williams, M. a., Pitt, W. R. & Ladbury, J. E. The Thermodynamics of Protein-Ligand Interaction and Solvation: Insights for Ligand Design. *J. Mol. Biol.* 384, 1002-1017 (2008).
2. Fox, J. M., Zhao, M., Fink, M. J., Kang, K. & Whitesides, G. M. The Molecular Origin of Enthalpy/Entropy Compensation in Biomolecular Recognition. *Annu. Rev. Biophys.* 47, (2018).
3. Mobley, D. L. & Gilson, M. K. Predicting Binding Free Energies: Frontiers and Benchmarks. *Annu. Rev. Biophys.* 46, 531-558 (2017).
4. Hert, J., Irwin, J. J., Laggner, C., Keiser, M. J. & Shoichet, B. K. Quantifying biogenic bias in screening libraries. *Nat. Chem. Biol.* 5, pages 479-483 (2009).
5. Smanski, M. J. et al. Synthetic biology to access and expand nature's chemical diversity. *Nature Reviews Microbiology* 14, 135-149 (2016).
6. Fürstenberg-Hägg, J., Zagrobelny, M. & Bak, S. Plant defense against insect herbivores. *Int. J. Mol. Sci.* 14, 10242-10297 (2013).
7. Maier, M. E. Design and synthesis of analogues of natural products. *Organic and Biomolecular Chemistry* 13, 5302-5343 (2015).
8. Chen, M. S. & White, M. C. A predictably selective aliphatic C—H oxidation reaction for complex molecule synthesis. *Science* (80-.). 318, 783-787 (2007).
9. Cho, I., Jia, Z. J. & Arnold, F. H. Site-selective enzymatic C—H amidation for synthesis of diverse lactams. *Science* (80-.). 364, 575-578 (2019).
10. Atanasov, A. G. et al. A Historical overview of natural products in drug discovery. *Metabolites* 33, 1582-1614 (2012).
11. Paul, S. M. et al. How to improve RD productivity: The pharmaceutical industry's grand challenge. *Nature Reviews Drug Discovery* 9, 203-214 (2010).
12. Li, J. W. H. & Vederas, J. C. Drug discovery and natural products: End of era or an endless frontier? *Biomeditsinskaya Khimiya* 57, 148-160 (2011).
13. Jensen, P. R., Chavarria, K. L., Fenical, W., Moore, B. S. & Ziemert, N. Challenges and triumphs to genomics-based natural product discovery. *J. Ind. Microbiol. Biotechnol.* 41, 203-209 (2014).
14. Medema, M. H. et al. AntiSMASH: Rapid identification, annotation and analysis of secondary metabolite biosynthesis gene clusters in bacterial and fungal genome sequences. *Nucleic Acids Res.* 39, W339-W346 (2011).
15. Jensen, P. R. Natural Products and the Gene Cluster Revolution. *Trends Microbiol.* 24, 968-977 (2016).
16. Yan, Y. et al. Resistance-gene-directed discovery of a natural-product herbicide with a new mode of action. *Nature* 559, 415-418 (2018).
17. Culp, E. J. et al. Evolution-guided discovery of antibiotics that inhibit peptidoglycan remodelling. *Nature* 578, 582-587 (2020).
18. Zhabinskii, V. N., Khripach, N. B. & Khripach, V. A. Steroid plant hormones: Effects outside plant kingdom. *Steroids* 97, 87-97 (2015).

19. Li, Y. et al. Complete biosynthesis of noscapine and halogenated alkaloids in yeast. *Proc. Natl. Acad. Sci. U.S.A* 115, E3922-E3931 (2018).
20. Luo, X. et al. Complete biosynthesis of cannabinoids and their unnatural analogues in yeast. *Nature* 567, 123-126 (2019).
21. He, R., Yu, Z., Zhang, R. & Zhang, Z. Protein tyrosine phosphatases as potential therapeutic targets. *Acta Pharmacol. Sin.* 35, 1227-1246 (2014).
22. Paul, M. K. & Mukhopadhyay, A. K. Tyrosine kinase-Role and significance in Cancer. *Int. J. Med. Sci.* 1, 101-115 (2012).
23. Ferguson, F. M. & Gray, N. S. Kinase inhibitors: The road ahead. *Nature Reviews Drug Discovery* 17, 353-376 (2018).
24. Stanford, S. M. & Bottini, N. Targeting Tyrosine Phosphatases: Time to End the Stigma. *Trends in Pharmacological Sciences* 38, 524-540 (2017).
25. Krishnan, N. et al. Targeting the disordered C terminus of PTP1B with an allosteric inhibitor. *Nat. Chem. Biol.* 10, 558-566 (2014).
26. Barr, A. J. et al. Large-Scale Structural Analysis of the Classical Human Protein Tyrosine Phosphatome. *Cell* 136, 352-363 (2009).
27. Banno, R. et al. PTP1B and SHP2 in POMC neurons reciprocally regulate energy balance in mice. *J. Clin. Invest.* 120, 720-734 (2010).
28. Zabolotny, J. M. et al. Protein-tyrosine phosphatase 1B. expression is induced by inflammation in vivo. *J. Biol. Chem.* 283, 14230-14241 (2008).
29. Matulka, K. et al. PTP1B is an effector of activin signaling and regulates neural specification of embryonic stem cells. *Cell Stem Cell* 13, 706-719 (2013).
30. Zhang, H., Wang, Y., Wu, J., Skalina, K. & Pfeifer, B. A. Complete biosynthesis of erythromycin A and designed analogs using *E. coli* as a heterologous host. *Chem. Biol.* 17, 1232-1240 (2010).
31. Antosch, J., Schaefers, F. & Gulder, T. A. M. Heterologous Reconstitution of Ikarugamycin Biosynthesis in *E. coli*. *Angew. Chemie Int. Ed.* 53, 3011-3014 (2014).
32. Montalibet, J. & Kennedy, B. P. Using yeast to screen for inhibitors of protein tyrosine phosphatase 1B. *Biochem. Pharmacol.* 68, 1807-1814 (2004).
33. Piserchio, A., Cowburn, D. & Ghose, R. Expression and purification of Src-family kinases for solution NMR studies. *Methods Mol. Biol.* 831, 111-131 (2012).
34. Badran, A. H. et al. Continuous evolution of *Bacillus thuringiensis* toxins overcomes insect resistance. *Nature* 533, 58-63 (2016).
35. Kaneko, T. et al. Superbinder SH2 domains act as antagonists of cell signaling. *Sci. Signal.* 5, ra68-ra68 (2012).
36. Jiang, C. S., Liang, L. F. & Guo, Y. W. Natural products possessing protein tyrosine phosphatase 1B (PTP1B) inhibitory activity found in the last decades. *Acta Pharmacologica Sinica* (2012). doi: 10.1038/aps.2012.90
37. Hjortness, M. K. et al. Abietane-Type Diterpenoids Inhibit Protein Tyrosine Phosphatases by Stabilizing an Inactive Enzyme Conformation. *Biochemistry* 57, 5886-5896 (2018).
38. Christianson, D. W. Structural and Chemical Biology of Terpenoid Cyclases. *Chem. Rev.* 106, 3412-3442 (2006).
39. Newman, D. J. & Cragg, G. M. Natural Products as Sources of New Drugs from 1981 to 2014. *Journal of Natural Products* 79, 629-661 (2016).
40. Martin, V. J. J., Pitera, D. J., Withers, S. T., Newman, J. D. & Keasling, J. D. Engineering a mevalonate pathway in *Escherichia coli* for production of terpenoids. *Nat. Biotechnol.* 21, 796-802 (2003).
41. Morrone, D. et al. Increasing diterpene yield with a modular metabolic engineering system in *E. coli*: Comparison of MEV and MEP isoprenoid precursor pathway engineering. *Appl. Microbiol. Biotechnol.* 85, 1893-1906 (2010).
42. Williams, D. C. et al. Heterologous expression and characterization of a 'pseudomature' form of taxadiene synthase involved in paclitaxel (Taxol) biosynthesis and evaluation of a potential intermediate and inhibitors of the multistep diterpene cyclization reaction. *Arch. Biochem. Biophys.* (2000). doi: 10.1006/abbi.2000.1865
43. Yoshikuni, Y., Ferrin, T. E. & Keasling, J. D. Designed divergent evolution of enzyme function. *Nature* 440, 1078-1082 (2006).
44. Peralta-Yahya, P. P. et al. Identification and microbial production of a terpene-based advanced biofuel. *Nat. Commun.* (2011). doi: 10.1038/ncomms1494
45. Wiesmann, C. et al. Allosteric inhibition of protein tyrosine phosphatase 1B. *Nat. Struct. Mol. Biol.* 11, 730-737 (2004).
46. Zhang, C., Chen, X., Stephanopoulos, G. & Too, H. P. Efflux transporter engineering markedly improves AD production in *Escherichia coli*. *Biotechnol. Bioeng.* (2016). doi: 10.1002/bit.25943
47. Keedy, D. A. et al. An expanded allosteric network in PTP1B by multitemperature crystallography, fragment screening, and covalent tethering. *Elife* 7, doi: 10.7554/eLife.36307 (2018).
48. Vallurupalli, P., Bouvignies, G. & Kay, L. E. Studying 'invisible' excited protein states in slow exchange with a major state conformation. *J. Am. Chem. Soc.* 134, 8148-8161 (2012).
49. Amamuddy, O. S. et al. Integrated computational approaches and tools for allosteric drug discovery. *Int. J. Mol. Sci.* 21, 847 (2020).
50. Shimada, T. et al. Selectivity of Polycyclic Inhibitors for Human Cytochrome P450s 1A1, 1A2, and 1B1. *Chem. Res. Toxicol.* 11, 1048-1056 (1998).
51. Goldstein, B. J., Bittner-Kowalczyk, A., White, M. F. & Harbeck, M. Tyrosine dephosphorylation and deactivation of insulin receptor substrate-1 by protein-tyrosine phosphatase 1B. Possible facilitation by the formation of a ternary complex with the GRB2 adaptor protein. *J. Biol. Chem.* 275, 4283-4289 (2000).
52. Choi, E. et al. Mitotic regulators and the SHP2-MAPK pathway promote IR endocytosis and feedback regulation of insulin signaling. *Nat. Commun.* 10, (2019).
53. Dubois, M. J. et al. The SHP-1 protein tyrosine phosphatase negatively modulates glucose homeostasis. *Nat. Med.* 12, 549-556 (2006).
54. Hubert, J., Nuzillard, J. M. & Renault, J. H. Dereplication strategies in natural product research: How many tools and methodologies behind the same concept? *Phytochemistry Reviews* 16, 55-95 (2017).
55. Manguso, R. T. et al. In vivo CRISPR screening identifies Ptpn2 as a cancer immunotherapy target. *Nature* 547, 413-418 (2017).
56. Varone, A., Spano, D. & Corda, D. Shp1 in Solid Cancers and Their Therapy. *Frontiers in Oncology* 10, 935 (2020).
57. Yang, C. F. et al. Targeting protein tyrosine phosphatase PTP-PEST (PTPN12) for therapeutic intervention in acute myocardial infarction. *Cardiovasc. Res.* 116, 1032-1046 (2020).

58. Zhang, S. & Zhang, Z. Y. PTP1B as a drug target: recent developments in PTP1B inhibitor discovery. *Drug Discov. Today* 12, 373-381 (2007).
59. Oleinikovas, V., Saladino, G., Cossins, B. P. & Gervasio, F. L. Understanding Cryptic Pocket Formation in Protein Targets by Enhanced Sampling Simulations. *J. Am. Chem. Soc.* 138, 14257-14263 (2016).
60. Rutledge, P. J. & Challis, G. L. Discovery of microbial natural products by activation of silent biosynthetic gene clusters. *Nature Reviews Microbiology* 13, 509-523 (2015).
61. Hartenfeller, M. & Schneider, G. De Novo Drug Design. in *Chemoinformatics and Computational Chemical Biology* (ed. Bajorath, J.) 299-323 (Humana Press, 2011). doi: 10.1007/978-1-60761-839-3_12
62. Packer, M. S. & Liu, D. R. Methods for the directed evolution of proteins. *Nat. Rev. Genet.* 16, 379-394 (2015).
63. Johnston, C. W., Badran, A. H. & Collins, J. J. Continuous bioactivity-dependent evolution of an antibiotic biosynthetic pathway. *Nat. Commun.* 11, 4202 (2020).
64. Chen, M. J., Dixon, J. E. & Manning, G. Genomics and evolution of protein phosphatases. *Sci. Signal.* 10, 1-17 (2017).
65. Galanie, S. et al. Complete biosynthesis of opioids in yeast. *Science* (80-.). 349, 1095-1100 (2015).
66. Paddon, C. J. & Keasling, J. D. Semi-synthetic artemisinin: a model for the use of synthetic biology in pharmaceutical development. *Nat. Rev. Microbiol.* 12, 355-367 (2014).
67. Grangeasse, C., Nessler, S. & Mijakovic, I. Bacterial tyrosine kinases: Evolution, biological function and structural insights. *Philos. Trans. R. Soc. B Biol. Sci.* 367, 2640-2655 (2012).
68. Montalibet, J. et al. Residues distant from the active site influence protein-tyrosine phosphatase 1B inhibitor binding. *J. Biol. Chem.* 281, 5258-5266 (2006).
69. Douzery, E. J. P., Snell, E. A., Bapteste, E., Delsuc, F. & Philippe, H. The timing of eukaryotic evolution: Does a relaxed molecular clock reconcile proteins and fossils? *Proc. Natl. Acad. Sci. U.S.A* 101, 15386-15391 (2004).
70. O'Brien, K. P., Remm, M. & Sonnhammer, E. L. L. Inparanoid: A comprehensive database of eukaryotic orthologs. *Nucleic Acids Res.* 33, D476-D480 (2005).
71. Kachroo, A. H. et al. Systematic humanization of yeast genes reveals conserved functions and genetic modularity. *Science* (80-.). 348, 921-925 (2015).
72. Carlson, J. C., Badran, A. H., Guggiana-Nilo, D. A. & Liu, D. R. Negative selection and stringency modulation in phage-assisted continuous evolution. *Nat. Chem. Biol.* 10, 216-222 (2014).
73. Hjortness, M. K. et al. Evolutionarily Conserved Allosteric Communication in Protein Tyrosine Phosphatases. *Biochemistry* 57, 6443-6451 (2018).
74. Chen, X. et al. Statistical experimental design guided optimization of a one-pot biphasic multienzyme total synthesis of *amorpha*-4,11-diene. *PLoS One* 8, e79650 (2013).
75. Edgar, S. et al. Mechanistic Insights into Taxadiene Epoxidation by Taxadiene-5α-Hydroxylase. *ACS Chem. Biol.* 11, 460-469 (2016).
76. Price, M. N., Dehal, P. S. & Arkin, A. P. FastTree 2-Approximately maximum-likelihood trees for large alignments. *PLoS One* 5, e9490 (2010).
77. Yu, G., Smith, D. K., Zhu, H., Guan, Y. & Lam, T. T. Y. ggtree: an r package for visualization and annotation of phylogenetic trees with their covariates and other associated data. *Methods Ecol. Evol.* 8, 28-36 (2017).
78. Burnham, K. P. & Anderson, D. R. *Model Selection and Multimodel Inference: a Practical Information-theoretic Approach, 2nd edn. Springer-Verlag, New York. New York Springer* 60, (2002).
79. Winter, G. Xia2: An expert system for macromolecular crystallography data reduction. *J. Appl. Crystallogr.* 43, 186-190 (2010).
80. Afonine, P. V et al. Towards automated crystallographic structure refinement with phenix.refine. *Acta Crystallogr. D. Biol. Crystallogr.* 68, 352-67 (2012).
81. Emsley, P. & Cowtan, K. Coot: Model-building tools for molecular graphics. *Acta Crystallogr. Sect. D Biol. Crystallogr.* 60, 2126-2132 (2004).
82. Joosten, R. P., Long, F., Murshudov, G. N. & Perrakis, A. The PDB_REDO server for macromolecular structure model optimization. *IUCrJ* 1, 213-220 (2014).
83. Vitalis, A. & Pappu, R. V. Chapter 3 Methods for Monte Carlo Simulations of Biomacromolecules. in (ed. Wheeler, R. A. B. T.-A. R. in C. C.) 5, 49-76 (Elsevier, 2009).
84. Vitalis, A. & Pappu, R. V. ABSINTH: A new continuum solvation model for simulations of polypeptides in aqueous solutions. *J. Comput. Chem.* 30, 673-699 (2009).
85. Choi, J.-M. & Pappu, R. V. Improvements to the ABSINTH Force Field for Proteins Based on Experimentally Derived Amino Acid Specific Backbone Conformational Statistics. *J. Chem. Theory Comput.* 15, 1367-1382 (2019).
86. Abraham, M. J. et al. Gromacs: High performance molecular simulations through multi-level parallelism from laptops to supercomputers. *SoftwareX* 1, 19-25 (2015).
87. Huang, J. et al. CHARMM36m: An improved force field for folded and intrinsically disordered proteins. *Nat. Methods* 14, 71-73 (2016).
88. MacKerell, A. D. et al. All-atom empirical potential for molecular modeling and dynamics studies of proteins. *J. Phys. Chem. B* 102, 3586-3616 (1998).
89. Vanommeslaeghe, K. et al. CHARMM general force field: A force field for drug-like molecules compatible with the CHARMM all-atom additive biological force fields. *J. Comput. Chem.* 31, 671-690 (2010).
90. Yu, W., He, X., Vanommeslaeghe, K. & MacKerell, A. D. Extension of the CHARMM general force field to sulfonyl-containing compounds and its utility in biomolecular simulations. *J. Comput. Chem.* 33, 2451-2468 (2012).
91 Hess, B., Bekker, H., Berendsen, H. J. C. & Fraaije, J. G. E. M. LINCS: A linear constraint solver for molecular simulations. *J. Comput. Chem.* 18, 1463-1472 (1997).
92. Darden, T., York, D. & Pedersen, L. Particle mesh Ewald: An N·log (N) method for Ewald sums in large systems. *J. Chem. Phys.* 98, 10089 (1993).
93. Bussi, G., Donadio, D. & Parrinello, M. Canonical sampling through velocity rescaling. *J. Chem. Phys.* 126, 014101 (2007).
94. Parrinello, M. Polymorphic transitions in single crystals: A new molecular dynamics method. *J. Appl. Phys.* 52, 7182 (1981).
95. Li, H. et al. Crystal Structure and Substrate Specificity of PTPN12. *Cell Rep.* (2016). doi: 10.1016/j.celrep.2016.04.016
96. Paling, N. R. D. & Welham, M. J. Role of the protein tyrosine phosphatase SHP-1 (Src homology phosphatase- 1) in the regulation of interleukin-3-induced survival, proliferation and signalling. *Biochem. J.* 368, 885-894 (2002).

97. Van Vliet, C. et al. Selective regulation of tumor necrosis factor-induced Erk signaling by Src family kinases and the T cell protein tyrosine phosphatase. *Nat. Immunol.* 6, 253-260 (2005).

TABLE 1

Gene Sources

| Component | Organism | Plasmid | Source |
|---|---|---|---|
| Src | *H. sapiens* | pDONR223_SRC_WT | Addgene: 82165 |
| CDC37 | *H. sapiens* | pBACgus4x/cdc37/RocCOR LRRK2 1867-2176 | Addgene: 40398 |
| PTP1B | *H. sapiens* | pGEX-2T PTP-1B | Addgene: 8602 |
| SHP2 | *H. sapiens* | PTPN11 | Addgene: 38965 |
| TC-PTP | *H. sapiens* | pBG100-TCPTP | Addgene: 33365 |
| LuxAB | | pAB078d8 | Addgene: 79206 |
| RpoZ | *Escherichia coli* | pAB094a | Addgene: 79241 |
| cI434 | *Escherichia virus Lambda* | pAB078d8 | Addgene: 79206 |
| SH2 | *Rous sarcoma virus* | | Addgene: 78302 |
| p130cas | *H. sapiens* | Synthetic | Integrated DNA Technologies, Inc. |
| midT | *H. sapiens* | Synthetic | Integrated DNA Technologies, Inc. |
| EGFR | *H. sapiens* | Synthetic | Integrated DNA Technologies, Inc. |
| ShcA | *H. sapiens* | Synthetic | Integrated DNA Technologies, Inc. |
| MBIS | *S. cerevisiae* | pMBIS | Addgene: 17817 |
| ADS | *Artemisia annua* | pADS | Addgene: 19040 |
| GHS | *Abies grandis* | pTrcHUM | Addgene: 19003 |
| ABS | *Abies grandis* | pSBET/AgAs | Ruben Peters, Iowa State University |
| TXS | *Taxus brevifola* | M60 | David W. Christianson, University of Pennsylvania |
| GGPPS | *Taxus Canadensis* | gBlock | Integrated DNA Technologies, Inc. |

TABLE 2

Plasmids

| Plasmid | Description | Antibiotic* | Addgene |
|---|---|---|---|
| F-plasmid | The F-plasmid from the S1030 strain of *E. coli*. | T | 105063 |
| $pB2H_{1b}$ | An early version of B2H that lacks PTP1B and contains LuxAB as the GOT | K | TBD |
| $pBAD_{1b.Src}$ | Enables inducible expression of Src and CDC37 | P | TBD |
| $pBAD_{1b.SH2}$ | Enables inducible expression of the SH2 domain. | P | TBD |
| $pBAD_{1b.S}$ | Enables inducible expression of the substrate domain. | P | TBD |
| $pBAD_{1b.All}$ | Enables inducible expression of Src, CDC37, the SH2 domain, and the substrate domain. | P | TBD |

TABLE 2-continued

Plasmids

| Plasmid | Description | Antibiotic* | Addgene |
|---|---|---|---|
| $pB2H_{1c.p130cas}$ | An early version of B2H that (i) lacks PTP1B and Src, (ii) contains LuxAB, and (iii) includes a substrate from p130cas. | K | TBD |
| $pB2H_{1c.midT}$ | An early version of B2H that (i) lacks PTP1B and Src, (ii) contains LuxAB, and (iii) includes a substrate from midT. | K | TBD |
| $pB2H_{1c.ShcA}$ | An early version of B2H that (i) lacks PTP1B and Src, (ii) contains LuxAB, and (iii) includes a substrate from ShCA. | K | TBD |
| $pB2H_{1c.EGFR}$ | An early version of B2H that (i) lacks PTP1B and Src, (ii) contains LuxAB, and (iii) includes a substrate from EGFR. | K | TBD |
| $pBAD_{1c}$ | Enables inducible expression of Src and CDC37. | P | TBD |
| $pBAD_{1d}$ | Enables inducible expression of Src and PTP1B. | P | TBD |
| $pBAD_{1d.mut}$ | Enables inducible expression of Src and catalytically inactive PTP1B (C215S). | P | TBD |
| $pB2H_{S1.1Pro1}$ | An early version of B2H that (i) lacks PTP1B, (ii) contains LuxAB, (iii) places expression of Src, CDC37, the SH2 domain, and the substrate domain under control of the same Pro1 promoter, and (iv) uses the BB034 RBS for Src. | K | TBD |
| $pB2H_{S1.1Pro1.mut}$ | Identical to $pB2H_{S1.1Pro1}$ except for a mutation in the substrate (Y4F) | K | TBD |
| $pB2H_{S1.1ProD}$ | An early version of B2H that (i) lacks PTP1B, (ii) contains LuxAB, and (iii) includes the ProD promoter and pro RBS for Src. | K | TBD |
| $pB2H_{S1.1ProD.mut}$ | Identical to $pB2H_{S1.1ProD}$ except for a mutation in the substrate (Y4F) | K | TBD |
| $pB2H_{S1.2pro}$ | An early version of B2H that (i) lacks PTP1B, (ii) contains LuxAB, and (iii) includes the pro RBS for Src. | K | TBD |
| $pB2H_{S1.2pro.mut}$ | Identical to $pB2H_{S1.2pro}$ except for a mutation in the substrate (Y4F) | K | TBD |
| $pB2H_{S1.2Sal28}$ | An early version of B2H that (i) lacks PTP1B, (ii) contains LuxAB, and (iii) includes the Sal28 RBS for Src. | K | TBD |
| $pB2H_{S1.2Sal28.mut}$ | Identical to $pB2H_{S1.2Sal28}$ except for a mutation in the substrate (Y4F) | K | TBD |
| $pB2H_{S1.3RBS30}$ | An early version of B2H that (i) contains LuxAB and (ii) includes the bb030 RBS for PTP1B. | K | TBD |
| $pB2H_{S1.3RBS30}$ | Identical to $pB2H_{S1.3RBS30}$ except for a mutation in the substrate (Y4F) | K | TBD |
| $pB2H_{S1.3RBS34}$ | An early version of B2H that (i) contains LuxAB and (ii) includes the bb034 RBS for PTP1B. | K | TBD |
| $pB2H_{S1.3RBS34}$ | Identical to $pB2H_{S1.3RBS34}$ except for a mutation in the substrate (Y4F) | K | TBD |
| $pB2H_{S2RBS30}$ | An early version of B2H that (i) contains SpecR and (ii) includes the bb030 RBS for PTP1B. | K | TBD |
| $pB2H_{S2RBS30.mut}$ | Identical to $pB2H_{S2RBS30}$ except for an inactivating mutation in PTP1B (C215S) | K | TBD |

TABLE 2-continued

| Plasmids | | | |
|---|---|---|---|
| Plasmid | Description | Anti-biotic* | Add-gene |
| $pB2H_{opt}$ | Final, optimized B2H that (i) contains SpecR and (ii) includes the bb034 RBS for PTP1B. | K | TBD |
| $pB2H_{opt}$* | Identical to $pB2H_{opt}$ except for an inactivating mutation in PTP1B (C215S) | K | TBD |
| $pB2H_{optX}$ | | K | TBD |
| pMBIS | A plasmid that harbors genes for the mevalonate-dependent isoprenoid pathway from *S. cerevisiae* and harbors a tetracycline resistance marker. | T | 17817 |
| $pMBIS_{CmR}$ | A plasmid that harbors genes for the mevalonate-dependent isoprenoid pathway from *S. cerevisiae* and harbors a chloramphenicol resistance marker. | P | TBD |
| pTrc99t | A pTrc99a variant with BsaI removed for use in Golden Gate cloning | C | TBD |
| $PTS_{ADS}$ | A plasmid that harbors ADS. | C | TBD |
| $PTS_{ADS(G349A)}$ | A plasmid that harbors ADS (G349A). | C | TBD |
| $PTS_{ADS(G400C)}$ | A plasmid that harbors ADS (G400C). | C | TBD |
| $PTS_{ADS(D299A)}$ | A plasmid that harbors ADS (D299A, inactivating). | C | TBD |
| $PTS_{ADS(F514E)}$ | A plasmid that harbors ADS (F514E). | C | TBD |
| $pTS_{ADS(G400L)}$ | A plasmid that harbors ADS (G400L). | C | TBD |
| $PTS_{ADS(F514S)}$ | A plasmid that harbors ADS (F514S). | C | TBD |
| $PTS_{ADS(F514V)}$ | A plasmid that harbors ADS (F514V). | C | TBD |
| $pTS_{ADS(V292I)}$ | A plasmid that harbors ADS (V292I). | C | TBD |
| $PTS_{ADS(I90S/F340S)}$ | A plasmid that harbors ADS (I90S/F340S). | C | TBD |
| $PTS_{ADS(I490V/M528K)}$ | A plasmid that harbors ADS (I490V/M528K). | C | TBD |
| $PTS_{ADS(G34S/K51N)}$ | A plasmid that harbors ADS (G34S/K51N). | C | TBD |
| $pTS_{ADSF370Y}$ | A plasmid that harbors ADS (F370Y). | C | TBD |
| $PTS_{ADSR527L}$ | A plasmid that harbors ADS (R527L). | C | TBD |
| $pTS_{GHS}$ | A plasmid that harbors GHS. | C | TBD |
| $pTS_{GHS(BFN)}$ | A plasmid that harbors GHS (W315P). | C | TBD |
| $PTS_{GHS(SIB)}$ | A plasmid that harbors GHS (F312Q/M339A/M447F). | C | TBD |
| $PTS_{GHS(HUM)}$ | A plasmid that harbors GHS (M339N/S484C/M565I). | C | TBD |
| $pTS_{GHS(BBA)}$ | A plasmid that harbors GHS (A336V/M447H/I562T). | C | TBD |
| $pTS_{GHS(ALP)}$ | A plasmid that harbors GHS (A336C/T445C/S484C/I562L/M565L). | C | TBD |
| $pTS_{GHS(LFN)}$ | A plasmid that harbors GHS (A317N/A337S/S484C/I562V). | C | TBD |
| $pTS_{GHS(A319Q)}$ | A plasmid that harbors GHS (A319Q). | C | TBD |
| pTSGHS (S561C) | A plasmid that harbors GHS (S561C). | C | TBD |
| pTSGHS (Y415C) | A plasmid that harbors GHS (Y415C). | C | TBD |
| $pTS_{GHS(S484L)}$ | A plasmid that harbors GHS (S484L). | C | TBD |
| $PTS_{GHS(450Y)}$ | A plasmid that harbors GHS (L450Y). | C | TBD |
| $PTS_{GHS(450G)}$ | A plasmid that harbors GHS (L450G). | C | TBD |
| $PTS_{GHS(450K)}$ | A plasmid that harbors GHS (L450K). | C | TBD |
| $PTS_{GHS(450T)}$ | A plasmid that harbors GHS (L450T). | C | TBD |
| $pTS_{GHS(T455I)}$ | A plasmid that harbors GHS (T455I). | C | TBD |
| $PTS_{ABS}$ | A plasmid that harbors ABS and GGPPS. | C | TBD |
| $PTS_{TXS}$ | A plasmid that harbors TXS and GGPPS. | C | TBD |

*Antibiotic resistance: carbenicillin (C, 50 μg/ml), kanamycin (K, 50 μg/ml), tetracycline (T, 10 μg/ml), chloramphenicol (P, 34 μg/ml), and spectinomycin (S, conditional).

TABLE 3

| Components of various B2H systems. | | | | | |
|---|---|---|---|---|---|
| Component | Name | DNA SEQ ID NO: | DNA | Amino Acid SEQ ID NO: | Amino Acid |
| Kinase | c-Src | 3 | ATGGGCTCCAAGCCGCAGACTCAGG GCCTGGCCAAGGATGCCTGGGAGAT CCCTCGGGAGTCGCTGCGGCTGGAG GTCAAGCTGGGCCAGGGCTGCTTTG GCGAGGTGTGGATGGGGACCTGGAA CGGTACCACCAGGGTGGCCATCAAA ACCCTGAAGCCTGGCACGATGTCTC CAGAGGCCTTCCTGCAGGAGGCCCA GGTCATGAAGAAGCTGAGGCATGAG AAGCTGGTGCAGTTGTATGCTGTGG TTTCAGAGGAGCCCATTTACATCGT CACGGAGTACATGAGCAAGGGGAG TTTGCTGGACTTTCTCAAGGGGGAG ACAGGCAAGTACCTGCGGCTGCCTC AGCTGGTGGACATGGCTGCTCAGAT CGCCTCAGGCATGGCGTACGTGGAG CGGATGAACTACGTCCACCGGGACC TTCGTGCAGCCAACATCCTGGTGGG AGAGAACCTGGTGTGCAAAGTGGCC GACTTTGGGCTGGCTCGGCTCATTG AAGACAATGAGTACACGGCGCGGC AAGGTGCCAAATTCCCCATCAAGTG GACGGCTCCAGAAGCTGCCCTCTAT GGCCGCTTCACCATCAAGTCGGACG TGTGGTCCTTCGGGATCCTGCTGACT GAGCTCACCACAAAGGGACGGGTGC CCTACCCTGGGATGGTGAACCGCGA | 21 | MGSKPQTQGLAKDAWEIP RESLRLEVKLGQGCFGEV WMGTWNGTTRVAIKTLKP GTMSPEAFLQEAQVMKKL RHEKLVQLYAVVSEEPIYIV TEYMSKGSLLDFLKGETGK YLRLPQLVDMAAQIASGM AYVERMNYVHRDLRAANI LVGENLVCKVADFGLARLI EDNEYTARQGAKFPIKWTA PEAALYGRFTIKSDVWSFGI LLTELTTKGRVPYPGMVNR EVLDQVERGYRMPCPPECP ESLHDLMCQCWRKEPEERP TFEYLQAFLEDYFTSTEPQY QPGENL* |

TABLE 3-continued

Components of various B2H systems.

| Component | Name | DNA SEQ ID NO: | DNA | Amino Acid SEQ ID NO: | Amino Acid |
|---|---|---|---|---|---|
| | | | GGTGCTGGACCAGGTGGAGCGGGGC<br>TACCGGATGCCCTGCCCGCCGGAGT<br>GTCCCGAGTCCCTGCACGACCTCAT<br>GTGCCAGTGCTGGCGGAAGGAGCCT<br>GAGGAGCGGCCCACCTTCGAGTACC<br>TGCAGGCCTTCCTGGAGGACTACTT<br>CACGTCCACCGAGCCCCAGTACCAG<br>CCCGGGGAGAACCTCTAA | | |
| Chaperone | CDC37 | 4 | ATGGTGGACTACAGCGTGTGGGACC<br>ACATTGAGGTGTCTGATGATGAAGA<br>CGAGACGCACCCCAACATCGACACG<br>GCCAGTCTCTTCCGCTGGCGGCATC<br>AGGCCCGGGTGGAACGCATGGAGC<br>AGTTCCAGAAGGAGAAGGAGGAAC<br>TGGACAGGGGCTGCCGCGAGTGCAA<br>GCGCAAGGTGGCCGAGTGCCAGAG<br>GAAACTGAAGGAGCTGGAGGTGGC<br>CGAGGGCGGCAAGGCAGAGCTGGA<br>GCGCCTGCAGGCCGAGGCACAGCAG<br>CTGCGCAAGGAGGAGCGGAGCTGG<br>GAGCAGAAGCTGGAGGAGATGCGC<br>AAGAAGGAGAAGAGCATGCCCTGG<br>AACGTGGACACGCTCAGCAAAGACG<br>GCTTCAGCAAGAGCATGGTAAATAC<br>CAAGCCCGAGAAGACGGAGGAGGA<br>CTCAGAGGAGGTGAGGGAGCAGAA<br>ACACAAGACCTTCGTGGAAAAATAC<br>GAGAAACAGATCAAGCACTTTGGCA<br>TGCTTCGCCGCTGGGATGACAGCCA<br>AAAGTACCTGTCAGACAACGTCCAC<br>CTGGTGTGCGAGGAGACAGCCAATT<br>ACCTGGTCATTTGGTGCATTGACCTA<br>GAGGTGGAGGAGAAATGTGCACTCA<br>TGGAGCAGGTGGCCCACCAGACAAT<br>CGTCATGCAATTTATCCTGGAGCTG<br>GCCAAGAGCCTAAAGGTGGACCCCC<br>GGGCCTGCTTCCGGCAGTTCTTCACT<br>AAGATTAAGACAGCCGATCGCCAGT<br>ACATGGAGGGCTTCAACGACGAGCT<br>GGAAGCCTTCAAGGAGCGTGTGCGG<br>GGCCGTGCCAAGCTGCGCATCGAGA<br>AGGCCATGAAGGAGTACGAGGAGG<br>AGGAGCGCAAGAAGCGGCTCGGCC<br>CCGGCGGCCTGGACCCCGTCGAGGT<br>CTACGAGTCCCTCCCTGAGGAACTC<br>CAGAAGTGCTTCGATGTGAAGGACG<br>TGCAGATGCTGCAGGACGCCATCAG<br>CAAGATGGACCCCACCGACGCAAAG<br>TACCACATGCAGCGCTGCATTGACT<br>CTGGCCTCTGGGTCCCCAACTCTAA<br>GGCCAGCGAGGCCAAGGAGGGAGA<br>GGAGGCAGGTCCTGGGGACCCATTA<br>CTGGAAGCTGTTCCCAAGACGGGCG<br>ATGAGAAGGATGTCAGTGTGTAA | 22 | MVDYSVWDHIEVSDDEDE<br>THPNIDTASLFRWRHQARV<br>ERMEQFQKEKEELDRGCRE<br>CKRKVAECQRKLKELEVA<br>EGGKAELERLQAEAQQLR<br>KEERSWEQKLEEMRKKEK<br>SMPWNVDTLSKDGFSKSM<br>VNTKPEKTEEDSEEVREQK<br>HKTFVEKYEKQIKHFGMLR<br>RWDDSQKYLSDNVHLVCE<br>ETANYLVIWCIDLEVEEKC<br>ALMEQVAHQTIVMQFILEL<br>AKSLKVDPRACFRQFFTKI<br>KTADRQYMEGFNDELEAF<br>KERVRGRAKLRIEKAMKE<br>YEEEERKKRLGPGGLDPVE<br>VYESLPEELQKCFDVKDVQ<br>MLQDAISKMDPTDAKYHM<br>QRCIDSGLWVPNSKASEAK<br>EGEEAGPGDPLLEAVPKTG<br>DEKDVSV* |
| Phosphatase | PTP1B | 5 | ATGGAGATGGAAAAGGAGTTCGAG<br>CAGATCGACAAGTCCGGGAGCTGGG<br>CGGCCATTTACCAGGATATCCGACA<br>TGAAGCCAGTGACTTCCCATGTAGA<br>GTGGCCAAGCTTCCTAAGAACAAAA<br>ACCGAAATAGGTACAGAGACGTCAG<br>TCCCTTTGACCATAGTCGGATTAAA<br>CTACATCAAGAAGATAATGACTATA<br>TCAACGCTAGTTTGATAAAAATGGA<br>AGAAGCCCAAAGGAGTTACATTCTT<br>ACCCAGGGCCCTTTGCCTAACACAT<br>GCGGTCACTTTTGGGAGATGGTGTG<br>GGAGCAGAAAAGCAGGGGTGTCGT<br>CATGCTCAACAGAGTGATGGAGAAA<br>GGTTCGTTAAAATGCGCACAATACT<br>GGCCACAAAAAGAAGAAAAAGAGA<br>TGATCTTTGAAGACACAAATTTGAA<br>ATTAACATTGATCTCTGAAGATATC | 23 | MEMEKEFEQIDKSGSWAAI<br>YQDIRHEASDFPCRVAKLP<br>KNKNRNRYRDVSPFDHSRI<br>KLHQEDNDYINASLIKMEE<br>AQRSYILTQGPLPNTCGHF<br>WEMVWEQKSRGVVMLNR<br>VMEKGSLKCAQYWPQKEE<br>KEMIFEDTNLKLTLISEDIK<br>SYYTVRQLELENLTTQETR<br>EILHFHYTTWPDFGVPESPA<br>SFLNFLFKVRESGSLSPEHG<br>PVVVHCSAGIGRSGTFCLA<br>DTCLLLMDKRKDPSSVDIK<br>KVLLEMRKFRMGLIQTAD<br>QLRFSYLAVIEGAKFIMGD<br>SSVQDQWKELSHEDLEPPP<br>EHIPPPPRPPKRILEPHN* |

TABLE 3-continued

| Components of various B2H systems. | | | | | |
|---|---|---|---|---|---|
| Component | Name | DNA SEQ ID NO: | DNA | Amino Acid SEQ ID NO: | Amino Acid |
| | | | AAGTCATATTATACAGTGCGACAGC TAGAATTGGAAAACCTTACAACCCA AGAAACTCGAGAGATCTTACATTTC CACTATACCACATGGCCTGACTTTG GAGTCCCTGAATCACCAGCCTCATT CTTGAACTTTCTTTTCAAAGTCCGAG AGTCAGGGTCACTCAGCCCGGAGCA CGGGCCCGTTGTGGTGCACTGCAGT GCAGGCATCGGCAGGTCTGGAACCT TCTGTCTGGCTGATACCTGCCTCTTG CTGATGGACAAGAGGAAAGACCCTT CTTCCGTTGATATCAAGAAAGTGCT GTTAGAAATGAGGAAGTTTCGGATG GGGCTGATCCAGACAGCCGACCAGC TGCGCTTCTCCTACCTGGCTGTGATC GAAGGTGCCAAATTCATCATGGGGG ACTCTTCCGTGCAGGATCAGTGGAA GGAGCTTTCCCACGAGGACCTGGAG CCCCCACCCGAGCATATCCCCCCAC CTCCCCGGCCACCCAAACGAATCCT GGAGCCACACAATTGA | | |
| Substrate | p130cas | 6 | TGGATGGAGGACTATGACTACGTCC ACCTACAGGGG | 24 | WMEDYDYVHLQG |
| Substrate | midT | 7 | GAACCGCAGTATGAAGAAATTCCGA TTTATCTG | 25 | EPQYEEIPIYL |
| Substrate | ShcA | 8 | GATCATCAGTATTATAACGATTTTCC GGGC | 26 | DHQYYNDFPG |
| Substrate | EGFR | 9 | CCGCAGCGCTATCTGGTGATTCAGG GCGAT | 27 | PQRYLVIQGD |
| Substrate | p130cas Y/F | 10 | TGGATGGAGGACTTTGACTTCGTCC ACCTACAGGGG | 28 | WMEDFDFVHLQG |
| Substrate | midT Y/F | 11 | GAACCGCAGTTTGAAGAAATTCCGA TTTATCTG | 29 | EPQFEEIPIYL |
| Promoter | pBAD | 12 | AGAAACCAATTGTCCATATTGCATC AGACATTGCCGTCACTGCGTCTTTTA CTGGCTCTTCTCGCTAACCAAACCG GTAACCCCGCTTATTAAAAGCATTC TGTAACAAAGCGGGACCAAAGCCAT GACAAAAACGCGTAACAAAAGTGTC TATAATCACGGCAGAAAAGTCCACA TTGATTATTTGCACGGCGTCACACTT TGCTATGCCATAGCATTTTTATCCAT AAGATTAGCG | — | N/A |
| Promoter | Pro1[57] | 13 | TTCTAGAGCACAGCTAACACCACGT CGTCCCTATCTGCTGCCCTAGGTCTA TGAGTGGTTGCTGGATAACTTTACG GGCATGCATAAGGCTCGGTATCTAT ATTCAGGGAGACCACAACGGTTTCC CTCTACAAATAATTTTGTTTAACTTT TACTAGAG | | N/A |
| Promoter | placZopt[39] | 14 | CATTAGGCACCCCGGGCTTTACTCG TAAAGCTTCCGGCGCGTATGTTGTG TCGACCG | | N/A |
| Promoter | ProD[57] | 13 | TTCTAGAGCACAGCTAACACCACGT CGTCCCTATCTGCTGCCCTAGGTCTA TGAGTGGTTGCTGGATAACTTTACG GGCATGCATAAGGCTCGGTATCTAT ATTCAGGGAGACCACAACGGTTTCC CTCTACAAATAATTTTGTTTAACTTT TACTAGAG | | N/A |
| RBS | Pro | 15 | GTGCAGTTAAAGAGGAGAAAGGTC | | N/A |
| RBS | Sal28[‡] | 16 | CGAAAAAAAGTAAGGCGGTAATCC | | N/A |

TABLE 3-continued

Components of various B2H systems.

| Component | Name | DNA SEQ ID NO: | DNA | Amino Acid SEQ ID NO: | Amino Acid |
|---|---|---|---|---|---|
| RBS | BB030 | 17 | TCTAGAGATTAAAGAGGAGAAATAC<br>TAG | | N/A |
| RBS | BB034 | 18 | TCTAGAAAAGAGGAGAAATACTAG | | N/A |
| GOI | LuxAB | 19 | ATGAAATTTGGAAACTTTTTGCTTAC<br>ATACCAACCTCCCCAATTTTCCCAA<br>ACAGAGGTAATGAAACGTTTGGTTA<br>AATTAGGTCGCATCTCTGAGGAGTG<br>TGGTTTTGATACCGTATGGTTACTGG<br>AGCATCATTTCACGGAGTTTGGTTTG<br>CTTGGTAACCCTTATGTCGCTGCTGC<br>ATATTTACTTGGCGCGACTAAAAAA<br>TTGAATGTAGGAACTGCCGCTATTG<br>TTCTTCCCACAGCCCATCCAGTACGC<br>CAACTTGAAGATGTGAATTTATTGG<br>ATCAAATGTCAAAAGGACGATTTCG<br>GTTTGGTATTTGCCGAGGGCTTTACA<br>ACAAGGACTTTCGCGTATTCGGCAC<br>AGATATGAATAACAGTCGCGCCTTA<br>GCGGAATGCTGGTACGGGCTGATAA<br>AGAATGGCATGACAGAGGGATATAT<br>GGAAGCTGATAATGAACATATCAAG<br>TTCCATAAGGTAAAAGTAAACCCCG<br>CGGCGTATAGCAGAGGTGGCGCACC<br>GGTTTATGTGGTGGCTGAATCAGCT<br>TCGACGACTGAGTGGGCTGCTCAAT<br>TTGGCCTACCGATGATATTAAGTTG<br>GATTATAAATACTAACGAAAAGAAA<br>GCACAACTTGAGCTTTATAATGAAG<br>TGGCTCAAGAATATGGGCACGATAT<br>TCATAATATCGACCATTGCTTATCAT<br>ATATAACATCTGTAGATCATGACTC<br>AATTAAAGCGAAAGAGATTTGCCGG<br>AAATTTCTGGGGCATTGGTATGATT<br>CTTATGTGAATGCTACGACTATTTTT<br>GATGATTCAGACCAAACAAGAGGTT<br>ATGATTTCAATAAAGGGCAGTGGCG<br>TGACTTTGTATTAAAAGGACATAAA<br>GATACTAATCGCCGTATTGATTACA<br>GTTACGAAATCAATCCCGTGGGAAC<br>GCCGCAGGAATGTATTGACATAATT<br>CAAAAAGACATTGATGCTACAGGAA<br>TATCAAATATTTGTTGTGGATTTGAA<br>GCTAATGGAACAGTAGACGAAATTA<br>TTGCTTCCATGAAGCTCTTCCAGTCT<br>GATGTCATGCCATTTCTTAAAGAAA<br>AACAACGTTCGCTATTATATTATGG<br>CGGTGGCGGTAGCGGCGGTGGCGGT<br>AGCGGCGGTGGCGGTAGCGGCGGTG<br>GCGGTAGCAAATTTGGATTGTTCTTC<br>CTTAACTTCATCAATTCAACAACTGT<br>TCAAGAACAGAGTATAGTTCGCATG<br>CAGGAAATAACGGAGTATGTTGATA<br>AGTTGAATTTTGAACAGATTTTAGT<br>GTATGAAAATCATTTTTCAGATAAT<br>GGTGTTGTCGGCGCTCCTCTGACTGT<br>TTCTGGTTTTCTGCTCGGTTTAACAG<br>AGAAAATTAAAATTGGTTCATTAAA<br>TCACATCATTACAACTCATCATCCTG<br>TCCGCATAGCGGAGGAAGCTTGCTT<br>ATTGGATCAGTTAAGTGAAGGGAGA<br>TttattTTAGGGTTTAGTGATTGCGA<br>AAAAAAAGATGAAATGCATTTTTTT<br>AATCGCCCGGTTGAATATCAACAGC<br>AACTATTTGAAGAGTGTTATGAAAT<br>CATTAACGATGCTTTAACAACAGGC<br>TATTGTAATCCAGATAACGATTTTTA<br>TAGCTTCCCTAAAATATCTGTAAATC<br>CCCATGCTTATACGCCAGGCGGACC<br>TCGGAAATATGTAACAGCAACCAGT<br>CATCATATTGTTGAGTGGGCGGCCA<br>AAAAAGGTATTCCTCTCATCTTTAA | 30 | MKFGNFLLTYQPPQFSQTE<br>VMKRLVKLGRISEECGFDT<br>VWLLEHHFTEFGLLGNPYV<br>AAAYLLGATKKLNVGTAA<br>IVLPTAHPVRQLEDVNLLD<br>QMSKGRFRFGICRGLYNKD<br>FRVFGTDMNNSRALAECW<br>YGLIKNGMTEGYMEADNE<br>HIKFHKVKVNPAAYSRGG<br>APVYVVAESASTTEWAAQ<br>FGLPMILSWIINTNEKKAQL<br>ELYNEVAQEYGHDIHNIDH<br>CLSYITSVDHDSIKAKEICR<br>KFLGHWYDSYVNATTIFDD<br>SDQTRGYDFNKGQWRDFV<br>LKGHKDTNRRIDYSYEINP<br>VGTPQECIDIIQKDIDATGIS<br>NICCGFEANGTVDEIIASMK<br>LFQSDVMPFLKEKQRSLLY<br>YGGGGSGGGGSGGGGSGG<br>GGSKFGLFFLNFINSTTVQE<br>QSIVRMQEITEYVDKLNFE<br>QILVYENHFSDNGVVGAPL<br>TVSGFLLGLTEKIKIGSLNHI<br>ITTHHPVRIAEEACLLDQLS<br>EGRFILGFSDCEKKDEMHF<br>FNRPVEYQQQLFEECYEIIN<br>DALTTGYCNPDNDFYSFPK<br>ISVNPHAYTPGGPRKYVTA<br>TSHHIVEWAAKKGIPLIFK<br>WDDSNDVRYEYAERYKAV<br>ADKYDVDLSEIDHQLMILV<br>NYNEDSNKAKQETRAFISD<br>YVLEMHPNENFENKLEEIIA<br>ENAVGNYTECITAAKLAIE<br>KCGAKSVLLSFEPMNDLMS<br>QKNVINIVDDNIKKYHTEY<br>T* |

TABLE 3-continued

Components of various B2H systems.

| Component | Name | DNA SEQ ID NO: | DNA | Amino Acid SEQ ID NO: | Amino Acid |
|---|---|---|---|---|---|
| | | | GTGGGATGATTCTAATGATGTTAGA TATGAATATGCTGAAAGATATAAAG CCGTTGCGGATAAATATGACGTTGA CCTATCAGAGATAGACCATCAGTTA ATGATATTAGTTAACTATAACGAAG ATAGTAATAAAGCTAAACAAGAGAC GCGTGCATTTATTAGTGATTATGTTC TTGAAATGCACCCTAATGAAAATTT CGAAAATAAACTTGAAGAAATAATT GCAGAAAACGCTGTCGGAAATTATA CGGAGTGTATAACTGCGGCTAAGTT GGCAATTGAAAAGTGTGGTGCGAAA AGTGTATTGCTGTCCTTTGAACCAAT GAATGATTTGATGAGCCAAAAAAAT GTAATCAATATTGTTGATGATAATA TTAAGAAGTACCACACGGAATATAC CTAA | | |
| GOI | SpecR | 20 | ATGAGGGAAGCGGTGATCGCCGAA GTATCGACTCAACTATCAGAGGTAG TTGGCGTCATCGAGCGCCATCTCGA ACCGACGTTGCTGGCCGTACATTTG TACGGCTCCGCAGTGGATGGCGGCC TGAAGCCACACAGTGATATTGATTT GCTGGTTACGGTGACCGTAAGGCTT GATGAAACAACGCGGCGAGCTTTGA TCAACGACCTTTTGGAAACTTCGGC TTCCCCTGGAGAGAGCGAGATTCTC CGCGCTGTAGAAGTCACCATTGTTG TGCACGACGACATCATTCCGTGGCG TTATCCAGCTAAGCGCGAACTGCAA TTTGGAGAATGGCAGCGCAATGACA TTCTTGCAGGTATCTTCGAGCCAGCC ACGATCGACATTGATCTGGCTATCTT GCTGACAAAAGCAAGAGAACATAG CGTTGCCTTGGTAGGTCCAGCGGCG GAGGAACTCTTTGATCCGGTTCCTG AACAGGATCTATTTGAGGCGCTAAA TGAAACCTTAACGCTATGGAACTCG CCGCCCGACTGGGCTGGCGATGAGC GAAATGTAGTGCTTACGTTGTCCCG CATTTGGTACAGCGCAGTAACCGGC AAAATCGCGCCGAAGGATGTCGCTG CCGACTGGGCAATGGAGCGCCTGCC GGCCCAGTATCAGCCCGTCATACTT GAAGCTAGACAGGCTTATCTTGGAC AAGAAGAAGATCGCTTGGCCTCGCG CGCAGATCAGTTGGAAGAATTTGTC CACTACGTGAAAGGCGAGATCACCA AGGTAGTCGGCAAATGA | 31 | MREAVIAEVSTQLSEVVGV IERHLEPTLLAVHLYGSAV DGGLKPH SDIDLLVTVTVR LDETTRRALINDLLETSASP GESEILRAVEVTIVVHDDIIP WRYPAKRELQFGEWQRND ILAGIFEPATIDIDLAILLTK AREHSVALVGPAAEELFDP VPEQDLFEALNETLTLWNS PPDWAGDERNVVLTLSRIW YSAVTGKIAPKDVAADWA MERLPAQYQPVILEARQAY LGQEEDRLASRADQLEEFV HYVKGEITKVVGK* |

†RBS designed computationally using the Ribosome Binding Site Calculator.[58]

TABLE 4

Primers used to assemble the bacterial two-hybrid system.

| Component | F Primer SEQ ID NO: | F Primer | R Primer SEQ ID NO: | R Primer |
|---|---|---|---|---|
| RpoZ/HA4 with pAB078d8 overhangs | 32 | GTGCAGTAAGGAGGAAAAAA | 54 | GTCAGGGGCGGGGTTTTTTTT TAGGGCCCTACTGACTGTTAG CAGGTGCGGTAATTGA |
| pAB078d8 with RpoZ/HA4 overhang piece 1 | 33 | CAGTCAGTAGGGCCCTAAAA | 55 | CACAGTTCTCGTCATCAGCTC TCTGGTTGCTTTAGCTAATAC ACCATAAGCATTTTCC |
| pAB078d8 with RpoZ/HA4 overhang piece 2 | 34 | TAGCTAAAGCAACCAGAGAG | 56 | CAGTTACGCGTGCCATTTTTT TTTCCTCCTTACTGCACTTAG CGTTTCGGCGCCGGAT |

TABLE 4-continued

| Primers used to assemble the bacterial two-hybrid system. | | | | |
|---|---|---|---|---|
| Component | F Primer SEQ ID NO: | F Primer | R Primer SEQ ID NO: | R Primer |
| Src/CDC37 into pAB078d8 | 35 | CAATTCCCCTCTAGAAATAA TTTTG | 57 | GTCAGGGGCGGGGTTTTTTTT TAGGGCCCTACTGACTGTTAC ACACTGACATCCTTCTCATCG |
| Insulin Receptor Substrate RpoZ fusion into pAB078d8* | 36 | CGCTGTAGAGAAAATTGGTA | 58 | CAGGGGCGGGGTTTTTTTTTA GGGCCCTACTGACTGTTATTA GCCAAGATCCATCTTCA |
| Insulin Receptor SH2_cI fusion into pAB078d8* | 37 | GACGCGGAATGGTACTGGGG | 59 | GTTACGCGTGCCATTTTTTTT TCCTCCTTACTGCACTTATTA CGAAACCGGATACAACA |
| Src/CDC37 into pBAD33t | 38 | ATATGGTCTCACATGTCCAA GCCGCAGACTCAG | 60 | ATATGGTCTCATTTACACACT GACATCCTTCTCATCG |
| RpoZ/p130cas substrate into pBAD33t | 39 | ATATGGTCTCACATGGCACG CGTAACTGTTC | 61 | ATATGGTCTCATTTACCCCTG TAGGTGGACG |
| cI/SH2 into pBAD33t | 40 | ATATGGTCTCACATGAGTAT CAGCAGCAGGGTAAAAAG | 62 | ATATGGTCTCATTTAGCAGAC GTTGGTCAGGC |
| pB2H$_{1b}$ Gibson piece 1 | 41 | ATGACTACGTCCACCTACAG GGGTAATAACAATTCCCCTC TAGAAATAATTTTGTTTAAC | 63 | AAGATAAAAAGAATAGATCCC AGCCCTGTGTATAACTCACTA CTTTAGTCAGTTCCGCA |
| pB2H$_{1b}$ Gibson piece 2 | 42 | TGAGTTATACACAGGGCTGG | 64 | CCCCTGTAGGTGGACGTAGTC ATAGTCCTCCATCCACGCAGC TGCACGACGA |
| pB2H$_{1b}$ Gibson piece 3 | 43 | GTGCAGTAAGGAGGAAAAAA AATGGC | 65 | GCCCATGGTATATCTCCTTCT TAAAGT |
| pB2H$_{1b}$ Gibson piece 4 | 44 | TAAAATTCGTAGACTACAAG GACGACGATGACAAGTGGTA TTTTGGGAAGATCACTCGT | 66 | ACAGTTACGCGTGCCATTTTT TTTTCCTCCTTACTGCACTTA GCAGACGTTGGTCAGGC |
| B2H ShcA substrate | 45 | TAATAACAATTCCCCTCTAG AAATAATTTTGTTTAACTTT AAG | 67 | GGGAATTGTTATTAGCCCGGA AAATCGTTATAATACTGATGA TCCGCAGCTGCACGACG |
| B2H EGFR Substrate | 45 | TAATAACAATTCCCCTCTAG AAATAATTTTGTTTAACTTT AAG | 68 | GGGAATTGTTATTAATCGCCC TGAATCACCAGATAGCGCTGC GGCGCAGCTGCACGACG |
| B2H MidT Substrate | 45 | TAATAACAATTCCCCTCTAG AAATAATTTTGTTTAACTTT AAG | 69 | GAATTGTTATTACAGATAAAT CGGAATTTCTTCATACTGCGG TTCCGCAGCTGCACGACG |
| BB034 PTP1B$_{1-321}$ into pBAD$_{1c}$ | 46 | GTCAGTGTGTAAGTGCAGAA AGAGGAGAAATACTAGATGG AGATGGAAAAGGAGTTCGAG | 70 | CTCATCCGCCAAAACAGCCTC AATTGTGTGGCTCCAGGATTC G |
| BB034 Src/CDC37 | 47 | TAATCTAGAGAAAGAGGAGA AATACTAGATGTCCAAGCCG CAGACTC | 71 | TTACACACTGACATCCTTCTC ATCG |
| ProD into B2H | 48 | CTCTAGTAAAAGTTAAACAA AATTATTTGTAGAGGG | 72 | TTCTAGAGCACAGCTAACACC AC |
| ProD Overhang ProRBS Src/CDC37 | 49 | AACTTTTACTAGAGGAATTC GAGCTCTTAAAGAGGAGAAA GGTCATGGGCTCCAAGCCGC | 63 | AAGATAAAAAGAATAGATCCC AGCCCTGTGTATAACTCACTA CTTTAGTCAGTTCCGCA |
| Sal28 RBS Src/CDC37 | 50 | AACTTTTACTAGAGCGAAAA AAAGTAAGGCGGTAATCCAT GGGCTCCAAGCCGC | 73 | GAACCAATGAATGATTTGATG AGC |
| BB030 PTP1B into pB2H$_{S1.2Sal28}$ | 51 | AGTGTGTAAGTGCAGATTAA AGAGGAGAAATACTAGATGG AGATGGAAAAGGAGTTCGAG | 74 | GTTTTTTTTTAGGGCCCTACT GACTGTCAATTGTGTGGCTCC AGGATTC |

TABLE 4-continued

Primers used to assemble the bacterial two-hybrid system.

| Component | F Primer SEQ ID NO: | F Primer | R Primer SEQ ID NO: | R Primer |
|---|---|---|---|---|
| BB034 PTP1B into pB2H$_{1.2Sal28}$ | 52 | TCAGTGTGTAAGTGCAGTCACACAGGAAAGTACTAGATGGAGATGGAAAAGGAGTTCGAG | 74 | GTTTTTTTTTAGGGCCCTACTGACTGTCAATTGTGTGGCTCCAGGATTC |
| B2H Swap LuxAB/SpecR | 53 | GCGTACATTGGCTCCGTTCATTTGCCGACTACCTTGGTGATC | 75 | GACCTGCAGATTAAAGAGGGAAAAATGAGGGAAGCGGTGATCG |

*Insulin receptor substrate/SH2 domains[59] were used initially, but failed to activate the operon (data not shown)

TABLE 5

Primers used to assemble pathways for terpenoid biosynthesis.

| Component | F Primer SEQ ID NO: | F Primer | R Primer SEQ ID NO: | R Primer |
|---|---|---|---|---|
| GGPPS into pTrc99t | 76 | TATTGAGCTCCACCGCGGAGGAGGAATG | 80 | TATTGTCGACTTATTTATTACGCTGGATGATGTAGTC |
| TXS into pTrc99t | 77 | TATTGGTCTCCCATGAGCAGCAGCACTGGCAC | 81 | TATTGGTCTCCGTCCTTCCAACGCATTCAACATGTTG |
| ABS into pTrc99t | 78 | ATAAAGGTCTCCCATGGTGAAACGAGAATTTCCTCCAG | 82 | TATTAGGTCTCGAGCTCTTAGGCAACTGGTTGGAAGAGGC |
| pMBIS TetR->CmR | 79 | AGATCACTACCGGGCGTATTTTTTGAGTTATCGAGATTTTCAGGAGCTAAGGAAGCTAAAATGGAGAAAAAAATCACTGGATATACCAC | 83 | GCCGCCGGCTTCCATTTATTACGCCCCGCCCTG |

TABLE 6

Primers used for site-directed mutagenesis.

| Mutant | F Primer SEQ ID NO: | F Primer | R Primer SEQ ID NO: | R Primer |
|---|---|---|---|---|
| PTP1B (C215S) | 84 | GTCCAGTACTTTATTGGGGTTCAGGCGGATGGAACTGAGCATGTCCGAGAT | 107 | ATCTCGGACATGCTCAGTTCCATCCGCCTGAACCCCAATAAAGTACTGGAC |
| ABS (D404A) | 85 | GAGAGAGAATCCTGTTCCTAGTATTGCGGATACAGCCATGGGCCTTC | 108 | GAAGGCCCATGGCTGTATCCGCAATATCAGGAACAGGATTCTCTCTC |
| ABS (D621A) | 86 | ACAAAAACTTCCAATTTCACTGTTATTTTAGCGGATCTTTATGACGCCCATGG | 109 | CCATGGGCGTCATAAAGATCCGCTAAAATAACAGTGAAATTGGAAGTTTTTGT |
| ADS (D299A) | 87 | CGTAAGCATCGTAAGTGTCCGCGATCAGGGTGATAACAGC | 110 | GCTGTTATCACCCTGATCGCGGACACTTACGATGCTTACG |
| GHS (D343A) | 88 | CCCATGCGTGTCGTATAAGTCCGCTAACATTGTCATCAAGATCG | 111 | CGATCTTGATGACAATGTTAGCGGACTTATACGACACGCATGGG |
| GHS (T455X) | 89 | CAATGGCACCCCCAACNNKGGTATGTGTGTACTTAATCTGATCCCG | 112 | GTTGGGGGTGCCATTGTTC |
| GHS (L450X) | 90 | CAACACCGGTATGTGTGTANNKAATCTGATCCCGTTGCTGCTTATG | 113 | TACACACATACCGGTGTTGGG |

TABLE 6-continued

Primers used for site-directed mutagenesis.

| Mutant | F Primer SEQ ID NO: | F Primer | R Primer SEQ ID NO: | R Primer |
|---|---|---|---|---|
| GHS (Y415X) | 91 | AAACGCTTGGGAACGCNNKCT GGAAGCGTATTTGCAGGATG | 114 | GCGTTCCCAAGCGTTTTTG |
| GHS (A319X) | 92 | CTTCTGGATGGCCGCGNNKAT TTCAGAACCAGAATTTAGTGG CTC | 115 | CGCGGCCATCCAGAAGT |
| GHS (S484X) | 93 | ACCATCTGATTGAACTGGCTN NKCGACTGGTCGATGATGCGA G | 116 | AGCCAGTTCAATCAGATGGTG G |
| GHS (S561X) | 94 | CGTCCTGGCGCGGNNKATTCA GTTTATGTATAACCAGGGGGA C | 117 | CCGCGCCAGGACGTG |
| ADS (F370X) | 95 | CAACTGCGGTAAAGAGTTTGT TAAAGAANNKGTACGTAACCT GATGGTTGAAGC | 118 | TTCTTTAACAAACTCTTTACC GCAGTTG |
| ADS (G400X) | 96 | CATGACCCGGTTGTTATCATC ACCNNKGGTGCAAACCTGCTG ACCAC | 119 | GGTGATGATAACAACCGGGTC ATG |
| ADS (L405X) | 97 | CCGGCGGTGCAAACCTGNNKA CCACCACTTGCTATCTGGG | 120 | CAGGTTTGCACCGCCGG |
| ADS (G439X) | 98 | CTGTTCCGTTACTCCGGTATT CTGNNKCGTCGTCTGAACGAC CTGATG | 121 | CAGAATACCGGAGTAACGGAA CAG |
| ADS (F514X) | 99 | GGCAGTAATCTACCTGTGCCA GNNKCTGGAAGTACAGTACGC TGGTAAAG | 122 | CTGGCACAGGTAGATTACTGC C |
| MidT Substrate (Y/F) | 100 | CAGCTGCGGAACCGCAGTTTG AAGAAATTCCGAT | 123 | ATCGGAATTTCTTCAAACTGC GGTTCCGCAGCTG |
| p130Cas Substrate (Y/F) | 101 | TGGATGGAGGACTTTGACTTC GTCCACCTACAGGGGTAATAA CAATTC | 124 | GTCAAAGTCCTCCATCCACGC AGCTGCACGACG |
| SH2 (Superbinder mutations) | 102 | CTCTCCGTTTCTGACTTTGAC AACGCCAAGGGGCTCAATGTG CTGCACTACAAGATCCGCAAG CTG | 125 | AAGTCAGAAACGGAGAGGGCA TAGGCACCTTTTACCGTCTCG CTCTCCCG |
| SH2 (L13K K15L)* | 103 | AAACACTACCTGATCCGCAAG CTGGACAGC | 126 | GCTGTCCAGCTTGCGGATCAG GTAGTGTTTCACATTGAGCCC CTTGGC* |
| pTrc99a (remove BsaI sites) piece 1 | 104 | TATTGGTCTCTCGCGGTATCA TTGCAGCAC | 127 | TATTGGTCTCAGTGACCCCAC ACTACCATCGG |
| pTrc99a (remove BsaI sites) piece 2 | 105 | TATTGGTCTCATCACCCCATG CGAGAGTAGG | 128 | TATTGGTCTCACGCGTGACCC ACGCTCACCG |
| ADS ep PCR | 106 | AACAATTTCACACAGGAAACA GACC | 129 | GCCTGCAGGTCGACTCTAGA |

*The original superbinder primer mutated the incorrect lysine residue (13 vs. 15). This primer corrects that error. The residue numbering system used for this protein matches that of Kaneko et. al.[40]

TABLE 7

| Gene sources. | | | |
|---|---|---|---|
| Component | Organism | Plasmid | Source |
| Src | *H. sapiens* | pDONR223_ SRC_WT | Addgene: 82165 |
| CDC37 | *H. sapiens* | pBACgus4x/ cdc37/RocCOR LRRK2 1867-2176 | Addgene: 40398 |
| PTP1B | *H. sapiens* | pET21B_ PTP1B | Nicholas Tonks, Cold Spring Harbor |
| TC-PTP | *H. sapiens* | pBG100- TCPTP | Addgene: 33365 |
| PTPN6 | *H. sapiens:* | pGEX-2T SHP1 WT | Addgene: 8594 |
| PTPN12 | *H. sapiens* | DONR223_ PTPN12_ p.E57D | Addgene: 81528 |
| LuxAB | | pAB078d8 | Addgene: 79206 |
| RpoZ | *Escherichia coli* | pAB094a | Addgene: 79241 |
| cI434 | *Escherichia virus Lambda* | pAB078d8 | Addgene: 79206 |
| SH2 | *Rous sarcoma virus* | Kras-SRC FRET Biosensor | Addgene: 78302 |
| p130cas | *H. sapiens* | Synthetic | Integrated DNA Technologies, Inc. |
| midT | *H. sapiens* | Synthetic | Integrated DNA Technologies, Inc. |
| EGFR | *H. sapiens* | Synthetic | Integrated DNA Technologies, Inc. |
| ShcA | *H. sapiens* | Synthetic | Integrated DNA Technologies, Inc. |
| MBIS | *S. cerevisiae* | pMBIS | Addgene: 17817 |
| ADS | *Artemisia annua* | pADS | Addgene: 19040 |
| GHS | *Abies grandis* | pTrcHUM | Addgene: 19003 |
| ABS | *Abies grandis* | pSBET/AgAs | Reuben Peters, Iowa State University |
| TXS | *Taxus brevifola* | M60 | David W. Christianson, University of Pennsylvania |
| ABA | *Abies grandis* | pTrc99a | Addgene: 35153 |
| GGPPS | *Taxus canadensis* | gBlock | Integrated DNA Technologies, Inc. |
| A0A166A5J3 | *S. Suecicum* HHB10207 ss-3 | Synthetic | Twist Bioscience |
| A0A0D9X487 | *L. perrieri* | Synthetic | Twist Bioscience |
| F2DRF1 | *H. vulgare* | Synthetic | Twist Bioscience |
| A2XI80 | *O. sativa* | Synthetic | Twist Bioscience |
| A0A0D9ZGD1 | *O. glumipatula* | Synthetic | Twist Bioscience |
| A0A0K9RZT8 | *S. olaracea* | Synthetic | Twist Bioscience |
| A0A1I1AC30 | *A.aquimarinus* | Synthetic | Twist Bioscience |
| A0A1S3XW43 | *N. tabacum* | Synthetic | Twist Bioscience |
| A0A0D3D8G7 | *B. oleracea* | Synthetic | Twist Bioscience |
| B9IF04 | *P. trichocarpa* | Synthetic | Twist Bioscience |
| A0A067L3D3 | *J. curcas* | Synthetic | Twist Bioscience |
| A0A0C2TFL3 | *A.Muscaria Koide* BX008 | Synthetic | Twist Bioscience |
| A0A022S1C8 | *E. guttata* | Synthetic | Twist Bioscience |
| G4TNA6 | *S. indica* | Synthetic | Twist Bioscience |
| A0A1L7WMZ8 | *P. subalpine* | Synthetic | Twist Bioscience |
| A0A078IZJ5 | *B. napus* | Synthetic | Twist Bioscience |
| A0A0C9VSL7 | *S. stellatus* SS14 | Synthetic | Twist Bioscience |
| G2QRS0 | *T. terrestris* ATCC 38088 | Synthetic | Twist Bioscience |
| A0A2H3DKU3 | *A. gallica* | Synthetic | Twist Bioscience |
| A0A0D2L718 | *H. sublateritium* FD-334 SS-4 | Synthetic | Twist Bioscience |
| S9Q0922 | *C. Fuscus* DSM 2262 | Synthetic | Twist Bioscience |
| T1LTV1 | *T. urartu* | Synthetic | Twist Bioscience |
| A0A287XU99 | *H. vulgare* | Synthetic | Twist Bioscience |
| A0A0G2ZSL3 | *A. gephyra* | Synthetic | Twist Bioscience |

TABLE 8

| Plasmids | | | |
|---|---|---|---|
| Plasmid | Description | Anti-biotic* | Avail-ability |
| F-plasmid | The F-plasmid from the S1030 strain of *E. coli.* | T | AG: 105063.* |
| pB2H$_{1b}$ | An early version of B2H that lacks PTP1B and contains LuxAB as the GOI. | K | Fox Lab |
| pBAD$_{1b.Src}$ | Enables inducible expression of Src and CDC37 | P | Fox Lab |
| pBAD$_{1b.SH2}$ | Enables inducible expression of the SH2 domain. | P | Fox Lab |
| pBAD$_{1b.S}$ | Enables inducible expression of the substrate domain. | P | Fox Lab |
| pBAD$_{1b.All}$ | Enables inducible expression of Src, CDC37, the SH2 domain, and the substrate domain. | P | Fox Lab |
| pB2H$_{1c.p130cas}$ | An early version of B2H that (i) lacks PTP1B and Src, (ii) contains LuxAB, and (iii) includes a substrate from p130cas. | K | Fox Lab |
| pB2H$_{1c.midT}$ | An early version of B2H that (i) lacks PTP1B and Src, (ii) contains LuxAB, and (iii) includes a substrate from midT. | K | Fox Lab |
| pB2H$_{1c.ShcA}$ | An early version of B2H that (i) lacks PTP1B and Src, (ii) contains LuxAB, and (iii) includes a substrate from ShCA. | K | Fox Lab |
| pB2H$_{1c.EGFR}$ | An early version of B2H that (i) lacks PTP1B and Src, (ii) contains LuxAB, and (iii) includes a substrate from EGFR. | K | Fox Lab |
| pBAD$_{1d}$ | Enables inducible expression of Src and PTP1B. | P | Fox Lab |
| pBAD$_{1d.mut}$ | Enables inducible expression of Src and catalytically inactive PTP1B (C215S). | P | Fox Lab |
| pB2H$_{S1.1Pro1}$ | An early version of B2H that (i) lacks PTP1B, (ii) contains LuxAB, (iii) places expression of Src, CDC37, the SH2 domain, and the substrate domain under control of the same Pro1 promoter, and (iv) uses the BB034 RBS for Src. | K | Fox Lab |
| pB2H$_{S1.1Pro1.mut}$ | Identical to pB2H$_{S1.1Pro1}$ except for a mutation in the substrate (Y4F) | K | Fox Lab |
| pB2H$_{S1.1ProD}$ | An early version of B2H that (i) lacks PTP1B, (ii) contains LuxAB, and (iii) includes the ProD promoter and pro RBS for Src. | K | Fox Lab |
| pB2H$_{S1.1ProD.mut}$ | Identical to pB2H$_{S1.1ProD}$ except for a mutation in the substrate (Y4F) | K | Fox Lab |
| pB2H$_{S1.2pro}$ | An early version of B2H that (i) lacks PTP1B, (ii) contains LuxAB, and (iii) includes the pro RBS for Src. | K | Fox Lab |
| pB2H$_{S1.2pro.mut}$ | Identical to pB2H$_{S1.2pro}$ except for a mutation in the substrate (Y4F) | K | Fox Lab |
| pB2H$_{S1.2Sal28}$ | An early version of B2H that (i) lacks PTP1B, (ii) contains LuxAB, and (iii) includes the Sal28 RBS for Src. | K | Fox Lab |
| pB2H$_{S1.2Sal28.mut}$ | Identical to pB2H$_{S1.2Sal28}$ except for a mutation in the substrate (Y4F) | K | Fox Lab |
| pB2H$_{S1.3RBS30}$ | An early version of B2H that (i) contains LuxAB and (ii) includes the bb030 RBS for PTP1B. | K | Fox Lab |

TABLE 8-continued

| Plasmids | | | |
|---|---|---|---|
| Plasmid | Description | Anti-biotic* | Avail-ability |
| pB2Hs$_{S1.3RBS30.mut}$ | Identical to pB2H$_{S1.3RBS30}$ except for a mutation in the substrate (Y4F) | K | Fox Lab |
| pB2H$_{S1.3RBS34}$ | An early version of B2H that (i) contains LuxAB and (ii) includes the bb034 RBS for PTP1B. | K | Fox Lab |
| pB2H$_{S1.3RBS34.mut}$ | Identical to pB2H$_{S1.3RBS34}$ except for a mutation in the substrate (Y4F) | K | Fox Lab |
| pB2H$_{S2RBS30}$ | An early version of B2H that (i) contains SpecR and (ii) includes the bb030 RBS for PTP1B. | K | Fox Lab |
| pB2H$_{S2RBS30.mut}$ | Identical to pB2H$_{S2RBS30}$ except for an inactivating mutation in PTP1B (C215S) | K | Fox Lab |
| pB2H$_{opt}$ | Final, optimized B2H that (i) contains SpecR and (ii) includes the bb034 RBS for PTP1B. | K | AG: 163830 |
| pBH$_{opt*}$ | Identical to pB2H$_{opt}$ except for an inactivating mutation in PTP1B (C215S) | K | AG: 163831 |
| pB2H$_{optX}$ | Identical to pB2H$_{opt}$ except for a mutation in the substrate domain (Y4F) | K | AG: 163832 |
| pB2H$_2$ | Identical to pB2H$_{opt}$ with TC-PTP in place of PTP1B | K | AG: 163833 |
| pB2H$_2$* | Identical to pB2H$_2$ except for an inactivating mutation in TC-PTP (R222M) | K | AG: 163834 |
| pB2H$_6$ | Identical to pB2H$_{opt}$ with SHP1 (catalytic domain) in place of PTP1B | K | AG: 163835 |
| pB2H$_6$* | Identical to pB2H$_6$ except for an inactivating mutation in SHP1 (R459M) | K | AG: 163836 |
| pB2H$_{12}$ | Identical to pB2H$_{opt}$ with PTPN12 in place of PTP1B | K | AG: 163837 |
| pB2H$_{12}$* | Identical to pB2H$_{12}$ except for an inactivating mutation in PTPN12 (Y64A) | K | AG: 163838 |
| pMBIS | A plasmid that harbors genes for the mevalonate-dependent isoprenoid pathway from *S. cerevisiae* and harbors a tetracycline resistance marker. | T | AG: 17817 |
| pMBIS$_{CmR}$ | A plasmid that harbors genes for the mevalonate-dependent isoprenoid pathway from *S. cerevisiae* and harbors a chloramphenicol resistance marker. | P | Fox Lab |
| pTrc99t | A pTrc99a variant with BsaI removed for use in Golden Gate cloning | C | Fox Lab |
| PTS$_{ADS}$ | A plasmid that harbors ADS. | C | AG: 19040 |
| pTS$_{ADS(D299A)}$ | A plasmid that harbors ADS (D299A, inactivating). | C | Fox Lab |
| pTS$_{GHS}$ | A plasmid that harbors GHS. | C | AG: 19003 |
| pTS$_{GHS(D343A)}$ | A plasmid that harbors GHS (D343A, inactivating). | C | Fox Lab |
| pTS$_{ABA}$ | A plasmid that harbors ABA. | C | Fox Lab |
| pTS$_{ABA(D566A)}$ | A plasmid that harbors ABA (D566A, inactivating). | C | Fox Lab |
| pTS$_{ABS}$ | A plasmid that harbors ABS and GGPPS. | C | AG: 163840 |
| pTS$_{ABS(D404A/D621A)}$ | A plasmid that harbors ABS (D404A/D621A, inactivating) and GGPPS. | C | Fox Lab |

TABLE 8-continued

| Plasmids | | | |
|---|---|---|---|
| Plasmid | Description | Anti-biotic* | Avail-ability |
| pTS$_{TXS}$ | A plasmid that harbors TXS and GGPPS. | C | AG: 163839 |
| pTS$_{A0A166A5J3}$ | A plasmid that harbors A0A166A5J3 (Clade 1) | C | Fox Lab |
| pTS$_{A0A0D9X4S7}$ | A plasmid that harbors A0A0D9X487 (Clade 1) | C | Fox Lab |
| pTS$_{F2DRF1}$ | A plasmid that harbors F2DRF1 (Clade 1) | C | Fox Lab |
| pTS$_{A2XI80}$ | A plasmid that harbors A2XI80 (Clade 2) | C | Fox Lab |
| pTS$_{A0AOD9ZGD1}$ | A plasmid that harbors A0A0D9ZGD1 (Clade 2) | C | Fox Lab |
| pTS$_{A0A0K9RZT8}$ | A plasmid that harbors A0A0K9RZT8 (Clade 2) | C | Fox Lab |
| pTS$_{A0A1I1AC30}$ | A plasmid that harbors A0A1I1AC30 (Clade 3) | C | Fox Lab |
| pTS$_{A0A1S3XW43}$ | A plasmid that harbors A0A1S3XW43 (Clade 3) | C | Fox Lab |
| pTS$_{A0A0D3D8G7}$ | A plasmid that harbors A0A0D3D8G7 (Clade 3) | C | Fox Lab |
| pTS$_{B9IF04}$ | A plasmid that harbors B9IF04 (Clade 4) | C | Fox Lab |
| pTS$_{A0A067L3D3}$ | A plasmid that harbors A0A067L3D3 (Clade 4) | C | Fox Lab |
| pTS$_{A0A0C2TFL3}$ | A plasmid that harbors A0A0C2TFL3 (Clade 4) | C | Fox Lab |
| pTS$_{A0A022S1C8}$ | A plasmid that harbors A0A022S1C8 (Clade 5) | C | Fox Lab |
| pTS$_{G4TNA6}$ | A plasmid that harbors G4TNA6 (Clade 5) | C | Fox Lab |
| pTS$_{A0A1L7WMZ8}$ | A plasmid that harbors A0A1L7WMZ8 (Clade 5) | C | Fox Lab |
| pTS$_{A0A078IZJ5}$ | A plasmid that harbors A0A078IZJ5 (Clade 6) | C | Fox Lab |
| pTS$_{A0A0C9VSL7}$ | A plasmid that harbors A0A0C9VSL7 (Clade 6) | C | AG: 163841 |
| pTS$_{G2QRS0}$ | A plasmid that harbors G2QRS0 (Clade 6) | C | Fox Lab |
| pTS$_{A0A2H3DKU3}$ | A plasmid that harbors A0A2H3DKU3 (Clade 7) | C | Fox Lab |
| pTS$_{A0A0D2L718}$ | A plasmid that harbors A0A0D2L718 (Clade 7) | C | Fox Lab |
| pTS$_{S9Q922}$ | A plasmid that harbors S9Q922 (Clade 7) | C | Fox Lab |
| pTS$_{T1LTV1}$ | A plasmid that harbors T1LTV1 (Clade 8) | C | Fox Lab |
| pTS$_{A0A2S7XU99}$ | A plasmid that harbors A0A287XU99 (Clade 8) | C | Fox Lab |
| pTSA$_{0A0G2ZSL3}$ | A plasmid that harbors A0A0G2ZSL3 (Clade 8) | C | Fox Lab |
| pET21b$_{ptp1b}$ | A plasmid that encodes a His-tagged catalytic domain of PTP1B (for protein expression) | C | N/A⁺ |
| pET16B$_{TCPTP}$ | A plasmid that encodes a His-tagged catalytic domain of TCPTP (for protein expression) | C | Fox Lab |

*Antibiotic resistance: carbenicillin (C, 50 μg/ml), kanamycin (K, 50 μg/ml), tetracycline (T, 10 μg/ml), chloramphenicol (P, 34 μg/ml), and spectinomycin (S, conditional).

⁺This plasmid was a kind gift from Nicholas Tonks of Cold Spring Harbor Laboratory.

**AG = Addgene accession # (Addgene.com).

TABLE 9

Primers used to assemble pathways for terpenoid biosynthesis.

| Component | F Primer SEQ ID NO: | F Primer | R Primer SEQ ID NO: | R Primer |
|---|---|---|---|---|
| GGPPS into pTrc99t | 76 | TATTGAGCTCCACCGCGGAGGAGGAATG | 80 | TATTGTCGACTTATTTATTACGCTGGATGATGTAGTC |
| TXS into pTrc99t | 77 | TATTGGTCTCCCATGAGCAGCAGCACTGGCAC | 81 | TATTGGTCTCCGTCCTTCCAACGCATTCAACATGTTG |
| ABS into pTrc99t | 78 | ATAAAGGTCTCCCATGGTGAAACGAGAATTTCCTCCAG | 82 | TATTAGGTCTCGAGCTCTTAGGCAACTGGTTGGAAGAGGC |
| pMBIS TetR->CmR | 79 | AGATCACTACCGGGCGTATTTTTTGAGTTATCGAGATTTTCAGGAGCTAAGGAAGCTAAAATGGAGAAAAAAATCACTGGATATACCAC | 83 | GCCGCCGGCTTCCATTTATTACGCCCCGCCCTG |
| ABA into pTrc99 | 130 | AACAATTTCACACAGGAAACAGACCATGGCGGGTGTTTCTGCG | 131 | GCCTGCAGGTCGACTCTAGATTACAGCGGCAGCGGTTC |

TABLE 10

Primers used for site-directed mutagenesis.

| Mutant | F Primer SEQ ID NO: | F Primer | R Primer SEQ ID NO: | R Primer |
|---|---|---|---|---|
| PTP1B (C215S) | 84 | GTCCAGTACTTTATTGGGGTTCAGGCGGATGGAACTGAGCATGTCCGAGAT | 107 | ATCTCGGACATGCTCAGTTCCATCCGCCTGAACCCCAATAAAGTACTGGAC |
| TCPTP (R222M) | 132 | CAGAGAGAAGGTGCCAGACATCCCAATGCCTGCACTACA | 136 | TGTAGTGCAGGCATTGGGATGTCTGGCACCTTCTCTCTG |
| SHP1 (R459M) | 133 | CAATGATGGTGCCTGTCATGCCGATGCCGGCGCTG | 137 | CAGCGCCGGCATCGGCATGACAGGCACCATCATTG |
| PTPN12 (Y64A) | 134 | GCTGTGATCAAATGGCAGTATGTCCTTCGCTCTGTTCTTTTTAACATTTTCTTCTTTTTC | 138 | GAAAAAGAAGAAAATGTTAAAAAGAACAGAGCGAAGGACATACTGCCATTTGATCACAGC |
| ABS (D404A) | 85 | GAGAGAGAATCCTGTTCCTGATATTGCGGATACAGCCATGGGCCTTC | 108 | GAAGGCCCATGGCTGTATCCGCAATATCAGGAACAGGATTCTCTCTC |
| ABS (D621A) | 86 | ACAAAAACTTCCAATTTCACTGTTATTTTAGCGGATCTTTATGACGCCCATGG | 109 | CCATGGGCGTCATAAAGATCCGCTAAAATAACAGTGAAATTGGAAGTTTTTGT |
| ADS (D299A) | 87 | CGTAAGCATCGTAAGTGTCCGCGATCAGGGTGATAACAGC | 110 | GCTGTTATCACCCTGATCGCGGACACTTACGATGCTTACG |
| GHS (D343A) | 88 | CCCATGCGTGTCGTATAAGTCCGCTAACATTGTCATCAAGATCG | 111 | CGATCTTGATGACAATGTTAGCGGACTTATACGACACGCATGGG |
| MidT Substrate (Y/F) | 100 | CAGCTGCGGAACCGCAGTTTGAAGAAATTCCGAT | 123 | ATCGGAATTTCTTCAAACTGCGGTTCCGCAGCTG |
| p130Cas Substrate (Y/F) | 101 | TGGATGGAGGACTTTGACTTCGTCCACCTACAGGGGTAATAACAATTC | 124 | GTCAAAGTCCTCCATCCACGCAGCTGCACGACG |

TABLE 10-continued

| Primers used for site-directed mutagenesis. | | | | |
|---|---|---|---|---|
| Mutant | F Primer SEQ ID NO: | F Primer | R Primer SEQ ID NO: | R Primer |
| SH2 (Superbinder mutations) | 102 | CTCTCCGTTTCTGACTTTGAC AACGCCAAGGGGCTCAATGTG CTGCACTACAAGATCCGCAAG CTG | 125 | AAGTCAGAAACGGAGAGGGCAT AGGCACCTTTTACCGTCTCGCT CTCCCG |
| SH2 (L13K K15L)* | 103 | AAACACTACCTGATCCGCAAG CTGGACAGC | 126 | GCTGTCCAGCTTGCGGATCAGG TAGTGTTTCACATTGAGCCCCT TGGC* |
| pTrc99a (remove BsaI sites) piece 1 | 104 | TATTGGTCTCTCGCGGTATCA TTGCAGCAC | 127 | TATTGGTCTCAGTGACCCCACA CTACCATCGG |
| pTrc99a (remove BsaI sites) piece 2 | 105 | TATTGGTCTCATCACCCCATG CGAGAGTAGG | 128 | TATTGGTCTCACGCGTGACCCA CGCTCACCG |
| ABA D/A | 135 | AGGTGTCGTACATGTCCGCCA GAACGGTCTGCAG | 139 | CTGCAGACCGTTCTGGCGGACA TGTACGACACCT |

*The original superbinder primer mutated the incorrect lysine residue (13 vs. 15). This primer corrects that error. The residue numbering system used for this protein matches that of Kaneko et. al.[20]

TABLE 11a

| Scaling factor for amorphadiene/caryophyllene (m/z = 204) | | | | | |
|---|---|---|---|---|---|
| Technical Replicate | $A_{std}$ (counts*min) | $A_{ref}$ (counts*min) | $C_{std}$ (μg/mL) | $C_{ref}$ (μg/mL) | R |
| 1 | 74520 | 88358 | 20 | 0.4 | 0.017 |
| 2 | 71037 | 142415 | 20 | 0.4 | 0.010 |
| 3 | 75761 | 49011 | 20 | 0.4 | 0.031 |
| | | | | Avg R | 0.019 (0.006) |

*R was computed using eq. 2. Standard error is shown in parentheses.

TABLE 11b

| Scaling factor for taxadiene/caryophyllene (m/z = 93) | | | | | |
|---|---|---|---|---|---|
| Technical Replicate | $A_{std}$ (counts*min) | $A_{ref}$ (counts*min) | $C_{std}$ (μg/mL) | $C_{ref}$ (μg/mL) | R |
| 1 | 1399872 | 847009 | 20 | 10 | 0.83 |
| 2 | 1247250 | 605265 | 20 | 10 | 1.0 |
| 3 | 1291028 | 547740 | 20 | 10 | 1.2 |
| | | | | Avg R | 1.0 (0.10) |

TABLE 11c

| Scaling factor for amorphadiene/methyl abietate (m/z = 121) | | | | | |
|---|---|---|---|---|---|
| Technical Replicate | $A_{std}$ (counts * min) | $A_{ref}$ (counts * min) | $C_{std}$ (μg/mL) | $C_{ref}$ (μg/mL) | R |
| 1 | 949492 | 868168 | 20 | 3.162 | 0.17 |
| 2 | 920694 | 908257 | 20 | 3.162 | 0.16 |
| 3 | 898594 | 1106474 | 20 | 3.162 | 0.13 |
| | | | | Avg R | 0.15 (0.01) |

TABLE 12a

| Analysis of the inhibition of $PTP1B_{1-321}$ by amorphadiene. | | | | | |
|---|---|---|---|---|---|
| Model | SSE ($\mu M^2/s^2$) | DF | Criteria | Reference | Fit par. (μM) |
| Competitive | 0.14 | 27 | $\Delta_i$ = 51.2 | noncompetitive | $K_i$ = 2.85 |
| Uncompetitive** | 0.023 | 27 | $\Delta_i$ = 1.16 | noncompetitive | $K_i$ = 46.3 |
| Noncompetitive** | 0.023 | 27 | | | $K_i$ = 52.6* |
| Mixed | 0.022 | 26 | F = 0.47 | noncompetitive | $K_{i,c}$ = 86.2 |
| | | | p = 0.972 | | $K_{i,u}$ = 50.1 |

*The SSEs of the uncompetitive and noncompetitive models are indistinguishable from one another.
**Indicate models of best fit.

TABLE 12b

| Analysis of the inhibition of $PTP1B_{1-321}$ by α-bisabolene. | | | | | |
|---|---|---|---|---|---|
| Model | SSE ($\mu M^2/s^2$) | DF | Criteria | Reference | Fit par. (μM)) |
| Competitive | 0.082 | 27 | $\Delta_i$ = 39.1 | noncompetitive | $K_i$ = 1.05 |
| Uncompetitive** | 0.023 | 27 | $\Delta_i$ = 3.81 | noncompetitive | $K_i$ = 11.7 |
| Noncompetitive** | 0.021 | 27 | | | $K_i$ = 13.1 |
| Mixed | 0.020 | 26 | F = 0.24 | noncompetitive | $K_{i,c}$ = 9.51 |
| | | | p = 1.0 | | $K_{i,u}$ = 13.7 |

TABLE 12c

| Analysis of the inhibition of $PTP1B_{1-321}$ by alpha bisabolol. | | | | | |
|---|---|---|---|---|---|
| Model | SSE ($\mu M^2/s^2$) | DF | Criteria | Reference | Fit par. (μM) |
| Competitive | 0.039 | 27 | $\Delta_i$ = 34.4 | uncompetitive | $K_i$ = 178 |
| Uncompetitive** | 0.011 | 27 | | | $K_i$ = 469 |
| Noncompetitive** | 0.013 | 27 | $\Delta_i$ = 4.65 | uncompetitive | $K_i$ = 541 |
| Mixed | 0.011 | 26 | F = 0 | uncompetitive | $K_{i,c}$ = $3.5e^{16}$ |
| | | | p = 1.0 | | $K_{i,u}$ = 469 |

TABLE 12d

Analysis of the inhibition of $PTP1B_{1-321}$ by dihydroartimesnic acid.

| Model | SSE ($\mu M^2/s^2$) | DF | Criteria | Reference | Fit par. ($\mu M$) |
|---|---|---|---|---|---|
| Competitive | 0.129 | 21 | $\Delta_i$ = 60.7 | noncompetitive | $K_i$ = 178 |
| Uncompetitive | 0.025 | 27 | $\Delta_i$ = 15.2 | noncompetitive | $K_i$ = 469 |
| Noncompetitive | 0.015 | 27 | | | $K_i$ = 541 |
| Mixed** | 0.013 | 26 | F = 2.69 | noncompetitive | $K_{i,c}$ = $3.5e^{16}$ |
| | | | p = $6.9e^{-3}$ | | $K_{i,u}$ = 469 |

TABLE 12e

Analysis of the inhibition of $TCPTP_{1-317}$ by amorphadiene.

| Model | SSE ($\mu M^2/s^2$) | DF | Criteria | Reference | Fit par. ($\mu M$) |
|---|---|---|---|---|---|
| Competitive | 0.053 | 27 | $\Delta_i$ = 41.1 | uncompetitive | $K_i$ = 87.2 |
| Uncompetitive** | 0.012 | 27 | | | $K_i$ = 356 |
| Noncompetitive** | 0.013 | 27 | $\Delta_i$ = 2.22 | uncompetitive | $K_i$ = 400 |
| Mixed | 0.012 | 26 | F = 0 | uncompetitive | $K_{i,c}$ = $3.7e^{15}$ |
| | | | p = 1.0 | | $K_{i,u}$ = 356 |

*The SSEs of the uncompetitive and noncompetitive models are indistinguishable from one another.

**Indicate models of best fit.

TABLE 12f

Analysis of the inhibition of $TCPTP_{1-317}$ by α-bisabolene.

| Model | SSE ($\mu M^2/s^2$) | DF | Criteria | Reference | Fit par. ($\mu M$) |
|---|---|---|---|---|---|
| Competitive | 0.046 | 27 | $\Delta_i$ = 37.6 | uncompetitive | $K_i$ = 13.7 |
| Uncompetitive** | 0.012 | 27 | | | $K_i$ = 69.2 |
| Noncompetitive** | 0.012 | 27 | $\Delta_i$ = 1.12 | uncompetitive | $K_i$ = 76.2 |
| Mixed | 0.012 | 26 | F = 0 | uncompetitive | $K_{i,c}$ = 3610 |
| | | | p = 1.0 | | $K_{i,u}$ = 69.3 |

TABLE 12g

Analysis of the inhibition of $PTP1B_{1-281}$ by amorphadiene.

| Model | SSE ($\mu M^2/s^2$) | DF | Criteria | Reference | Fit par. ($\mu M$) |
|---|---|---|---|---|---|
| Competitive | 0.010 | 27 | $\Delta_i$ = 16.3 | noncompetitive | $K_i$ = 37.9 |
| Uncompetitive** | 0.006 | 27 | $\Delta_i$ = 3.51 | noncompetitive | $K_i$ = 210 |
| Noncompetitive** | 0.006 | 27 | | | $K_i$ = 244 |
| Mixed | 0.006 | 26 | F = 0.41 | noncompetitive | $K_{i,c}$ = 157 |
| | | | p = 0.99 | | $K_{i,u}$ = 271 |

TABLE 12h

Analysis of the inhibition of $PTP1B_{1-281}$ by α-bisabolene.

| Model | SSE ($\mu M^2/s^2$) | DF | Criteria | Reference | Fit par. ($\mu M$) |
|---|---|---|---|---|---|
| Competitive | 0.012 | 27 | $\Delta_i$ = 14.4 | noncompetitive | $K_i$ = 6.51 |
| Uncompetitive** | 0.008 | 27 | $\Delta_i$ = 1.41 | noncompetitive | $K_i$ = 40.0 |
| Noncompetitive** | 0.007 | 27 | | | $K_i$ = 46.3 |
| Mixed | 0.007 | 26 | F = 0 | noncompetitive | $K_{i,c}$ = 39.0 |
| | | | p = 1.0 | | $K_{i,u}$ = 47.7 |

TABLE 12i

Analysis of the inhibition of $TCPTP_{1-281}$ by amorphadiene.

| Model | SSE ($\mu M^2/s^2$) | DF | Criteria | Reference | Fit par. ($\mu M$) |
|---|---|---|---|---|---|
| Competitive | 0.005 | 27 | $\Delta_i$ = 22.9 | uncompetitive | $K_i$ = 87.2 |
| Uncompetitive** | 0.002 | 27 | | | $K_i$ = 356 |
| Noncompetitive** | 0.002 | 27 | $\Delta_i$ = 0.83 | uncompetitive | $K_i$ = 400 |
| Mixed | 0.002 | 26 | F = 0.03 | uncompetitive | $K_{i,c}$ = $3.7e^{15}$ |
| | | | p = 1.0 | | $K_{i,u}$ = 356 |

TABLE 12j

Analysis of the inhibition of $TCPTP_{1-281}$ by α-bisabolene.

| Model | SSE ($\mu M^2/s^2$) | DF | Criteria | Reference | Fit par. ($\mu M$) |
|---|---|---|---|---|---|
| Competitive | 0.083 | 27 | $\Delta_i$ = 39.1 | noncompetitive | $K_i$ = 13.7 |
| Uncompetitive** | 0.023 | 27 | $\Delta_i$ = 3.81 | noncompetitive | $K_i$ = 69.2 |
| Noncompetitive** | 0.021 | 27 | | | $K_i$ = 76.2 |
| Mixed | 0.020 | 26 | F = 0 | noncompetitive | $K_{i,c}$ = 3610 |
| | | | p = 1.0 | | $K_{i,u}$ = 69.3 |

TABLE 12k

Analysis of the inhibition of $PTP1B_{1-321}$ by (+)1-(10),4-cadinadiene

| Model | SSE ($\mu M^2/s^2$) | DF | Criteria | Reference | Fit par. ($\mu M$) |
|---|---|---|---|---|---|
| Competitive | 0.115 | 27 | $\Delta_i$ = 48.3 | uncompetitive | $K_i$ = 14.75 |
| Uncompetitive** | 0.020 | 27 | | | $K_i$ = 168.09 |
| Noncompetitive** | 0.022 | 27 | $\Delta_i$ = 2.5 | uncompetitive | $K_i$ = 190.44 |
| Mixed | 0.020 | 26 | F = 0 | uncompetitive | $K_{i,c}$ = 5689.38 |
| | | | p = 1.0 | | $K_{i,u}$ = 168.78 |

TABLE 12l

Analysis of the inhibition of $SHP2_{223-565}$ by Amorphadiene

| Model | SSE ($\mu M^2/s^2$) | DF | Criteria | Reference | Fit par. ($\mu M$) |
|---|---|---|---|---|---|
| Competitive | .0024 | 27 | $\Delta_i$ = 10.6 | noncompetitive | $K_i$ = 25.1 |
| Uncompetitive** | .0017 | 27 | $\Delta_i$ = 0.5 | noncompetitive | $K_i$ = 116.51 |
| Noncompetitive** | .0017 | 27 | | | $K_i$ = 145.69 |
| Mixed | 0.0017 | 26 | F = 0.15 | noncompetitive | $K_{i,c}$ = 236.21 |
| | | | p = 1.0 | | $K_{i,u}$ = 132.37 |

TABLE 13

Data collection and refinement statistics (molecular replacement)

| | PTP1B: amorphadiene (6W30) | PTP1B: α-bisabolol (N/A***) |
|---|---|---|
| Data collection | | |
| Space group | | |
| Cell dimensions | | |
| a, b, c (Å) | 89.03, 89.03, 105.56 | 89.28, 89.28, 105.51 |
| α, β, γ (°) | 90.00, 90.00, 120.00 | 90.00, 90.00, 120.00 |
| Resolution (Å) | 62.26-2.10 (2.13-2.10)* | 77.32-2.11 (2.15-2.11) |
| $R_{sym}$ or $R_{merge}$ | 0.130 (0.442) | 0.086 (0.331) |
| I/σI | 5.4 (1.0) | 6.7 (1.1) |

TABLE 13-continued

Data collection and refinement statistics (molecular replacement)

| | PTP1B: amorphadiene (6W30) | PTP1B: α-bisabolol (N/A***) |
|---|---|---|
| Completeness (%) | 99.8 (93.3) | 100.0 (98.5) |
| Redundancy | 10.7 (10.8) | 12.1 (12.3) |
| Refinement | | |
| Resolution (Å) | 44.52-2.10 (2.17-2.10) | 62.37-2.11 (2.18-2.11) |
| No. reflections | 28,654 | 28,479 |
| $R_{work}/R_{free}$ | 0.20/0.24 | 0.19/0.24 |
| No. atoms | | |
| Protein | 2355 | 2320 |
| Ligand/ion | 22 | 17 |
| Water | 170 | 270 |
| B-factors | | |
| Protein | 37 | 30 |
| Ligand/ion | 90/61 | 66/37 |
| Water | 47 | 43 |
| R.m.s. deviations | | |
| Bond lengths (Å) | 0.42 | 0.42 |
| Bond angles (°) | 0.56 | 0.54 |

*Values in parentheses correspond to the highest-resolution shell.

**Number of crystals used for each structure: 1

***In light of the results detailed in FIG. 31, we elected not to deposit this structure into the protein data bank.

TABLE 14

Details of hypothesis testing

| FIG. | Null hypothesis | Δμ | Test | DF | t | 95% confidence intervals | P-value |
|---|---|---|---|---|---|---|---|
| 3h | AD-(−) = 0 | 0.212 | t-test, unequal variance | 2 | 6.61 | (0.092, 0.332) | 0.02 |
| 3h | AB-(−) = 0 | 0.310 | t-test, unequal variance | 2 | 13.5 | (0.138, 0.482) | 0.005 |
| 3h | AD-DHA = 0 | 0.124 | t-test, unequal variance | 3 | 3.59 | (0.069, 0.179) | 0.04 |
| 3h | AB-ABOL = 0 | 0.309 | t-test, unequal variance | 3 | 12.6 | (0.170, 0.447) | 0.001 |

TABLE 15

Ligand efficiency.

| Ligand | $IC_{50}$ (μM) | # Heavy Atoms | Ligand Efficiency (kcal/mol-atom)* |
|---|---|---|---|
| Amorphadiene | 50 | 15 | 0.39 |
| α-bisabolene | 13 | 15 | 0.44 |
| BBR | 8 | 41 | 0.17 |
| MSI-1436 | 0.6 | 47 | 0.17 |

*Ligand efficiency = (−2.303RT)/HAC * log($IC_{50}$), where R is the gas constant, T is the temperature in K, and HAC is the number of heavy atoms.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCES
<210> 1
<211> 10
<212> PRT
<213> Homo sapiens
<400> 1
Glu Pro Gln Tyr Glu Glu Ile Pro Tyr Leu
1 5 10

<210> 2
<211> 10
<212> PRT
<213> Artificial Sequence
<220>
<223> Synthetic
<400> 2
Glu Pro Gln Phe Glu Glu Ile Pro Tyr Leu
1 5 10

<210> 3
<211> 867
<212> DNA
<213> Artificial Sequence
<220>
<223> Synthetic
<400> 3
atgggctcca agccgcagac tcagggcctg gccaaggatg cctgggagat ccctcgggag 60
tcgctgcggc tggaggtcaa gctgggccag ggctgctttg gcgaggtgtg gatggggacc 120
tggaacggta ccaccagggt ggccatcaaa accctgaagc ctggcacgat gtctccagag 180
gccttcctgc aggaggccca ggtcatgaag aagctgaggc atgagaagct ggtgcagttg 240
tatgctgtgg tttcagagga gcccatttac atcgtcacgg agtacatgag caaggggagt 300
ttgctggact ttctcaaggg ggagacaggc aagtacctgc ggctgcctca gctggtggac 360
atggctgctc agatcgcctc aggcatggcg tacgtggagc ggatgaacta cgtccaccgg 420
gaccttcgtg cagccaacat cctggtggga gagaacctgg tgtgcaaagt ggccgacttt 480
gggctggctc ggctcattga agacaatgag tacacggcgc ggcaaggtgc caaattcccc 540
atcaagtgga cggctccaga agctgccctc tatggccgct tcaccatcaa gtcggacgtg 600
tggtccttcg ggatcctgct gactgagctc accacaaagg gacgggtgcc ctaccctggg 660
atggtgaacc gcgaggtgct ggaccaggtg gagcggggct accggatgcc ctgcccgccg 720
gagtgtcccg agtccctgca cgacctcatg tgccagtgct ggcggaagga gcctgaggag 780
cggcccacct tcgagtacct gcaggccttc ctggaggact acttcacgtc caccgagccc 840
cagtaccagc ccggggagaa cctctaa 867

<210> 4
<211> 1137
<212> DNA
<213> Artificial Sequence
<220>
<223> Synthetic
<400> 4
atggtggact acagcgtgtg ggaccacatt gaggtgtctg atgatgaaga cgagacgcac 60
cccaacatcg acacggccag tctcttccgc tggcggcatc aggcccgggt ggaacgcatg 120
gagcagttcc agaaggagaa ggaggaactg gacaggggct gccgcgagtg caagcgcaag 180
gtggccgagt gccagaggaa actgaaggag ctggaggtgg ccgagggcgg caaggcagag 240
ctggagcgcc tgcaggccga ggcacagcag ctgcgcaagg aggagcggag ctgggagcag 300

-continued

```
aagctggagg agatgcgcaa gaaggagaag agcatgccct ggaacgtgga cacgctcagc  360
aaagacggct tcagcaagag catggtaaat accaagcccg agaagacgga ggaggactca  420
gaggaggtga gggagcagaa acacaagacc ttcgtggaaa aatacgagaa acagatcaag  480
cactttggca tgcttcgccg ctgggatgac agccaaaagt acctgtcaga caacgtccac  540
ctggtgtgcg aggagacagc caattacctg gtcatttggt gcattgacct agaggtggag  600
gagaaatgtg cactcatgga gcaggtggcc caccagacaa tcgtcatgca atttatcctg  660
gagctggcca agagcctaaa ggtggacccc cgggcctgct tccggcagtt cttcactaag  720
attaagacag ccgatcgcca gtacatggag ggcttcaacg acgagctgga agccttcaag  780
gagcgtgtgc ggggccgtgc caagctgcgc atcgagaagg ccatgaagga gtacgaggag  840
gaggagcgca agaagcggct cggccccggc ggcctggacc ccgtcgaggt ctacgagtcc  900
ctccctgagg aactccagaa gtgcttcgat gtgaaggacg tgcagatgct gcaggacgcc  960
atcagcaaga tggaccccac cgacgcaaag taccacatgc agcgctgcat tgactctggc 1020
ctctgggtcc ccaactctaa ggccagcgag gccaaggagg gagaggaggc aggtcctggg 1080
gacccattac tggaagctgt tcccaagacg ggcgatgaga aggatgtcag tgtgtaa    1137
```

<210> 5
<211> 966
<212> DNA
<213> Artificial Sequence
<220>
<223> Synthetic
<400> 5

```
atggagatgg aaaaggagtt cgagcagatc gacaagtccg ggagctgggc ggccatttac   60
caggatatcc gacatgaagc cagtgacttc ccatgtagag tggccaagct tcctaagaac  120
aaaaaccgaa ataggtacag agacgtcagt ccctttgacc atagtcggat taaactacat  180
caagaagata atgactatat caacgctagt ttgataaaaa tggaagaagc ccaaaggagt  240
tacattctta cccagggccc tttgcctaac acatgcggtc acttttggga gatggtgtgg  300
gagcagaaaa gcaggggtgt cgtcatgctc aacagagtga tggagaaagg ttcgttaaaa  360
tgcgcacaat actggccaca aaaagaagaa aaagagatga tctttgaaga cacaaatttg  420
aaattaacat tgatctctga agatatcaag tcatattata cagtgcgaca gctagaattg  480
gaaaacctta caacccaaga aactcgagag atcttacatt tccactatac cacatggcct  540
gactttggag tccctgaatc accagcctca ttcttgaact ttcttttcaa agtccgagag  600
tcagggtcac tcagcccgga gcacgggccc gttgtggtgc actgcagtgc aggcatcggc  660
aggtctggaa ccttctgtct ggctgatacc tgcctcttgc tgatggacaa gaggaaagac  720
ccttcttccg ttgatatcaa gaaagtgctg ttagaaatga ggaagtttcg gatggggctg  780
atccagacag ccgaccagct gcgcttctcc tacctggctg tgatcgaagg tgccaaattc  840
atcatggggg actcttccgt gcaggatcag tggaaggagc tttcccacga ggacctggag  900
cccccacccg agcatatccc cccacctccc cggccaccca aacgaatcct ggagccacac  960
aattga                                                              966
```

<210> 6
<211> 36
<212> DNA
<213> Artificial Sequence
<220>
<223> Synthetic
<400> 6

```
tggatggagg actatgacta cgtccaccta cagggg                              36
```

<210> 7
<211> 33
<212> DNA
<213> Artificial Sequence
<220>
<223> Synthetic
<400> 7

```
gaaccgcagt atgaagaaat tccgatttat ctg                                 33
```

<210> 8
<211> 30
<212> DNA
<213> Artificial Sequence
<220>
<223> Synthetic
<400> 8

```
gatcatcagt attataacga ttttccgggc                                     30
```

<210> 9
<211> 30
<212> DNA
<213> Artificial Sequence
<220>
<223> Synthetic
<400> 9

```
ccgcagcgct atctggtgat tcagggcgat                                     30
```

<210> 10
<211> 36
<212> DNA
<213> Artificial Sequence
<220>

<223> Synthetic
<400> 10
tggatggagg actttgactt cgtccaccta cagggg 36

<210> 11
<211> 33
<212> DNA
<213> Artificial Sequence
<220>
<223> Synthetic
<400> 11
gaaccgcagt ttgaagaaat tccgatttat ctg 33

<210> 12
<211> 238
<212> DNA
<213> Artificial Sequence
<220>
<223> Synthetic
<400> 12
agaaaccaat tgtccatatt gcatcagaca ttgccgtcac tgcgtctttt actggctctt 60
ctcgctaacc aaaccggtaa ccccgcttat taaaagcatt ctgtaacaaa gcgggaccaa 120
agccatgaca aaaacgcgta acaaaagtgt ctataatcac ggcagaaaag tccacattga 180
ttatttgcac ggcgtcacac tttgctatgc catagcattt ttatccataa gattagcg 238

<210> 13
<211> 160
<212> DNA
<213> Artificial Sequence
<220>
<223> Synthetic
<400> 13
ttctagagca cagctaacac cacgtcgtcc ctatctgctg ccctaggtct atgagtggtt 60
gctggataac tttacgggca tgcataaggc tcggtatcta tattcaggga gaccacaacg 120
gtttccctct acaaataatt ttgtttaact tttactagag 160

<210> 14
<211> 57
<212> DNA
<213> Artificial Sequence
<220>
<223> Synthetic
<400> 14
cattaggcac cccgggcttt actcgtaaag cttccggcgc gtatgttgtg tcgaccg 57

<210> 15
<211> 24
<212> DNA
<213> Artificial Sequence
<220>
<223> Synthetic
<400> 15
gtgcagttaa agaggagaaa ggtc 24

<210> 16
<211> 24
<212> DNA
<213> Artificial Sequence
<220>
<223> Synthetic
<400> 16
cgaaaaaaag taaggcggta atcc 24

<210> 17
<211> 28
<212> DNA
<213> Artificial Sequence
<220>
<223> Synthetic
<400> 17
tctagagatt aaagaggaga aatactag 28

<210> 18
<211> 24
<212> DNA
<213> Artificial Sequence
<220>
<223> Synthetic
<400> 18
tctagaaaag aggagaaata ctag 24

-continued

<210> 19
<211> 2124
<212> DNA
<213> Artificial Sequence
<220>
<223> Synthetic
<400> 19

```
atgaaatttg gaaacttttt gcttacatac caacctcccc aattttccca aacagaggta   60
atgaaacgtt tggttaaatt aggtcgcatc tctgaggagt gtggttttga taccgtatgg  120
ttactggagc atcatttcac ggagtttggt ttgcttggta acccttatgt cgctgctgca  180
tatttacttg gcgcgactaa aaaattgaat gtaggaactg ccgctattgt tcttcccaca  240
gcccatccag tacgccaact tgaagatgtg aatttattgg atcaaatgtc aaaaggacga  300
tttcggtttg gtatttgccg agggctttac aacaaggact ttcgcgtatt cggcacagat  360
atgaataaca gtcgcgcctt agcggaatgc tggtacgggc tgataaagaa tggcatgaca  420
gagggatata tggaagctga taatgaacat atcaagttcc ataaggtaaa agtaaacccc  480
gcggcgtata gcagaggtgg cgcaccggtt tatgtggtgg ctgaatcagc ttcgacgact  540
gagtgggctg ctcaatttgg cctaccgatg atattaagtt ggattataaa tactaacgaa  600
aagaaagcac aacttgagct ttataatgaa gtggctcaag aatatgggca cgatattcat  660
aatatcgacc attgcttatc atatataaca tctgtagatc atgactcaat taaagcgaaa  720
gagatttgcc ggaaatttct ggggcattgg tatgattctt atgtgaatgc tacgactatt  780
tttgatgatt cagaccaaac aagaggttat gatttcaata aagggcagtg gcgtgacttt  840
gtattaaaag gacataaaga tactaatcgc cgtattgatt acagttacga aatcaatccc  900
gtgggaacgc cgcaggaatg tattgacata attcaaaaag acattgatgc tacaggaata  960
tcaaatattt gttgtggatt tgaagctaat ggaacagtag acgaaattat tgcttccatg 1020
aagctcttcc agtctgatgt catgccattt cttaaagaaa aacaacgttc gctattatat 1080
tatggcggtg gcggtagcgg cggtggoggt agcggcggtg gcggtagcgg cggtggcggt 1140
agcaaatttg gattgttctt ccttaacttc atcaattcaa caactgttca agaacagagt 1200
atagttcgca tgcaggaaat aacggagtat gttgataagt tgaattttga acagatttta 1260
gtgtatgaaa atcatttttc agataatggt gttgtcggcg ctcctctgac tgtttctggt 1320
tttctgctcg gtttaacaga gaaaattaaa attggttcat taaatcacat cattacaact 1380
catcatcctg tccgcatagc ggaggaagct tgcttattgg atcagttaag tgaagggaga 1440
tttattttag ggtttagtga ttgcgaaaaa aaagatgaaa tgcatttttt taatcgcccg 1500
gttgaatatc aacagcaact atttgaagag tgttatgaaa tcattaacga tgctttaaca 1560
acaggctatt gtaatccaga taacgatttt tatagcttcc ctaaaatatc tgtaaatccc 1620
catgcttata cgccaggcgg acctcggaaa tatgtaacag caaccagtca tcatattgtt 1680
gagtgggcgg ccaaaaaagg tattcctctc atctttaagt gggatgattc taatgatgtt 1740
agatatgaat atgctgaaag atataaagcc gttgcggata aatatgacgt tgacctatca 1800
gagatagacc atcagttaat gatattagtt aactataacg aagatagtaa taaagctaaa 1860
caagagacgc gtgcatttat tagtgattat gttcttgaaa tgcaccctaa tgaaaatttc 1920
gaaaataaac ttgaagaaat aattgcagaa aacgctgtcg gaaattatac ggagtgtata 1980
actgcggcta agttggcaat tgaaaagtgt ggtgcgaaaa gtgtattgct gtcctttgaa 2040
ccaatgaatg atttgatgag ccaaaaaaat gtaatcaata ttgttgatga taatattaag 2100
aagtaccaca cggaatatac ctaa                                        2124
```

<210> 20
<211> 792
<212> DNA
<213> Artificial Sequence
<220>
<223> Synthetic
<400> 20

```
atgagggaag cggtgatcgc cgaagtatcg actcaactat cagaggtagt tggcgtcatc   60
gagcgccatc tcgaaccgac gttgctggcc gtacatttgt acggctccgc agtggatggc  120
ggcctgaagc cacacagtga tattgatttg ctggttacgg tgaccgtaag gcttgatgaa  180
acaacgcggc gagctttgat caacgacctt ttggaaactt cggcttcccc tggagagagc  240
gagattctcc gcgctgtaga agtcaccatt gttgtgcacg acgacatcat tccgtggegt  300
tatccagcta agcgcgaact gcaatttgga gaatggcagc gcaatgacat tcttgcaggt  360
atcttcgagc cagccacgat cgacattgat ctggctatct tgctgacaaa agcaagagaa  420
catagcgttg ccttggtagg tccagcggcg gaggaactct ttgatccggt tcctgaacag  480
gatctatttg aggcgctaaa tgaaacctta acgctatgga actcgccgcc cgactgggct  540
ggcgatgagc gaaatgtagt gcttacgttg tcccgcattt ggtacagcgc agtaaccggc  600
aaaatcgcgc cgaaggatgt cgctgccgac tgggcaatgg agcgcctgcc ggcccagtat  660
cagcccgtca tacttgaagc tagacaggct tatcttggac aagaagaaga tcgcttggcc  720
tcgcgcgcag atcagttgga agaatttgtc cactacgtga aaggcgagat caccaaggta  780
gtcggcaaat ga                                                      792
```

<210> 21
<211> 288
<212> PRT
<213> Artificial Sequence
<220>
<223> Synthetic
<400> 21

```
Met Gly Ser Lys Pro Gln Thr Gln Gly Leu Ala Lys Asp Ala Trp Glu
1               5                   10                  15
Ile Pro Arg Glu Ser Leu Arg Leu Glu Val Lys Leu Gly Gln Gly Cys
            20                  25                  30
Phe Gly Glu Val Trp Met Gly Thr Trp Asn Gly Thr Thr Arg Val Ala
        35                  40                  45
Ile Lys Thr Leu Lys Pro Gly Thr Met Ser Pro Glu Ala Phe Leu Gln
    50                  55                  60
```

-continued

```
Glu Ala Gln Val Met Lys Lys Leu Arg His Glu Lys Leu Val Gln Leu
65              70                  75                  80
Tyr Ala Val Val Ser Glu Glu Pro Ile Tyr Ile Val Thr Glu Tyr Met
                85                  90                  95
Ser Lys Gly Ser Leu Leu Asp Phe Leu Lys Gly Glu Thr Gly Lys Tyr
            100                 105                 110
Leu Arg Leu Pro Gln Leu Val Asp Met Ala Ala Gln Ile Ala Ser Gly
        115                 120                 125
Met Ala Tyr Val Glu Arg Met Asn Tyr Val His Arg Asp Leu Arg Ala
    130                 135                 140
Ala Asn Ile Leu Val Gly Glu Asn Leu Val Cys Lys Val Ala Asp Phe
145                 150                 155                 160
Gly Leu Ala Arg Leu Ile Glu Asp Asn Glu Tyr Thr Ala Arg Gln Gly
                165                 170                 175
Ala Lys Phe Pro Ile Lys Trp Thr Ala Pro Glu Ala Ala Leu Tyr Gly
            180                 185                 190
Arg Phe Thr Ile Lys Ser Asp Val Trp Ser Phe Gly Ile Leu Leu Thr
        195                 200                 205
Glu Leu Thr Thr Lys Gly Arg Val Pro Tyr Pro Gly Met Val Asn Arg
    210                 215                 220
Glu Val Leu Asp Gln Val Glu Arg Gly Tyr Arg Met Pro Cys Pro Pro
225                 230                 235                 240
Glu Cys Pro Glu Ser Leu His Asp Leu Met Cys Gln Cys Trp Arg Lys
                245                 250                 255
Glu Pro Glu Glu Arg Pro Thr Phe Glu Tyr Leu Gln Ala Phe Leu Glu
            260                 265                 270
Asp Tyr Phe Thr Ser Thr Glu Pro Gln Tyr Gln Pro Gly Glu Asn Leu
        275                 280                 285

<210> 22
<211> 378
<212> PRT
<213> Artificial Sequence
<220>
<223> Synthetic
<400> 22
Met Val Asp Tyr Ser Val Trp Asp His Ile Glu Val Ser Asp Asp Glu
1               5                   10                  15
Asp Glu Thr His Pro Asn Ile Asp Thr Ala Ser Leu Phe Arg Trp Arg
            20                  25                  30
His Gln Ala Arg Val Glu Arg Met Glu Gln Phe Gln Lys Glu Lys Glu
        35                  40                  45
Glu Leu Asp Arg Gly Cys Arg Glu Cys Lys Arg Lys Val Ala Glu Cys
    50                  55                  60
Gln Arg Lys Leu Lys Glu Leu Glu Val Ala Glu Gly Gly Lys Ala Glu
65                  70                  75                  80
Leu Glu Arg Leu Gln Ala Glu Ala Gln Gln Leu Arg Lys Glu Glu Arg
                85                  90                  95
Ser Trp Glu Gln Lys Leu Glu Glu Met Arg Lys Lys Glu Lys Ser Met
            100                 105                 110
Pro Trp Asn Val Asp Thr Leu Ser Lys Asp Gly Phe Ser Lys Ser Met
        115                 120                 125
Val Asn Thr Lys Pro Glu Lys Thr Glu Glu Asp Ser Glu Glu Val Arg
    130                 135                 140
Glu Gln Lys His Lys Thr Phe Val Glu Lys Tyr Glu Lys Gln Ile Lys
145                 150                 155                 160
His Phe Gly Met Leu Arg Arg Trp Asp Asp Ser Gln Lys Tyr Leu Ser
                165                 170                 175
Asp Asn Val His Leu Val Cys Glu Glu Thr Ala Asn Tyr Leu Val Ile
            180                 185                 190
Trp Cys Ile Asp Leu Glu Val Glu Glu Lys Cys Ala Leu Met Glu Gln
        195                 200                 205
Val Ala His Gln Thr Ile Val Met Gln Phe Ile Leu Glu Leu Ala Lys
    210                 215                 220
Ser Leu Lys Val Asp Pro Arg Ala Cys Phe Arg Gln Phe Phe Thr Lys
225                 230                 235                 240
Ile Lys Thr Ala Asp Arg Gln Tyr Met Glu Gly Phe Asn Asp Glu Leu
                245                 250                 255
Glu Ala Phe Lys Glu Arg Val Arg Gly Arg Ala Lys Leu Arg Ile Glu
            260                 265                 270
Lys Ala Met Lys Glu Tyr Glu Glu Glu Glu Arg Lys Lys Arg Leu Gly
        275                 280                 285
Pro Gly Gly Leu Asp Pro Val Glu Val Tyr Glu Ser Leu Pro Glu Glu
    290                 295                 300
Leu Gln Lys Cys Phe Asp Val Lys Asp Val Gln Met Leu Gln Asp Ala
305                 310                 315                 320
Ile Ser Lys Met Asp Pro Thr Asp Ala Lys Tyr His Met Gln Arg Cys
                325                 330                 335
Ile Asp Ser Gly Leu Trp Val Pro Asn Ser Lys Ala Ser Glu Ala Lys
            340                 345                 350
Glu Gly Glu Glu Ala Gly Pro Gly Asp Pro Leu Leu Glu Ala Val Pro
```

-continued

```
    355           360           365
Lys Thr Gly Asp Glu Lys Asp Val Ser Val
  370           375

<210> 23
<211> 321
<212> PRT
<213> Artificial Sequence
<220>
<223> Synthetic
<400> 23
Met Glu Met Glu Lys Glu Phe Glu Gln Ile Asp Lys Ser Gly Ser Trp
1         5           10           15
Ala Ala Ile Tyr Gln Asp Ile Arg His Glu Ala Ser Asp Phe Pro Cys
       20           25           30
Arg Val Ala Lys Leu Pro Lys Asn Lys Asn Arg Asn Arg Tyr Arg Asp
    35           40           45
Val Ser Pro Phe Asp His Ser Arg Ile Lys Leu His Gln Glu Asp Asn
  50           55           60
Asp Tyr Ile Asn Ala Ser Leu Ile Lys Met Glu Glu Ala Gln Arg Ser
65           70           75           80
Tyr Ile Leu Thr Gln Gly Pro Leu Pro Asn Thr Cys Gly His Phe Trp
          85           90           95
Glu Met Val Trp Glu Gln Lys Ser Arg Gly Val Val Met Leu Asn Arg
      100           105           110
Val Met Glu Lys Gly Ser Leu Lys Cys Ala Gln Tyr Trp Pro Gln Lys
    115           120           125
Glu Glu Lys Glu Met Ile Phe Glu Asp Thr Asn Leu Lys Leu Thr Leu
  130           135           140
Ile Ser Glu Asp Ile Lys Ser Tyr Tyr Thr Val Arg Gln Leu Glu Leu
145           150           155           160
Glu Asn Leu Thr Thr Gln Glu Thr Arg Glu Ile Leu His Phe His Tyr
         165           170           175
Thr Thr Trp Pro Asp Phe Gly Val Pro Glu Ser Pro Ala Ser Phe Leu
       180           185           190
Asn Phe Leu Phe Lys Val Arg Glu Ser Gly Ser Leu Ser Pro Glu His
    195           200           205
Gly Pro Val Val Val His Cys Ser Ala Gly Ile Gly Arg Ser Gly Thr
  210           215           220
Phe Cys Leu Ala Asp Thr Cys Leu Leu Leu Met Asp Lys Arg Lys Asp
225           230           235           240
Pro Ser Ser Val Asp Ile Lys Lys Val Leu Leu Glu Met Arg Lys Phe
          245           250           255
Arg Met Gly Leu Ile Gln Thr Ala Asp Gln Leu Arg Phe Ser Tyr Leu
      260           265           270
Ala Val Ile Glu Gly Ala Lys Phe Ile Met Gly Asp Ser Ser Val Gln
    275           280           285
Asp Gln Trp Lys Glu Leu Ser His Glu Asp Leu Glu Pro Pro Pro Glu
  290           295           300
His Ile Pro Pro Pro Pro Arg Pro Pro Lys Arg Ile Leu Glu Pro His
305           310           315           320
Asn

<210> 24
<211> 12
<212> PRT
<213> Artificial Sequence
<220>
<223> Synthetic
<400> 24
Trp Met Glu Asp Tyr Asp Tyr Val His Leu Gln Gly
1         5           10

<210> 25
<211> 11
<212> PRT
<213> Artificial Sequence
<220>
<223> Synthetic
<400> 25
Glu Pro Gln Tyr Glu Glu Ile Pro Ile Tyr Leu
1         5           10

<210> 26
<211> 10
<212> PRT
<213> Artificial Sequence
<220>
<223> Synthetic
<400> 26
Asp His Gln Tyr Tyr Asn Asp Phe Pro Gly
```

-continued 1 5 10

<210> 27
<211> 10
<212> PRT
<213> Artificial Sequence
<220>
<223> Synthetic
<400> 27
Pro Gln Arg Tyr Leu Val Ile Gln Gly Asp
1 5 10

<210> 28
<211> 12
<212> PRT
<213> Artificial Sequence
<220>
<223> Synthetic
<400> 28
Trp Met Glu Asp Phe Asp Phe Val His Leu Gln Gly
1 5 10

<210> 29
<211> 11
<212> PRT
<213> Artificial Sequence
<220>
<223> Synthetic
<400> 29
Glu Pro Gln Phe Glu Glu Ile Pro Ile Tyr Leu
1 5 10

<210> 30
<211> 707
<212> PRT
<213> Artificial Sequence
<220>
<223> Synthetic
<400> 30
Met Lys Phe Gly Asn Phe Leu Leu Thr Tyr Gln Pro Pro Gln Phe Ser
1 5 10 15
Gln Thr Glu Val Met Lys Arg Leu Val Lys Leu Gly Arg Ile Ser Glu
20 25 30
Glu Cys Gly Phe Asp Thr Val Trp Leu Leu Glu His His Phe Thr Glu
35 40 45
Phe Gly Leu Leu Gly Asn Pro Tyr Val Ala Ala Ala Tyr Leu Leu Gly
50 55 60
Ala Thr Lys Lys Leu Asn Val Gly Thr Ala Ala Ile Val Leu Pro Thr
65 70 75 80
Ala His Pro Val Arg Gln Leu Glu Asp Val Asn Leu Leu Asp Gln Met
85 90 95
Ser Lys Gly Arg Phe Arg Phe Gly Ile Cys Arg Gly Leu Tyr Asn Lys
100 105 110
Asp Phe Arg Val Phe Gly Thr Asp Met Asn Asn Ser Arg Ala Leu Ala
115 120 125
Glu Cys Trp Tyr Gly Leu Ile Lys Asn Gly Met Thr Glu Gly Tyr Met
130 135 140
Glu Ala Asp Asn Glu His Ile Lys Phe His Lys Val Lys Val Asn Pro
145 150 155 160
Ala Ala Tyr Ser Arg Gly Gly Ala Pro Val Tyr Val Val Ala Glu Ser
165 170 175
Ala Ser Thr Thr Glu Trp Ala Ala Gln Phe Gly Leu Pro Met Ile Leu
180 185 190
Ser Trp Ile Ile Asn Thr Asn Glu Lys Lys Ala Gln Leu Glu Leu Tyr
195 200 205
Asn Glu Val Ala Gln Glu Tyr Gly His Asp Ile His Asn Ile Asp His
210 215 220
Cys Leu Ser Tyr Ile Thr Ser Val Asp His Asp Ser Ile Lys Ala Lys
225 230 235 240
Glu Ile Cys Arg Lys Phe Leu Gly His Trp Tyr Asp Ser Tyr Val Asn
245 250 255
Ala Thr Thr Ile Phe Asp Asp Ser Asp Gln Thr Arg Gly Tyr Asp Phe
260 265 270
Asn Lys Gly Gln Trp Arg Asp Phe Val Leu Lys Gly His Lys Asp Thr
275 280 285
Asn Arg Arg Ile Asp Tyr Ser Tyr Glu Ile Asn Pro Val Gly Thr Pro
290 295 300
Gln Glu Cys Ile Asp Ile Ile Gln Lys Asp Ile Asp Ala Thr Gly Ile
305 310 315 320
Ser Asn Ile Cys Cys Gly Phe Glu Ala Asn Gly Thr Val Asp Glu Ile
325 330 335

-continued

```
Ile Ala Ser Met Lys Leu Phe Gln Ser Asp Val Met Pro Phe Leu Lys
        340             345             350
Glu Lys Gln Arg Ser Leu Leu Tyr Tyr Gly Gly Gly Gly Ser Gly Gly
    355             360             365
Gly Gly Ser Gly Gly Gly Gly Ser Gly Gly Gly Gly Ser Lys Phe Gly
  370             375             380
Leu Phe Phe Leu Asn Phe Ile Asn Ser Thr Thr Val Gln Glu Gln Ser
385             390             395             400
Ile Val Arg Met Gln Glu Ile Thr Glu Tyr Val Asp Lys Leu Asn Phe
            405             410             415
Glu Gln Ile Leu Val Tyr Glu Asn His Phe Ser Asp Asn Gly Val Val
        420             425             430
Gly Ala Pro Leu Thr Val Ser Gly Phe Leu Leu Gly Leu Thr Glu Lys
    435             440             445
Ile Lys Ile Gly Ser Leu Asn His Ile Ile Thr Thr His His Pro Val
   450             455             460
Arg Ile Ala Glu Glu Ala Cys Leu Leu Asp Gln Leu Ser Glu Gly Arg
465             470             475             480
Phe Ile Leu Gly Phe Ser Asp Cys Glu Lys Lys Asp Glu Met His Phe
            485             490             495
Phe Asn Arg Pro Val Glu Tyr Gln Gln Gln Leu Phe Glu Glu Cys Tyr
        500             505             510
Glu Ile Ile Asn Asp Ala Leu Thr Thr Gly Tyr Cys Asn Pro Asp Asn
     515             520             525
Asp Phe Tyr Ser Phe Pro Lys Ile Ser Val Asn Pro His Ala Tyr Thr
  530             535             540
Pro Gly Gly Pro Arg Lys Tyr Val Thr Ala Thr Ser His His Ile Val
545             550             555             560
Glu Trp Ala Ala Lys Lys Gly Ile Pro Leu Ile Phe Lys Trp Asp Asp
            565             570             575
Ser Asn Asp Val Arg Tyr Glu Tyr Ala Glu Arg Tyr Lys Ala Val Ala
        580             585             590
Asp Lys Tyr Asp Val Asp Leu Ser Glu Ile Asp His Gln Leu Met Ile
    595             600             605
Leu Val Asn Tyr Asn Glu Asp Ser Asn Lys Ala Lys Gln Glu Thr Arg
  610             615             620
Ala Phe Ile Ser Asp Tyr Val Leu Glu Met His Pro Asn Glu Asn Phe
625             630             635             640
Glu Asn Lys Leu Glu Glu Ile Ile Ala Glu Asn Ala Val Gly Asn Tyr
            645             650             655
Thr Glu Cys Ile Thr Ala Ala Lys Leu Ala Ile Glu Lys Cys Gly Ala
        660             665             670
Lys Ser Val Leu Leu Ser Phe Glu Pro Met Asn Asp Leu Met Ser Gln
     675             680             685
Lys Asn Val Ile Asn Ile Val Asp Asp Asn Ile Lys Lys Tyr His Thr
  690             695             700
Glu Tyr Thr
705

<210> 31
<211> 263
<212> PRT
<213> Artificial Sequence
<220>
<223> Synthetic
<400> 31
Met Arg Glu Ala Val Ile Ala Glu Val Ser Thr Gln Leu Ser Glu Val
1               5               10              15
Val Gly Val Ile Glu Arg His Leu Glu Pro Thr Leu Leu Ala Val His
        20              25              30
Leu Tyr Gly Ser Ala Val Asp Gly Gly Leu Lys Pro His Ser Asp Ile
    35              40              45
Asp Leu Leu Val Thr Val Thr Val Arg Leu Asp Glu Thr Thr Arg Arg
  50              55              60
Ala Leu Ile Asn Asp Leu Leu Glu Thr Ser Ala Ser Pro Gly Glu Ser
65              70              75              80
Glu Ile Leu Arg Ala Val Glu Val Thr Ile Val Val His Asp Asp Ile
            85              90              95
Ile Pro Trp Arg Tyr Pro Ala Lys Arg Glu Leu Gln Phe Gly Glu Trp
        100             105             110
Gln Arg Asn Asp Ile Leu Ala Gly Ile Phe Glu Pro Ala Thr Ile Asp
    115             120             125
Ile Asp Leu Ala Ile Leu Leu Thr Lys Ala Arg Glu His Ser Val Ala
   130             135             140
Leu Val Gly Pro Ala Ala Glu Glu Leu Phe Asp Pro Val Pro Glu Gln
145             150             155             160
Asp Leu Phe Glu Ala Leu Asn Glu Thr Leu Thr Leu Trp Asn Ser Pro
            165             170             175
Pro Asp Trp Ala Gly Asp Glu Arg Asn Val Val Leu Thr Leu Ser Arg
        180             185             190
Ile Trp Tyr Ser Ala Val Thr Gly Lys Ile Ala Pro Lys Asp Val Ala
```

-continued

```
     195            200            205
Ala Asp Trp Ala Met Glu Arg Leu Pro Ala Gln Tyr Gln Pro Val Ile
  210            215            220
Leu Glu Ala Arg Gln Ala Tyr Leu Gly Gln Glu Glu Asp Arg Leu Ala
225            230            235            240
Ser Arg Ala Asp Gln Leu Glu Glu Phe Val His Tyr Val Lys Gly Glu
         245            250            255
Ile Thr Lys Val Val Gly Lys
        260

<210> 32
<211> 20
<212> DNA
<213> Artificial Sequence
<220>
<223> Synthetic
<400> 32
gtgcagtaag gaggaaaaaa                                                 20

<210> 33
<211> 20
<212> DNA
<213> Artificial Sequence
<220>
<223> Synthetic
<400> 33
cagtcagtag ggccctaaaa                                                 20

<210> 34
<211> 20
<212> DNA
<213> Artificial Sequence
<220>
<223> Synthetic
<400> 34
tagctaaagc aaccagagag                                                 20

<210> 35
<211> 25
<212> DNA
<213> Artificial Sequence
<220>
<223> Synthetic
<400> 35
caattcccct ctagaaataa ttttg                                           25

<210> 36
<211> 20
<212> DNA
<213> Artificial Sequence
<220>
<223> Synthetic
<400> 36
cgctgtagag aaaattggta                                                 20

<210> 37
<211> 20
<212> DNA
<213> Artificial Sequence
<220>
<223> Synthetic
<400> 37
gacgcggaat ggtactgggg                                                 20

<210> 38
<211> 33
<212> DNA
<213> Artificial Sequence
<220>
<223> Synthetic
<400> 38
atatggtctc acatgtccaa gccgcagact cag                                  33

<210> 39
<211> 31
<212> DNA
<213> Artificial Sequence
<220>
<223> Synthetic
<400> 39
atatggtctc acatggcacg cgtaactgtt c                                    31
```

<210> 40
<211> 38
<212> DNA
<213> Artificial Sequence
<220>
<223> Synthetic
<400> 40
atatggtctc acatgagtat cagcagcagg gtaaaaag 38

<210> 41
<211> 60
<212> DNA
<213> Artificial Sequence
<220>
<223> Synthetic
<400> 41
atgactacgt ccacctacag gggtaataac aattcccctc tagaaataat tttgtttaac 60

<210> 42
<211> 20
<212> DNA
<213> Artificial Sequence
<220>
<223> Synthetic
<400> 42
tgagttatac acagggctgg 20

<210> 43
<211> 27
<212> DNA
<213> Artificial Sequence
<220>
<223> Synthetic
<400> 43
gtgcagtaag gaggaaaaaa aaatggc 27

<210> 44
<211> 59
<212> DNA
<213> Artificial Sequence
<220>
<223> Synthetic
<400> 44
taaaattcgt agactacaag gacgacgatg acaagtggta ttttgggaag atcactcgt 59

<210> 45
<211> 43
<212> DNA
<213> Artificial Sequence
<220>
<223> Synthetic
<400> 45
taataacaat tcccctctag aaataatttt gtttaacttt aag 43

<210> 46
<211> 60
<212> DNA
<213> Artificial Sequence
<220>
<223> Synthetic
<400> 46
gtcagtgtgt aagtgcagaa agaggagaaa tactagatgg agatggaaaa ggagttcgag 60

<210> 47
<211> 47
<212> DNA
<213> Artificial Sequence
<220>
<223> Synthetic
<400> 47
taatctagag aaagaggaga aatactagat gtccaagccg cagactc 47

<210> 48
<211> 36
<212> DNA
<213> Artificial Sequence
<220>
<223> Synthetic
<400> 48
ctctagtaaa agttaaacaa aattatttgt agaggg 36

<210> 49
<211> 60
<212> DNA
<213> Artificial Sequence
<220>
<223> Synthetic
<400> 49
aacttttact agaggaattc gagctcttaa agaggagaaa ggtcatgggc tccaagccgc 60

<210> 50
<211> 54
<212> DNA
<213> Artificial Sequence
<220>
<223> Synthetic
<400> 50
aacttttact agagcgaaaa aaagtaaggc ggtaatccat gggctccaag ccgc 54

<210> 51
<211> 60
<212> DNA
<213> Artificial Sequence
<220>
<223> Synthetic
<400> 51
agtgtgtaag tgcagattaa agaggagaaa tactagatgg agatggaaaa ggagttcgag 60

<210> 52
<211> 60
<212> DNA
<213> Artificial Sequence
<220>
<223> Synthetic
<400> 52
tcagtgtgta agtgcagtca cacaggaaag tactagatgg agatggaaaa ggagttcgag 60

<210> 53
<211> 42
<212> DNA
<213> Artificial Sequence
<220>
<223> Synthetic
<400> 53
gcgtacattg gctccgttca tttgccgact accttggtga tc 42

<210> 54
<211> 58
<212> DNA
<213> Artificial Sequence
<220>
<223> Synthetic
<400> 54
gtcaggggcg gggttttttt ttagggccct actgactgtt agcaggtgcg gtaattga 58

<210> 55
<211> 58
<212> DNA
<213> Artificial Sequence
<220>
<223> Synthetic
<400> 55
cacagttctc gtcatcagct ctctggttgc tttagctaat acaccataag cattttcc 58

<210> 56
<211> 58
<212> DNA
<213> Artificial Sequence
<220>
<223> Synthetic
<400> 56
cagttacgcg tgccattttt ttttcctcct tactgcactt agcgtttcgg cgccggat 58

<210> 57
<211> 63
<212> DNA
<213> Artificial Sequence
<220>
<223> Synthetic
<400> 57
gtcaggggcg ggtttttttt ttagggccct actgactgtt acacactgac atccttctca 60

-continued tcg 63

<210> 58
<211> 59
<212> DNA
<213> Artificial Sequence
<220>
<223> Synthetic
<400> 58
caggggcggg gttttttttt agggccctac tgactgttat tagccaagat ccatcttca 59

<210> 59
<211> 59
<212> DNA
<213> Artificial Sequence
<220>
<223> Synthetic
<400> 59
gttacgcgtg ccattttttt ttcctcctta ctgcacttat tacgaaaccg gatacaaca 59

<210> 60
<211> 37
<212> DNA
<213> Artificial Sequence
<220>
<223> Synthetic
<400> 60
atatggtctc atttacacac tgacatcctt ctcatcg 37

<210> 61
<211> 31
<212> DNA
<213> Artificial Sequence
<220>
<223> Synthetic
<400> 61
atatggtctc atttacccct gtaggtggac g 31

<210> 62
<211> 32
<212> DNA
<213> Artificial Sequence
<220>
<223> Synthetic
<400> 62
atatggtctc atttagcaga cgttggtcag gc 32

<210> 63
<211> 59
<212> DNA
<213> Artificial Sequence
<220>
<223> Synthetic
<400> 63
aagataaaaa gaatagatcc cagccctgtg tataactcac tactttagtc agttccgca 59

<210> 64
<211> 52
<212> DNA
<213> Artificial Sequence
<220>
<223> Synthetic
<400> 64
cccctgtagg tggacgtagt catagtcctc catccacgca gctgcacgac ga 52

<210> 65
<211> 27
<212> DNA
<213> Artificial Sequence
<220>
<223> Synthetic
<400> 65
gcccatggta tatctccttc ttaaagt 27

<210> 66
<211> 59
<212> DNA
<213> Artificial Sequence
<220>
<223> Synthetic
<400> 66

-continued acagttacgc gtgccatttt tttttcctcc ttactgcact tagcagacgt tggtcaggc 59

<210> 67
<211> 59
<212> DNA
<213> Artificial Sequence
<220>
<223> Synthetic
<400> 67
gggaattgtt attagcccgg aaaatcgtta taatactgat gatccgcagc tgcacgacg 59

<210> 68
<211> 59
<212> DNA
<213> Artificial Sequence
<220>
<223> Synthetic
<400> 68
gggaattgtt attaatcgcc ctgaatcacc agatagcgct gcggcgcagc tgcacgacg 59

<210> 69
<211> 60
<212> DNA
<213> Artificial Sequence
<220>
<223> Synthetic
<400> 69
gaattgttat tacagataaa tcggaatttc ttcatactgc ggttccgcag ctgcacgacg 60

<210> 70
<211> 43
<212> DNA
<213> Artificial Sequence
<220>
<223> Synthetic
<400> 70
ctcatccgcc aaaacagcct caattgtgtg gctccaggat tcg 43

<210> 71
<211> 25
<212> DNA
<213> Artificial Sequence
<220>
<223> Synthetic
<400> 71
ttacacactg acatccttct catcg 25

<210> 72
<211> 23
<212> DNA
<213> Artificial Sequence
<220>
<223> Synthetic
<400> 72
ttctagagca cagctaacac cac 23

<210> 73
<211> 24
<212> DNA
<213> Artificial Sequence
<220>
<223> Synthetic
<400> 73
gaaccaatga atgatttgat gagc 24

<210> 74
<211> 49
<212> DNA
<213> Artificial Sequence
<220>
<223> Synthetic
<400> 74
gttttttttt agggccctac tgactgtcaa ttgtgtggct ccaggattc 49

<210> 75
<211> 43
<212> DNA
<213> Artificial Sequence
<220>
<223> Synthetic
<400> 75

-continued gacctgcaga ttaaagagga gaaaatgagg gaagcggtga tcg 43

<210> 76
<211> 28
<212> DNA
<213> Artificial Sequence
<220>
<223> Synthetic
<400> 76
tattgagctc caccgcggag gaggaatg 28

<210> 77
<211> 32
<212> DNA
<213> Artificial Sequence
<220>
<223> Synthetic
<400> 77
tattggtctc ccatgagcag cagcactggc ac 32

<210> 78
<211> 38
<212> DNA
<213> Artificial Sequence
<220>
<223> Synthetic
<400> 78
ataaaggtct cccatggtga aacgagaatt tcctccag 38

<210> 79
<211> 89
<212> DNA
<213> Artificial Sequence
<220>
<223> Synthetic
<400> 79
agatcactac cgggcgtatt ttttgagtta tcgagatttt caggagctaa ggaagctaaa 60
atggagaaaa aaatcactgg atataccac 89

<210> 80
<211> 37
<212> DNA
<213> Artificial Sequence
<220>
<223> Synthetic
<400> 80
tattgtcgac ttatttatta cgctggatga tgtagtc 37

<210> 81
<211> 37
<212> DNA
<213> Artificial Sequence
<220>
<223> Synthetic
<400> 81
tattggtctc cgtccttcca acgcattcaa catgttg 37

<210> 82
<211> 40
<212> DNA
<213> Artificial Sequence
<220>
<223> Synthetic
<400> 82
tattaggtct cgagctctta ggcaactggt tggaagaggc 40

<210> 83
<211> 33
<212> DNA
<213> Artificial Sequence
<220>
<223> Synthetic
<400> 83
gccgccggct tccatttatt acgccccgcc ctg 33

<210> 84
<211> 51
<212> DNA
<213> Artificial Sequence
<220>
<223> Synthetic

-continued

<400> 84
gtccagtact ttattggggt tcaggcggat ggaactgagc atgtccgaga t 51

<210> 85
<211> 47
<212> DNA
<213> Artificial Sequence
<220>
<223> Synthetic
<400> 85
gagagagaat cctgttcctg atattgcgga tacagccatg ggccttc 47

<210> 86
<211> 53
<212> DNA
<213> Artificial Sequence
<220>
<223> Synthetic
<400> 86
acaaaaactt ccaatttcac tgttatttta gcggatcttt atgacgccca tgg 53

<210> 87
<211> 40
<212> DNA
<213> Artificial Sequence
<220>
<223> Synthetic
<400> 87
cgtaagcatc gtaagtgtcc gcgatcaggg tgataacagc 40

<210> 88
<211> 44
<212> DNA
<213> Artificial Sequence
<220>
<223> Synthetic
<400> 88
cccatgcgtg tcgtataagt ccgctaacat tgtcatcaag atcg 44

<210> 89
<211> 46
<212> DNA
<213> Artificial Sequence
<220>
<223> Synthetic
<220>
<221> misc_feature
<222> (17) . . . (18)
<223> n is a, c, g, or t
<400> 89
caatggcacc cccaacnnkg gtatgtgtgt acttaatctg atcccg 46

<210> 90
<211> 46
<212> DNA
<213> Artificial Sequence
<220>
<223> Synthetic
<220>
<221> misc_feature
<222> (20) . . . (21)
<223> n is a, c, g, or t
<400> 90
caacaccggt atgtgtgtan nkaatctgat cccgttgctg cttatg 46

<210> 91
<211> 41
<212> DNA
<213> Artificial Sequence
<220>
<223> Synthetic
<220>
<221> misc_feature
<222> (17) . . . (18)
<223> n is a, c, g, or t
<400> 91
aaacgcttgg gaacgcnnkc tggaagcgta tttgcaggat g 41

<210> 92
<211> 45
<212> DNA

<213> Artificial Sequence
<220>
<223> Synthetic
<220>
<221> misc_feature
<222> (17) . . . (18)
<223> n is a, c, g, or t
<400> 92
cttctggatg gccgcgnnka tttcagaacc agaatttagt ggctc 45

<210> 93
<211> 43
<212> DNA
<213> Artificial Sequence
<220>
<223> Synthetic
<220>
<221> misc_feature
<222> (21) . . . (22)
<223> n is a, c, g, or t
<400> 93
accatctgat tgaactggct nnkcgactgg togatgatgc gag 43

<210> 94
<211> 43
<212> DNA
<213> Artificial Sequence
<220>
<223> Synthetic
<220>
<221> misc_feature
<222> (14) . . . (15)
<223> n is a, c, g, or t
<400> 94
cgtcctggcg cggnnkattc agtttatgta taaccagggg gac 43

<210> 95
<211> 54
<212> DNA
<213> Artificial Sequence
<220>
<223> Synthetic
<220>
<221> misc_feature
<222> (29) . . . (30)
<223> n is a, c, g, or t
<400> 95
caactgcggt aaagagtttg ttaaagaann kgtacgtaac ctgatggttg aagc 54

<210> 96
<211> 47
<212> DNA
<213> Artificial Sequence
<220>
<223> Synthetic
<220>
<221> misc_feature
<222> (25) . . . (26)
<223> n is a, c, g, or t
<400> 96
catgacccgg ttgttatcat caccnnkggt gcaaacctgc tgaccac 47

<210> 97
<211> 40
<212> DNA
<213> Artificial Sequence
<220>
<223> Synthetic
<220>
<221> misc_feature
<222> (18) . . . (19)
<223> n is a, c, g, or t
<400> 97
ccggcggtgc aaacctgnnk accaccactt gctatctggg 40

<210> 98
<211> 48
<212> DNA
<213> Artificial Sequence
<220>
<223> Synthetic

<220>
<221> misc_feature
<222> (25) . . . (26)
<223> n is a, c, g, or t
<400> 98
ctgttccgtt actccggtat tctgnnkcgt cgtctgaacg acctgatg 48

<210> 99
<211> 50
<212> DNA
<213> Artificial Sequence
<220>
<223> Synthetic
<220>
<221> misc_feature
<222> (23) . . . (24)
<223> n is a, c, g, or t
<400> 99
ggcagtaatc tacctgtgcc agnnkctgga agtacagtac gctggtaaag 50

<210> 100
<211> 34
<212> DNA
<213> Artificial Sequence
<220>
<223> Synthetic
<400> 100
cagctgcgga accgcagttt gaagaaattc cgat 34

<210> 101
<211> 48
<212> DNA
<213> Artificial Sequence
<220>
<223> Synthetic
<400> 101
tggatggagg actttgactt cgtccaccta caggggtaat aacaattc 48

<210> 102
<211> 66
<212> DNA
<213> Artificial Sequence
<220>
<223> Synthetic
<400> 102
ctctccgttt ctgactttga caacgccaag gggctcaatg tgctgcacta caagatccgc 60
aagctg 66

<210> 103
<211> 30
<212> DNA
<213> Artificial Sequence
<220>
<223> Synthetic
<400> 103
aaacactacc tgatccgcaa gctggacagc 30

<210> 104
<211> 30
<212> DNA
<213> Artificial Sequence
<220>
<223> Synthetic
<400> 104
tattggtctc tcgcggtatc attgcagcac 30

<210> 105
<211> 31
<212> DNA
<213> Artificial Sequence
<220>
<223> Synthetic
<400> 105
tattggtctc atcaccccat gcgagagtag g 31

<210> 106
<211> 25
<212> DNA
<213> Artificial Sequence
<220>
<223> Synthetic

<400> 106
aacaatttca cacaggaaac agacc 25

<210> 107
<211> 51
<212> DNA
<213> Artificial Sequence
<220>
<223> Synthetic
<400> 107
atctcggaca tgctcagttc catccgcctg aaccccaata aagtactgga c 51

<210> 108
<211> 47
<212> DNA
<213> Artificial Sequence
<220>
<223> Synthetic
<400> 108
gaaggcccat ggctgtatcc gcaatatcag gaacaggatt ctctctc 47

<210> 109
<211> 53
<212> DNA
<213> Artificial Sequence
<220>
<223> Synthetic
<400> 109
ccatgggcgt cataaagatc cgctaaaata acagtgaaat tggaagtttt tgt 53

<210> 110
<211> 40
<212> DNA
<213> Artificial Sequence
<220>
<223> Synthetic
<400> 110
gctgttatca ccctgatcgc ggacacttac gatgcttacg 40

<210> 111
<211> 44
<212> DNA
<213> Artificial Sequence
<220>
<223> Synthetic
<400> 111
cgatcttgat gacaatgtta gcggacttat acgacacgca tggg 44

<210> 112
<211> 19
<212> DNA
<213> Artificial Sequence
<220>
<223> Synthetic
<400> 112
gttgggggtg ccattgttc 19

<210> 113
<211> 21
<212> DNA
<213> Artificial Sequence
<220>
<223> Synthetic
<400> 113
tacacacata ccggtgttgg g 21

<210> 114
<211> 19
<212> DNA
<213> Artificial Sequence
<220>
<223> Synthetic
<400> 114
gcgttcccaa gcgtttttg 19

<210> 115
<211> 17
<212> DNA
<213> Artificial Sequence
<220>
<223> Synthetic

<400> 115
cgcggccatc cagaagt 17

<210> 116
<211> 22
<212> DNA
<213> Artificial Sequence
<220>
<223> Synthetic
<400> 116
agccagttca atcagatggt gg 22

<210> 117
<211> 15
<212> DNA
<213> Artificial Sequence
<220>
<223> Synthetic
<400> 117
ccgcgccagg acgtg 15

<210> 118
<211> 28
<212> DNA
<213> Artificial Sequence
<220>
<223> Synthetic
<400> 118
ttctttaaca aactctttac cgcagttg 28

<210> 119
<211> 24
<212> DNA
<213> Artificial Sequence
<220>
<223> Synthetic
<400> 119
ggtgatgata acaaccgggt catg 24

<210> 120
<211> 17
<212> DNA
<213> Artificial Sequence
<220>
<223> Synthetic
<400> 120
caggtttgca ccgccgg 17

<210> 121
<211> 24
<212> DNA
<213> Artificial Sequence
<220>
<223> Synthetic
<400> 121
cagaataccg gagtaacgga acag 24

<210> 122
<211> 22
<212> DNA
<213> Artificial Sequence
<220>
<223> Synthetic
<400> 122
ctggcacagg tagattactg cc 22

<210> 123
<211> 34
<212> DNA
<213> Artificial Sequence
<220>
<223> Synthetic
<400> 123
atcggaattt cttcaaactg cggttccgca gctg 34

<210> 124
<211> 33
<212> DNA
<213> Artificial Sequence
<220>
<223> Synthetic

-continued

<400> 124
gtcaaagtcc tccatccacg cagctgcacg acg 33

<210> 125
<211> 50
<212> DNA
<213> Artificial Sequence
<220>
<223> Synthetic
<400> 125
aagtcagaaa cggagagggc ataggcacct tttaccgtct cgctctcccg 50

<210> 126
<211> 48
<212> DNA
<213> Artificial Sequence
<220>
<223> Synthetic
<400> 126
gctgtccagc ttgcggatca ggtagtgttt cacattgagc cccttggc 48

<210> 127
<211> 32
<212> DNA
<213> Artificial Sequence
<220>
<223> Synthetic
<400> 127
tattggtctc agtgacccca cactaccatc gg 32

<210> 128
<211> 31
<212> DNA
<213> Artificial Sequence
<220>
<223> Synthetic
<400> 128
tattggtctc acgcgtgacc cacgctcacc g 31

<210> 129
<211> 20
<212> DNA
<213> Artificial Sequence
<220>
<223> Synthetic
<400> 129
gcctgcaggt cgactctaga 20

<210> 130
<211> 43
<212> DNA
<213> Artificial Sequence
<220>
<223> Synthetic
<400> 130
aacaatttca cacaggaaac agaccatggc gggtgtttct gcg 43

<210> 131
<211> 38
<212> DNA
<213> Artificial Sequence
<220>
<223> Synthetic
<400> 131
gcctgcaggt cgactctaga ttacagcggc agcggttc 38

<210> 132
<211> 39
<212> DNA
<213> Artificial Sequence
<220>
<223> Synthetic
<400> 132
cagagagaag gtgccagaca tcccaatgcc tgcactaca 39

<210> 133
<211> 35
<212> DNA
<213> Artificial Sequence
<220>
<223> Synthetic

-continued

<400> 133
caatgatggt gcctgtcatg ccgatgccgg cgctg 35

<210> 134
<211> 60
<212> DNA
<213> Artificial Sequence
<220>
<223> Synthetic
<400> 134
gctgtgatca aatggcagta tgtccttcgc tctgttcttt ttaacatttt cttctttttc 60

<210> 135
<211> 34
<212> DNA
<213> Artificial Sequence
<220>
<223> Synthetic
<400> 135
aggtgtcgta catgtccgcc agaacggtct gcag 34

<210> 136
<211> 39
<212> DNA
<213> Artificial Sequence
<220>
<223> Synthetic
<400> 136
tgtagtgcag gcattgggat gtctggcacc ttctctctg 39

<210> 137
<211> 35
<212> DNA
<213> Artificial Sequence
<220>
<223> Synthetic
<400> 137
cagcgccggc atcggcatga caggcaccat cattg 35

<210> 138
<211> 60
<212> DNA
<213> Artificial Sequence
<220>
<223> Synthetic
<400> 138
gaaaaagaag aaaatgttaa aaagaacaga gcgaaggaca tactgccatt tgatcacagc 60

<210> 139
<211> 34
<212> DNA
<213> Artificial Sequence
<220>
<223> Synthetic
<400> 139
ctgcagaccg ttctggcgga catgtacgac acct 34

<210> 140
<211> 34
<212> PRT
<213> *Homo sapiens*
<400> 140
Ile Gln Thr Ala Asp Gln Leu Arg Phe Ser Tyr Leu Ala Val Ile Glu
1 5 10 15
Gly Ala Lys Phe Ile Met Gly Asp Ser Ser Val Gln Asp Gln Trp Lys
20 25 30
Glu Leu <210> 141
<211> 34
<212> PRT
<213> *Homo sapiens*
<400> 141
Ile Gln Thr Pro Asp Gln Leu Arg Phe Ser Tyr Met Ala Ile Ile Glu
1 5 10 15
Gly Ala Lys Tyr Thr Lys Gly Asp Ser Asn Ile Gin Lys Arg Trp Lys
20 25 30
Glu Leu

SEQUENCE LISTING

```
Sequence total quantity: 141
SEQ ID NO: 1            moltype = AA  length = 10
FEATURE                 Location/Qualifiers
REGION                  1..10
                        note = Synthetic
source                  1..10
                        mol_type = protein
                        organism = synthetic construct
SEQUENCE: 1
EPQYEEIPYL                                                         10

SEQ ID NO: 2            moltype = AA  length = 10
FEATURE                 Location/Qualifiers
REGION                  1..10
                        note = Synthetic
source                  1..10
                        mol_type = protein
                        organism = synthetic construct
SEQUENCE: 2
EPQFEEIPYL                                                         10

SEQ ID NO: 3            moltype = DNA  length = 867
FEATURE                 Location/Qualifiers
misc_feature            1..867
                        note = Synthetic
source                  1..867
                        mol_type = other DNA
                        organism = synthetic construct
SEQUENCE: 3
atgggctcca agccgcagac tcagggcctg gccaaggatg cctgggagat ccctcgggag  60
tcgctgcggc tggaggtcaa gctgggccag ggctgctttg gcgaggtgtg gatggggacc  120
tggaacggta ccaccagggt ggccatcaaa accctgaagc ctggcacgat gtctccagag  180
gccttcctgc aggaggccca ggtcatgaag aagctgaggc atgagaagct ggtgcagttg  240
tatgctgtgg tttcagagga gcccatttac atcgtcacgg agtacatgag caaggggagt  300
ttgctggact ttctcaaggg ggagacaggc aagtacctgc ggctgcctca gctggtggac  360
atggctgctc agatcgcctc aggcatggcg tacgtggagc ggatgaacta cgtccaccgg  420
gaccttcgtg cagccaacat cctggtggga gagaacctgg tgtgcaaagt ggccgacttt  480
gggctggctc ggctcattga agacaatgag tacacggcgc ggcaaggtgc caaattcccc  540
atcaagtgga cggctccaga agctgccctc tatggccgct tcaccatcaa gtcggacgtg  600
tggtccttcg ggatcctgct gactgagctc accacaaagg gacgggtgcc ctaccctggg  660
atggtgaacc gcgaggtgct ggaccaggtg gagcggggct accggatgcc ctgcccgccg  720
gagtgtcccg agtccctgca cgacctcatg tgccagtgct ggcggaagga gcctgaggag  780
cggcccacct tcgagtacct gcaggccttc ctggaggact acttcacgtc caccgagccc  840
cagtaccagc ccggggagaa cctctaa                                      867

SEQ ID NO: 4            moltype = DNA  length = 1137
FEATURE                 Location/Qualifiers
misc_feature            1..1137
                        note = Synthetic
source                  1..1137
                        mol_type = other DNA
                        organism = synthetic construct
SEQUENCE: 4
atggtggact acagcgtgtg ggaccacatt gaggtgtctg atgatgaaga cgagacgcac  60
cccaacatcg acacggccag tctcttccgc tggcggcatc aggcccgggt ggaacgcatg  120
gagcagttcc agaaggagaa ggaggaactg gacaggggct gccgcgagtg caagcgcaag  180
gtggccgagt gccagaggaa actgaaggag ctggaggtgg ccgagggcgg caaggcagag  240
ctggagcgcc tgcaggccga ggcacagcag ctgcgcaagg aggagcggag ctgggagcag  300
aagctggagg agatgcgcaa gaaggagaag agcatgccct ggaacgtgga cacgctcagc  360
aaagacggct tcagcaagag catggtaaat accaagcccg agaagacgga ggaggactca  420
gaggaggtga gggagcagaa acacaagacc ttcgtggaaa aatacgagaa acagatcaag  480
cactttggca tgcttcgccg ctgggatgac agccaaaagt acctgtcaga caacgtccac  540
ctggtgtgcg aggagacagc caattacctg gtcatttggt gcattgacct agaggtggag  600
gagaaatgtg cactcatgga gcaggtggcc caccagacaa tcgtcatgca atttatcctg  660
gagctggcca agagcctaaa ggtggacccc cggggcctgct tccggcagtt cttcactaag  720
attaagacag ccgatcgcca gtacatggag ggcttcaacg acgagctgga agccttcaag  780
gagcgtgtgc ggggccgtgc caagctgcgc atcgagaagg ccatgaagga gtacgaggag  840
gaggagcgca agaagcggct cggccccggc ggcctggacc ccgtcgaggt ctacgagtcc  900
ctccctgagg aactccagaa gtgcttcgat gtgaaggacg tgcagatgct gcaggacgcc  960
atcagcaaga tggaccccac cgacgcaaag taccacatgc agcgctgcat tgactctggc  1020
ctctgggtcc ccaactctaa ggccagcgag gccaaggagg gagaggaggc aggtcctggg  1080
gacccattac tggaagctgt tcccaagacg ggcgatgaga aggatgtcag tgtgtaa     1137

SEQ ID NO: 5            moltype = DNA  length = 966
FEATURE                 Location/Qualifiers
misc_feature            1..966
                        note = Synthetic
source                  1..966
```

```
                        mol_type = other DNA
                        organism = synthetic construct
SEQUENCE: 5
atggagatgg aaaaggagtt cgagcagatc gacaagtccg ggagctgggc ggccatttac  60
caggatatcc gacatgaagc cagtgacttc ccatgtagag tggccaagct tcctaagaac  120
aaaaaccgaa ataggtacag agacgtcagt ccctttgacc atagtcggat taaactacat  180
caagaagata atgactatat caacgctagt ttgataaaaa tggaagaagc ccaaaggagt  240
tacattctta cccagggccc tttgcctaac acatgcggtc acttttggga gatggtgtgg  300
gagcagaaaa gcaggggtgt cgtcatgctc aacagagtga tggagaaagg ttcgttaaaa  360
tgcgcacaat actggccaca aaaagaagaa aaagagatga tctttgaaga cacaaatttg  420
aaattaacat tgatctctga agatatcaag tcatattata cagtgcgaca gctagaattg  480
gaaaacctta caacccaaga aactcgagag atcttacatt tccactatac cacatggcct  540
gactttggag tccctgaatc accagcctca ttcttgaact ttcttttcaa agtccgagag  600
tcagggtcac tcagcccgga gcacgggccc gttgtggtgc actgcagtgc aggcatcggc  660
aggtctggaa ccttctgtct ggctgatacc tgcctcttgc tgatggacaa gaggaaagac  720
ccttcttccg ttgatatcaa gaaagtgctg ttagaaatga ggaagtttcg gatggggctg  780
atccagacag ccgaccagct gcgcttctcc tacctggctg tgatcgaagg tgccaaattc  840
atcatggggg actcttccgt gcaggatcag tggaaggagc tttcccacga ggacctggag  900
cccccacccg agcatatccc cccacctccc cggccaccca aacgaatcct ggagccacac  960
aattga                                                             966

SEQ ID NO: 6            moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 6
tggatggagg actatgacta cgtccaccta cagggg                            36

SEQ ID NO: 7            moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 7
gaaccgcagt atgaagaaat tccgatttat ctg                               33

SEQ ID NO: 8            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 8
gatcatcagt attataacga ttttccgggc                                   30

SEQ ID NO: 9            moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 9
ccgcagcgct atctggtgat tcagggcgat                                   30

SEQ ID NO: 10           moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 10
tggatggagg actttgactt cgtccaccta cagggg                            36

SEQ ID NO: 11           moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 11
```

```
gaaccgcagt ttgaagaaat tccgatttat ctg                           33

SEQ ID NO: 12          moltype = DNA  length = 238
FEATURE                Location/Qualifiers
misc_feature           1..238
                       note = Synthetic
source                 1..238
                       mol_type = other DNA
                       organism = synthetic construct
SEQUENCE: 12
agaaaccaat tgtccatatt gcatcagaca ttgccgtcac tgcgtctttt actggctctt  60
ctcgctaacc aaaccggtaa ccccgcttat taaaagcatt ctgtaacaaa gcgggaccaa  120
agccatgaca aaaacgcgta acaaaagtgt ctataatcac ggcagaaaag tccacattga  180
ttatttgcac ggcgtcacac tttgctatgc catagcattt ttatccataa gattagcg    238

SEQ ID NO: 13          moltype = DNA  length = 160
FEATURE                Location/Qualifiers
misc_feature           1..160
                       note = Synthetic
source                 1..160
                       mol_type = other DNA
                       organism = synthetic construct
SEQUENCE: 13
ttctagagca cagctaacac cacgtcgtcc ctatctgctg ccctaggtct atgagtggtt  60
gctggataac tttacgggca tgcataaggc tcggtatcta tattcaggga gaccacaacg  120
gtttccctct acaaataatt ttgtttaact tttactagag                        160

SEQ ID NO: 14          moltype = DNA  length = 57
FEATURE                Location/Qualifiers
misc_feature           1..57
                       note = Synthetic
source                 1..57
                       mol_type = other DNA
                       organism = synthetic construct
SEQUENCE: 14
cattaggcac cccgggcttt actcgtaaag cttccggcgc gtatgttgtg tcgaccg     57

SEQ ID NO: 15          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 15
gtgcagttaa agaggagaaa ggtc                                     24

SEQ ID NO: 16          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 16
cgaaaaaaag taaggcggta atcc                                     24

SEQ ID NO: 17          moltype = DNA  length = 28
FEATURE                Location/Qualifiers
misc_feature           1..28
                       note = Synthetic
source                 1..28
                       mol_type = other DNA
                       organism = synthetic construct
SEQUENCE: 17
tctagagatt aaagaggaga aatactag                                 28

SEQ ID NO: 18          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 18
tctagaaaag aggagaaata ctag                                     24

SEQ ID NO: 19          moltype = DNA  length = 2124
FEATURE                Location/Qualifiers
```

```
misc_feature            1..2124
                        note = Synthetic
source                  1..2124
                        mol_type = other DNA
                        organism = synthetic construct
SEQUENCE: 19
atgaaatttg gaaacttttt gcttacatac caacctcccc aattttccca aacagaggta  60
atgaaacgtt tggttaaatt aggtcgcatc tctgaggagt gtggttttga taccgtatgg  120
ttactggagc atcatttcac ggagtttggt ttgcttggta acccttatgt cgctgctgca  180
tatttacttg gcgcgactaa aaaattgaat gtaggaactg ccgctattgt tcttcccaca  240
gcccatccag tacgccaact tgaagatgtg aatttattgg atcaaatgtc aaaaggacga  300
tttcggtttg gtatttgccg agggctttac aacaaggact ttcgcgtatt cggcacagat  360
atgaataaca gtcgcgcctt agcggaatgc tggtacgggc tgataaagaa tggcatgaca  420
gagggatata tggaagctga taatgaacat atcaagttcc ataaggtaaa agtaaacccc  480
gcggcgtata gcagaggtgg cgcaccggtt tatgtggtgg ctgaatcagc ttcgacgact  540
gagtgggctg ctcaatttgg cctaccgatg atattaagtt ggattataaa tactaacgaa  600
aagaaagcac aacttgagct ttataatgaa gtggctcaag aatatgggca cgatattcat  660
aatatcgacc attgcttatc atatataaca tctgtagatc atgactcaat taaagcgaaa  720
gagatttgcc ggaaatttct ggggcattgg tatgattctt atgtgaatgc tacgactatt  780
tttgatgatt cagaccaaac aagaggttat gatttcaata aagggcagtg gcgtgacttt  840
gtattaaaag gacataaaga tactaatcgc cgtattgatt acagttacga aatcaatccc  900
gtgggaacgc cgcaggaatg tattgacata attcaaaaag acattgatgc tacaggaata  960
tcaaatattt gttgtggatt tgaagctaat ggaacagtag acgaaattat tgcttccatg  1020
aagctcttcc agtctgatgt catgccattt cttaaagaaa aacaacgttc gctattatat  1080
tatggcggtg gcggtagcgg cggtggcggt agcggcggtg gcggtagcgg cggtggcggt  1140
agcaaatttg gattgttctt ccttaacttc atcaattcaa caactgttca agaacagagt  1200
atagttcgca tgcaggaaat aacggagtat gttgataagt tgaattttga acagatttta  1260
gtgtatgaaa atcatttttc agataatggt gttgtcggcg ctcctctgac tgtttctggt  1320
tttctgctcg gtttaacaga gaaaattaaa attggttcat taaatcacat cattacaact  1380
catcatcctg tccgcatagc ggaggaagct tgcttattgg atcagttaag tgaagggaga  1440
tttattttag ggtttagtga ttgcgaaaaa aaagatgaaa tgcatttttt taatcgcccg  1500
gttgaatatc aacagcaact atttgaagag tgttatgaaa tcattaacga tgctttaaca  1560
acaggctatt gtaatccaga taacgatttt tatagcttcc ctaaaatatc tgtaaatccc  1620
catgcttata cgccaggcgg acctcggaaa tatgtaacag caaccagtca tcatattgtt  1680
gagtgggcgg ccaaaaaagg tattcctctc atctttaagt gggatgattc taatgatgtt  1740
agatatgaat atgctgaaag atataaagcc gttgcggata aatatgacgt tgacctatca  1800
gagatagacc atcagttaat gatattagtt aactataacg aagatagtaa taaagctaaa  1860
caagagacgc gtgcatttat tagtgattat gttcttgaaa tgcaccctaa tgaaaatttc  1920
gaaaataaac ttgaagaaat aattgcagaa aacgctgtcg gaaattatac ggagtgtata  1980
actgcggcta agttggcaat tgaaaagtgt ggtgcgaaaa gtgtattgct gtcctttgaa  2040
ccaatgaatg atttgatgag ccaaaaaaat gtaatcaata ttgttgatga taatattaag  2100
aagtaccaca cggaatatac ctaa                                         2124

SEQ ID NO: 20           moltype = DNA  length = 792
FEATURE                 Location/Qualifiers
misc_feature            1..792
                        note = Synthetic
source                  1..792
                        mol_type = other DNA
                        organism = synthetic construct
SEQUENCE: 20
atgagggaag cggtgatcgc cgaagtatcg actcaactat cagaggtagt tggcgtcatc  60
gagcgccatc tcgaaccgac gttgctggcc gtacatttgt acggctccgc agtggatggc  120
ggcctgaagc cacacagtga tattgatttg ctggttacgg tgaccgtaag gcttgatgaa  180
acaacgcggc gagctttgat caacgacctt ttggaaactt cggcttcccc tggagagagc  240
gagattctcc gcgctgtaga agtcaccatt gttgtgcacg acgacatcat tccgtggcgt  300
tatccagcta agcgcgaact gcaatttgga gaatggcagc gcaatgacat tcttgcaggt  360
atcttcgagc cagccacgat cgacattgat ctggctatct tgctgacaaa agcaagagaa  420
catagcgttg ccttggtagg tccagcggcg gaggaactct ttgatccggt tcctgaacag  480
gatctatttg aggcgctaaa tgaaacctta acgctatgga actcgccgcc cgactgggct  540
ggcgatgagc gaaatgtagt gcttacgttg tcccgcattt ggtacagcgc agtaaccggc  600
aaaatcgcgc cgaaggatgt cgctgccgac tgggcaatgg agcgcctgcc ggcccagtat  660
cagcccgtca tacttgaagc tagacaggct tatcttggac aagaagaaga tcgcttggcc  720
tcgcgcgcag atcagttgga agaatttgtc cactacgtga aaggcgagat caccaaggta  780
gtcggcaaat ga                                                       792

SEQ ID NO: 21           moltype = AA  length = 288
FEATURE                 Location/Qualifiers
REGION                  1..288
                        note = Synthetic
source                  1..288
                        mol_type = protein
                        organism = synthetic construct
SEQUENCE: 21
MGSKPQTQGL AKDAWEIPRE SLRLEVKLGQ GCFGEVWMGT WNGTTRVAIK TLKPGTMSPE  60
AFLQEAQVMK KLRHEKLVQL YAVVSEEPIY IVTEYMSKGS LLDFLKGETG KYLRLPQLVD  120
MAAQIASGMA YVERMNYVHR DLRAANILVG ENLVCKVADF GLARLIEDNE YTARQGAKFP  180
IKWTAPEAAL YGRFTIKSDV WSFGILLTEL TTKGRVPYPG MVNREVLDQV ERGYRMPCPP  240
ECPESLHDLM CQCWRKEPEE RPTFEYLQAF LEDYFTSTEP QYQPGENL                288
```

```
SEQ ID NO: 22          moltype = AA  length = 378
FEATURE                Location/Qualifiers
REGION                 1..378
                       note = Synthetic
source                 1..378
                       mol_type = protein
                       organism = synthetic construct
SEQUENCE: 22
MVDYSVWDHI EVSDDEDETH PNIDTASLFR WRHQARVERM EQFQKEKEEL DRGCRECKRK  60
VAECQRKLKE LEVAEGGKAE LERLQAEAQQ LRKEERSWEQ KLEEMRKKEK SMPWNVDTLS  120
KDGFSKSMVN TKPEKTEEDS EEVREQKHKT FVEKYEKQIK HFGMLRRWDD SQKYLSDNVH  180
LVCEETANYL VIWCIDLEVE EKCALMEQVA HQTIVMQFIL ELAKSLKVDP RACFRQFFTK  240
IKTADRQYME GFNDELEAFK ERVRGRAKLR IEKAMKEYEE EERKKRLGPG GLDPVEVYES  300
LPEELQKCFD VKDVQMLQDA ISKMDPTDAK YHMQRCIDSG LWVPNSKASE AKEGEEAGPG  360
DPLLEAVPKT GDEKDVSV                                                378

SEQ ID NO: 23          moltype = AA  length = 321
FEATURE                Location/Qualifiers
REGION                 1..321
                       note = Synthetic
source                 1..321
                       mol_type = protein
                       organism = synthetic construct
SEQUENCE: 23
MEMEKEFEQI DKSGSWAAIY QDIRHEASDF PCRVAKLPKN KNRNRYRDVS PFDHSRIKLH  60
QEDNDYINAS LIKMEEAQRS YILTQGPLPN TCGHFWEMVW EQKSRGVVML NRVMEKGSLK  120
CAQYWPQKEE KEMIFEDTNL KLTLISEDIK SYYTVRQLEL ENLTTQETRE ILHFHYTTWP  180
DFGVPESPAS FLNFLFKVRE SGSLSPEHGP VVVHCSAGIG RSGTFCLADT CLLLMDKRKD  240
PSSVDIKKVL LEMRKFRMGL IQTADQLRFS YLAVIEGAKF IMGDSSVQDQ WKELSHEDLE  300
PPPEHIPPPP RPPKRILEPH N                                            321

SEQ ID NO: 24          moltype = AA  length = 12
FEATURE                Location/Qualifiers
REGION                 1..12
                       note = Synthetic
source                 1..12
                       mol_type = protein
                       organism = synthetic construct
SEQUENCE: 24
WMEDYDYVHL QG                                                      12

SEQ ID NO: 25          moltype = AA  length = 11
FEATURE                Location/Qualifiers
REGION                 1..11
                       note = Synthetic
source                 1..11
                       mol_type = protein
                       organism = synthetic construct
SEQUENCE: 25
EPQYEEIPIY L                                                       11

SEQ ID NO: 26          moltype = AA  length = 10
FEATURE                Location/Qualifiers
REGION                 1..10
                       note = Synthetic
source                 1..10
                       mol_type = protein
                       organism = synthetic construct
SEQUENCE: 26
DHQYYNDFPG                                                         10

SEQ ID NO: 27          moltype = AA  length = 10
FEATURE                Location/Qualifiers
REGION                 1..10
                       note = Synthetic
source                 1..10
                       mol_type = protein
                       organism = synthetic construct
SEQUENCE: 27
PQRYLVIQGD                                                         10

SEQ ID NO: 28          moltype = AA  length = 12
FEATURE                Location/Qualifiers
REGION                 1..12
                       note = Synthetic
source                 1..12
                       mol_type = protein
                       organism = synthetic construct
```

```
SEQUENCE: 28
WMEDFDFVHL QG                                                12

SEQ ID NO: 29          moltype = AA  length = 11
FEATURE                Location/Qualifiers
REGION                 1..11
                       note = Synthetic
source                 1..11
                       mol_type = protein
                       organism = synthetic construct
SEQUENCE: 29
EPQFEEIPIY L                                                 11

SEQ ID NO: 30          moltype = AA  length = 707
FEATURE                Location/Qualifiers
REGION                 1..707
                       note = Synthetic
source                 1..707
                       mol_type = protein
                       organism = synthetic construct
SEQUENCE: 30
MKFGNFLLTY QPPQFSQTEV MKRLVKLGRI SEECGFDTVW LLEHHFTEFG LLGNPYVAAA  60
YLLGATKKLN VGTAAIVLPT AHPVRQLEDV NLLDQMSKGR FRFGICRGLY NKDFRVFGTD  120
MNNSRALAEC WYGLIKNGMT EGYMEADNEH IKFHKVKVNP AAYSRGGAPV YVVAESASTT  180
EWAAQFGLPM ILSWIINTNE KKAQLELYNE VAQEYGHDIH NIDHCLSYIT SVDHDSIKAK  240
EICRKFLGHW YDSYVNATTI FDDSDQTRGY DFNKGQWRDF VLKGHKDTNR RIDYSYEINP  300
VGTPQECIDI IQKDIDATGI SNICCGFEAN GTVDEIIASM KLFQSDVMPF LKEKQRSLLY  360
YGGGGSGGGG SGGGGSGGGG SKFGLPFLNF INSTTVQEQS IVRMQEITEY VDKLNFEQIL  420
VYENHFSDNG VVGAPLTVSG FLLGLTEKIK IGSLNHIITT HHPVRIAEEA CLLDQLSEGR  480
FILGFSDCEK KDEMHFFNRP VEYQQQLFEE CYEIINDALT TGYCNPDNDF YSFPKISVNP  540
HAYTPGGPRK YVTATSHHIV EWAAKKGIPL IFKWDDSNDV RYEYAERYKA VADKYDVDLS  600
EIDHQLMILV NYNEDSNKAK QETRAFISDY VLEMHPNENF ENKLEEIIAE NAVGNYTECI  660
TAAKLAIEKC GAKSVLLSFE PMNDLMSQKN VINIVDDNIK KYHTEYT             707

SEQ ID NO: 31          moltype = AA  length = 263
FEATURE                Location/Qualifiers
REGION                 1..263
                       note = Synthetic
source                 1..263
                       mol_type = protein
                       organism = synthetic construct
SEQUENCE: 31
MREAVIAEVS TQLSEVVGVI ERHLEPTLLA VHLYGSAVDG GLKPHSDIDL LVTVTVRLDE  60
TTRRALINDL LETSASPGES EILRAVEVTI VVHDDIIPWR YPAKRELQFG EWQRNDILAG  120
IFEPATIDID LAILLTKARE HSVALVGPAA EELFDPVPEQ DLFEALNETL TLWNSPPDWA  180
GDERNVVLTL SRIWYSAVTG KIAPKDVAAD WAMERLPAQY QPVILEARQA YLGQEEDRLA  240
SRADQLEEFV HYVKGEITKV VGK                                    263

SEQ ID NO: 32          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 32
gtgcagtaag gaggaaaaaa                                        20

SEQ ID NO: 33          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 33
cagtcagtag ggccctaaaa                                        20

SEQ ID NO: 34          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 34
tagctaaagc aaccagagag                                        20

SEQ ID NO: 35          moltype = DNA  length = 25
```

```
FEATURE                Location/Qualifiers
misc_feature           1..25
                       note = Synthetic
source                 1..25
                       mol_type = other DNA
                       organism = synthetic construct
SEQUENCE: 35
caattcccct ctagaaataa ttttg                                      25

SEQ ID NO: 36          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 36
cgctgtagag aaaattggta                                            20

SEQ ID NO: 37          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 37
gacgcggaat ggtactgggg                                            20

SEQ ID NO: 38          moltype = DNA  length = 33
FEATURE                Location/Qualifiers
misc_feature           1..33
                       note = Synthetic
source                 1..33
                       mol_type = other DNA
                       organism = synthetic construct
SEQUENCE: 38
atatggtctc acatgtccaa gccgcagact cag                             33

SEQ ID NO: 39          moltype = DNA  length = 31
FEATURE                Location/Qualifiers
misc_feature           1..31
                       note = Synthetic
source                 1..31
                       mol_type = other DNA
                       organism = synthetic construct
SEQUENCE: 39
atatggtctc acatggcacg cgtaactgtt c                               31

SEQ ID NO: 40          moltype = DNA  length = 38
FEATURE                Location/Qualifiers
misc_feature           1..38
                       note = Synthetic
source                 1..38
                       mol_type = other DNA
                       organism = synthetic construct
SEQUENCE: 40
atatggtctc acatgagtat cagcagcagg gtaaaaag                        38

SEQ ID NO: 41          moltype = DNA  length = 60
FEATURE                Location/Qualifiers
misc_feature           1..60
                       note = Synthetic
source                 1..60
                       mol_type = other DNA
                       organism = synthetic construct
SEQUENCE: 41
atgactacgt ccacctacag gggtaataac aattcccctc tagaaataat tttgtttaac  60

SEQ ID NO: 42          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 42
tgagttatac acagggctgg                                            20
```

```
SEQ ID NO: 43          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 43
gtgcagtaag gaggaaaaaa aaatggc                                         27

SEQ ID NO: 44          moltype = DNA  length = 59
FEATURE                Location/Qualifiers
misc_feature           1..59
                       note = Synthetic
source                 1..59
                       mol_type = other DNA
                       organism = synthetic construct
SEQUENCE: 44
taaaattcgt agactacaag gacgacgatg acaagtggta ttttgggaag atcactcgt   59

SEQ ID NO: 45          moltype = DNA  length = 43
FEATURE                Location/Qualifiers
misc_feature           1..43
                       note = Synthetic
source                 1..43
                       mol_type = other DNA
                       organism = synthetic construct
SEQUENCE: 45
taataacaat tcccctctag aaataatttt gtttaacttt aag                       43

SEQ ID NO: 46          moltype = DNA  length = 60
FEATURE                Location/Qualifiers
misc_feature           1..60
                       note = Synthetic
source                 1..60
                       mol_type = other DNA
                       organism = synthetic construct
SEQUENCE: 46
gtcagtgtgt aagtgcagaa agaggagaaa tactagatgg agatggaaaa ggagttcgag  60

SEQ ID NO: 47          moltype = DNA  length = 47
FEATURE                Location/Qualifiers
misc_feature           1..47
                       note = Synthetic
source                 1..47
                       mol_type = other DNA
                       organism = synthetic construct
SEQUENCE: 47
taatctagag aaagaggaga aatactagat gtccaagccg cagactc                   47

SEQ ID NO: 48          moltype = DNA  length = 36
FEATURE                Location/Qualifiers
misc_feature           1..36
                       note = Synthetic
source                 1..36
                       mol_type = other DNA
                       organism = synthetic construct
SEQUENCE: 48
ctctagtaaa agttaaacaa aattatttgt agaggg                               36

SEQ ID NO: 49          moltype = DNA  length = 60
FEATURE                Location/Qualifiers
misc_feature           1..60
                       note = Synthetic
source                 1..60
                       mol_type = other DNA
                       organism = synthetic construct
SEQUENCE: 49
aacttttact agaggaattc gagctcttaa agaggagaaa ggtcatgggc tccaagccgc  60

SEQ ID NO: 50          moltype = DNA  length = 54
FEATURE                Location/Qualifiers
misc_feature           1..54
                       note = Synthetic
source                 1..54
                       mol_type = other DNA
                       organism = synthetic construct
SEQUENCE: 50
aacttttact agagcgaaaa aaagtaaggc ggtaatccat gggctccaag ccgc          54
```

```
SEQ ID NO: 51          moltype = DNA  length = 60
FEATURE                Location/Qualifiers
misc_feature           1..60
                       note = Synthetic
source                 1..60
                       mol_type = other DNA
                       organism = synthetic construct
SEQUENCE: 51
agtgtgtaag tgcagattaa agaggagaaa tactagatgg agatggaaaa ggagttcgag  60

SEQ ID NO: 52          moltype = DNA  length = 60
FEATURE                Location/Qualifiers
misc_feature           1..60
                       note = Synthetic
source                 1..60
                       mol_type = other DNA
                       organism = synthetic construct
SEQUENCE: 52
tcagtgtgta agtgcagtca cacaggaaag tactagatgg agatggaaaa ggagttcgag  60

SEQ ID NO: 53          moltype = DNA  length = 42
FEATURE                Location/Qualifiers
misc_feature           1..42
                       note = Synthetic
source                 1..42
                       mol_type = other DNA
                       organism = synthetic construct
SEQUENCE: 53
gcgtacattg gctccgttca tttgccgact accttggtga tc                     42

SEQ ID NO: 54          moltype = DNA  length = 58
FEATURE                Location/Qualifiers
misc_feature           1..58
                       note = Synthetic
source                 1..58
                       mol_type = other DNA
                       organism = synthetic construct
SEQUENCE: 54
gtcaggggcg gggttttttt ttagggccct actgactgtt agcaggtgcg gtaattga    58

SEQ ID NO: 55          moltype = DNA  length = 58
FEATURE                Location/Qualifiers
misc_feature           1..58
                       note = Synthetic
source                 1..58
                       mol_type = other DNA
                       organism = synthetic construct
SEQUENCE: 55
cacagttctc gtcatcagct ctctggttgc tttagctaat acaccataag cattttcc    58

SEQ ID NO: 56          moltype = DNA  length = 58
FEATURE                Location/Qualifiers
misc_feature           1..58
                       note = Synthetic
source                 1..58
                       mol_type = other DNA
                       organism = synthetic construct
SEQUENCE: 56
cagttacgcg tgccattttt ttttcctcct tactgcactt agcgtttcgg cgccggat    58

SEQ ID NO: 57          moltype = DNA  length = 63
FEATURE                Location/Qualifiers
misc_feature           1..63
                       note = Synthetic
source                 1..63
                       mol_type = other DNA
                       organism = synthetic construct
SEQUENCE: 57
gtcaggggcg gggttttttt ttagggccct actgactgtt acacactgac atccttctca  60
tcg                                                                63

SEQ ID NO: 58          moltype = DNA  length = 59
FEATURE                Location/Qualifiers
misc_feature           1..59
                       note = Synthetic
source                 1..59
                       mol_type = other DNA
                       organism = synthetic construct
```

```
SEQUENCE: 58
caggggcggg gttttttttt agggccctac tgactgttat tagccaagat ccatcttca   59

SEQ ID NO: 59          moltype = DNA  length = 59
FEATURE                Location/Qualifiers
misc_feature           1..59
                       note = Synthetic
source                 1..59
                       mol_type = other DNA
                       organism = synthetic construct
SEQUENCE: 59
gttacgcgtg ccattttttt ttcctcctta ctgcacttat tacgaaaccg gatacaaca   59

SEQ ID NO: 60          moltype = DNA  length = 37
FEATURE                Location/Qualifiers
misc_feature           1..37
                       note = Synthetic
source                 1..37
                       mol_type = other DNA
                       organism = synthetic construct
SEQUENCE: 60
atatggtctc atttacacac tgacatcctt ctcatcg                           37

SEQ ID NO: 61          moltype = DNA  length = 31
FEATURE                Location/Qualifiers
misc_feature           1..31
                       note = Synthetic
source                 1..31
                       mol_type = other DNA
                       organism = synthetic construct
SEQUENCE: 61
atatggtctc atttacccct gtaggtggac g                                 31

SEQ ID NO: 62          moltype = DNA  length = 32
FEATURE                Location/Qualifiers
misc_feature           1..32
                       note = Synthetic
source                 1..32
                       mol_type = other DNA
                       organism = synthetic construct
SEQUENCE: 62
atatggtctc atttagcaga cgttggtcag gc                                32

SEQ ID NO: 63          moltype = DNA  length = 59
FEATURE                Location/Qualifiers
misc_feature           1..59
                       note = Synthetic
source                 1..59
                       mol_type = other DNA
                       organism = synthetic construct
SEQUENCE: 63
aagataaaaa gaatagatcc cagccctgtg tataactcac tactttagtc agttccgca   59

SEQ ID NO: 64          moltype = DNA  length = 52
FEATURE                Location/Qualifiers
misc_feature           1..52
                       note = Synthetic
source                 1..52
                       mol_type = other DNA
                       organism = synthetic construct
SEQUENCE: 64
cccctgtagg tggacgtagt catagtcctc catccacgca gctgcacgac ga           52

SEQ ID NO: 65          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 65
gcccatggta tatctccttc ttaaagt                                      27

SEQ ID NO: 66          moltype = DNA  length = 59
FEATURE                Location/Qualifiers
misc_feature           1..59
                       note = Synthetic
source                 1..59
                       mol_type = other DNA
```

```
                        organism = synthetic construct
SEQUENCE: 66
acagttacgc gtgccatttt tttttcctcc ttactgcact tagcagacgt tggtcaggc   59

SEQ ID NO: 67           moltype = DNA  length = 59
FEATURE                 Location/Qualifiers
misc_feature            1..59
                        note = Synthetic
source                  1..59
                        mol_type = other DNA
                        organism = synthetic construct
SEQUENCE: 67
gggaattgtt attagcccgg aaaatcgtta taatactgat gatccgcagc tgcacgacg   59

SEQ ID NO: 68           moltype = DNA  length = 59
FEATURE                 Location/Qualifiers
misc_feature            1..59
                        note = Synthetic
source                  1..59
                        mol_type = other DNA
                        organism = synthetic construct
SEQUENCE: 68
gggaattgtt attaatcgcc ctgaatcacc agatagcgct gcggcgcagc tgcacgacg   59

SEQ ID NO: 69           moltype = DNA  length = 60
FEATURE                 Location/Qualifiers
misc_feature            1..60
                        note = Synthetic
source                  1..60
                        mol_type = other DNA
                        organism = synthetic construct
SEQUENCE: 69
gaattgttat tacagataaa tcggaatttc ttcatactgc ggttccgcag ctgcacgacg  60

SEQ ID NO: 70           moltype = DNA  length = 43
FEATURE                 Location/Qualifiers
misc_feature            1..43
                        note = Synthetic
source                  1..43
                        mol_type = other DNA
                        organism = synthetic construct
SEQUENCE: 70
ctcatccgcc aaaacagcct caattgtgtg gctccaggat tcg                    43

SEQ ID NO: 71           moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 71
ttacacactg acatccttct catcg                                        25

SEQ ID NO: 72           moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 72
ttctagagca cagctaacac cac                                          23

SEQ ID NO: 73           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 73
gaaccaatga atgatttgat gagc                                         24

SEQ ID NO: 74           moltype = DNA  length = 49
FEATURE                 Location/Qualifiers
misc_feature            1..49
                        note = Synthetic
source                  1..49
```

```
                        mol_type = other DNA
                        organism = synthetic construct
SEQUENCE: 74
gttttttttt agggccctac tgactgtcaa ttgtgtggct ccaggattc               49

SEQ ID NO: 75           moltype = DNA  length = 43
FEATURE                 Location/Qualifiers
misc_feature            1..43
                        note = Synthetic
source                  1..43
                        mol_type = other DNA
                        organism = synthetic construct
SEQUENCE: 75
gacctgcaga ttaaagagga gaaaatgagg gaagcggtga tcg                     43

SEQ ID NO: 76           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 76
tattgagctc caccgcggag gaggaatg                                      28

SEQ ID NO: 77           moltype = DNA  length = 32
FEATURE                 Location/Qualifiers
misc_feature            1..32
                        note = Synthetic
source                  1..32
                        mol_type = other DNA
                        organism = synthetic construct
SEQUENCE: 77
tattggtctc ccatgagcag cagcactggc ac                                 32

SEQ ID NO: 78           moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 78
ataaaggtct cccatggtga aacgagaatt tcctccag                           38

SEQ ID NO: 79           moltype = DNA  length = 89
FEATURE                 Location/Qualifiers
misc_feature            1..89
                        note = Synthetic
source                  1..89
                        mol_type = other DNA
                        organism = synthetic construct
SEQUENCE: 79
agatcactac cgggcgtatt ttttgagtta tcgagatttt caggagctaa ggaagctaaa  60
atggagaaaa aaatcactgg atataccac                                     89

SEQ ID NO: 80           moltype = DNA  length = 37
FEATURE                 Location/Qualifiers
misc_feature            1..37
                        note = Synthetic
source                  1..37
                        mol_type = other DNA
                        organism = synthetic construct
SEQUENCE: 80
tattgtcgac ttatttatta cgctggatga tgtagtc                            37

SEQ ID NO: 81           moltype = DNA  length = 37
FEATURE                 Location/Qualifiers
misc_feature            1..37
                        note = Synthetic
source                  1..37
                        mol_type = other DNA
                        organism = synthetic construct
SEQUENCE: 81
tattggtctc cgtccttcca acgcattcaa catgttg                            37

SEQ ID NO: 82           moltype = DNA  length = 40
FEATURE                 Location/Qualifiers
misc_feature            1..40
```

```
                        note = Synthetic
source                  1..40
                        mol_type = other DNA
                        organism = synthetic construct
SEQUENCE: 82
tattaggtct cgagctctta ggcaactggt tggaagaggc                        40

SEQ ID NO: 83           moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 83
gccgccggct tccatttatt acgccccgcc ctg                               33

SEQ ID NO: 84           moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 84
gtccagtact ttattggggt tcaggcggat ggaactgagc atgtccgaga t           51

SEQ ID NO: 85           moltype = DNA  length = 47
FEATURE                 Location/Qualifiers
misc_feature            1..47
                        note = Synthetic
source                  1..47
                        mol_type = other DNA
                        organism = synthetic construct
SEQUENCE: 85
gagagagaat cctgttcctg atattgcgga tacagccatg ggccttc                47

SEQ ID NO: 86           moltype = DNA  length = 53
FEATURE                 Location/Qualifiers
misc_feature            1..53
                        note = Synthetic
source                  1..53
                        mol_type = other DNA
                        organism = synthetic construct
SEQUENCE: 86
acaaaaactt ccaatttcac tgttatttta gcggatcttt atgacgccca tgg         53

SEQ ID NO: 87           moltype = DNA  length = 40
FEATURE                 Location/Qualifiers
misc_feature            1..40
                        note = Synthetic
source                  1..40
                        mol_type = other DNA
                        organism = synthetic construct
SEQUENCE: 87
cgtaagcatc gtaagtgtcc gcgatcaggg tgataacagc                        40

SEQ ID NO: 88           moltype = DNA  length = 44
FEATURE                 Location/Qualifiers
misc_feature            1..44
                        note = Synthetic
source                  1..44
                        mol_type = other DNA
                        organism = synthetic construct
SEQUENCE: 88
cccatgcgtg tcgtataagt ccgctaacat tgtcatcaag atcg                   44

SEQ ID NO: 89           moltype = DNA  length = 46
FEATURE                 Location/Qualifiers
misc_feature            1..46
                        note = Synthetic
misc_feature            17..18
                        note = n is a, c, g, or t
source                  1..46
                        mol_type = other DNA
                        organism = synthetic construct
SEQUENCE: 89
caatggcacc cccaacnnkg gtatgtgtgt acttaatctg atcccg                 46
```

```
SEQ ID NO: 90           moltype = DNA  length = 46
FEATURE                 Location/Qualifiers
misc_feature            1..46
                        note = Synthetic
misc_feature            20..21
                        note = n is a, c, g, or t
source                  1..46
                        mol_type = other DNA
                        organism = synthetic construct
SEQUENCE: 90
caacaccggt atgtgtgtan nkaatctgat cccgttgctg cttatg                46

SEQ ID NO: 91           moltype = DNA  length = 41
FEATURE                 Location/Qualifiers
misc_feature            1..41
                        note = Synthetic
misc_feature            17..18
                        note = n is a, c, g, or t
source                  1..41
                        mol_type = other DNA
                        organism = synthetic construct
SEQUENCE: 91
aaacgcttgg gaacgcnnkc tggaagcgta tttgcaggat g                     41

SEQ ID NO: 92           moltype = DNA  length = 45
FEATURE                 Location/Qualifiers
misc_feature            1..45
                        note = Synthetic
misc_feature            17..18
                        note = n is a, c, g, or t
source                  1..45
                        mol_type = other DNA
                        organism = synthetic construct
SEQUENCE: 92
cttctggatg gccgcgnnka tttcagaacc agaatttagt ggctc                 45

SEQ ID NO: 93           moltype = DNA  length = 43
FEATURE                 Location/Qualifiers
misc_feature            1..43
                        note = Synthetic
misc_feature            21..22
                        note = n is a, c, g, or t
source                  1..43
                        mol_type = other DNA
                        organism = synthetic construct
SEQUENCE: 93
accatctgat tgaactggct nnkcgactgg tcgatgatgc gag                   43

SEQ ID NO: 94           moltype = DNA  length = 43
FEATURE                 Location/Qualifiers
misc_feature            1..43
                        note = Synthetic
misc_feature            14..15
                        note = n is a, c, g, or t
source                  1..43
                        mol_type = other DNA
                        organism = synthetic construct
SEQUENCE: 94
cgtcctggcg cggnnkattc agtttatgta taaccagggg gac                   43

SEQ ID NO: 95           moltype = DNA  length = 54
FEATURE                 Location/Qualifiers
misc_feature            1..54
                        note = Synthetic
misc_feature            29..30
                        note = n is a, c, g, or t
source                  1..54
                        mol_type = other DNA
                        organism = synthetic construct
SEQUENCE: 95
caactgcggt aaagagtttg ttaaagaann kgtacgtaac ctgatggttg aagc       54

SEQ ID NO: 96           moltype = DNA  length = 47
FEATURE                 Location/Qualifiers
misc_feature            1..47
                        note = Synthetic
misc_feature            25..26
                        note = n is a, c, g, or t
source                  1..47
```

```
                        mol_type = other DNA
                        organism = synthetic construct
SEQUENCE: 96
catgacccgg ttgttatcat caccnnkggt gcaaacctgc tgaccac                47

SEQ ID NO: 97           moltype = DNA  length = 40
FEATURE                 Location/Qualifiers
misc_feature            1..40
                        note = Synthetic
misc_feature            18..19
                        note = n is a, c, g, or t
source                  1..40
                        mol_type = other DNA
                        organism = synthetic construct
SEQUENCE: 97
ccggcggtgc aaacctgnnk accaccactt gctatctggg                        40

SEQ ID NO: 98           moltype = DNA  length = 48
FEATURE                 Location/Qualifiers
misc_feature            1..48
                        note = Synthetic
misc_feature            25..26
                        note = n is a, c, g, or t
source                  1..48
                        mol_type = other DNA
                        organism = synthetic construct
SEQUENCE: 98
ctgttccgtt actccggtat tctgnnkcgt cgtctgaacg acctgatg               48

SEQ ID NO: 99           moltype = DNA  length = 50
FEATURE                 Location/Qualifiers
misc_feature            1..50
                        note = Synthetic
misc_feature            23..24
                        note = n is a, c, g, or t
source                  1..50
                        mol_type = other DNA
                        organism = synthetic construct
SEQUENCE: 99
ggcagtaatc tacctgtgcc agnnkctgga agtacagtac gctggtaaag             50

SEQ ID NO: 100          moltype = DNA  length = 34
FEATURE                 Location/Qualifiers
misc_feature            1..34
                        note = Synthetic
source                  1..34
                        mol_type = other DNA
                        organism = synthetic construct
SEQUENCE: 100
cagctgcgga accgcagttt gaagaaattc cgat                              34

SEQ ID NO: 101          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 101
tggatggagg actttgactt cgtccaccta caggggtaat aacaattc               48

SEQ ID NO: 102          moltype = DNA  length = 66
FEATURE                 Location/Qualifiers
misc_feature            1..66
                        note = Synthetic
source                  1..66
                        mol_type = other DNA
                        organism = synthetic construct
SEQUENCE: 102
ctctccgttt ctgactttga caacgccaag ggctcaatg tgctgcacta caagatccgc  60
aagctg                                                             66

SEQ ID NO: 103          moltype = DNA  length = 30
FEATURE                 Location/Qualifiers
misc_feature            1..30
                        note = Synthetic
source                  1..30
                        mol_type = other DNA
                        organism = synthetic construct
```

```
SEQUENCE: 103
aaacactacc tgatccgcaa gctggacagc                                   30

SEQ ID NO: 104          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 104
tattggtctc tcgcggtatc attgcagcac                                   30

SEQ ID NO: 105          moltype = DNA  length = 31
FEATURE                 Location/Qualifiers
misc_feature            1..31
                        note = Synthetic
source                  1..31
                        mol_type = other DNA
                        organism = synthetic construct
SEQUENCE: 105
tattggtctc atcaccccat gcgagagtag g                                 31

SEQ ID NO: 106          moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 106
aacaatttca cacaggaaac agacc                                        25

SEQ ID NO: 107          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 107
atctcggaca tgctcagttc catccgcctg aaccccaata aagtactgga c           51

SEQ ID NO: 108          moltype = DNA  length = 47
FEATURE                 Location/Qualifiers
misc_feature            1..47
                        note = Synthetic
source                  1..47
                        mol_type = other DNA
                        organism = synthetic construct
SEQUENCE: 108
gaaggcccat ggctgtatcc gcaatatcag gaacaggatt ctctctc                47

SEQ ID NO: 109          moltype = DNA  length = 53
FEATURE                 Location/Qualifiers
misc_feature            1..53
                        note = Synthetic
source                  1..53
                        mol_type = other DNA
                        organism = synthetic construct
SEQUENCE: 109
ccatgggcgt cataaagatc cgctaaaata acagtgaaat tggaagtttt tgt         53

SEQ ID NO: 110          moltype = DNA  length = 40
FEATURE                 Location/Qualifiers
misc_feature            1..40
                        note = Synthetic
source                  1..40
                        mol_type = other DNA
                        organism = synthetic construct
SEQUENCE: 110
gctgttatca ccctgatcgc ggacacttac gatgcttacg                        40

SEQ ID NO: 111          moltype = DNA  length = 44
FEATURE                 Location/Qualifiers
misc_feature            1..44
                        note = Synthetic
source                  1..44
                        mol_type = other DNA
```

```
                         organism = synthetic construct
SEQUENCE: 111
cgatcttgat gacaatgtta gcggacttat acgacacgca tggg                  44

SEQ ID NO: 112           moltype = DNA  length = 19
FEATURE                  Location/Qualifiers
misc_feature             1..19
                         note = Synthetic
source                   1..19
                         mol_type = other DNA
                         organism = synthetic construct
SEQUENCE: 112
gttgggggtg ccattgttc                                              19

SEQ ID NO: 113           moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 113
tacacacata ccggtgttgg g                                           21

SEQ ID NO: 114           moltype = DNA  length = 19
FEATURE                  Location/Qualifiers
misc_feature             1..19
                         note = Synthetic
source                   1..19
                         mol_type = other DNA
                         organism = synthetic construct
SEQUENCE: 114
gcgttcccaa gcgtttttg                                              19

SEQ ID NO: 115           moltype = DNA  length = 17
FEATURE                  Location/Qualifiers
misc_feature             1..17
                         note = Synthetic
source                   1..17
                         mol_type = other DNA
                         organism = synthetic construct
SEQUENCE: 115
cgcggccatc cagaagt                                                17

SEQ ID NO: 116           moltype = DNA  length = 22
FEATURE                  Location/Qualifiers
misc_feature             1..22
                         note = Synthetic
source                   1..22
                         mol_type = other DNA
                         organism = synthetic construct
SEQUENCE: 116
agccagttca atcagatggt gg                                          22

SEQ ID NO: 117           moltype = DNA  length = 15
FEATURE                  Location/Qualifiers
misc_feature             1..15
                         note = Synthetic
source                   1..15
                         mol_type = other DNA
                         organism = synthetic construct
SEQUENCE: 117
ccgcgccagg acgtg                                                  15

SEQ ID NO: 118           moltype = DNA  length = 28
FEATURE                  Location/Qualifiers
misc_feature             1..28
                         note = Synthetic
source                   1..28
                         mol_type = other DNA
                         organism = synthetic construct
SEQUENCE: 118
ttctttaaca aactctttac cgcagttg                                    28

SEQ ID NO: 119           moltype = DNA  length = 24
FEATURE                  Location/Qualifiers
misc_feature             1..24
                         note = Synthetic
source                   1..24
```

```
                        mol_type = other DNA
                        organism = synthetic construct
SEQUENCE: 119
ggtgatgata acaaccgggt catg                                          24

SEQ ID NO: 120          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 120
caggtttgca ccgccgg                                                  17

SEQ ID NO: 121          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 121
cagaataccg gagtaacgga acag                                          24

SEQ ID NO: 122          moltype = DNA  length = 22
FEATURE                 Location/Qualifiers
misc_feature            1..22
                        note = Synthetic
source                  1..22
                        mol_type = other DNA
                        organism = synthetic construct
SEQUENCE: 122
ctggcacagg tagattactg cc                                            22

SEQ ID NO: 123          moltype = DNA  length = 34
FEATURE                 Location/Qualifiers
misc_feature            1..34
                        note = Synthetic
source                  1..34
                        mol_type = other DNA
                        organism = synthetic construct
SEQUENCE: 123
atcggaattt cttcaaactg cggttccgca gctg                               34

SEQ ID NO: 124          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 124
gtcaaagtcc tccatccacg cagctgcacg acg                                33

SEQ ID NO: 125          moltype = DNA  length = 50
FEATURE                 Location/Qualifiers
misc_feature            1..50
                        note = Synthetic
source                  1..50
                        mol_type = other DNA
                        organism = synthetic construct
SEQUENCE: 125
aagtcagaaa cggagagggc ataggcacct tttaccgtct cgctctcccg              50

SEQ ID NO: 126          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 126
gctgtccagc ttgcggatca ggtagtgttt cacattgagc cccttggc                48

SEQ ID NO: 127          moltype = DNA  length = 32
FEATURE                 Location/Qualifiers
misc_feature            1..32
                        note = Synthetic
```

```
source                  1..32
                        mol_type = other DNA
                        organism = synthetic construct
SEQUENCE: 127
tattggtctc agtgacccca cactaccatc gg                                32

SEQ ID NO: 128          moltype = DNA  length = 31
FEATURE                 Location/Qualifiers
misc_feature            1..31
                        note = Synthetic
source                  1..31
                        mol_type = other DNA
                        organism = synthetic construct
SEQUENCE: 128
tattggtctc acgcgtgacc cacgctcacc g                                 31

SEQ ID NO: 129          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 129
gcctgcaggt cgactctaga                                              20

SEQ ID NO: 130          moltype = DNA  length = 43
FEATURE                 Location/Qualifiers
misc_feature            1..43
                        note = Synthetic
source                  1..43
                        mol_type = other DNA
                        organism = synthetic construct
SEQUENCE: 130
aacaatttca cacaggaaac agaccatggc gggtgtttct gcg                    43

SEQ ID NO: 131          moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 131
gcctgcaggt cgactctaga ttacagcggc agcggttc                          38

SEQ ID NO: 132          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 132
cagagagaag gtgccagaca tcccaatgcc tgcactaca                         39

SEQ ID NO: 133          moltype = DNA  length = 35
FEATURE                 Location/Qualifiers
misc_feature            1..35
                        note = Synthetic
source                  1..35
                        mol_type = other DNA
                        organism = synthetic construct
SEQUENCE: 133
caatgatggt gcctgtcatg ccgatgccgg cgctg                             35

SEQ ID NO: 134          moltype = DNA  length = 60
FEATURE                 Location/Qualifiers
misc_feature            1..60
                        note = Synthetic
source                  1..60
                        mol_type = other DNA
                        organism = synthetic construct
SEQUENCE: 134
gctgtgatca aatggcagta tgtccttcgc tctgttcttt ttaacatttt cttctttttc  60

SEQ ID NO: 135          moltype = DNA  length = 34
FEATURE                 Location/Qualifiers
misc_feature            1..34
```

-continued

```
                         note = Synthetic
source                   1..34
                         mol_type = other DNA
                         organism = synthetic construct
SEQUENCE: 135
aggtgtcgta catgtccgcc agaacggtct gcag                         34

SEQ ID NO: 136           moltype = DNA  length = 39
FEATURE                  Location/Qualifiers
misc_feature             1..39
                         note = Synthetic
source                   1..39
                         mol_type = other DNA
                         organism = synthetic construct
SEQUENCE: 136
tgtagtgcag gcattgggat gtctggcacc ttctctctg                    39

SEQ ID NO: 137           moltype = DNA  length = 35
FEATURE                  Location/Qualifiers
misc_feature             1..35
                         note = Synthetic
source                   1..35
                         mol_type = other DNA
                         organism = synthetic construct
SEQUENCE: 137
cagcgccggc atcggcatga caggcaccat cattg                        35

SEQ ID NO: 138           moltype = DNA  length = 60
FEATURE                  Location/Qualifiers
misc_feature             1..60
                         note = Synthetic
source                   1..60
                         mol_type = other DNA
                         organism = synthetic construct
SEQUENCE: 138
gaaaaagaag aaaatgttaa aaagaacaga gcgaaggaca tactgccatt tgatcacagc  60

SEQ ID NO: 139           moltype = DNA  length = 34
FEATURE                  Location/Qualifiers
misc_feature             1..34
                         note = Synthetic
source                   1..34
                         mol_type = other DNA
                         organism = synthetic construct
SEQUENCE: 139
ctgcagaccg ttctggcgga catgtacgac acct                         34

SEQ ID NO: 140           moltype = AA  length = 34
FEATURE                  Location/Qualifiers
REGION                   1..34
                         note = Synthetic
source                   1..34
                         mol_type = protein
                         organism = synthetic construct
SEQUENCE: 140
IQTADQLRFS YLAVIEGAKF IMGDSSVQDQ WKEL                         34

SEQ ID NO: 141           moltype = AA  length = 34
FEATURE                  Location/Qualifiers
REGION                   1..34
                         note = Synthetic
source                   1..34
                         mol_type = protein
                         organism = synthetic construct
SEQUENCE: 141
IQTPDQLRFS YMAIIEGAKY TKGDSNIQKR WKEL                         34
```

What is claimed is:

1. A method for the discovery and evolution of metabolic pathways that produce molecules that modulate protein activity, comprising:

contacting a plurality of host cells that comprise a protein of interest with a plurality of expression vectors that each comprise a different metabolic pathway of a plurality of metabolic pathways under conditions sufficient to express components of the plurality of metabolic pathways in the plurality of host cells, wherein each metabolic pathway of the plurality of metabolic pathways produces one or more metabolites, wherein the protein of interest comprises an enzyme, wherein the enzyme comprises a protein tyrosine phosphatase;

expressing the plurality of metabolic pathways in the plurality of host cells, wherein a host cell of the plurality of host cells or a subset of the plurality of host cells produces a detectable output when a metabolic pathway of the plurality of metabolic pathways produces one or more products comprising a metabolite of the one or more metabolites that modulates an activity of the enzyme, wherein the activity of the enzyme controls an assembly of a protein complex, and wherein assembly of the protein complex enhances transcription of a gene of interest to produce the detectable output;

screening the host cell or the subset of the plurality of host cells under conditions that enable measurement of the detectable output in the host cell or the subset of the plurality of host cells;

isolating the host cell or the subset of the plurality of host cells that produce the detectable output;

analyzing an expression vector of the plurality of expression vectors that yields a detectable output that is higher than an output of a reference vector comprising a reference pathway that causes a threshold level of transcription of the gene of interest; and characterizing the one or more products of metabolic pathways of the plurality of metabolic pathways comprised by the expression vector that yielded the detectable output that is higher than the output of the reference vector.

2. The method of claim 1, wherein the plurality of host cells further comprises a genetically encoded system in which the activity of the enzyme controls the assembly of the protein complex with an activity that is not possessed by components of the protein complex when the components are dissociated, such that the detectable output is proportionate to an amount of the protein complex formed.

3. The method of claim 2, wherein the enzyme adds a post-translational modification to a component of the protein complex that causes the component to form the protein complex with another component of the protein complex, wherein the component and the another component are two proteins that are initially dissociated.

4. The method of claim 2, wherein the components of the protein complex comprise two proteins with a dissociation constant ($K_d$) less than or equal to the $K_d$ of binding between SH2 domains and their phosphorylated substrates.

5. The method of claim 1, wherein the one or more products comprises phenylpropanoids or nonribosomal peptides.

6. The method of claim 1, wherein each of the plurality of metabolic pathways comprises a mutation in one or more genes within a starting metabolic pathway relative to an otherwise identical starting metabolic pathway that does not comprise the mutation.

7. The method of claim 1, wherein one or more of the plurality of metabolic pathways comprises a set of genes of unknown biosynthetic capability.

8. The method of claim 1, wherein the expression vector that is analyzed comprises one or more metabolic pathways of the plurality of metabolic pathways that produces a product of the one or more products that differs from a reference product of another metabolic pathway of the plurality of metabolic pathways.

9. The method of claim 1, wherein the expression vector that is analyzed comprises one or more metabolic pathways of the plurality of metabolic pathways that produce a larger quantity of a product of the one or more products than a quantity of a reference product generated by another metabolic pathway of the plurality of metabolic pathways.

10. The method of claim 1, wherein the expression vector that is analyzed comprises one or more metabolic pathways of the plurality of metabolic pathways that exhibit a lower cellular toxicity than a reference cellular toxicity exhibited by another metabolic pathway of the plurality of metabolic pathways.

11. The method of claim 1, wherein the characterizing the one or more products of the metabolic pathways is performed by analytical methods comprising one or more of gas chromatography-mass spectrometry (GC/MS), liquid chromatography-mass spectrometry (LC/MS), and/or nuclear magnetic resonance (NMR) spectroscopy.

12. The method of claim 1, further comprising isolating the one or more products of the metabolic pathways encoded by the expression vector that yielded the detectable output that is higher than the output of the reference vector.

13. The method of claim 12, further comprising:

concentrating the one or more products of the metabolic pathways encoded by the expression vector that yielded the detectable output that is higher than the output of the reference vector.

14. The method of claim 1, further comprising testing an effect of the one or more products on the protein of interest.

15. The method of claim 12, further comprising:

testing the effects of the one or more products of the metabolic pathways encoded by the expression vectors that yield the detectable outputs that are higher than the output of the reference vector in the host cell or the subset of the plurality of host cells on the protein of interest.

16. The method of claim 13, wherein the concentrating the one or more products is performed using a rotary evaporator.

17. The method of claim 3, wherein the components of the protein complex are covalently coupled to each other to form the protein complex.

18. The method of claim 1, wherein the reference pathway does not produce molecules with concentrations, potencies, or a combination thereof that are sufficient to modulate the activity of the enzyme in the host cell or the subset of the population of host cells.

* * * * *